(12) United States Patent
Szafranowska et al.

(10) Patent No.: US 11,882,765 B2
(45) Date of Patent: Jan. 23, 2024

(54) ORGANIC MOLECULES FOR OPTOELECTRONIC DEVICES

(71) Applicant: SAMSUNG DISPLAY CO., LTD., Yongin-si (KR)

(72) Inventors: Barbara Szafranowska, Bruchsal (DE); Dagmara Raczynska, Eppelheim (DE); Daniel Zink, Graben-Neudorf (DE)

(73) Assignee: Samsung Display Co., Ltd., Yongin-si (KR)

( * ) Notice: Subject to any disclaimer, the term of this patent is extended or adjusted under 35 U.S.C. 154(b) by 795 days.

(21) Appl. No.: 16/979,418

(22) PCT Filed: Mar. 4, 2019

(86) PCT No.: PCT/EP2019/055281
§ 371 (c)(1),
(2) Date: Sep. 9, 2020

(87) PCT Pub. No.: WO2019/174945
PCT Pub. Date: Sep. 19, 2019

(65) Prior Publication Data
US 2021/0005823 A1     Jan. 7, 2021

(30) Foreign Application Priority Data
Mar. 16, 2018     (DE) ..................... 10 2018 106 250.8

(51) Int. Cl.
*H10K 85/60* (2023.01)
*C07D 403/14* (2006.01)
(Continued)

(52) U.S. Cl.
CPC ......... *H10K 85/654* (2023.02); *C07D 403/14* (2013.01); *C07D 405/14* (2013.01);
(Continued)

(58) Field of Classification Search
CPC .................... H10K 2101/20; C09K 2211/1018
See application file for complete search history.

(56) References Cited

U.S. PATENT DOCUMENTS

2017/0186962 A1   6/2017 Ren et al.
2018/0026202 A1*  1/2018 Danz ................. C07D 403/04
                                                      257/40

FOREIGN PATENT DOCUMENTS

JP     2017108006 A    6/2017
KR   20160041768 A    4/2016
(Continued)

*Primary Examiner* — Sean M DeGuire
(74) *Attorney, Agent, or Firm* — Lewis Roca Rothgerber Christie LLP

(57) ABSTRACT

An organic molecule is disclosed having:
a first chemical moiety with a structure of Formula I, Formula I (Continued)

and
two second chemical moieties, each independently from another with a structure of Formula II,

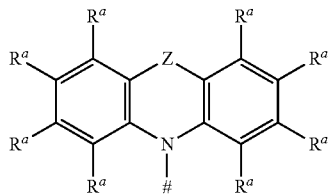

Formula II wherein the first chemical moiety is linked to each of the two second chemical moieties via a single bond.

20 Claims, 2 Drawing Sheets

(51) Int. Cl.
*C07D 405/14* (2006.01)
*C09K 11/06* (2006.01)
*H10K 50/11* (2023.01)

(52) U.S. Cl.
CPC .......... *C09K 11/06* (2013.01); *H10K 85/6572* (2023.02); *H10K 85/6574* (2023.02); *C09K 2211/1007* (2013.01); *C09K 2211/1018* (2013.01); *H10K 50/11* (2023.02)

(56) References Cited

FOREIGN PATENT DOCUMENTS

| WO | 2014208755 A1 | 12/2014 |
| WO | 2017005699 A1 | 1/2017 |
| WO | PCT/EP2019/055281 | 6/2019 |

* cited by examiner

ORGANIC MOLECULES FOR OPTOELECTRONIC DEVICES

CROSS-REFERENCE TO RELATED APPLICATIONS

This application claims priority under 35 U.S.C. § 371 to International Application No. PCT/EP2019/055281, filed Mar. 4, 2019, which claims priority to German Patent Application No. 10 2018 106 250.8, filed Mar. 16, 2018, the disclosures of which are incorporated by reference herein in their entireties.

FIELD OF INVENTION

The invention relates to organic molecules and their use in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
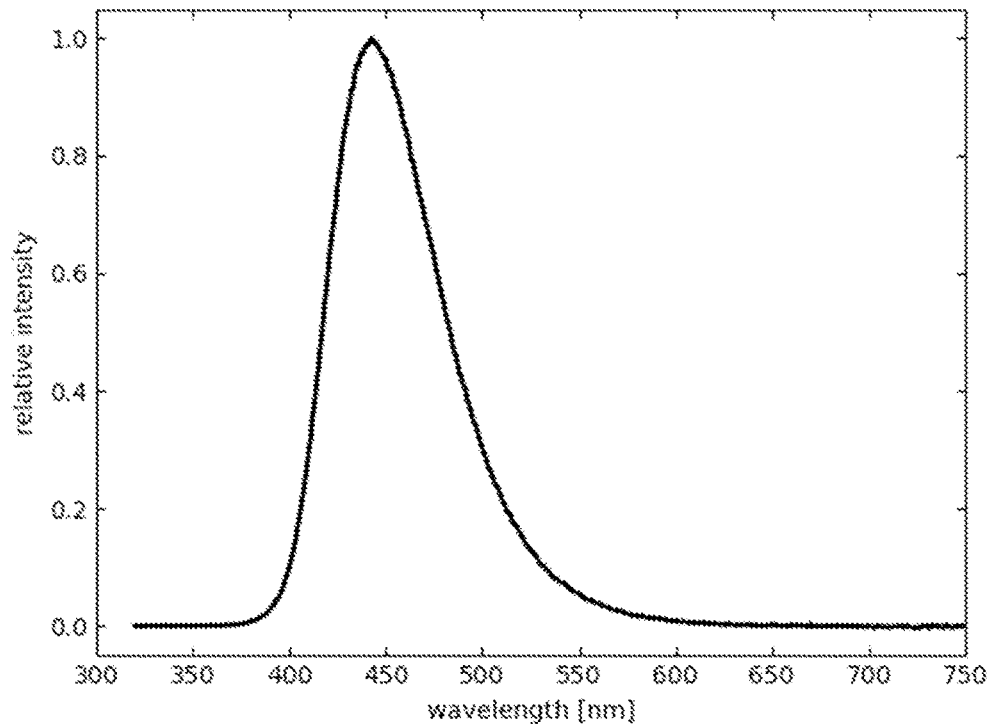
FIG. 1 is an emission spectrum of example 1 (10% by weight) in PMMA.

Exemplary embodiments of the invention will now be discussed in further detail. This invention may, however, be embodied in many different forms and should not be construed as limited to the embodiments set forth herein.

The object of the present invention is to provide molecules which are suitable for use in optoelectronic devices.

This object is achieved by the invention, which provides a new class of organic molecules.

The organic molecules of the invention are purely organic molecules, i.e. they do not contain any metal ions in contrast to metal complexes known for use in optoelectronic devices.

According to the present invention, the organic molecules exhibit emission maxima in the blue, sky-blue or green spectral range. The organic molecules exhibit, in particular, emission maxima between 420 nm and 520 nm, between 440 nm and 495 nm, or between 450 nm and 470 nm. The photoluminescence quantum yields of the organic molecules according to the invention are, in particular, 20% or more. The molecules according to the invention show, in particular, thermally activated delayed fluorescence (TADF). The use of the molecules according to the invention in an optoelectronic device, for example, in an organic light-emitting diode (OLED), leads to higher efficiencies of the device. Corresponding OLEDs have a higher stability than OLEDs with known emitter materials and comparable color.

The organic light-emitting molecules of the invention comprise or consist of a first chemical moiety comprising or consisting of a structure of Formula I,

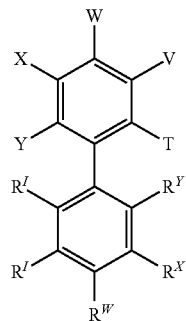

Formula I and two second chemical moieties, each independently from another comprising or consisting of a structure of Formula II,

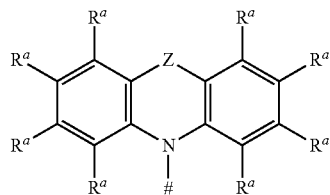

Formula II wherein the first chemical moiety is linked to each of the two second chemical moieties via a single bond.

T is selected from the group consisting of $R^A$ and $R^1$.

V is selected from the group consisting of $R^A$ and $R^1$.

W is the binding site of a single bond linking the first chemical moiety to one of the two second chemical moieties or is selected from the group consisting of $R^A$ and $R^2$.

X is the binding site of a single bond linking the first chemical moiety to one of the two second chemical moieties or is selected from the group consisting of $R^A$ and $R^2$.

Y is the binding site of a single bond linking the first chemical moiety to one of the two second chemical moieties or is selected from the group consisting of $R^A$ and $R^2$.

$R^A$ comprises or consists of a structure of Formula Py:

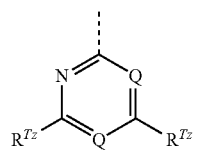

Formula Py wherein exactly one (one and only one) Q (i.e. a first Q) is N and exactly one Q (i.e. a second Q) is C—$R^{PY}$, wherein the dashed bond represents the binding site of Py (=$R^A$) to the single bond linking the first chemical moiety and $R^A$ as shown in Formula I;

$R^W$ is the binding site of a single bond linking the first chemical moiety to one of the two second chemical moieties or is $R^I$.

$R^X$ is the binding site of a single bond linking the first chemical moiety to one of the two second chemical moieties or is $R^I$.

$R^Y$ is the binding site of a single bond linking the first chemical moiety to one of the two second chemical moieties or is $R^I$.

\# represents the binding site of a single bond linking the second chemical moieties to the first chemical moiety;

Z is at each occurrence independently from another selected from the group consisting of a direct bond, $CR^3R^4$, $C=CR^3R^4$, $C=O$, $C=NR^3$, $NR^3$, O, $SiR^3R^4$, S, S(O) and $S(O)_2$;

$R^1$ is at each occurrence independently from another selected from the group consisting of:

hydrogen, deuterium, $C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^2$ is at each occurrence independently from another selected from the group consisting of:

hydrogen, deuterium, $C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^I$ is at each occurrence independently from another selected from the group consisting of:

hydrogen, deuterium, $C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^{Tz}$ is at each occurrence independently from another selected from the group consisting of:

hydrogen, deuterium, $C_1$-$C_5$-alkyl, wherein one or more hydrogen atoms are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$.

$R^{PY}$ is at each occurrence independently from another selected from the group consisting of:

hydrogen, deuterium, $C_1$-$C_5$-alkyl, wherein one or more hydrogen atoms are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$.

$R^a$, $R^3$ and $R^4$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl, which is optionally substituted with one or more substituents $R^5$ and wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

$R^5$ is at each occurrence independently from another selected from the group consisting of: hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;

$C_1$-$C_{40}$-alkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;

$C_1$-$C_{40}$-thioalkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;

$C_2$-$C_{40}$-alkenyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;

$C_2$-$C_{40}$-alkynyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;

$C_6$-$C_{60}$-aryl,
which is optionally substituted with one or more substituents $R^6$; and $C_3$-$C_{57}$-heteroaryl,
which is optionally substituted with one or more substituents $R^6$.

$R^6$ is at each occurrence independently from another selected from the group consisting of: hydrogen, deuterium, OPh, $CF_3$, CN, F, $C_1$-$C_5$-alkyl,
wherein optionally one or more hydrogen atoms are independently from each other substituted by deuterium, CN, $CF_3$, or F;

$C_1$-$C_5$-alkoxy,
wherein optionally one or more hydrogen atoms are independently from each other substituted by deuterium, CN, $CF_3$, or F;

$C_1$-$C_5$-thioalkoxy,
wherein optionally one or more hydrogen atoms are independently from each other substituted by deuterium, CN, $CF_3$, or F;

$C_2$-$C_5$-alkenyl,
wherein optionally one or more hydrogen atoms are independently from each other substituted by deuterium, CN, $CF_3$, or F;

$C_2$-$C_5$-alkynyl,
wherein optionally one or more hydrogen atoms are independently from each other substituted by deuterium, CN, $CF_3$, or F;

$C_6$-$C_{18}$-aryl,
which is optionally substituted with one or more $C_1$-$C_5$-alkyl substituents;

$C_3$-$C_{17}$-heteroaryl,
which is optionally substituted with one or more $C_1$-$C_5$-alkyl substituents;

$N(C_6$-$C_{18}$-aryl$)_2$, $N(C_3$-$C_{17}$-heteroaryl$)_2$; and $N(C_3$-$C_{17}$-heteroaryl)($C_6$-$C_{18}$-aryl).

The substituents $R^a$, $R^3$, $R^4$ or $R^5$ independently from each other can optionally form a mono- or polycyclic, aliphatic, aromatic and/or benzo-fused ring system with one or more substituents $R^a$, $R^3$, $R^4$ or $R^5$.

According to the invention exactly one substituent selected from the group consisting of T, V, W, X and Y is $R^A$; exactly one substituent selected from the group consisting of W, Y and X represents the binding site of a single bond linking the first chemical moiety and one of the two second chemical moieties and exactly one substituent selected from the group consisting of $R^W$, $R^Y$ and $R^X$ represents the binding site of a single bond linking the first chemical moiety and one of the two second chemical moieties.

According to the invention $R^X$ is $R^I$ in case X represents the binding site of a single bond linking the first chemical moiety and one of the two second chemical moieties.

In one embodiment of the invention, first chemical moiety comprises or consists of a structure of Formula Ia:

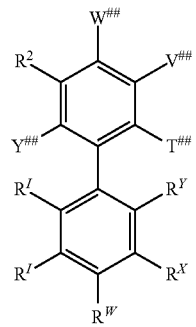

Formula Ia wherein $R^I$, $R^W$, $R^X$ and $R^Y$ are defined as above, $T^{\#\#}$ is selected from the group consisting of $R^A$ and $R^1$, $V^{\#\#}$ is selected from the group consisting of $R^A$ and $R^1$, $W^{\#\#}$ is the binding site of a single bond linking the first chemical moiety to one of the two second chemical moieties or is selected from the group consisting of $R^A$ and $R^2$, $Y^{\#\#}$ is the binding site of a single bond linking the first chemical moiety to one of the two second chemical moieties or is $R^2$, wherein exactly one substituent selected from the group consisting of $W^{\#\#}$ and $Y^{\#\#}$ represents the binding site of a single bond linking the first chemical moiety and one of the two second chemical moieties, exactly one substituent selected from the group consisting of $R^W$, $R^Y$ and $R^X$ represents the binding site of a single bond linking the first chemical moiety and one of the two second chemical moieties, and wherein exactly one substituent selected from the group consisting of $T^{\#\#}$, $V^{\#\#}$ and $W^{\#\#}$ is $R^A$.

In one embodiment of the invention, first chemical moiety comprises or consists of a structure of Formula Iaa:

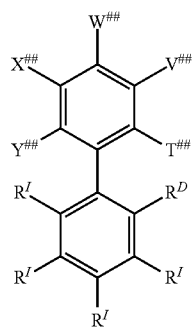

Formula Iaa wherein $R^I$ is defined as above, $R^D$ is the binding site of a single bond linking the first chemical moiety to one of the two second chemical moieties, $T^{\#\#\#}$ is selected from the group consisting of $R^A$ and $R^1$, $V^{\#\#\#}$ is selected from the group consisting of $R^A$ and $R^1$, $W^{\#\#\#}$ is the binding site of a single bond linking the first chemical moiety to one of the two second chemical moieties or is selected from the group consisting of $R^A$ and $R^2$, $X^{\#\#\#}$ is the binding site of a single bond linking the first chemical moiety to one of the two second chemical moieties or is $R^2$, $Y^{\#\#\#}$ is the binding site of a single bond linking the first chemical moiety to one of the two second chemical moieties or is $R^2$, wherein exactly one substituent selected from the group consisting of $W^{\#\#\#}$, $Y^{\#\#\#}$ and $X^{\#\#\#}$ represents the binding site of a single bond linking the first chemical moiety and one of the two second chemical moieties, and wherein exactly one substituent selected from the group consisting of $T^{\#\#\#}$, $V^{\#\#\#}$ and $W^{\#\#\#}$ is $R^A$.

In one embodiment of the invention, the first chemical moiety comprises or consists of a structure of Formula Iaaa or Formula Iaab:

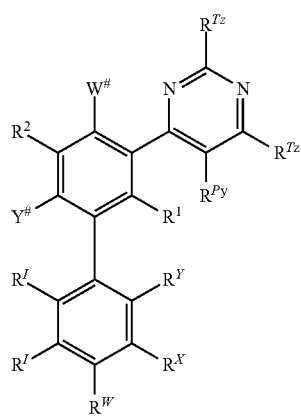

Formula Iaaa

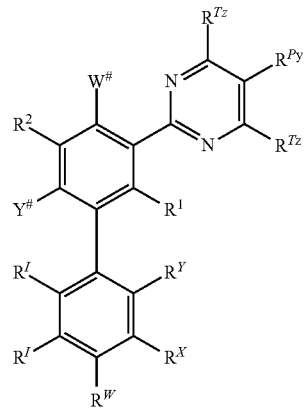

Formula Iaab wherein $R^1$, $R^I$, $R^W$, $R^X$, $R^Y$, $R^{PY}$ and $R^{Tz}$ are defined as above, $W^\#$ is the binding site of a single bond linking the first chemical moiety to one of the two second chemical moieties or is $R^2$, $Y^\#$ is the binding site of a single bond linking the first chemical moiety to one of the two second chemical moieties or is $R^2$, exactly one substituent selected from the group consisting of $R^W$, $R^Y$ and $R^X$ represents the binding site of a single bond linking the first chemical moiety and one of the two second chemical moieties, wherein exactly one substituent selected from the group consisting of $W^{\#\#}$ and $Y^{\#\#}$ represents the binding site of a single bond linking the first chemical moiety and one of the two second chemical moieties.

In one embodiment of the invention, first chemical moiety comprises or consists of a structure of Formula Iaaaa or Formula Iaaab:

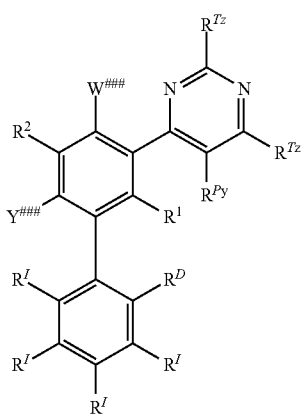

Formula Iaaaa

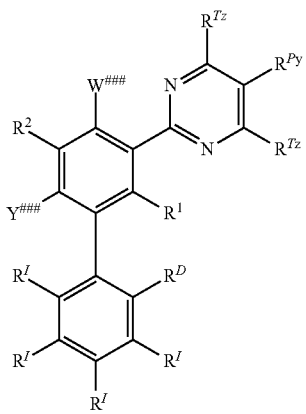

Formula Iaaab wherein $R^1$, $R^2$, $R^{Py}$, $R^{Tz}$ and $R^I$ are defined as above,
$R^D$ is the binding site of a single bond linking the first chemical moiety to one of the two second chemical moieties,
$Y^{\#\#\#\#}$ is the binding site of a single bond linking the first chemical moiety to one of the two second chemical moieties or is $R^2$,
$X^{\#\#\#\#}$ is the binding site of a single bond linking the first chemical moiety to one of the two second chemical moieties or is $R^2$,
wherein exactly one substituent selected from the group consisting of $W^{\#\#\#\#}$ and $Y^{\#\#\#\#}$ represents the binding site of a single bond linking the first chemical moiety and one of the two second chemical moieties.

In one embodiment, $R^1$, $R^2$, and $R^I$ is at each occurrence independently from another selected from the group consisting of hydrogen (H), methyl, mesityl, tolyl and phenyl. The term tolyl refers to 2-tolyl, 3-tolyl, and 4-tolyl.

In one embodiment, $R^1$, $R^2$, and $R^I$ is at each occurrence independently from another selected from the group consisting of hydrogen (H) and phenyl.

In one embodiment, $R^1$, $R^2$, and $R^I$ is at each occurrence hydrogen (H).

In one embodiment, V is $R^A$.
In one embodiment, T is $R^A$.
In one embodiment, W is $R^A$.
In one embodiment, X is $R^A$.
In one embodiment, Y is $R^A$.

In a further embodiment of the invention $R^{Tz}$ is independently from each other selected from the group consisting of H, methyl,
 phenyl, which is optionally substituted with one or more substituents $R^6$;
 1,3,5-triazinyl, which is optionally substituted with one or more substituents $R^6$;
 pyridinyl, which is optionally substituted with one or more substituents $R^6$; and
 pyrimidinyl, which is optionally substituted with one or more substituents $R^6$.

In a further embodiment of the invention, $R^{Tz}$ is independently from each other selected from the group consisting of H, methyl, and phenyl.

In a further embodiment of the invention, $R^{Tz}$ is phenyl at each occurrence.

In a further embodiment of the invention $R^{PY}$ is independently from each other selected from the group consisting of H, methyl,
 phenyl, which is optionally substituted with one or more substituents $R^6$;
 1,3,5-triazinyl, which is optionally substituted with one or more substituents $R^6$;
 pyridinyl, which is optionally substituted with one or more substituents $R^6$; and
 pyrimidinyl, which is optionally substituted with one or more substituents $R^6$.

In a further embodiment of the invention, $R^{PY}$ is independently from each other selected from the group consisting of H, methyl, and phenyl.

In a further embodiment of the invention, $R^{PY}$ is hydrogen at each occurrence.

In a further embodiment of the invention, $R^{Tz}$ and $R^{Py}$ is independently from each other at each occurrence selected from the group consisting of H, methyl, and phenyl.

In certain embodiments of the invention, the two second chemical moieties are identical in structure. In other embodiments, the two second chemical moieties are different from each other in an organic molecule of the invention. The possible structures of the second chemical moiety are described herein as Formula II and its numerous possible substructures (e.g. Formula IIa, Formula IIb, Formula IIb-2, etc.)

In a further embodiment of the invention, at least one of, or each of the two second chemical moieties at each occurrence independently from another comprise or consist of a structure of Formula IIa:

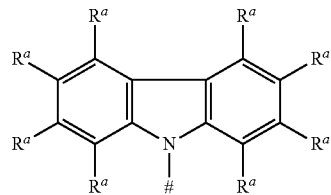

Formula IIa wherein # and $R^a$ are defined as above.

In a further embodiment of the invention, $R^a$ is at each occurrence independently from another selected from the group consisting of: H,
Me,
$^iPr$,
$^tBu$,
CN,
$CF_3$,
phenyl (Ph), which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph,
carbazolyl, which is optionally substituted with one or more substituents independently from each other selected from the group consisting of Me, $^iPr$, $^tBu$, CN, $CF_3$, and Ph, triazinyl, which is optionally substituted with one or more substituents independently from each other selected from the group consisting of Me, $^i$Pr, $^t$Bu, CN, CF$_3$, and Ph, and N(Ph)$_2$.

In a further embodiment of the invention, R$^a$ is at each occurrence independently from another selected from the group consisting of: H, Me, $^i$Pr, $^t$Bu,

CN,

CF$_3$,

Ph, which is optionally substituted with one or more substituents independently from each other selected from the group consisting of Me, $^i$Pr, $^t$Bu, CN, CF$_3$, and Ph, pyridinyl, which is optionally substituted with one or more substituents independently from each other selected from the group consisting of Me, $^i$Pr, $^t$Bu, CN, CF$_3$, and Ph, pyrimidinyl, which is optionally substituted with one or more substituents independently from each other selected from the group consisting of Me, $^i$Pr, $^t$Bu, CN, CF$_3$, and Ph, and triazinyl, which is optionally substituted with one or more substituents independently from each other selected from the group consisting of Me, $^i$Pr, $^t$Bu, CN, CF$_3$, and Ph.

In a further embodiment of the invention, R$^a$ is at each occurrence independently from another selected from the group consisting of: H, Me, $^t$Bu, Ph, which is optionally substituted with one or more substituents independently from each other selected from the group consisting of Me, $^i$Pr, $^t$Bu, CN, CF$_3$, and Ph, triazinyl, which is optionally substituted with one or more substituents independently from each other selected from the group consisting of Me, $^i$Pr, $^t$Bu, CN, CF$_3$, and Ph.

In a further embodiment of the invention, R$^a$ is H at each occurrence.

In a further embodiment of the invention, at least one second chemical moiety, or both second chemical moieties each at each occurrence independently from another comprise or consist of a structure of Formula IIb, a structure of Formula IIb-2, a structure of Formula IIb-3 or a structure of Formula IIb-4:

Formula IIb

Formula IIb-2

Formula IIb-3

Formula IIb-4 wherein R$^b$ is at each occurrence independently from another selected from the group consisting of:

H, deuterium,

N(R$^5$)$_2$,

OR$^5$,

Si(R$^5$)$_3$,

B(OR$^5$)$_2$,

OSO$_2$R$^5$,

CF$_3$,

CN,

F

Br,

I,

C$_1$-C$_{40}$-alkyl, which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-alkoxy, which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_1$-C$_{40}$-thioalkoxy, which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkenyl, which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_2$-C$_{40}$-alkynyl, which is optionally substituted with one or more substituents R$^5$ and wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

C$_6$-C$_{60}$-aryl,
which is optionally substituted with one or more substituents R$^5$; and C$_3$-C$_{57}$-heteroaryl,
which is optionally substituted with one or more substituents R$^5$.

Apart from that, the aforementioned definitions apply.

In one additional embodiment of the invention, at least one second chemical moiety, or both second chemical moieties each at each occurrence independently from another comprise or consist of a structure of Formula IIc, a structure of Formula IIc-2, a structure of Formula IIc-3, or a structure of Formula IIc-4:

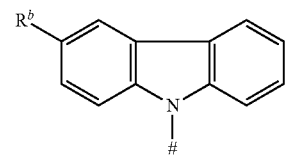

Formula IIc

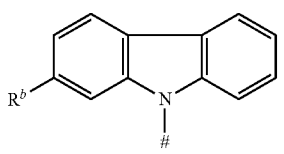

Formula IIc-2

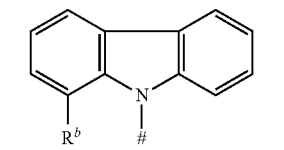

Formula IIc-3

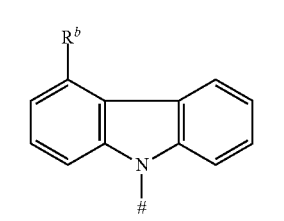

Formula IIc-4 wherein the aforementioned definitions apply.

In a further embodiment of the invention, R$^b$ is at each occurrence independently from another selected from the group consisting of:
H,
Me,
$^i$Pr,
$^t$Bu,
CN,
CF$_3$,
Ph, which is optionally substituted with one or more substituents independently from each other selected from the group consisting of Me, $^i$Pr, $^t$Bu, CN, CF$_3$, and Ph;
pyridinyl, which is optionally substituted with one or more substituents independently from each other selected from the group consisting of Me, $^i$Pr, $^t$Bu, CN, CF$_3$, and Ph;
carbazolyl, which is optionally substituted with one or more substituents independently from each other selected from the group consisting of Me, $^i$Pr, $^t$Bu, CN, CF$_3$, and Ph;
triazinyl, which is optionally substituted with one or more substituents independently from each other selected from the group consisting of Me, $^i$Pr, $^t$Bu, CN, CF$_3$, and Ph;
and N(Ph)$_2$.

In a further embodiment of the invention, R$^b$ is at each occurrence independently from another selected from the group consisting of:
H,
Me,
$^i$Pr,
$^t$Bu,
CN,
CF$_3$,
Ph, which is optionally substituted with one or more substituents independently from each other selected from the group consisting of Me, $^i$Pr, $^t$Bu, CN, CF$_3$, and Ph;
pyridinyl, which is optionally substituted with one or more substituents independently from each other selected from the group consisting of Me, $^i$Pr, $^t$Bu, CN, CF$_3$, and Ph;
pyrimidinyl, which is optionally substituted with one or more substituents independently from each other selected from the group consisting of Me, $^i$Pr, $^t$Bu, CN, CF$_3$, and Ph; and
triazinyl, which is optionally substituted with one or more substituents independently from each other selected from the group consisting of Me, $^i$Pr, $^t$Bu, CN, CF$_3$, and Ph.

In a further embodiment of the invention, R$^b$ is at each occurrence independently from another selected from the group consisting of:
H,
Me,
$^t$Bu,
Ph, which is optionally substituted with one or more substituents independently from each other selected from the group consisting of Me, $^i$Pr, $^t$Bu, CN, CF$_3$, and Ph;
triazinyl, which is optionally substituted with one or more substituents independently from each other selected from the group consisting of Me, $^i$Pr, $^t$Bu, CN, CF$_3$, and Ph.

In the following, examples of the second chemical moiety are shown. As mentioned above, the two second chemical moieties of the organic molecule can be identical or different.

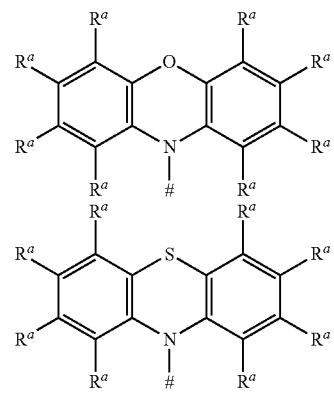

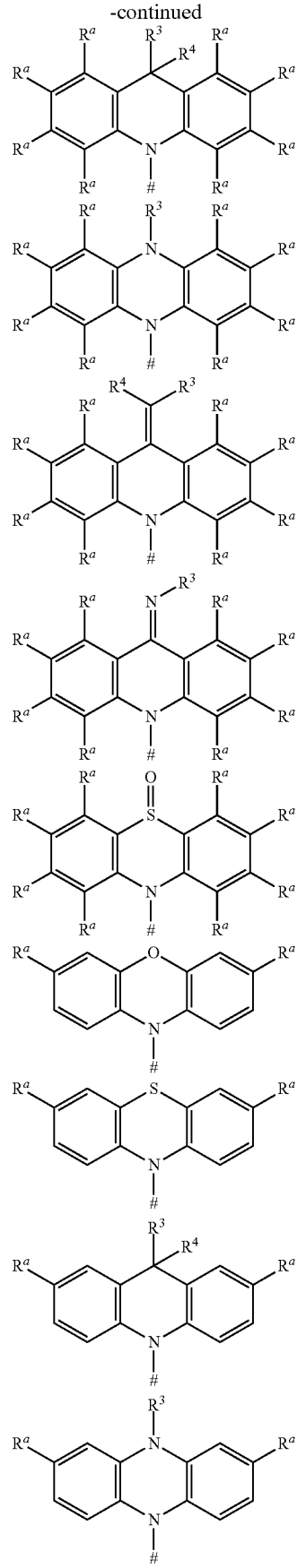
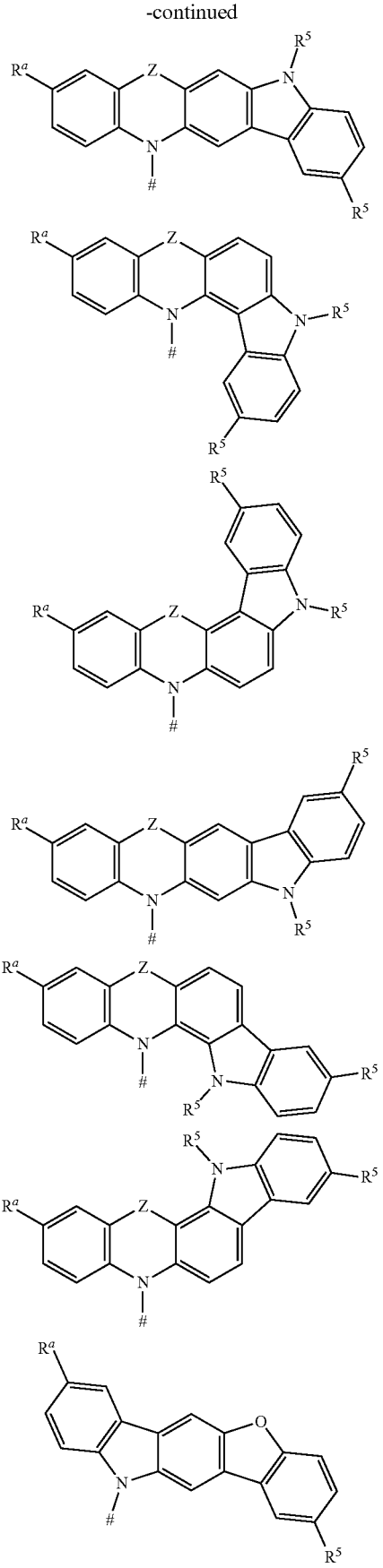

-continued
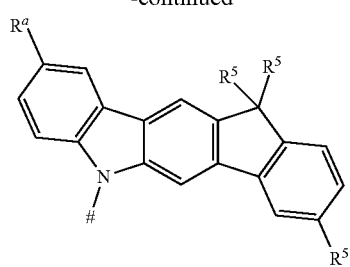
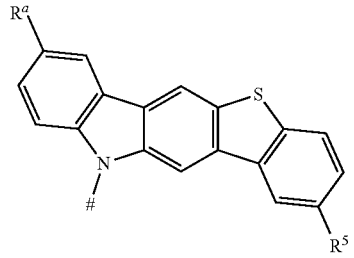
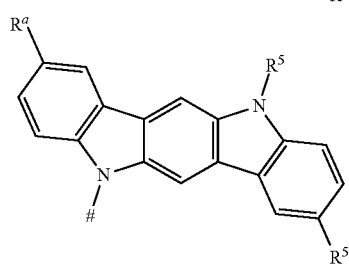
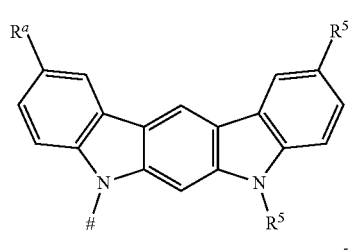
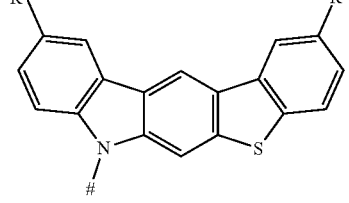
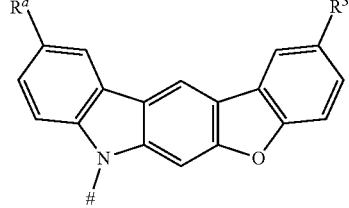
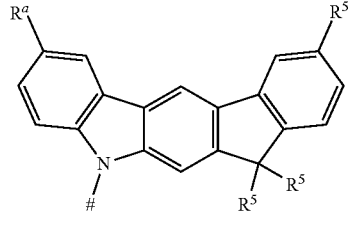
-continued
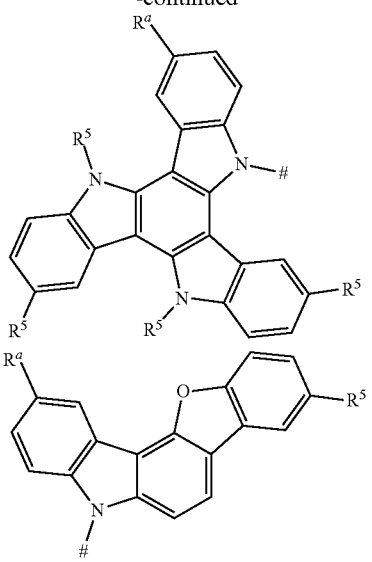
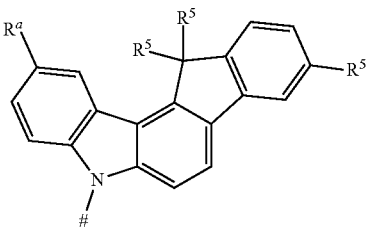
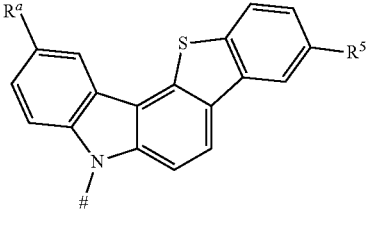
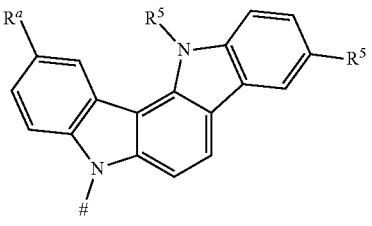
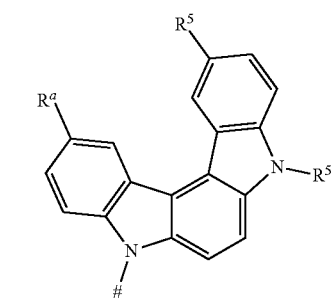

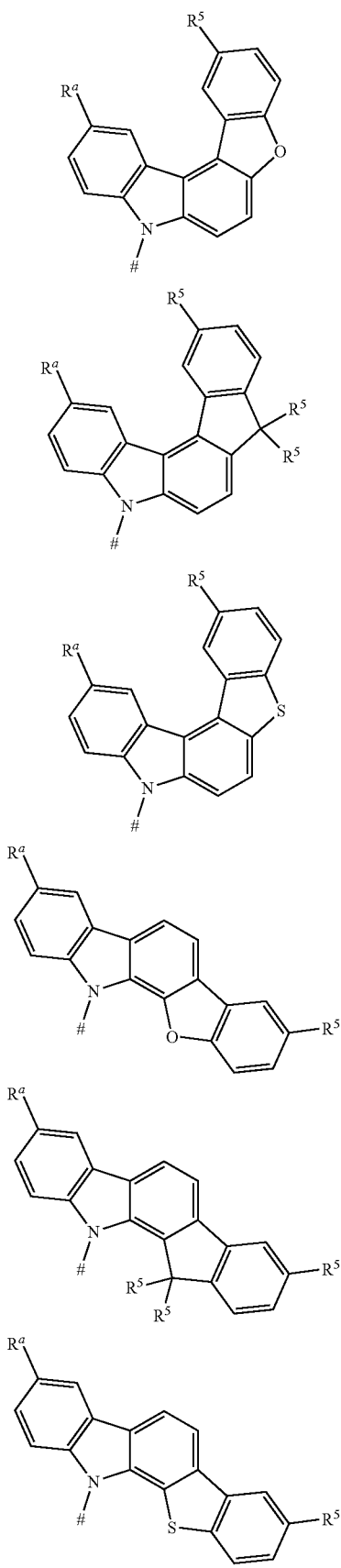
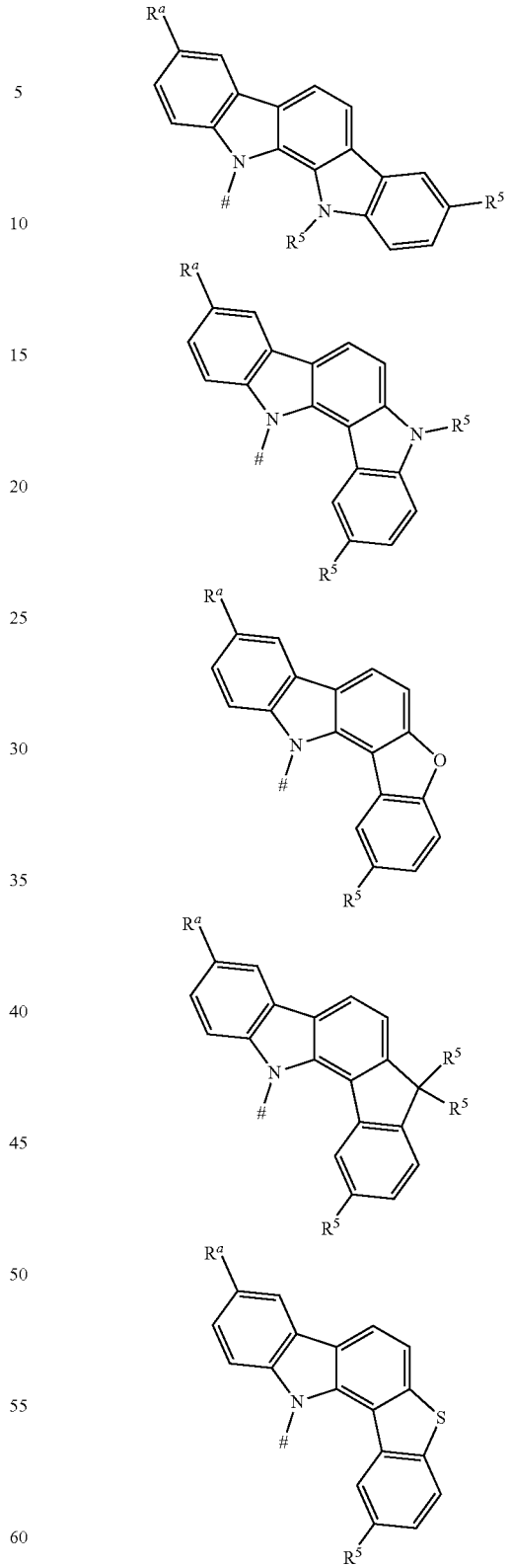
wherein for #, Z, $R^a$, $R^3$, $R^4$ and $R^5$, the aforementioned definitions apply.
In one embodiment, $R^a$ and $R^5$ is at each occurrence independently from another selected from the group consisting of hydrogen (H), methyl (Me), i-propyl (CH(CH$_3$)$_2$) ($^i$Pr), t-butyl ($^t$Bu), phenyl (Ph), CN, CF$_3$, and diphenylamine (NPh$_2$).

In one embodiment of the invention, the organic molecules comprise or consist of a structure of Formula III or Formula III-2:

Formula III

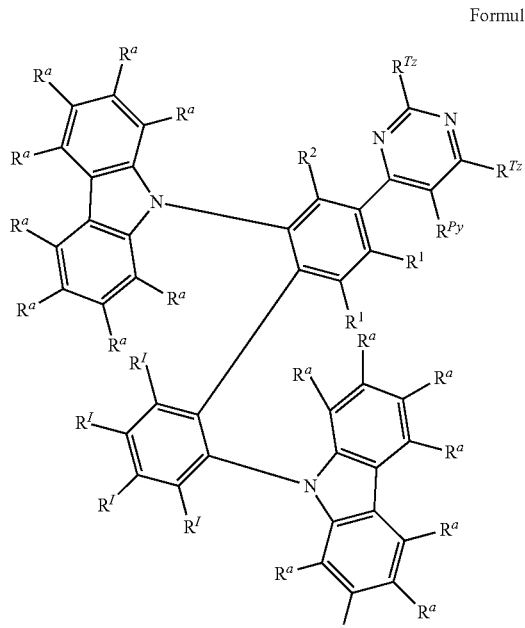

Formula III-2

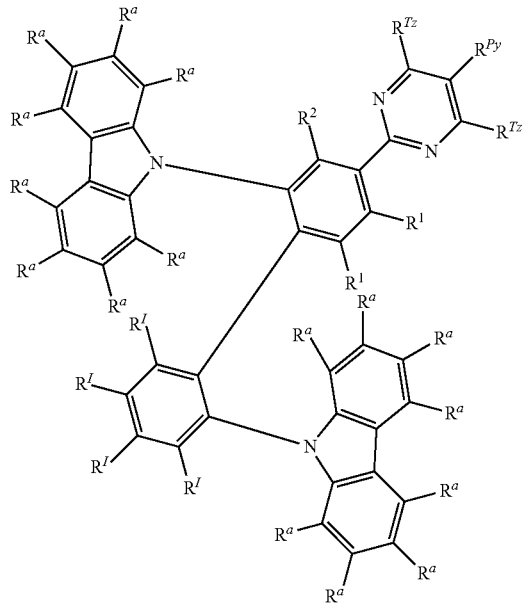

wherein the aforementioned definitions apply.

In a further embodiment of the invention, the organic molecules comprise or consist of a structure of Formula IIIa or Formula IIIa-2:

Formula IIIa

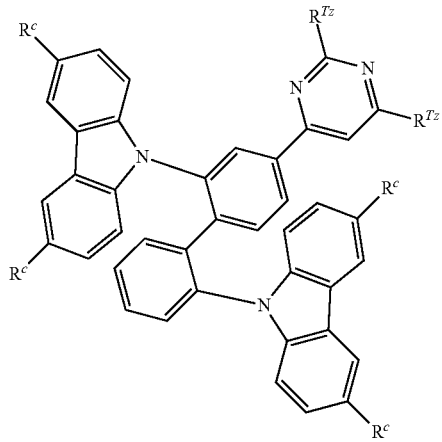

Formula IIIa-2

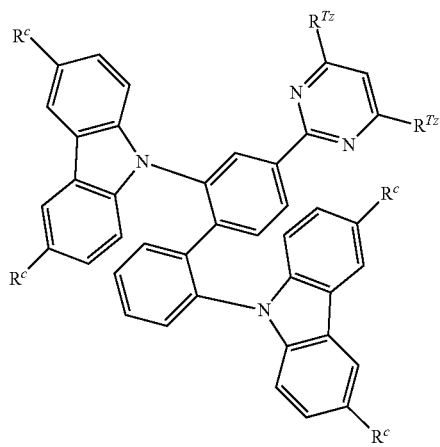

wherein R$^c$ is at each occurrence independently from another selected from the group consisting of:

H,

Me, $^i$Pr, $^t$Bu,

Ph, which is optionally substituted with one or more substituents independently from each other selected from the group consisting of Me, $^i$Pr, $^t$Bu, CN, CF$_3$, and Ph;

pyridinyl, which is optionally substituted with one or more substituents independently from each other selected from the group consisting of Me, $^i$Pr, $^t$Bu, CN, CF$_3$, and Ph;

pyrimidinyl, which is optionally substituted with one or more substituents independently from each other selected from the group consisting of Me, $^i$Pr, $^t$Bu, CN, CF$_3$, and Ph;

carbazolyl, which is optionally substituted with one or more substituents independently from each other selected from the group consisting of Me, $^i$Pr, $^t$Bu, CN, CF$_3$, and Ph;

triazinyl, which is optionally substituted with one or more substituents independently from each other selected from the group consisting of Me, $^i$Pr, $^t$Bu, CN, CF$_3$, and Ph;

and N(Ph)$_2$.

In a further embodiment of the invention, the organic molecules comprise or consist of a structure Formula IIIb or Formula IIIb-2:

Formula IIIb

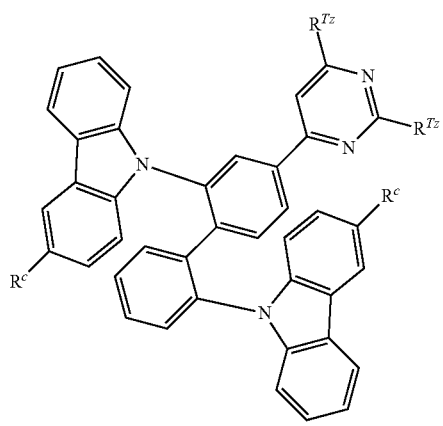

Formula IIIb-2

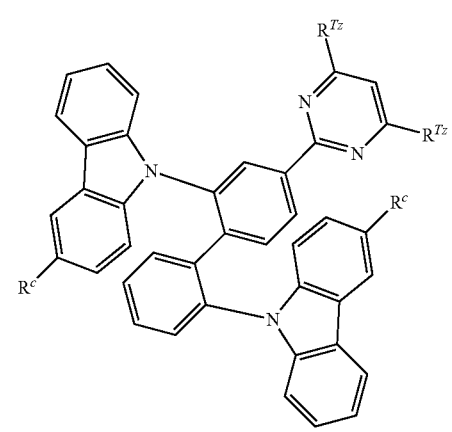

wherein the aforementioned definitions apply.

In one embodiment of the invention, the organic molecules comprise or consist of a structure of Formula IV or Formula IV-2:

Formula IV

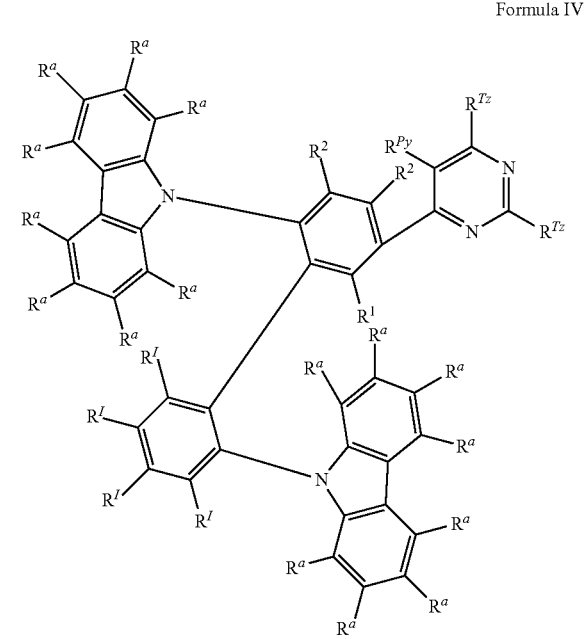

Formula IV-2

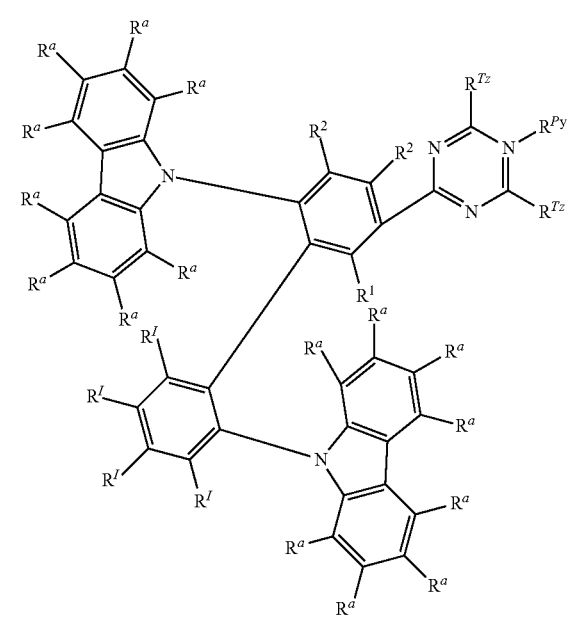

wherein the aforementioned definitions apply.

In a further embodiment of the invention, the organic molecules comprise or consist of a structure of Formula IVa or Formula IVa-2

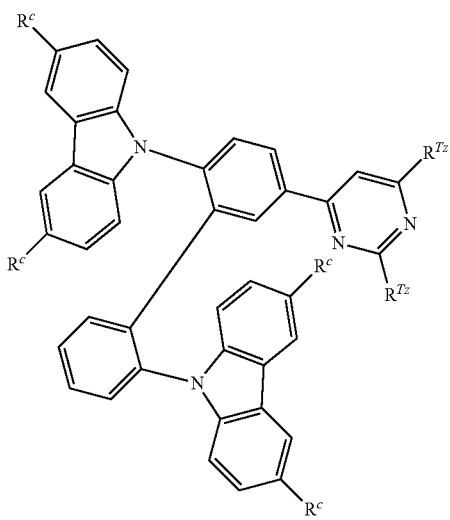

Formula IVa

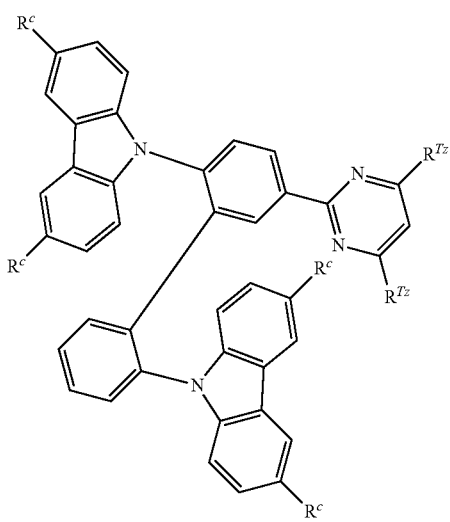

Formula IVa-2 wherein the aforementioned definitions apply.

In a further embodiment of the invention, the organic molecules comprise or consist of a structure selected from the group of Formula IVb or Formula IVb-2

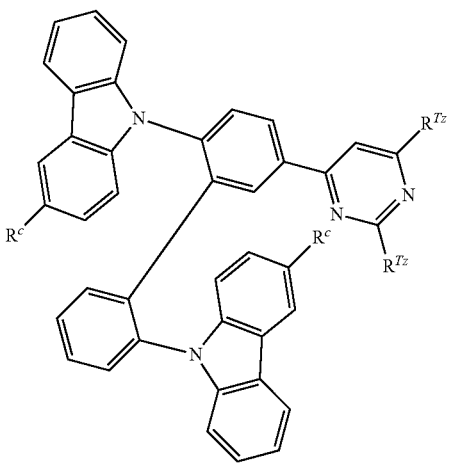

Formula IVb

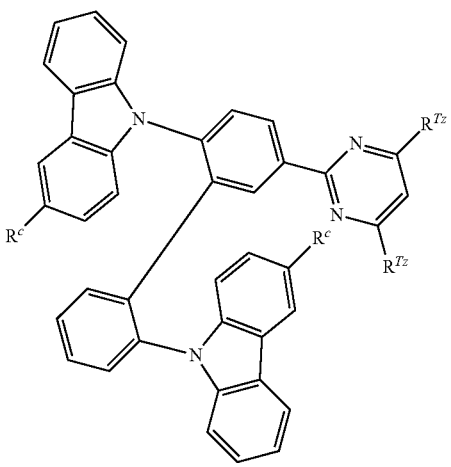

Formula IVb-2 wherein the aforementioned definitions apply.

In one embodiment of the invention, the organic molecules comprise or consist of a structure of Formula V or Formula V-2:

Formula V

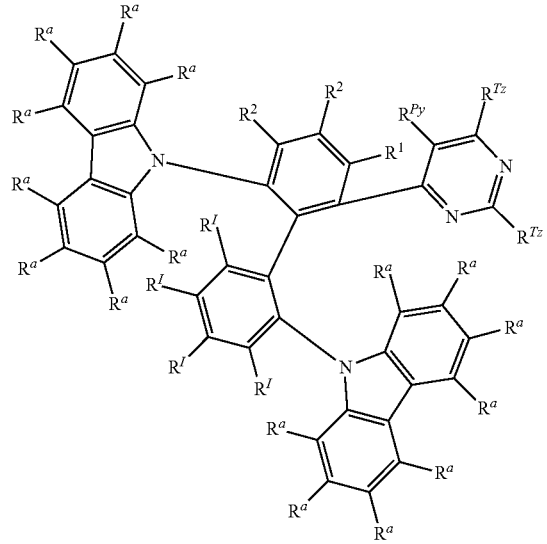

In one embodiment of the invention, the organic molecules comprise or consist of a structure of Formula VI or Formula VI-2:

Formula VI

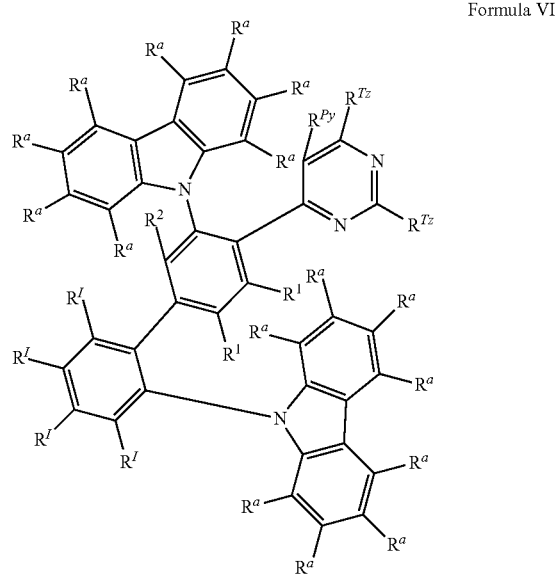

Formula V-2

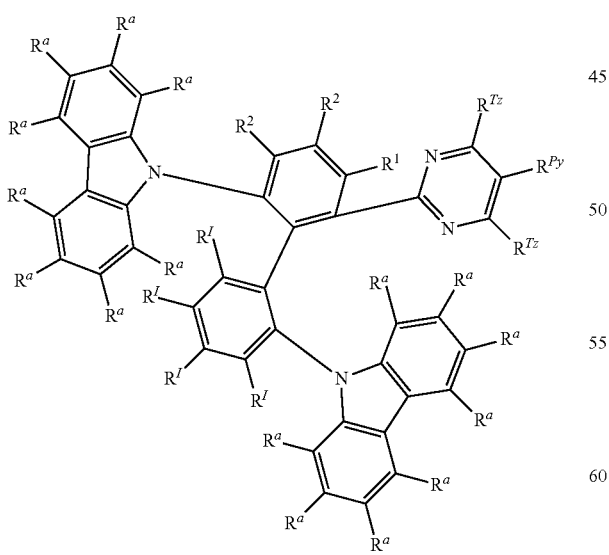

Formula VI-2

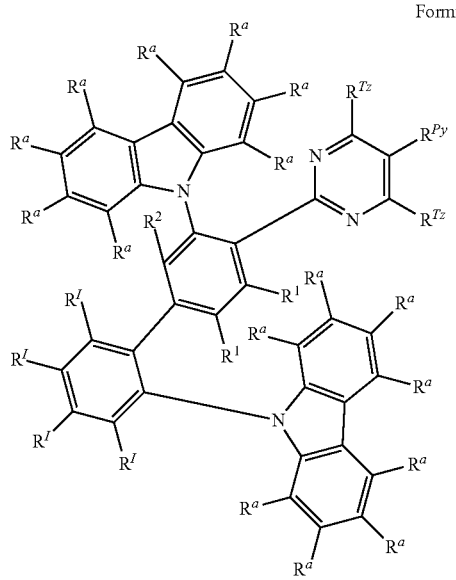

wherein the aforementioned definitions apply.

wherein the aforementioned definitions apply.

In one embodiment of the invention, the organic molecules comprise or consist of a structure of Formula VII or Formula VII-2:

Formula VII

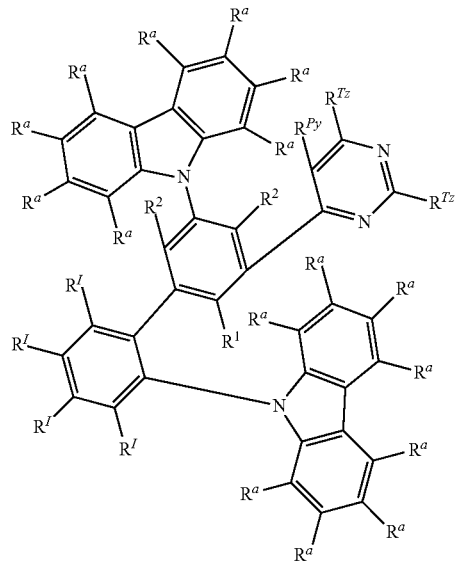

In one embodiment of the invention, the organic molecules comprise or consist of a structure of Formula VIII or Formula VIII-2:

Formula VIII

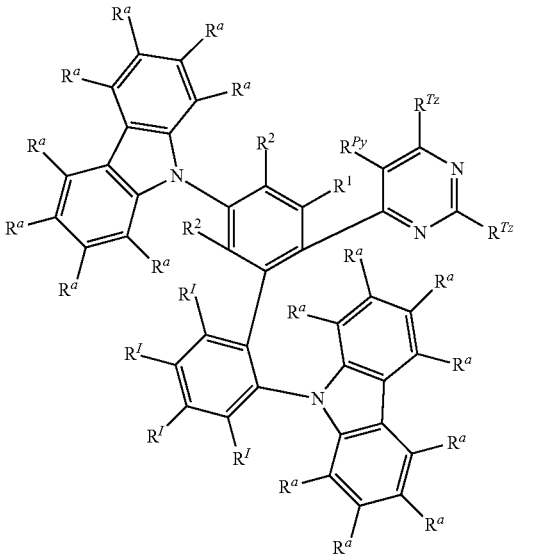

Formula VII-2

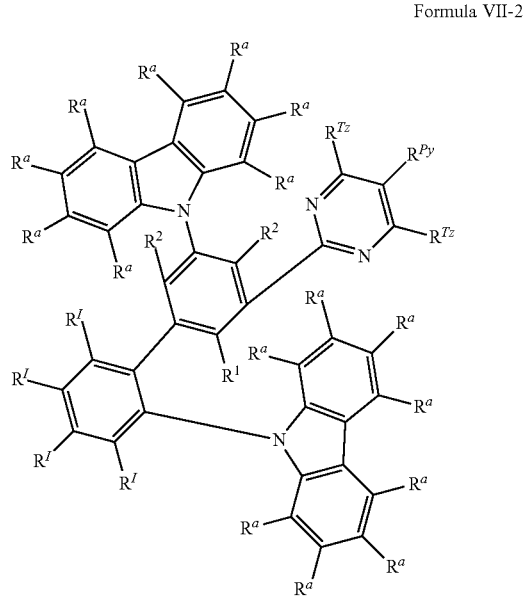

Formula VIII-2

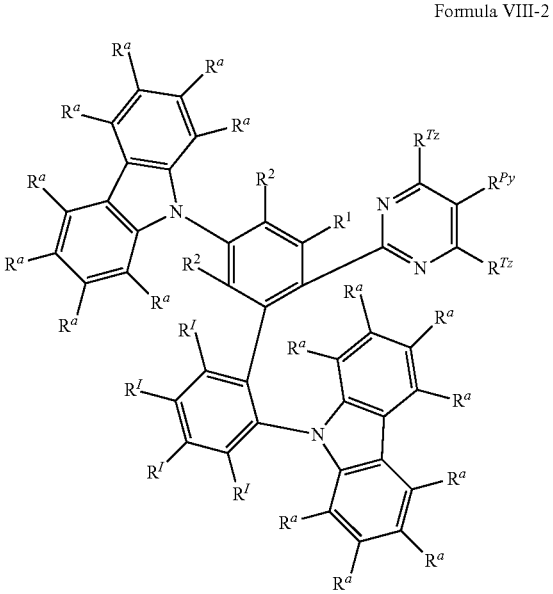

wherein the aforementioned definitions apply.

wherein the aforementioned definitions apply.

In one embodiment of the invention, the organic molecules comprise or consist of a structure of Formula IX or Formula IX-2:

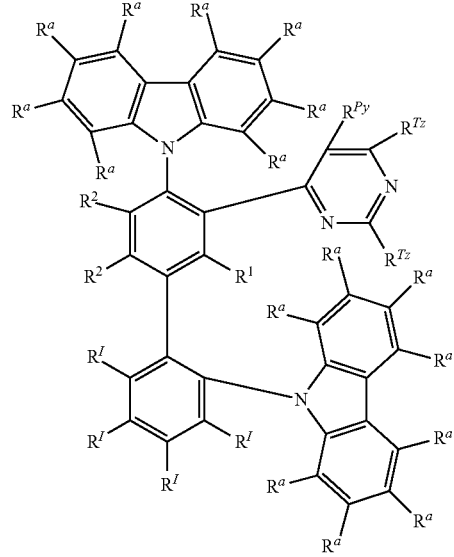

Formula IX

In one embodiment of the invention, the organic molecules comprise or consist of a structure of Formula IXa or Formula IXa-2:

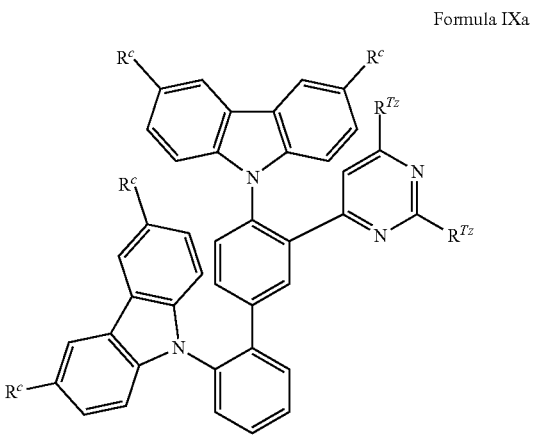

Formula IXa

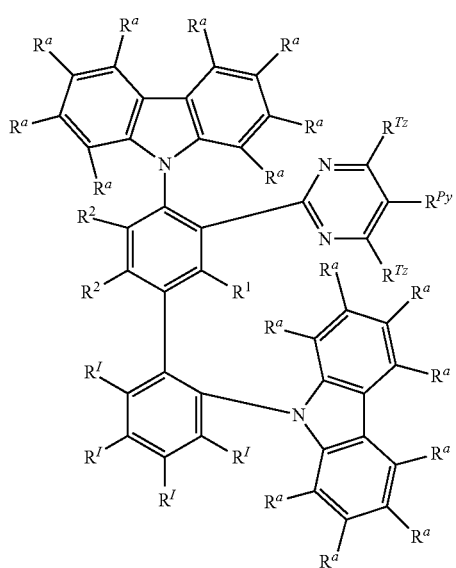

Formula IX-2

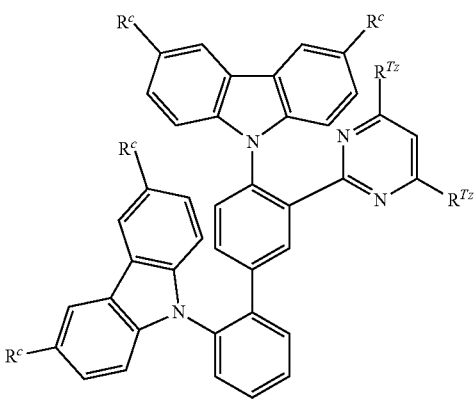

Formula IXa-2 wherein the aforementioned definitions apply.

wherein the aforementioned definitions apply.

In one embodiment of the invention, the organic molecules comprise or consist of a structure of Formula IXb or Formula IXb-2:

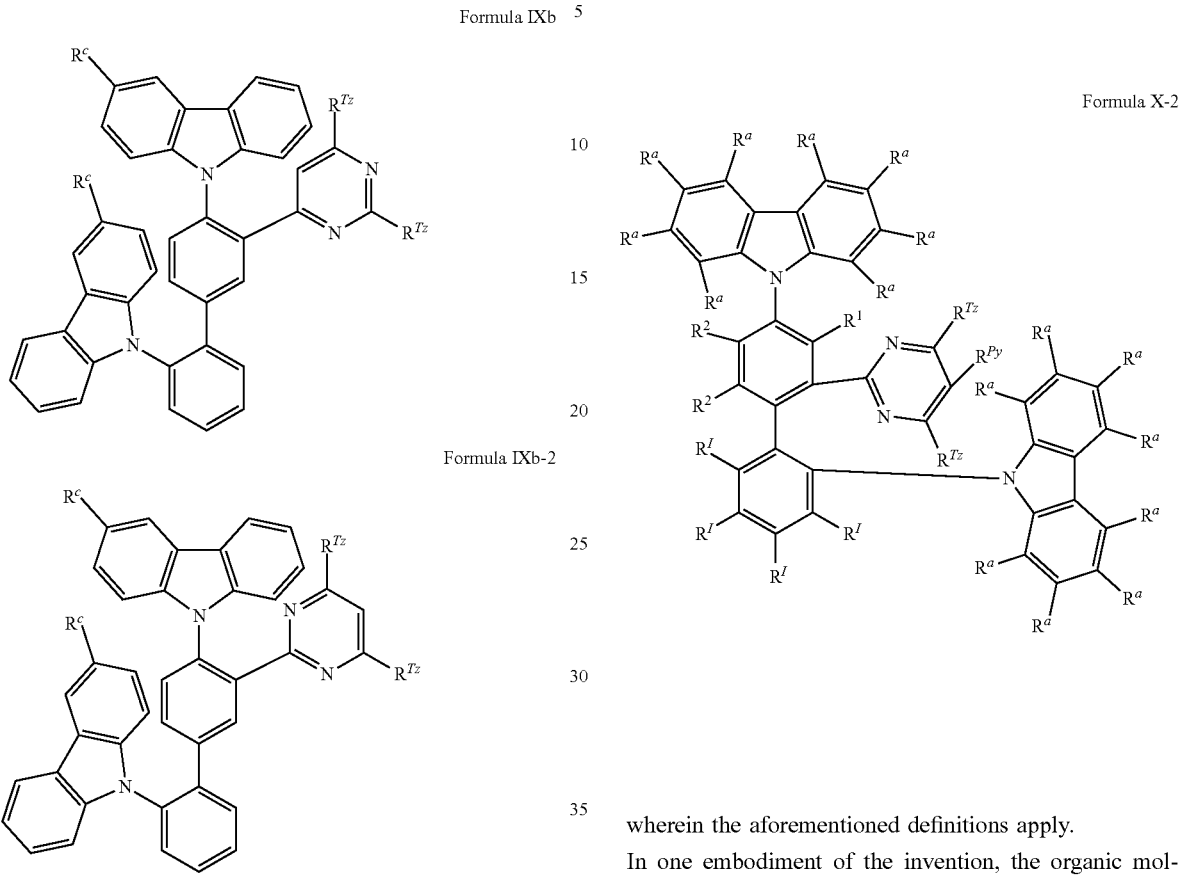

wherein the aforementioned definitions apply.

In one embodiment of the invention, the organic molecules comprise or consist of a structure of Formula X or Formula X-2:

wherein the aforementioned definitions apply.

In one embodiment of the invention, the organic molecules comprise or consist of a structure of Formula XI or Formula XI-2:

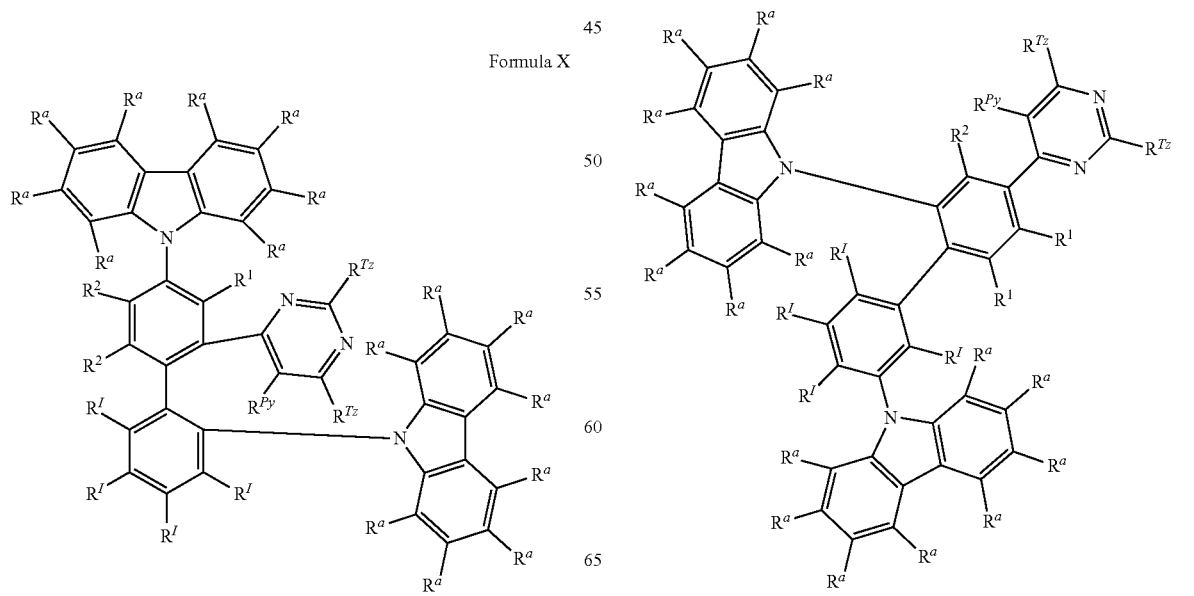

Formula XI-2

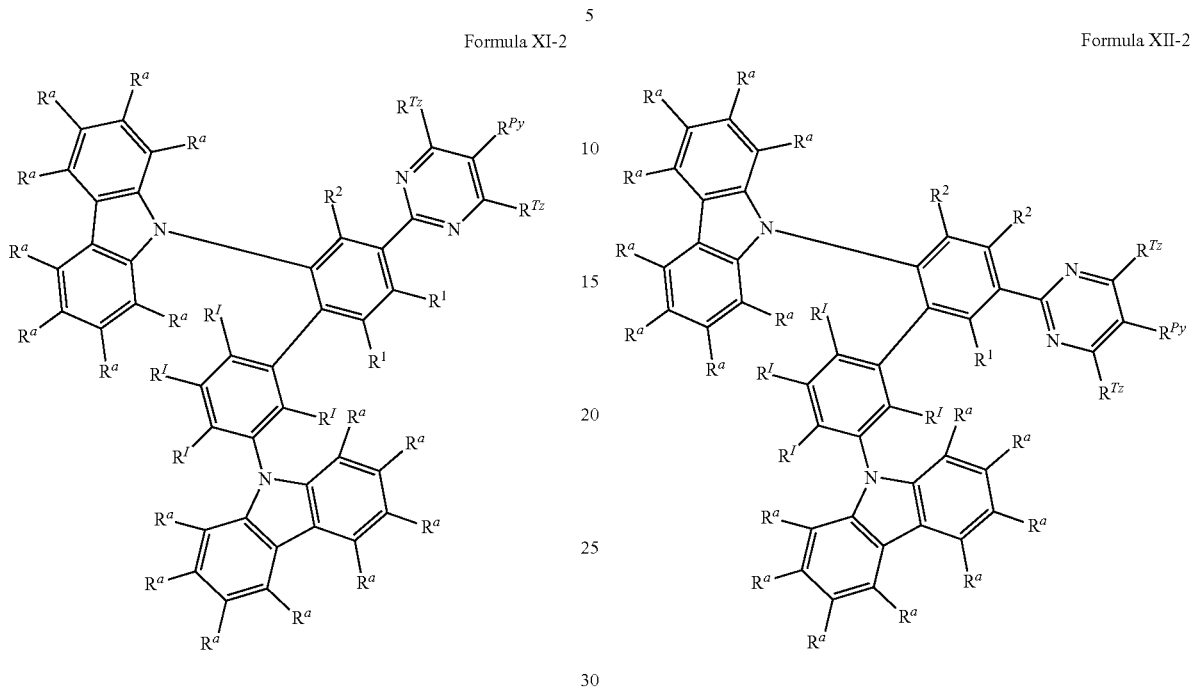

wherein the aforementioned definitions apply.

In one embodiment of the invention, the organic molecules comprise or consist of a structure of Formula XII or Formula XII-2:

Formula XII

Formula XII-2 wherein the aforementioned definitions apply.

In one embodiment of the invention, the organic molecules comprise or consist of a structure of Formula XIII or Formula XIII-2:

Formula XIII

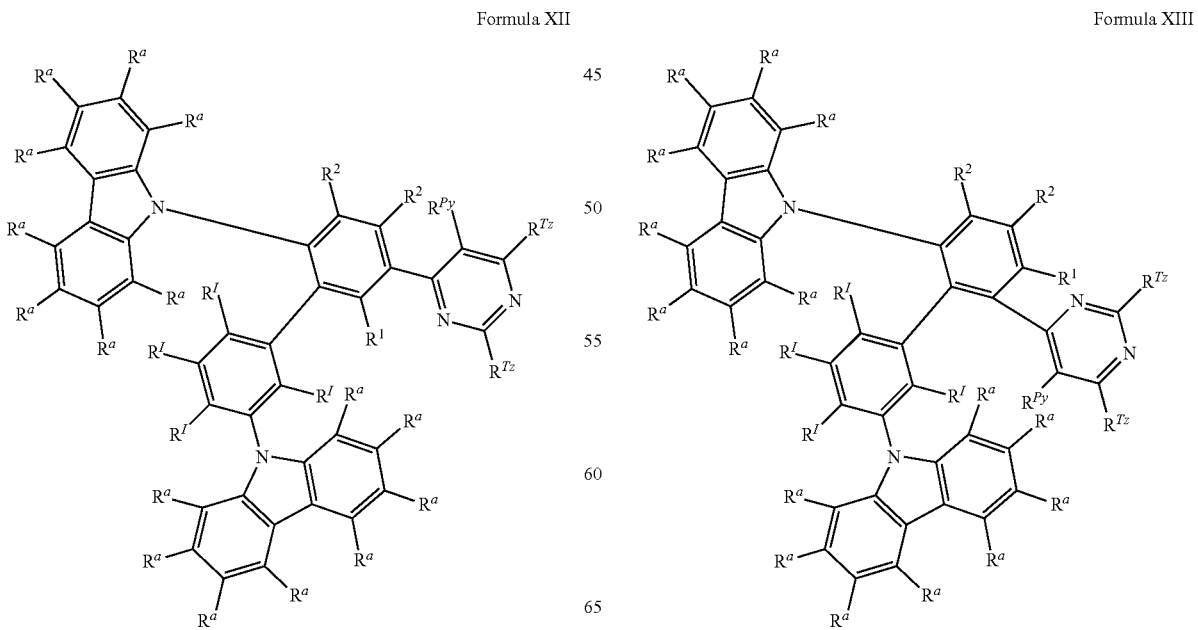

Formula XIII-2

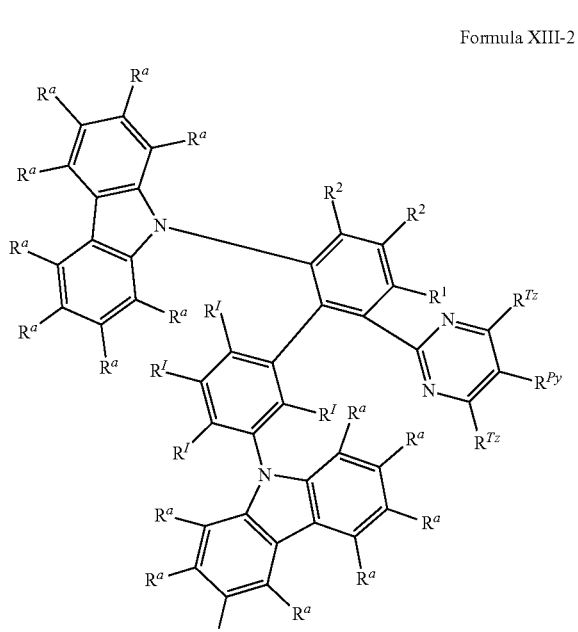

wherein the aforementioned definitions apply.

In one embodiment of the invention, the organic molecules comprise or consist of a structure of Formula XIII or Formula XIII-2:

Formula XIII

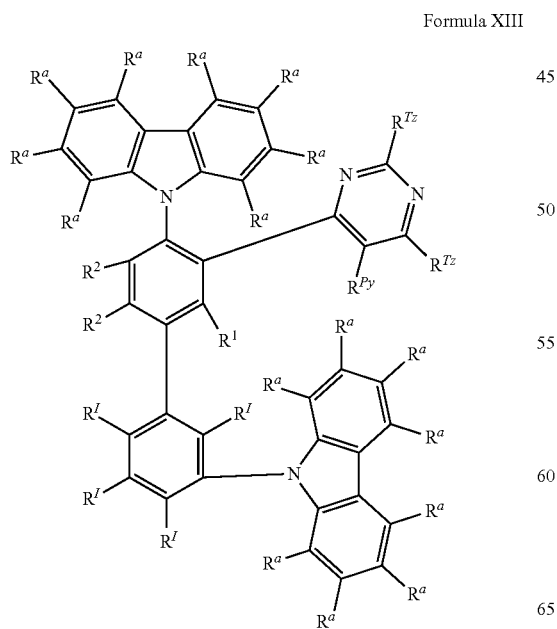

Formula XIII-2

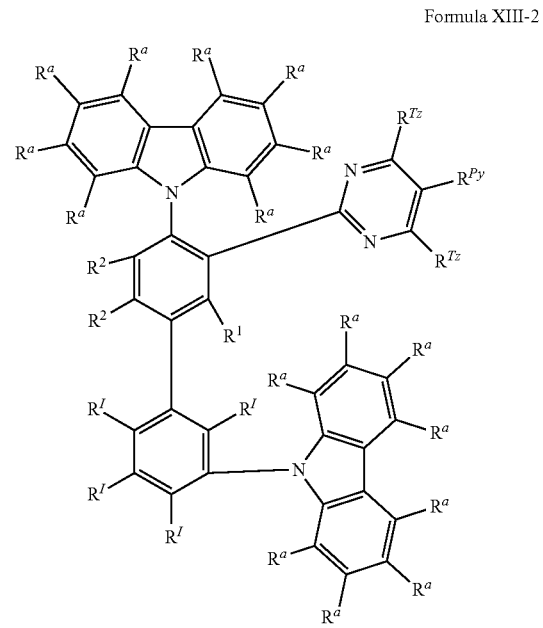

wherein the aforementioned definitions apply.

In one embodiment of the invention, the organic molecules comprise or consist of a structure of Formula XIIIa or Formula XIIIa-2:

Formula XIIIa

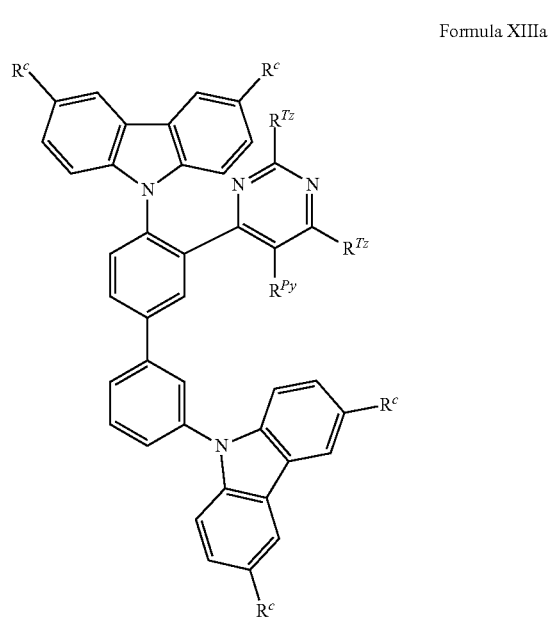

Formula XIIIa-2

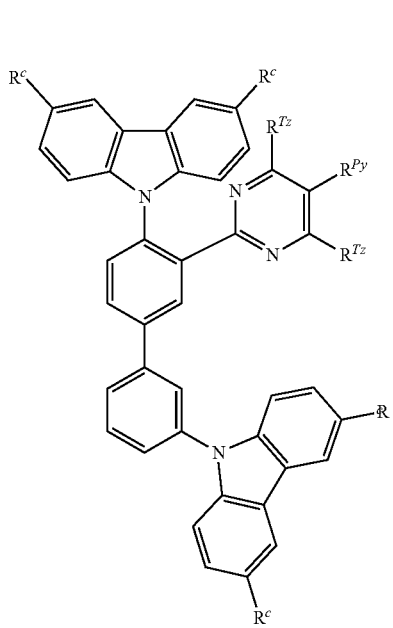

wherein the aforementioned definitions apply.

In one embodiment of the invention, the organic molecules comprise or consist of a structure of XIIIb or Formula XIIIb-2:

Formula XIIIb

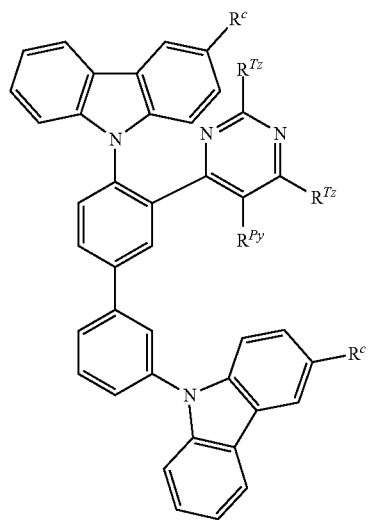

Formula XIIIb-2

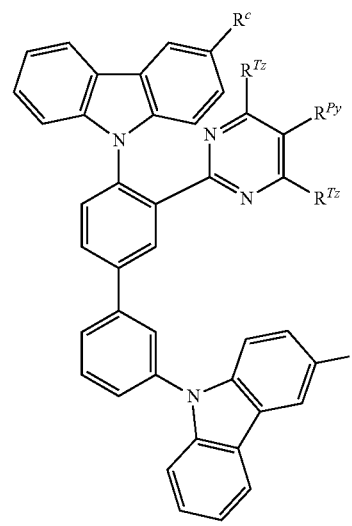

wherein the aforementioned definitions apply.

In one embodiment of the invention, the organic molecules comprise or consist of a structure of Formula XIV or Formula XIV-2:

Formula XIV

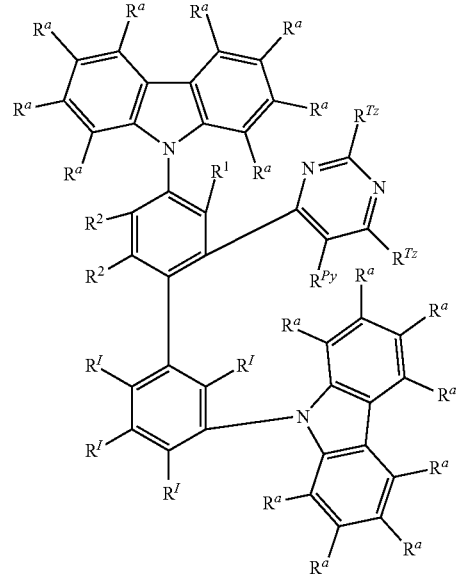

Formula XIV-2

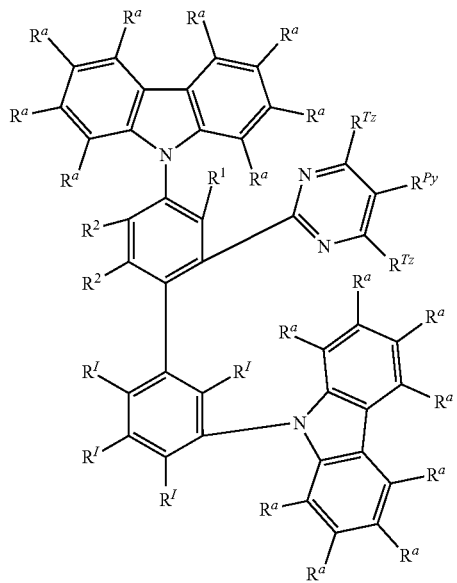

Formula XV-2

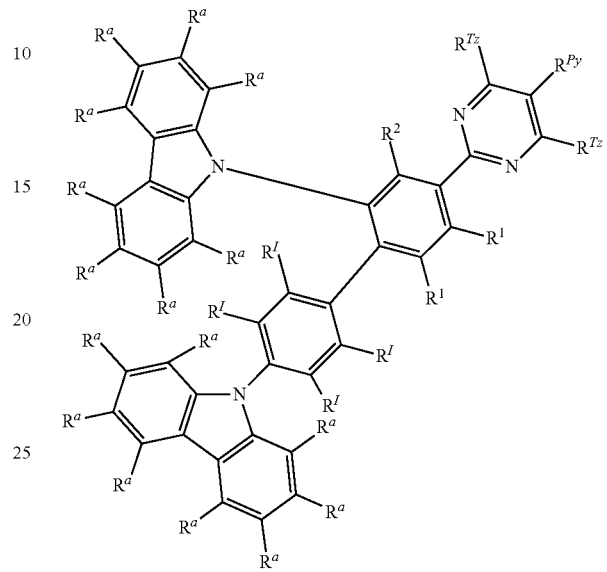

wherein the aforementioned definitions apply.

In one embodiment of the invention, the organic molecules comprise or consist of a structure of Formula XV or Formula XV-2:

wherein the aforementioned definitions apply.

In one embodiment of the invention, the organic molecules comprise or consist of a structure of Formula XVI or Formula XVI-2:

Formula XV

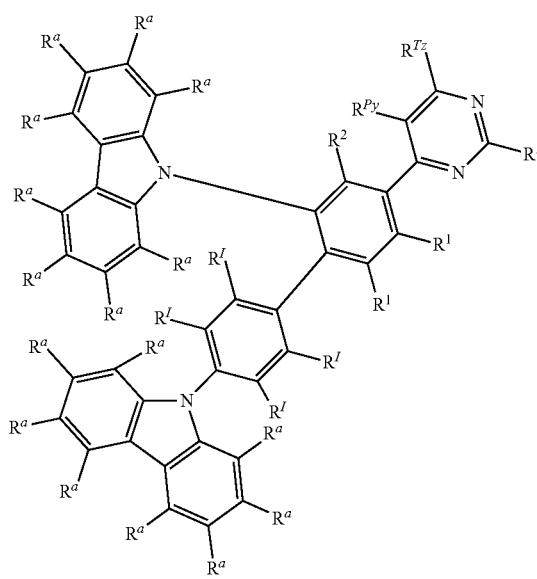

Formula XVI

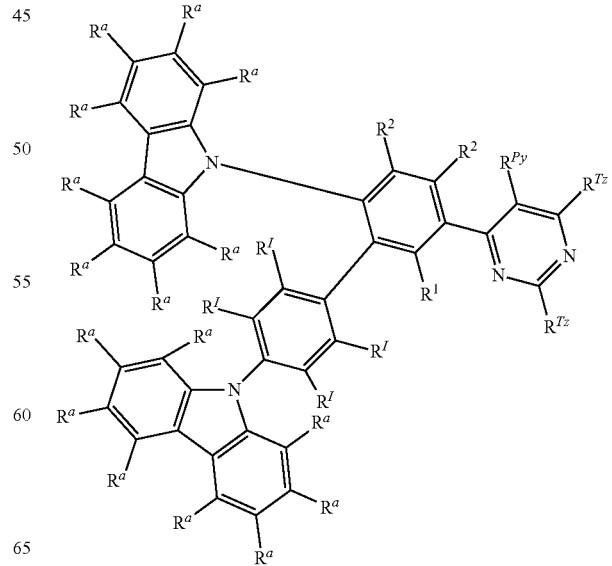

Formula XVI-2

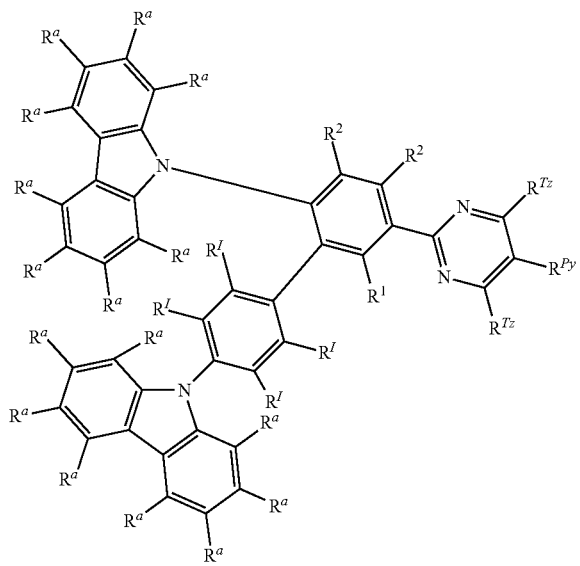

wherein the aforementioned definitions apply.

In one embodiment of the invention, the organic molecules comprise or consist of a structure of Formula XVII or Formula XVII-2:

Formula XVII

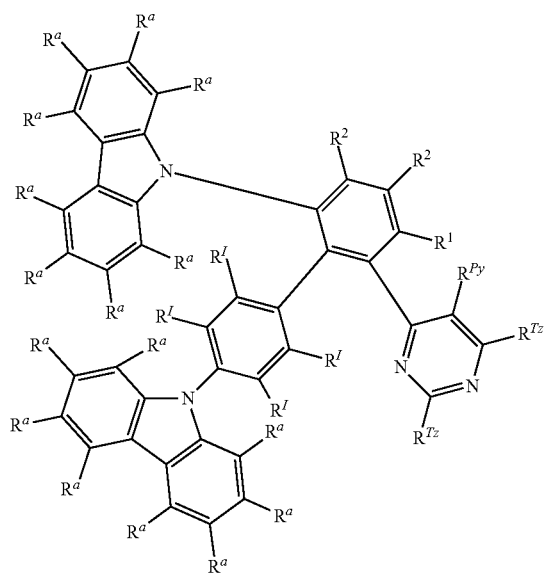

Formula XVII-2

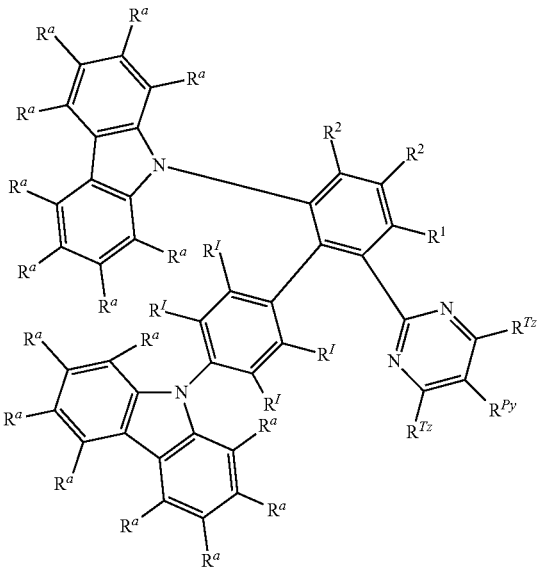

wherein the aforementioned definitions apply.

In one embodiment of the invention, the organic molecules comprise or consist of a structure of Formula XVIII or Formula XVIII-2:

Formula XVIII

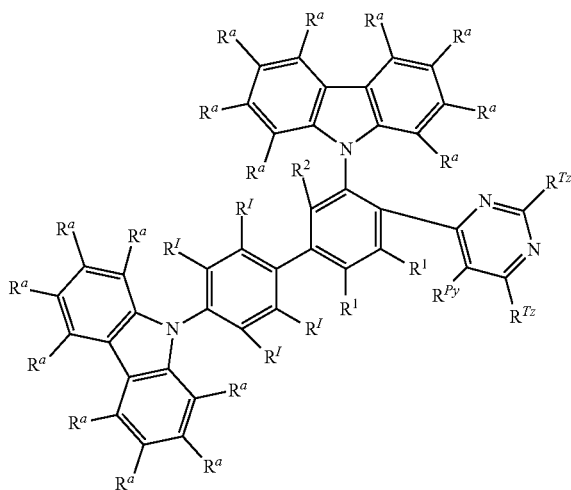

Formula XVIII-2

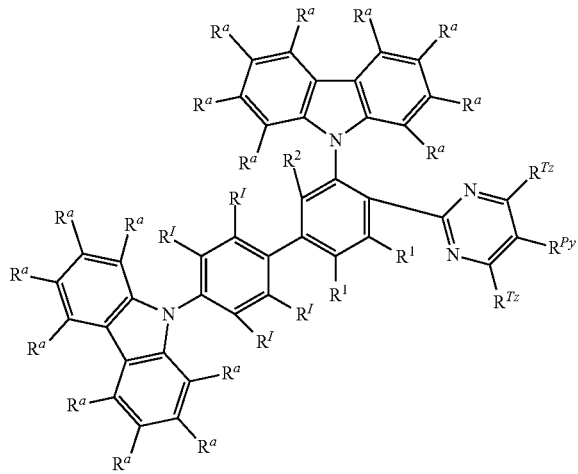

wherein the aforementioned definitions apply.

In one embodiment of the invention, the organic molecules comprise or consist of a structure of Formula XIX or Formula XIX2:

Formula XIX

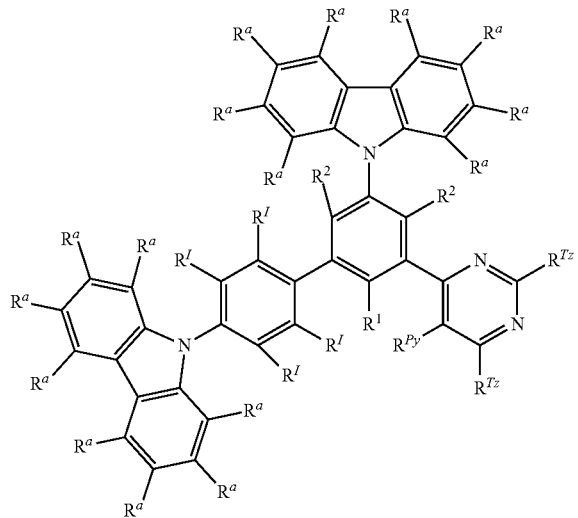

Formula XIX-2

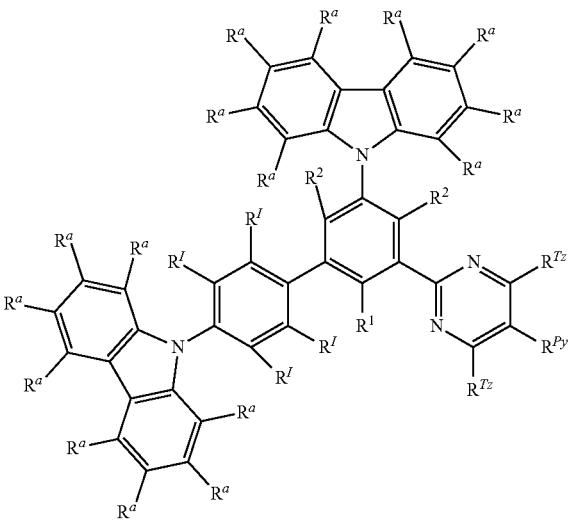

wherein the aforementioned definitions apply.

In one embodiment of the invention, the organic molecules comprise or consist of a structure of Formula XX or Formula XX-2:

Formula XX

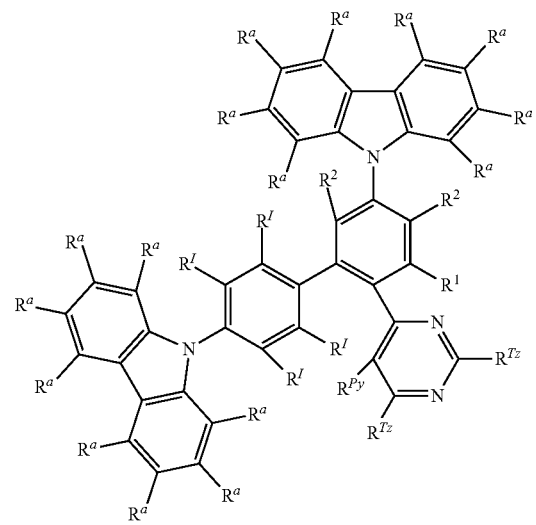

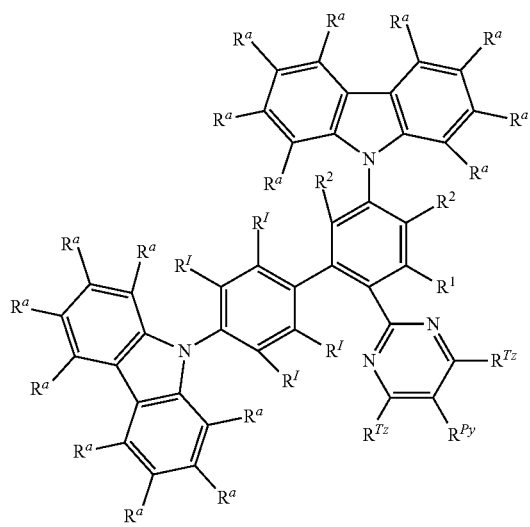

Formula XX-2 wherein the aforementioned definitions apply.

In one embodiment of the invention, the organic molecules comprise or consist of a structure of Formula XXI or Formula XXI-2:

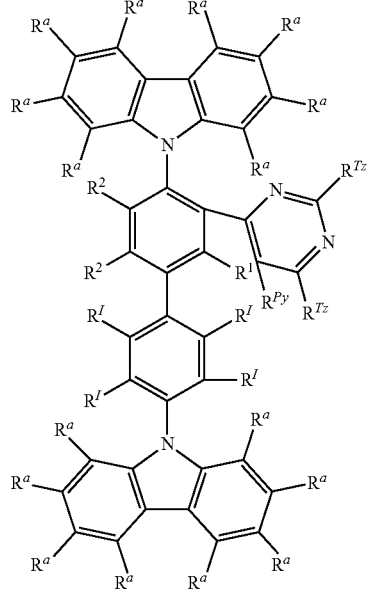

Formula XXI

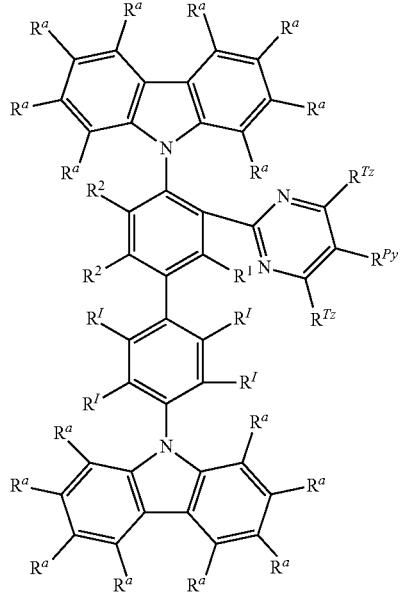

Formula XXI-2 wherein the aforementioned definitions apply.

In one embodiment of the invention, the organic molecules comprise or consist of a structure of Formula XXIa or Formula XXIa-2:

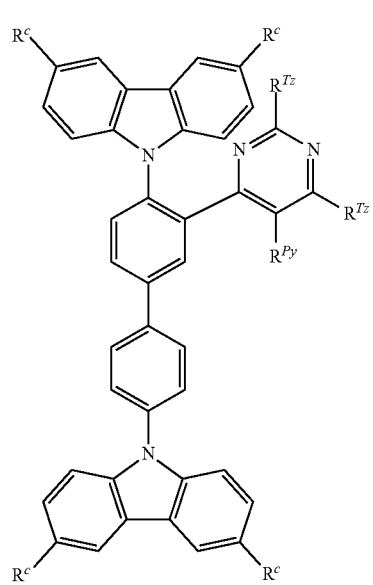

Formula XXIa

Formula XXIa-2

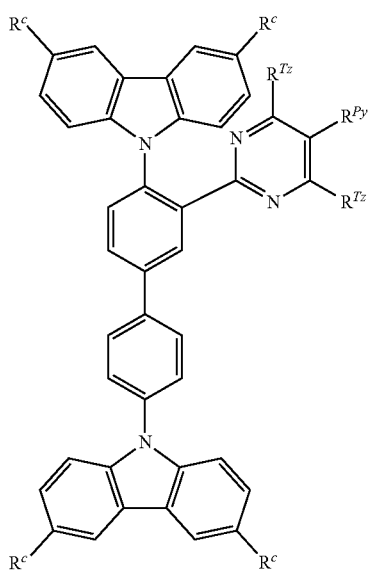

wherein the aforementioned definitions apply.

In one embodiment of the invention, the organic molecules comprise or consist of a structure of Formula XXIb or Formula XXIb-2:

Formula XXIb

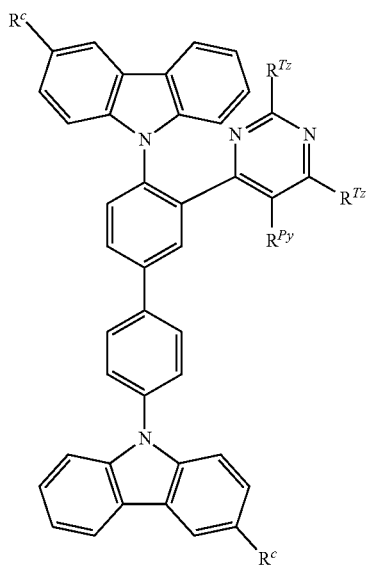

Formula XXIb-2

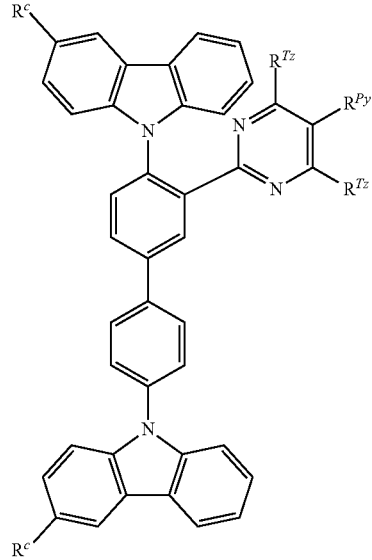

wherein the aforementioned definitions apply.

In one embodiment of the invention, the organic molecules comprise or consist of a structure of Formula XXII or Formula XXII-2:

Formula XXII

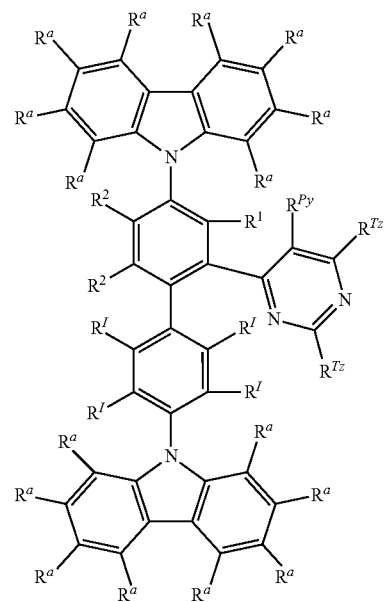

Formula XXII-2

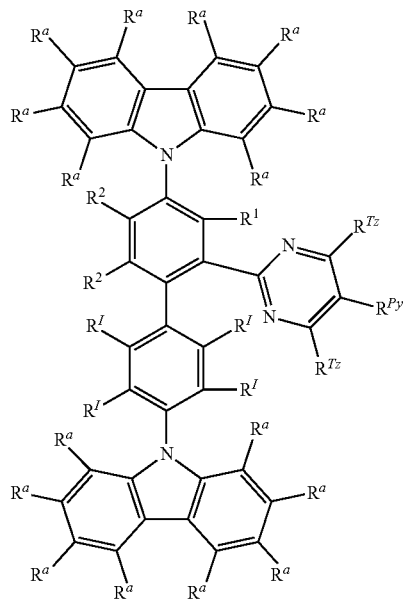

wherein the aforementioned definitions apply.

In one embodiment of the invention, the organic molecules comprise or consist of a structure of Formula XXIII or Formula XXIII-2:

Formula XXIII

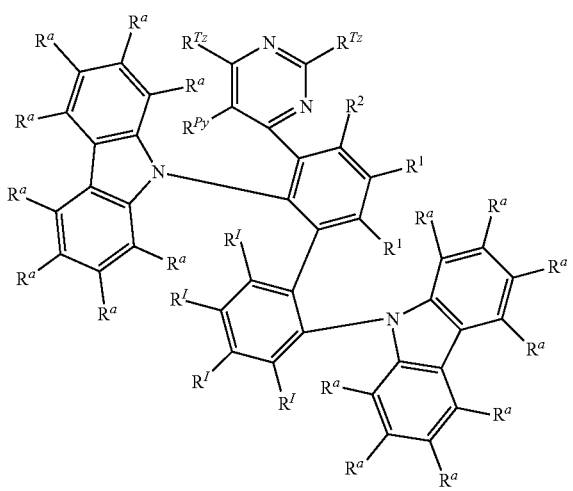

Formula XXIII-2

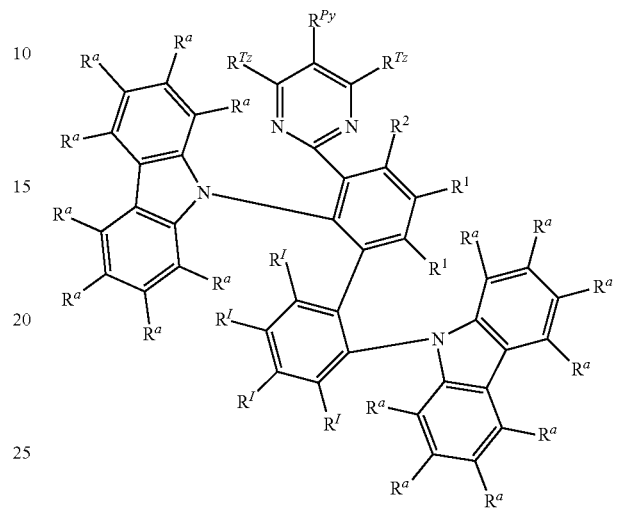

wherein the aforementioned definitions apply.

In one embodiment of the invention, the organic molecules comprise or consist of a structure of Formula XXIV or Formula XXIV-2:

Formula XXIV

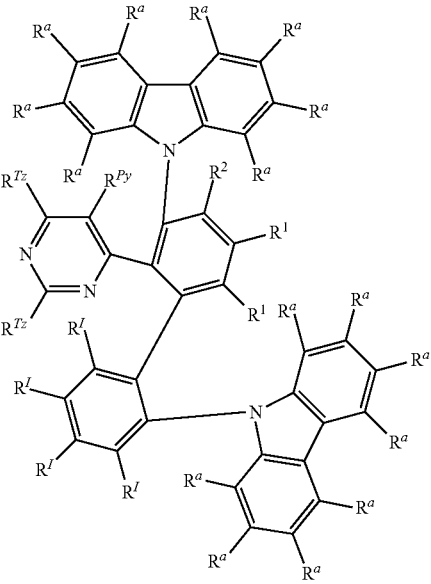

Formula XXIV-2

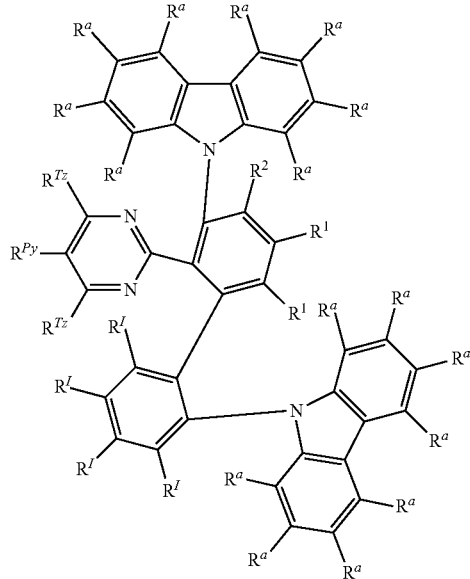

wherein the aforementioned definitions apply.

In one embodiment of the invention, $R^c$ is at each occurrence independently from another selected from the group consisting of:
H,
Me,
$^iPr$,
$^tBu$,
Ph, which is optionally substituted with one or more substituents independently from each other selected from the group consisting of Me, $^iPr$, $^tBu$, CN, $CF_3$ and Ph; and
triazinyl, which is optionally substituted with one or more substituents independently from each other selected from the group consisting of Me, $^iPr$, $^tBu$, CN, $CF_3$ and Ph.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application, the term "aryl group" or "heteroaryl group" comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application, the term "cyclic group" may be understood in the broadest sense as any mono-, bi- or polycyclic moieties.

As used throughout the present application, the term biphenyl as a substituent may be understood in the broadest sense as ortho-biphenyl, meta-biphenyl, or para-biphenyl, wherein ortho, meta and para is defined in regard to the binding site to another chemical moiety.

As used throughout the present application, the term "alkyl group" may be understood in the broadest sense as any linear, branched, or cyclic alkyl substituent. In particular, the term alkyl comprises the substituents methyl (Me), ethyl (Et), n-propyl ($^nPr$), i-propyl ($^iPr$), cyclopropyl, n-butyl ($^nBu$), i-butyl ($^iBu$), s-butyl ($^sBu$), t-butyl ($^tBu$), cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout the present application, the term "alkenyl" comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application, the term "alkynyl" comprises linear, branched, and cyclic alkynyl substituents. The term "alkynyl group" exemplarily comprises ethynyl, propynyl, butynyl, pentynyl, hexynyl, heptynyl or octynyl.

As used throughout the present application, the term "alkoxy" comprises linear, branched, and cyclic alkoxy substituents. The term "alkoxy group" exemplarily comprises methoxy, ethoxy, n-propoxy, i-propoxy, n-butoxy, i-butoxy, s-butoxy, t-butoxy and 2-methylbutoxy.

As used throughout the present application, the term "thioalkoxy" comprises linear, branched, and cyclic thioalkoxy substituents, in which the O of the exemplarily alkoxy groups is replaced by S.

As used throughout the present application, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 μs, of not more than 100 μs, in particular of not more than 50 μs, more preferably of not more than 10 μs or not more than 7 μs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular, density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly (methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing organic molecules (with an optional subsequent reaction) according to the invention, wherein a $R^I$ substituted 1-bromo-fluorophenyl is used as a reactant:

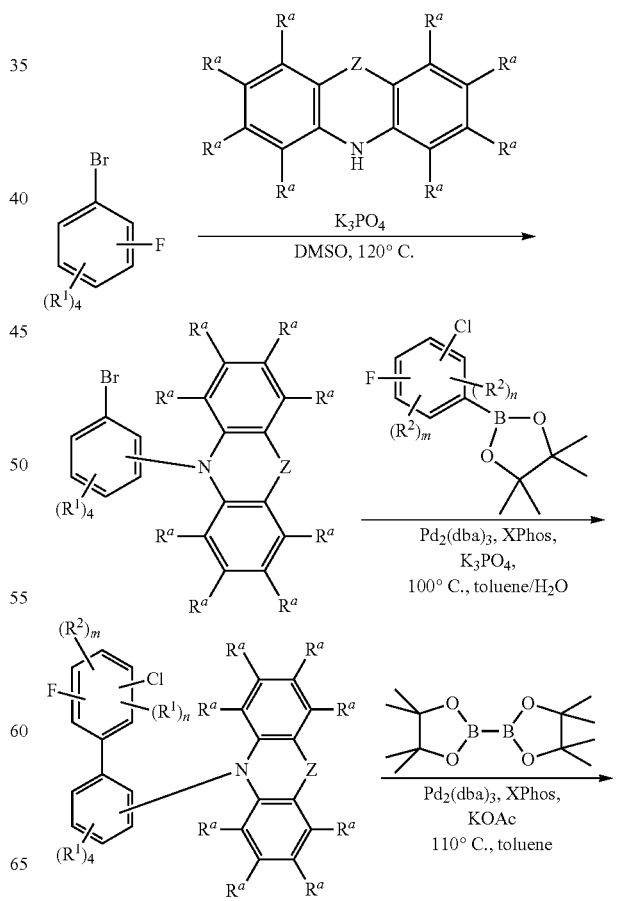

-continued
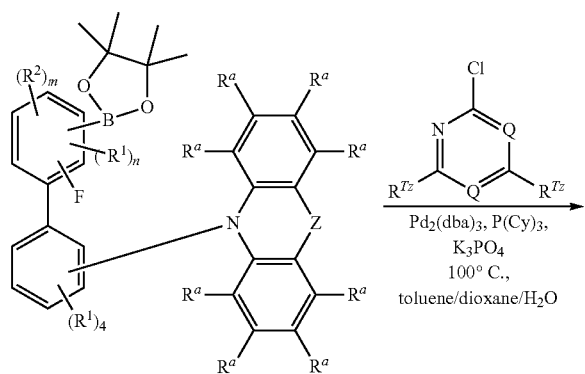
wherein the $R^{PY}$ substituted 2-($R^1$-, $R^2$-substituted bromo-fluoro-phenyl)-4,6-di-$R^{Tz}$-pyrdimidine is selected from the group consisting of:
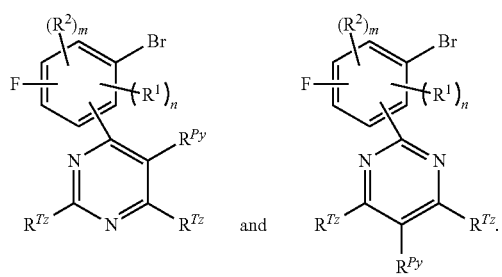
An alternative process for preparing organic molecules (with an optional subsequent reaction) according to the invention is described in the following:
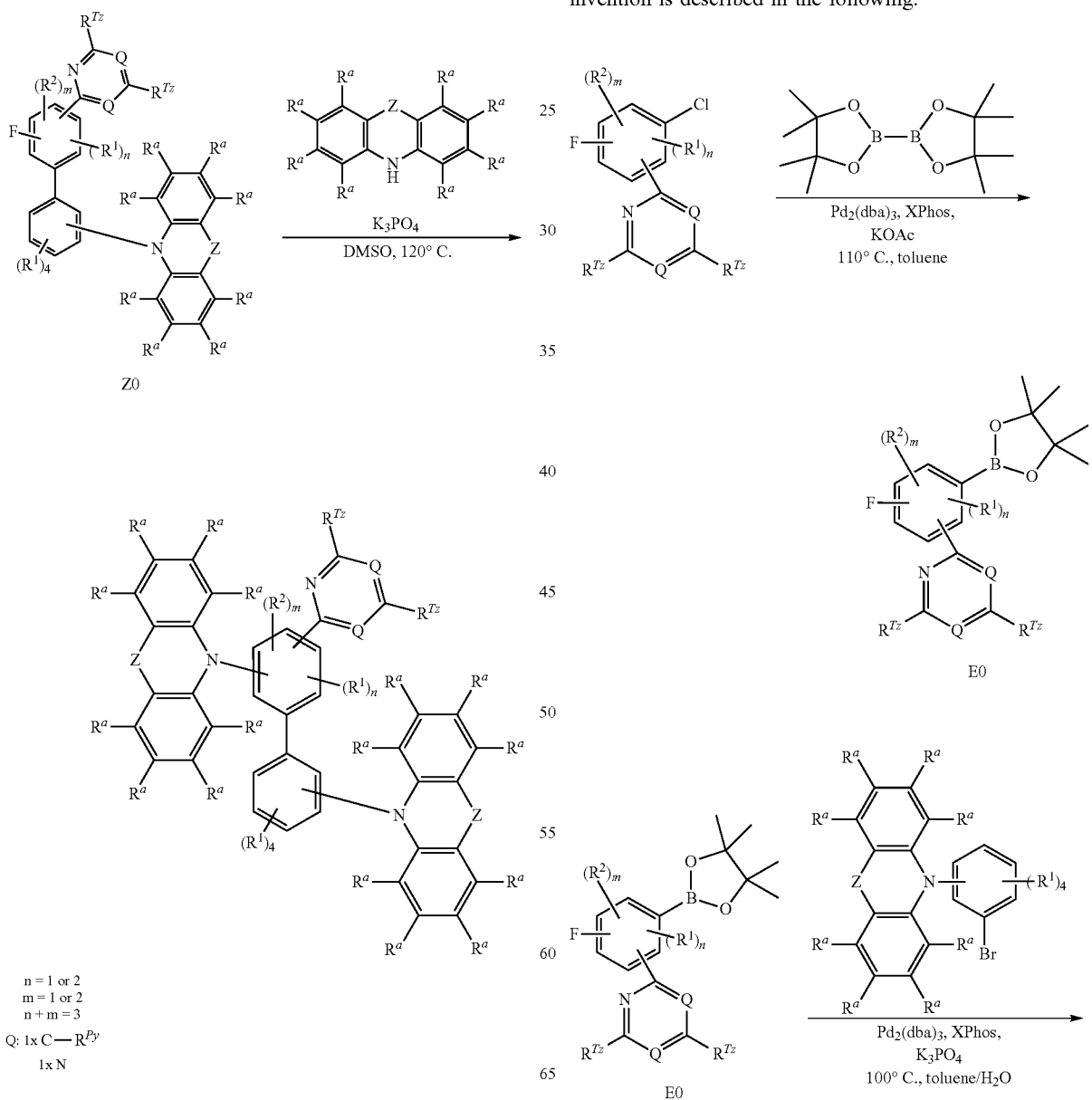
n = 1 or 2
m = 1 or 2
n + m = 3
Q: 1x C—$R^{Py}$
1x N

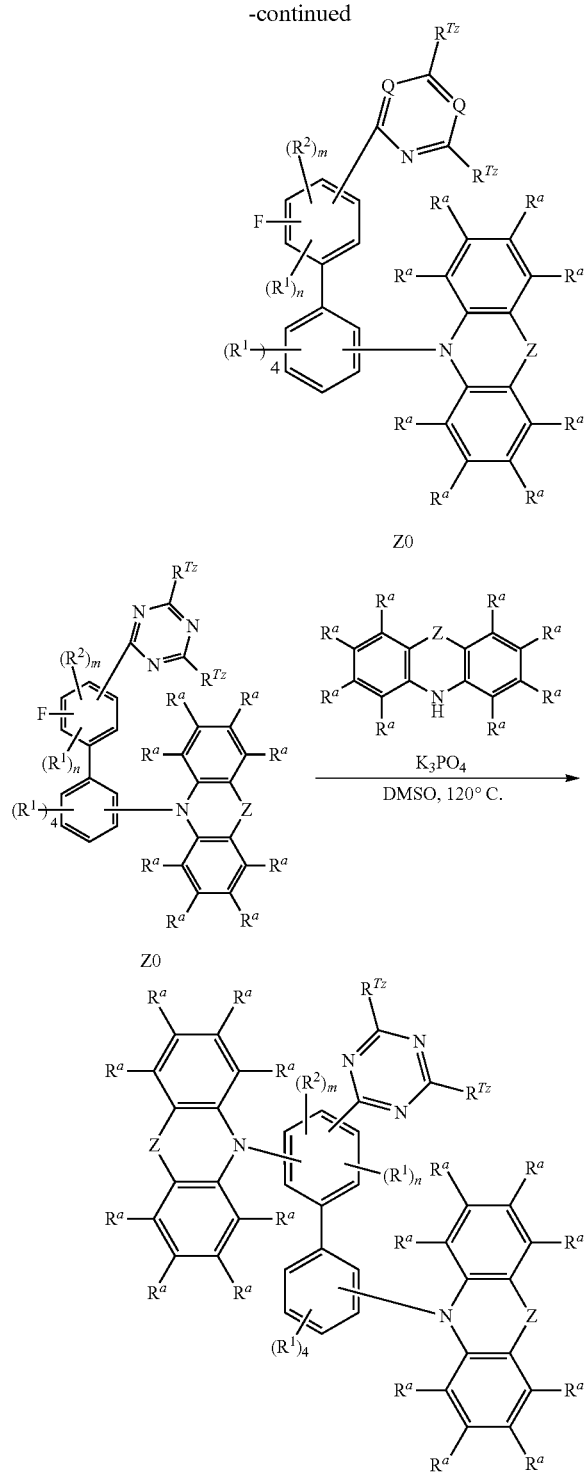

hexylphosphino)-2",4",6"-triisopropylbiphenyl; or XPhos), and P(Cy)$_3$ (tricyclohexylphosphine). The salt is, for example, selected from tribasic potassium phosphate and potassium acetate and the solvent can be a pure solvent, such as toluene or dioxane, or a mixture, such as toluene/dioxane/water or dioxane/toluene. A person of skill in the art can determine which Pd catalyst, ligand, salt and solvent combination will result in high reaction yields.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

A further aspect of the invention relates to the use of an organic molecule according to the invention as a luminescent emitter or as an absorber, and/or as host material and/or as electron transport material, and/or as hole injection material, and/or as hole blocking material in an optoelectronic device.

The optoelectronic device, also referred to as organic optoelectronic device, may be understood in the broadest sense as any device based on organic materials that is suitable for emitting light in the visible or nearest ultraviolet (UV) range, i.e., in the range of a wavelength of from 380 nm to 800 nm. More preferably, the optoelectronic device may be able to emit light in the visible range, i.e., of from 400 nm to 800 nm.

In the context of such use, the optoelectronic device is more particularly selected from the group consisting of:
organic light-emitting diodes (OLEDs),
light-emitting electrochemical cells,
OLED sensors, especially in gas and vapour sensors not hermetically externally shielded,
organic diodes,
organic solar cells,
organic transistors,
organic field-effect transistors,
organic lasers, and
down-conversion elements.

In a preferred embodiment in the context of such use, the optoelectronic device is a device selected from the group consisting of an organic light emitting diode (OLED), a light emitting electrochemical cell (LEC), and a light-emitting transistor.

In the case of the use, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention but also a host material whose triplet (T1) and singlet (S1) energy levels are energetically higher than the triplet (T1) and singlet (S1) energy levels of the organic molecule.

A further aspect of the invention relates to a composition comprising or consisting of:
(a) at least one organic molecule according to the invention, in particular in the form of an emitter and/or a host, and Typically, Pd$_2$(dba)$_3$ (tris(dibenzylideneacetone)dipalladium(0)) is used as a Pd catalyst, but alternatives are known in the art. For example, the ligand may be selected from the group consisting of S-Phos ([2-dicyclohexylphoshino-2',6'-dimethoxy-1,1'-biphenyl]; or SPhos), X-Phos (2-(dicyclo- (b) one or more emitter and/or host materials, which differ from the organic molecule according to the invention, and (c) optionally, one or more dyes and/or one or more solvents.

In one embodiment, the light-emitting layer comprises (or essentially consists of) a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

Particularly preferably the light-emitting layer EML comprises (or essentially consists of) a composition comprising or consisting of:
(i) 1-50% by weight, preferably 5-40% by weight, in particular 10-30% by weight, of one or more organic molecules according to the invention E;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally, 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention (E), in particular transferred from the first excited triplet state T1 (H) of the host compound H to the first excited triplet state T1 (E) of the one or more organic molecules according to the invention E and/or from the first excited singlet state S1(H) of the host compound H to the first excited singlet state S1(E) of the one or more organic molecules according to the invention E.

In a further embodiment, the light-emitting layer EML comprises (or essentially consists of) a composition comprising or consisting of:
(i) 1-50% by weight, preferably 5-40% by weight, in particular 10-30% by weight, of one organic molecule according to the invention E;
(ii) 5-99% by weight, preferably 30-94.9% by weight, in particular 40-89% by weight, of one host compound H; and
(iii) optionally, 0-94% by weight, preferably 0.1-65% by weight, in particular 1-50% by weight, of at least one further host compound D with a structure differing from the structure of the molecules according to the invention; and
(iv) optionally, 0-94% by weight, preferably 0-65% by weight, in particular 0-50% by weight, of a solvent; and
(v) optionally, 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H) > E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and
the at least one further host compound D has a highest occupied molecular orbital HOMO(D) having an energy $E^{HOMO}(D)$ and a lowest unoccupied molecular orbital LUMO(D) having an energy $E^{LUMO}(D)$
the organic molecule according to the invention (E) has a highest occupied molecular orbital HOMO(E) having an energy $E^{HOMO}(E)$ and a lowest unoccupied molecular orbital LUMO(E) having an energy $E^{LUMO}(E)$,
wherein $E^{HOMO}(H) > E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H) > E^{LUMO}(D)$ and the difference between the energy level of the lowest unoccupied molecular orbital LUMO(E) of the organic molecule according to the invention E ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to an optoelectronic device comprising an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention E is used as emission material in a light-emitting layer EML.

In one embodiment of the optoelectronic device of the invention the light-emitting layer EML consists of the composition according to the invention described here.

Exemplarily, when the optoelectronic device is an OLED, it may exhibit the following layer structure:
1. substrate
2. anode layer A
3. hole injection layer, HIL 4. hole transport layer, HTL
5. electron blocking layer, EBL
6. emitting layer, EML
7. hole blocking layer, HBL
8. electron transport layer, ETL
9. electron injection layer, EIL
10. cathode layer,
wherein the OLED comprises each layer only optionally, different layers may be merged and the OLED may comprise more than one layer of each layer type defined above.

Furthermore, the optoelectronic device may optionally comprise one or more protective layers protecting the device from damaging exposure to harmful species in the environment including, exemplarily moisture, vapor and/or gases.

In one embodiment of the invention, the optoelectronic device is an OLED, which exhibits the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A,
wherein the OLED with an inverted layer structure comprises each layer only optionally, different layers may be merged and the OLED may comprise more than one layer of each layer types defined above.

In one embodiment of the invention, the optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an essentially transparent film. As at least one of both electrodes should be essentially transparent in order to allow light emission from the OLED, either the anode layer A or the cathode layer C is transparent. Preferably, the anode layer A comprises a large content or even consists of transparent conductive oxides (TCOs). Such anode layer A may, for example, comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

The anode layer A essentially may consist of indium tin oxide (ITO) (e.g., $(InO_3)0.9(SnO_2)0.1$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may, for example, comprise PEDOT:PSS (poly-3,4-ethylendioxy thiophene: polystyrene sulfonate), PEDOT (poly-3,4-ethylendioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenylamino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL), a hole transport layer (HTL) is typically located. Herein, any hole transport compound may be used. For example, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. For example, the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane ($F_4$-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particularly, the EML comprises at least one light emitting molecule according to the invention E. In one embodiment, the light-emitting layer comprises only the organic molecules according to the invention E. Typically, the EML additionally comprises one or more host materials H. Exemplarily, the host material H is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl]ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule according to the invention E and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq$_3$ (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl).

Optionally, the ETL may be doped with materials such as Liq. The electron transport layer (ETL) may also block holes or a holeblocking layer (HBL) is introduced.

The HBL may, for example, comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq$_3$ (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl) benzene).

Adjacent to the electron transport layer (ETL), a cathode layer C may be located. For example, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of essentially non-transparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), Li$_2$O, BaF$_2$, MgO and/or NaF.

Optionally, also the electron transport layer (ETL) and/or a hole blocking layer (HBL) may comprise one or more host compounds H.

In order to modify the emission spectrum and/or the absorption spectrum of the light-emitting layer EML further, the light-emitting layer EML may further comprise one or more further emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the emitter molecule according to the invention E to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an optoelectronic device (e.g., an OLED) may exemplarily be an essentially white optoelectronic device. For example, such a white optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
  violet: wavelength range of >380-420 nm;
  deep blue: wavelength range of >420-480 nm;
  sky blue: wavelength range of >480-500 nm;
  green: wavelength range of >500-560 nm;
  yellow: wavelength range of >560-580 nm;

orange: wavelength range of >580-620 nm;
red: wavelength range of >620-800 nm.

With respect to emitter molecules, such colors refer to the emission maximum. Therefore, for example, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

Accordingly, a further aspect of the present invention relates to an OLED, which exhibits an external quantum efficiency at 1000 cd/m$^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/m$^2$ of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The optoelectronic device, in particular the OLED according to the present invention can be produced by any means of vapor deposition and/or liquid processing. Accordingly, at least one layer is:
  prepared by means of a sublimation process,
  prepared by means of an organic vapor phase deposition process,
  prepared by means of a carrier gas sublimation process,
  solution processed or printed.

The methods used to produce the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes may comprise thermal (co) evaporation, chemical vapor deposition and physical vapor deposition. For active matrix OLED display, an AMOLED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General Synthesis Scheme I

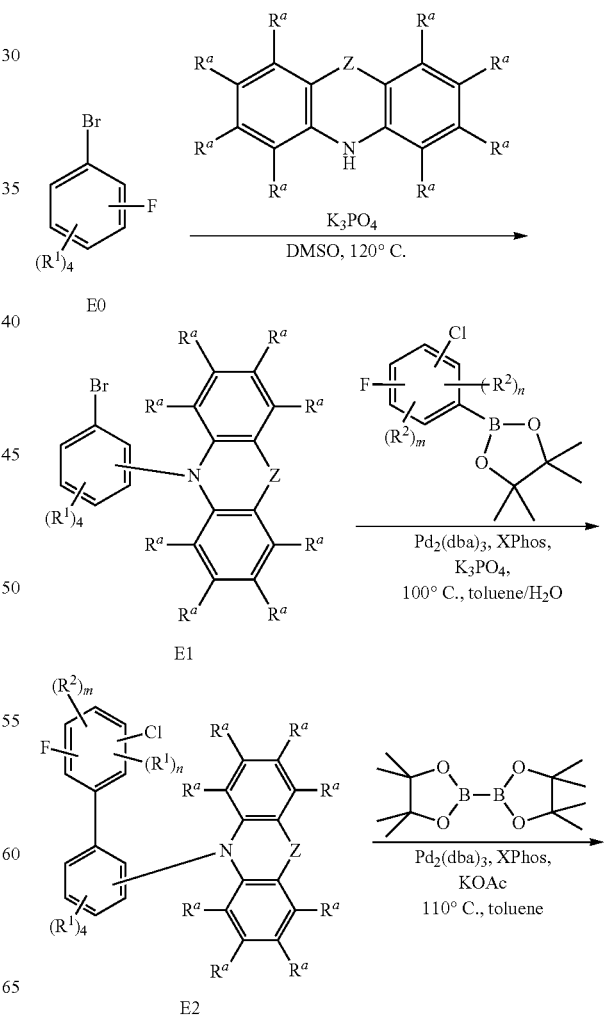

-continued

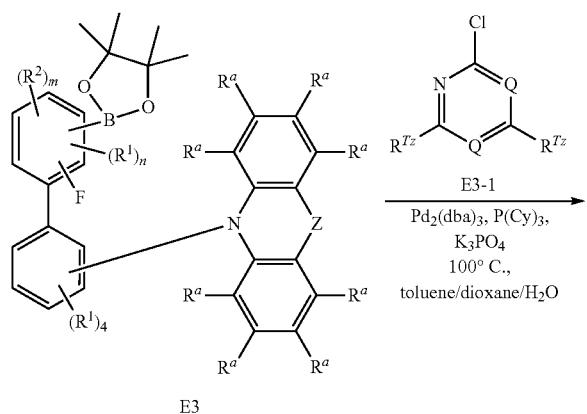

E3

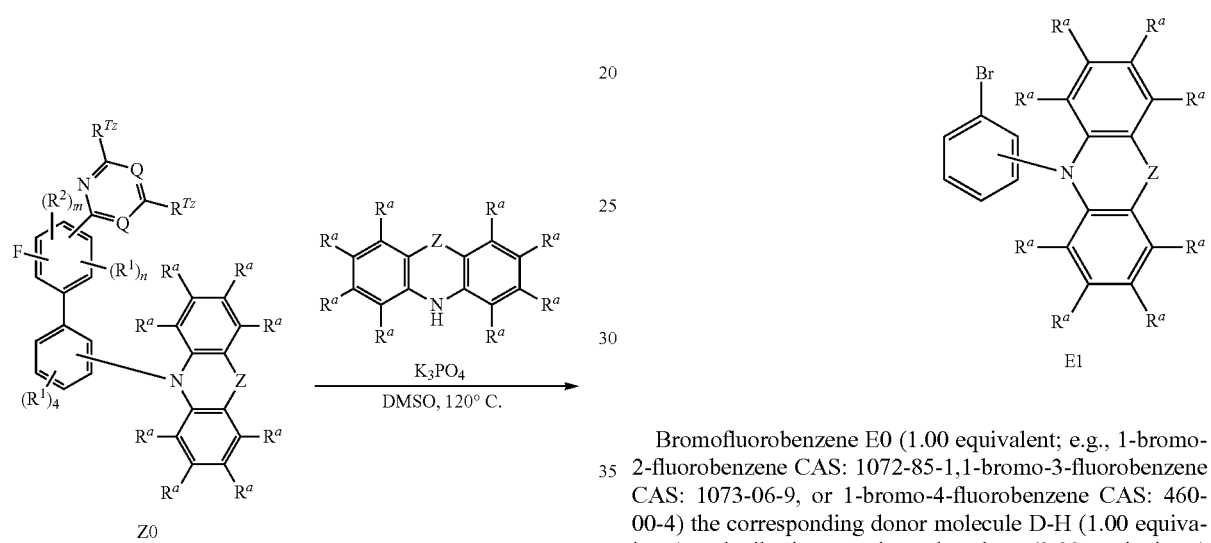

Z0 n = 1 or 2
m = 1 or 2
n + m = 3
Q: 1x C—R$^{Py}$
1x N

General Procedure for Synthesis AAV0:

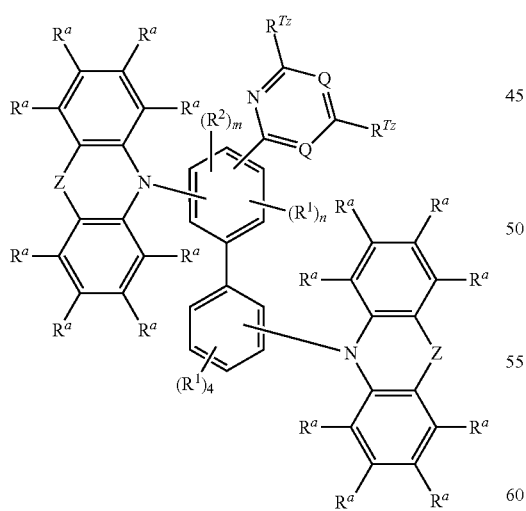

Bromofluorobenzene E0 (1.00 equivalent; e.g., 1-bromo-2-fluorobenzene CAS: 1072-85-1,1-bromo-3-fluorobenzene CAS: 1073-06-9, or 1-bromo-4-fluorobenzene CAS: 460-00-4) the corresponding donor molecule D-H (1.00 equivalents) and tribasic potassium phosphate (3.00 equivalents) are suspended under nitrogen atmosphere in DMSO and stirred at 120° C. (16 h). After cooling to room temperature the reaction mixture is extracted with ethyl acetate/brine. Organic phases are collected, washed with brine and dried over MgSO$_4$. The solvents are removed under reduced pressure. The crude product E1 is purified by recrystallization or by flash chromatography.

General Procedure for Synthesis AAV1:

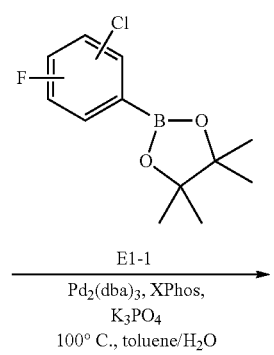

E1

-continued

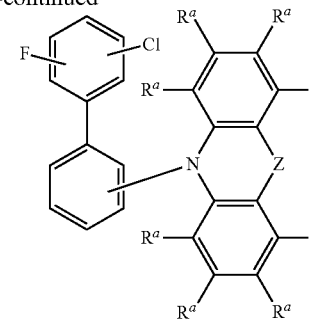

E2

E1 (1.00 equivalent), E1-1 (1.00 equivalent), tris(dibenzylideneacetone)dipalladium(0) Pd₂(dba)₃ (0.04 equivalents; CAS 51364-51-3), XPhos (0.08 equivalents, CAS 564483-18-7) and potassium phosphate (K₃PO₄, 3.00 equivalents) are stirred under nitrogen atmosphere in dry toluene/H2O (10:1) at 100° C. for 16 h. After cooling down to room temperature (RT), the reaction mixture is extracted with ethyl acetate/brine. Organic phase is collected, washed with brine and dried over MgSO₄. The organic solvent is removed, the crude oily product E2 is additionally filtrated through silica filter column to remove rest of catalyst and further purified by recrystallization or by flash chromatography.

General Procedure for Synthesis AAV2:

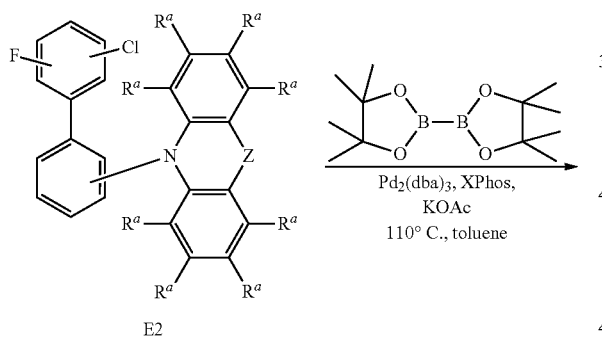

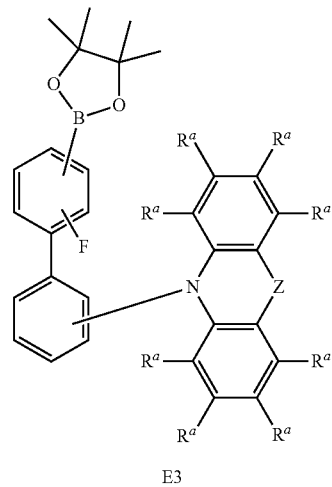

E2 (1.00 equivalent), bis-(pinacolato)diboron (1.50 equivalents, CAS 73183-34-3), tris(dibenzylideneacetone)dipalladium(0) Pd₂(dba)₃ (0.04 equivalents, CAS 51364-51-3), XPhos (0.08 equivalents, CAS 564483-18-7) and potassium acetate (KOAc, 3.00 equivalents) are stirred under nitrogen atmosphere in dry toluene at 110° C. for 16 h. After cooling down to room temperature (RT) the reaction mixture is extracted with ethyl acetate/brine. The organic phases are collected, washed with brine and dried over MgSO₄. The organic solvent is removed, the crude oily product is purified by recrystallization or by flash chromatography.

General Procedure for Synthesis AAV3:

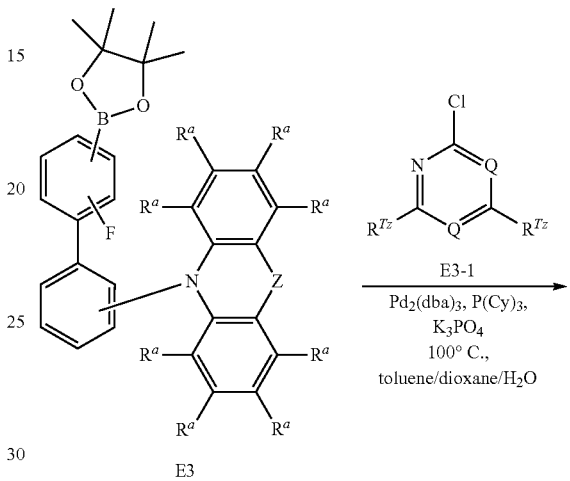

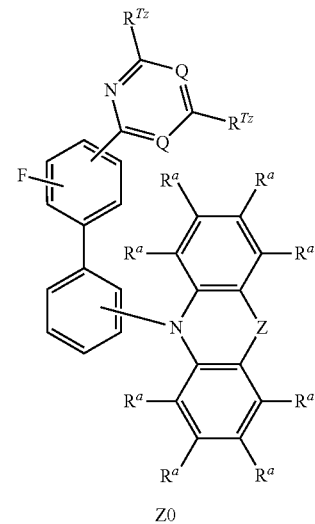

Z0

E3 (1.00 equivalent), E3-1 (1.50 equivalent; e.g., 4-chloro-2,6-diphenyl-pyrimidine CAS 29509-91-9 or 2-chloro-4,6-diphenyl-pyrimidine CAS 2915-16-4), tris(dibenzylideneacetone)dipalladium(0) Pd₂(dba)₃ (0.06 equivalents, CAS 51364-51-3), tricyclohexylphosphine P(Cy)₃ (0.16 equivalents; CAS 2622-14-2), and potassium phosphate (K₃PO₄, 3.00 equivalents) are stirred under nitrogen atmosphere in dry toluene/dioxane/H₂O (3:3:1) at 100° C. for 16 h. After cooling down to room temperature (RT) the reaction mixture is extracted with ethyl acetate/brine. Organic phase is collected, washed with brine and dried over MgSO₄. The organic solvent is removed, the crude product is further purified by recrystallization or flash chromatography.

General Procedure for Synthesis AAV4:

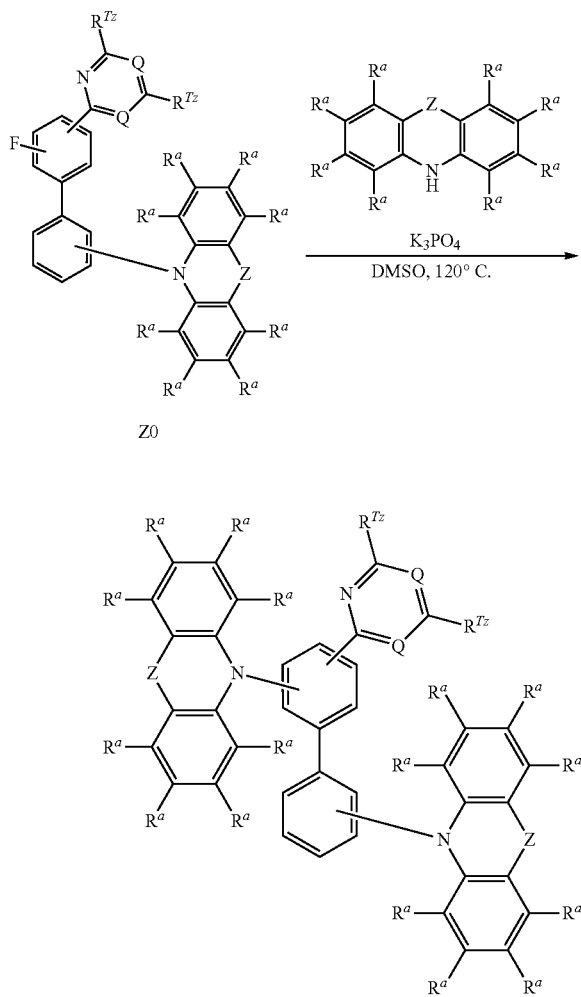

Z0 (1.00 equivalent each), the corresponding donor molecule D-H (1.00 equivalents) and tribasic potassium phosphate (3.00 equivalents) are suspended under nitrogen atmosphere in DMSO and stirred at 120° C. (16 h). After cooling to room temperature the reaction mixture is extracted with ethyl acetate/brine. Organic phases are collected, washed with brine and dried over MgSO$_4$. The solvents are removed under reduced pressure. The crude product is purified by recrystallization or by flash chromatography.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily, a halogen-substituted carbazole, particularly 3-bromocarbazole, can be used as D-H.

In a subsequent reaction, a boronic acid ester functional group or boronic acid functional group may be, for example, introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents $R^a$ may be introduced in place of the boronic acid ester group or the boronic acid group via a coupling reaction with the corresponding halogenated reactant $R^a$-Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—B(OH)$_2$] or a corresponding boronic acid ester.

Cyclic Voltammetry

Cyclic voltammograms are measured from solutions having concentration of $10^{-3}$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using FeCp$_2$/FeCp$_2^+$ as internal standard. The HOMO data was corrected using ferrocene as internal standard against a saturated calomel electrode (SCE).

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence Spectroscopy and TCSPC (Time-Correlated Single-Photon Counting)

Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Φ in % and CIE coordinates as x,y values.

PLQY is determined using the following protocol:

1) Quality assurance: Anthracene in ethanol (known concentration) is used as reference
2) Excitation wavelength: the absorption maximum of the organic molecule is determined and the molecule is excited using this wavelength
3) Measurement Quantum yields are measured for sample of solutions or films under nitrogen atmosphere. The yield is calculated using the equation:

$$\Phi_{PL} = \frac{n_{photon}, \text{emited}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

wherein $n_{photon}$ denotes the photon count and Int. the intensity.

Production and Characterization of Optoelectronic Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The (not fully optimized) OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc.

Accelerated lifetime measurements are performed (e.g. applying increased current densities). Exemplarily LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given.

HPLC-MS:

HPLC-MS spectroscopy is performed on a HPLC by Agilent (1100 series) with MS-detector (Thermo LTQ XL). A typical HPLC method is as follows: a reverse phase column 4.6 mm×150 mm, particle size 3.5 μm from Agilent (ZORBAX Eclipse Plus 95 Å C18, 4.6×150 mm, 3.5 μm HPLC column) is used in the HPLC. The HPLC-MS measurements are performed at room temperature (rt) following gradients:

| Flow rate [ml/min] | time [min] | A[%] | B[%] | C[%] |
|---|---|---|---|---|
| 2.5 | 0 | 40 | 50 | 10 |
| 2.5 | 5 | 40 | 50 | 10 |
| 2.5 | 25 | 10 | 20 | 70 |
| 2.5 | 35 | 10 | 20 | 70 |
| 2.5 | 35.01 | 40 | 50 | 10 |
| 2.5 | 40.01 | 40 | 50 | 10 |
| 2.5 | 41.01 | 40 | 50 | 10 | using the following solvent mixtures:

| Solvent A: | H₂O (90%) | MeCN (10%) |
|---|---|---|
| Solvent B: | H₂O (10%) | MeCN (90%) |
| Solvent C: | THF (50%) | MeCN (50%) |

An injection volume of 5 μL from a solution with a concentration of 0.5 mg/mL of the analyte is taken for the measurements.

Ionization of the probe is performed using an APCI (atmospheric pressure chemical ionization) source either in positive (APCI+) or negative (APCI−) ionization mode.

Example 1

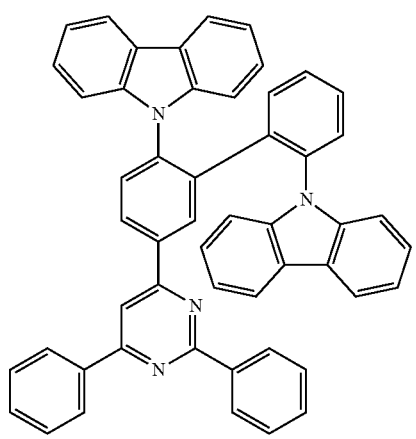 [SMILES: c1ccc(-c2cc(-c3ccc(-n4c5ccccc5c5ccccc54)c(-c4ccccc4-n4c5ccccc5c5ccccc54)c3)nc(-c3ccccc3)n2)cc1]

Example 1 was synthesized according to

AAV0 (yield=63%), wherein carbazole was used as reactant D-H and 2-bromofluorobenzene (CAS 1072-85-1) as reactant E0;

AAV1 (yield=92%), wherein 5-chloro-2-fluorobenzeneboronic acid pinacol ester was used as reactant E1-1 and 9-(2-bromophenyl)-9H-carbazole (CAS 902518-11-0) was used as reactant E1;

AAV2 (yield=59%) wherein E2 was used as reactant;

AAV3 (yield=69%), wherein 4-chloro-2,6-diphenyl-pyrimidine (CAS 29509-91-9) was used as reactant E3-1;

AAV4 (yield=69%).

HPLC-MS: 714.64 m/z, 100%

FIG. 1 depicts the emission spectrum of example 1 (10% by weight in PMMA). The emission maximum ($\lambda_{max}$) is at 443 nm. The photoluminescence quantum yield (PLQY) is 72% and the full width at half maximum (FWHM) is 0.41 eV.

Example 2

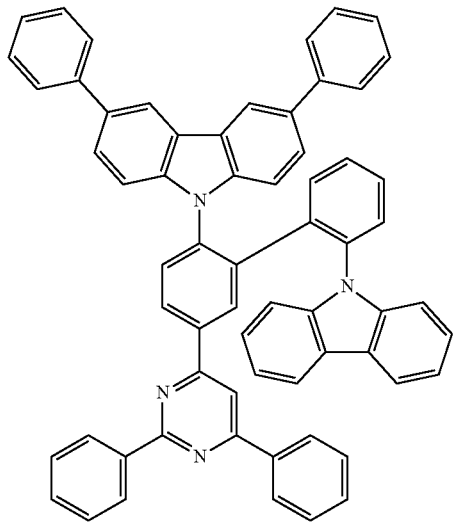 [SMILES: c1ccc(-c2ccc3c(c2)c2cc(-c4ccccc4)ccc2n3-c2ccc(-c3cc(-c4ccccc4)nc(-c4ccccc4)n3)cc2-c2ccccc2-n2c3ccccc3c3ccccc32)cc1]

Example 2 was synthesized according to

AAV0 (yield=63%), wherein carbazole was used as reactant D-H and 2-bromofluorobenzene (CAS 1072-85-1) as reactant E0;

AAV1 (yield=92%), wherein 5-chloro-2-fluorobenzeneboronic acid pinacol ester was used as reactant E1-1 and 9-(2-bromophenyl)-9H-carbazole (CAS 902518-11-0) was used as reactant E1;

AAV2 (yield=59%) wherein E2 was used as reactant;

AAV3 (yield=69%), wherein 4-chloro-2,6-diphenyl-pyrimidine (CAS 29509-91-9) was used as reactant E3-1;

AAV4 (yield=64%).

HPLC-MS: 866.84 m/z, 100%

Figure 2:
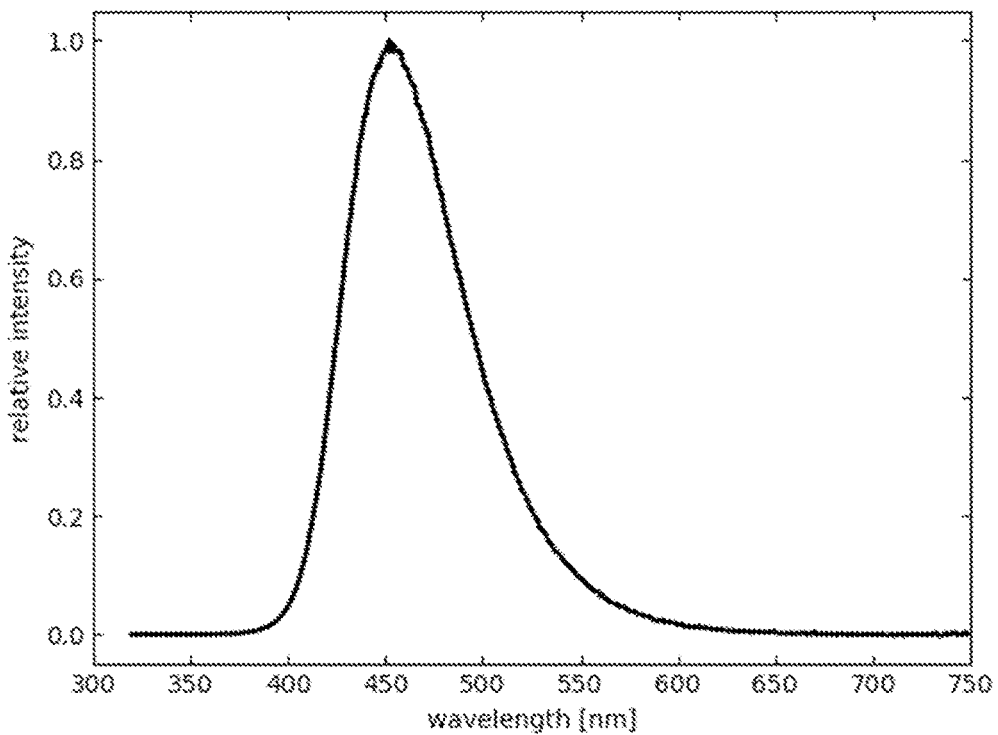
FIG. 2 is an emission spectrum of example 2 (10% by weight) in PMMA.

FIG. 2 depicts the emission spectrum of example 2 (10% by weight in PMMA). The emission maximum ($\lambda_{max}$) is at 454 nm. The photoluminescence quantum yield (PLQY) is 82% and the full width at half maximum (FWHM) is 0.42 eV.

Example 3

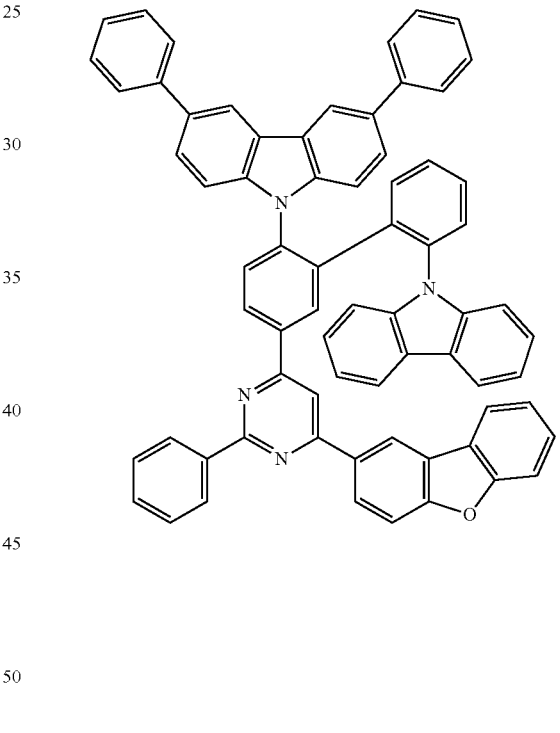

Example 3 was synthesized according to

AAV0 (yield=63%), wherein carbazole was used as reactant D-H and 2-bromofluorobenzene (CAS 1072-85-1) as reactant E0;

AAV1 (yield=92%), wherein 5-chloro-2-fluorobenzeneboronic acid pinacol ester was used as reactant E1-1 and 9-(2-bromophenyl)-9H-carbazole (CAS 902518-11-0) was used as reactant E1;

AAV2 (yield=59%) wherein E2 was used as reactant;

AAV3 (yield=74%), wherein 4-chloro-2-(2-dibenzofuryl)-6-phenyl-pyrimidine was used as reactant E3-1;

AAV4 (yield=57%).

HPLC-MS: 955.28 m/z, 100%

Figure 3:
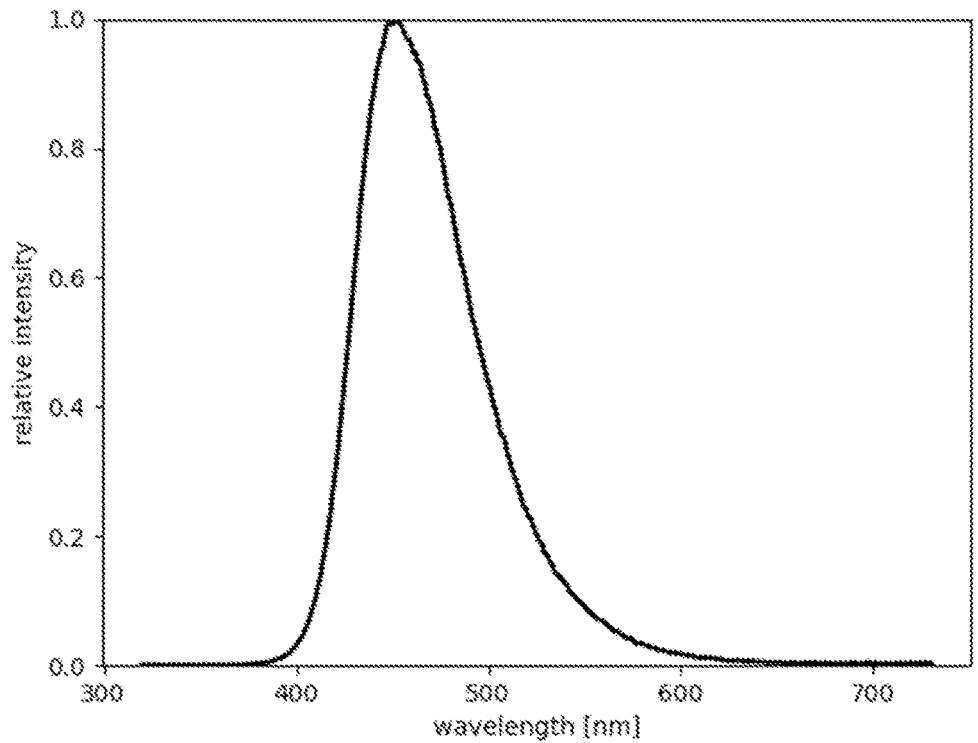
FIG. 3 is an emission spectrum of example 3 (10% by weight) in PMMA.

FIG. 3 depicts the emission spectrum of example 3 (10% by weight in PMMA). The emission maximum ($\lambda_{max}$) is at 453 nm. The photoluminescence quantum yield (PLQY) is 81% and the full width at half maximum (FWHM) is 0.40 eV.

Example 4

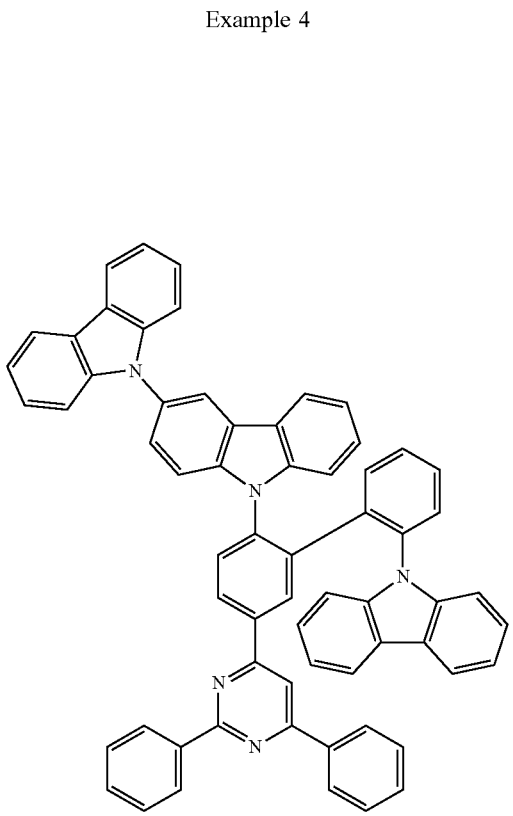

Example 4 was synthesized according to

AAV0 (yield=63%), wherein carbazole was used as reactant D-H and 2-bromofluorobenzene (CAS 1072-85-1) as reactant E0;

AAV1 (yield=92%), wherein 5-chloro-2-fluorobenzeneboronic acid pinacol ester was used as reactant E1-1 and 9-(2-bromophenyl)-9H-carbazole (CAS 902518-11-0) was used as reactant E1;

AAV2 (yield=59%) wherein E2 was used as reactant;

AAV3 (yield=69%), wherein 4-chloro-2,6-diphenyl-pyrimidine (CAS 29509-91-9) was used as reactant E3-1;

AAV4 (yield=53%).

HPLC-MS: 879.55 m/z, 100%

Figure 4:
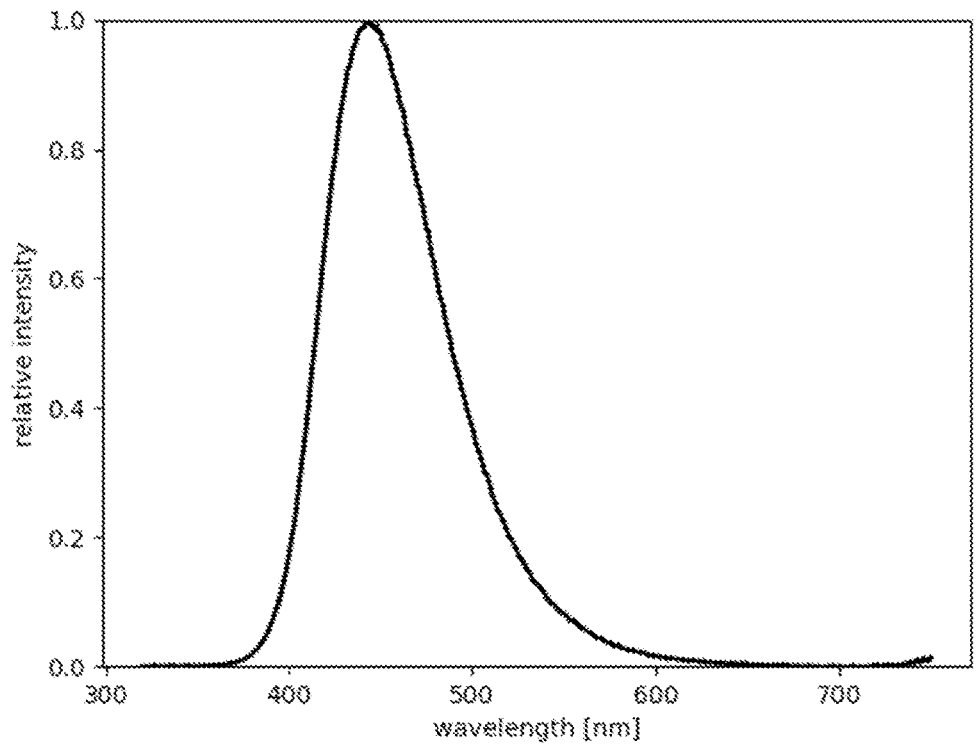
FIG. 4 is an emission spectrum of example 4 (10% by weight) in PMMA.

FIG. 4 depicts the emission spectrum of example 4 (10% by weight in PMMA). The emission maximum ($\lambda_{max}$) is at 444 nm. The photoluminescence quantum yield (PLQY) is 74% and the full width at half maximum (FWHM) is 0.45 eV.

Additional Examples of Organic Molecules of the Invention

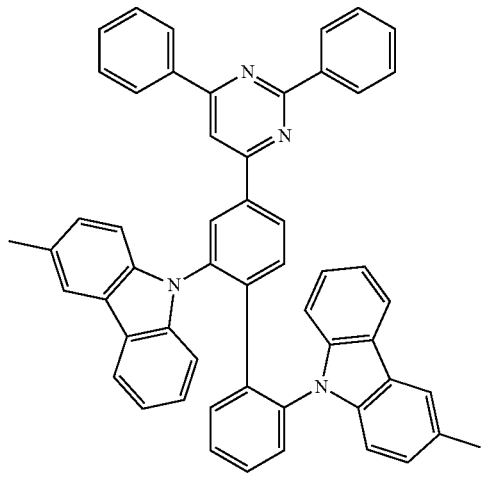

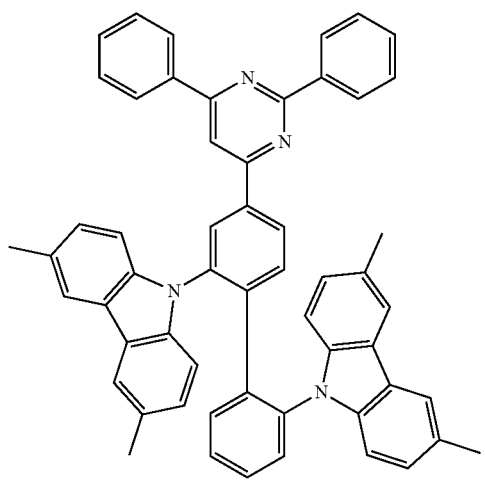

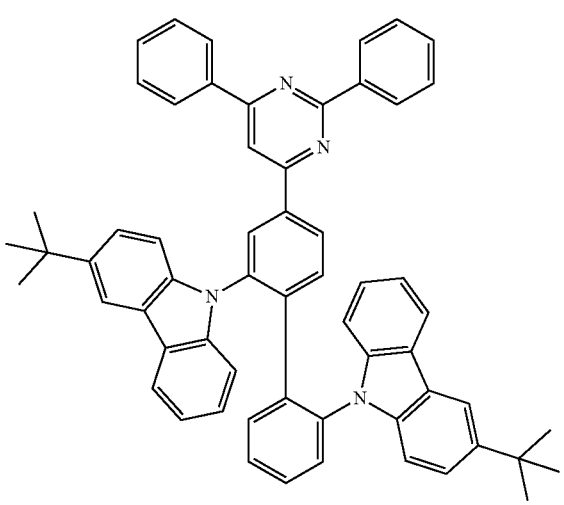

81
-continued
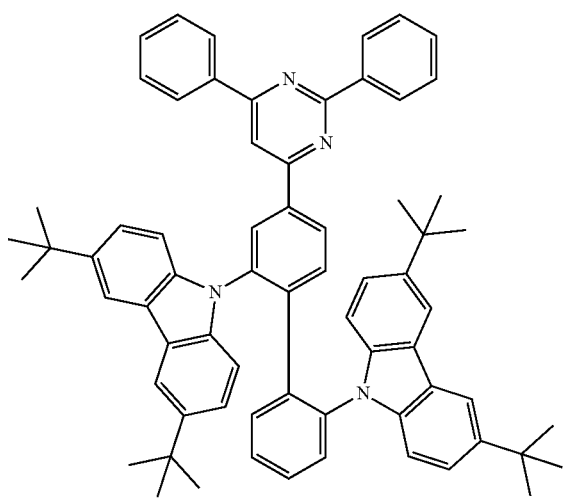
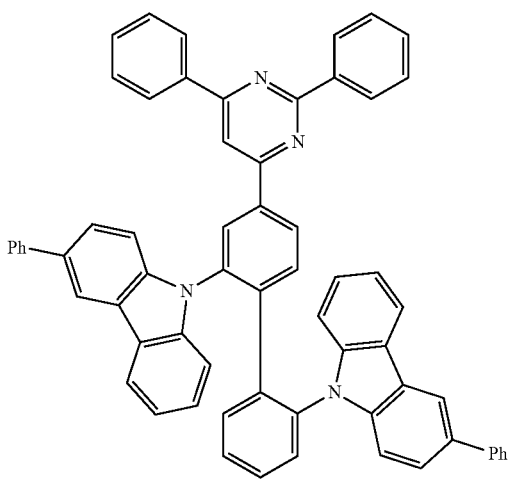
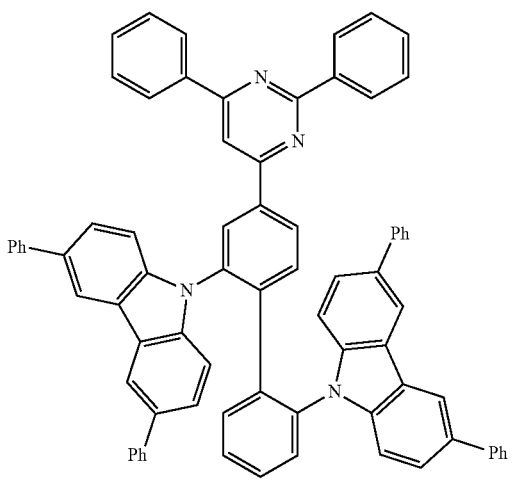
82
-continued
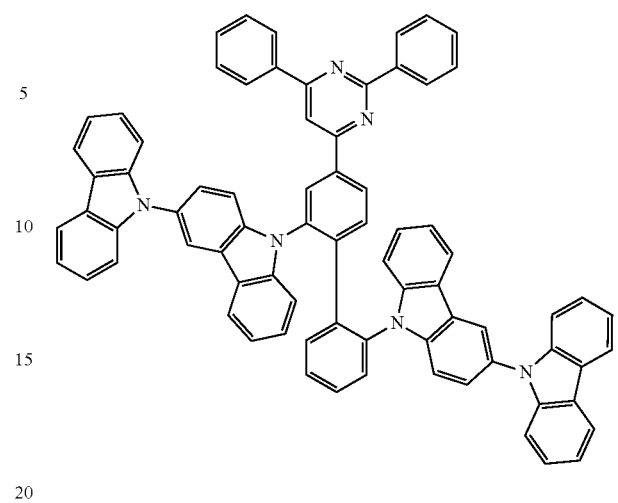
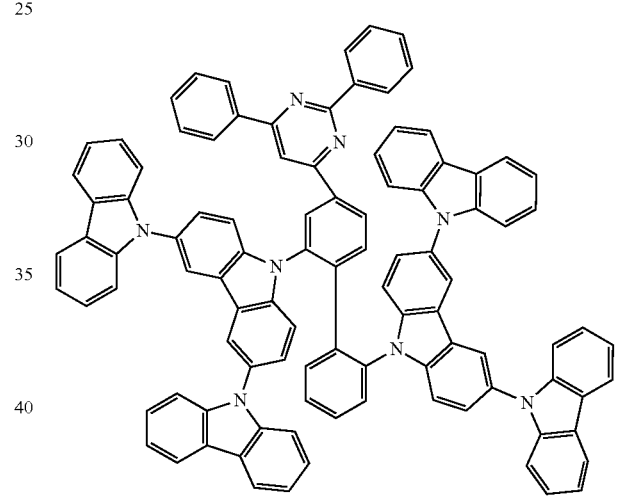
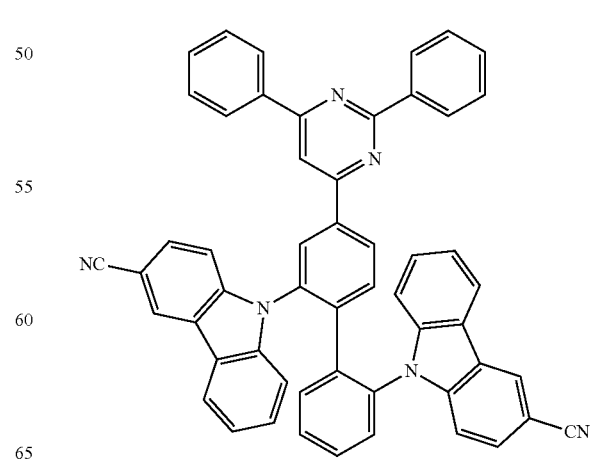

83
-continued
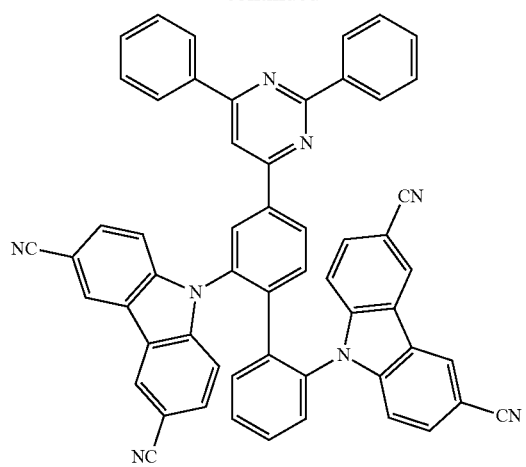
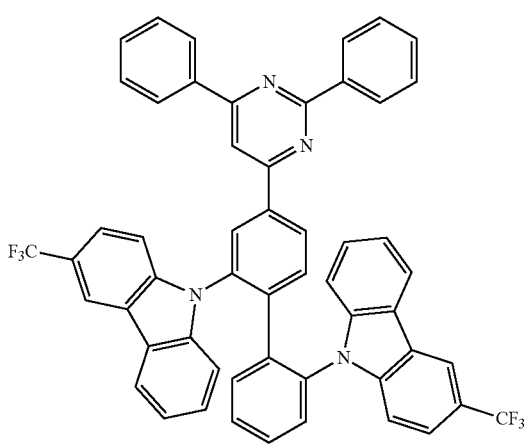
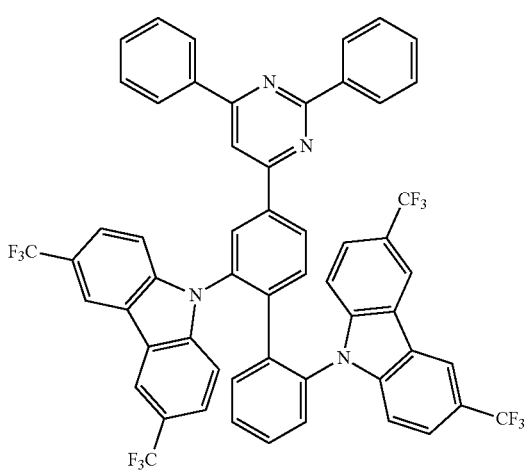
84
-continued
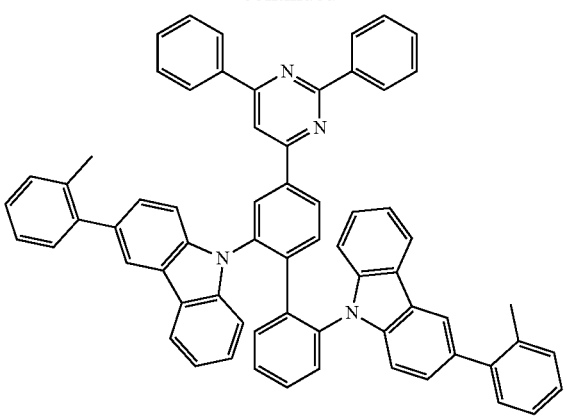
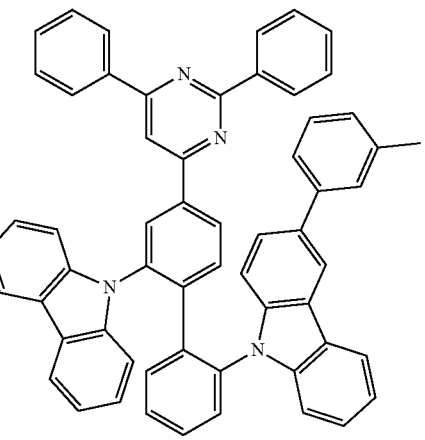
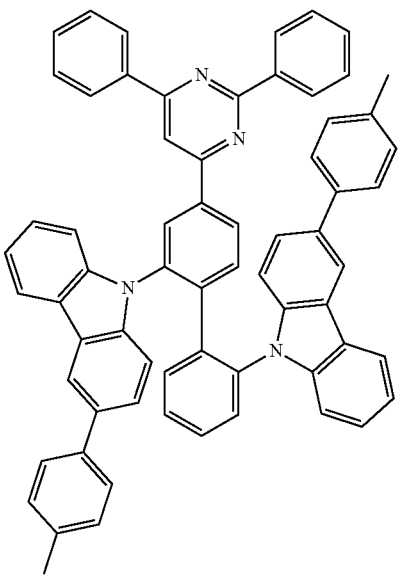

85
-continued
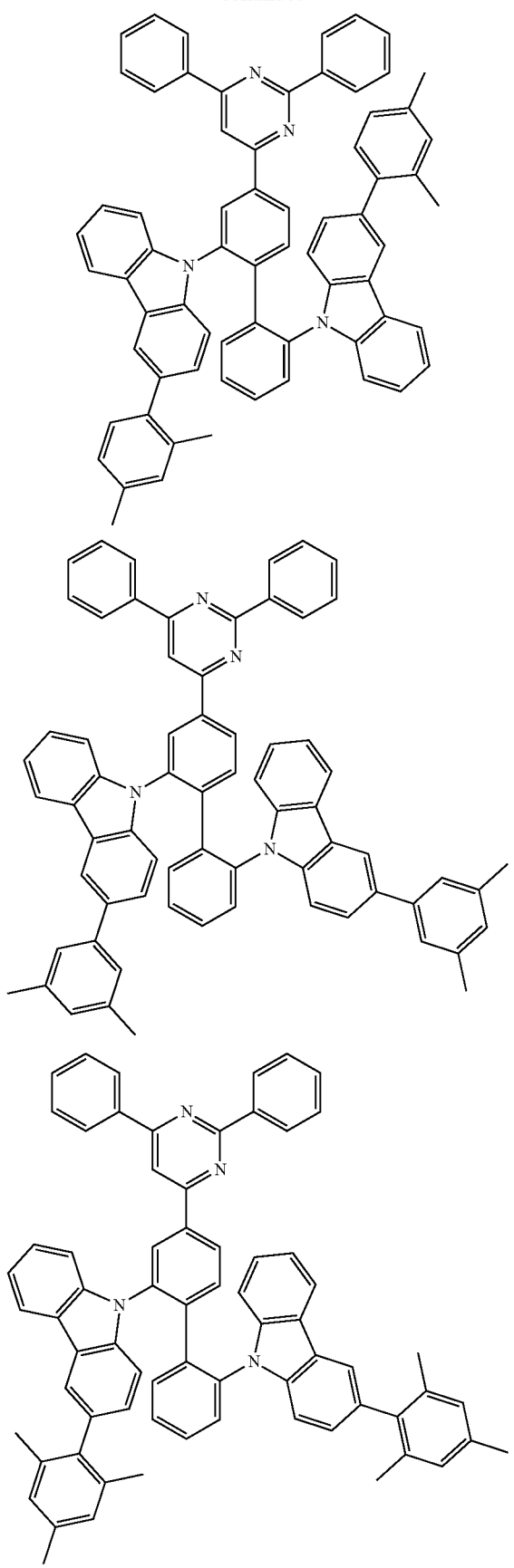
86
-continued
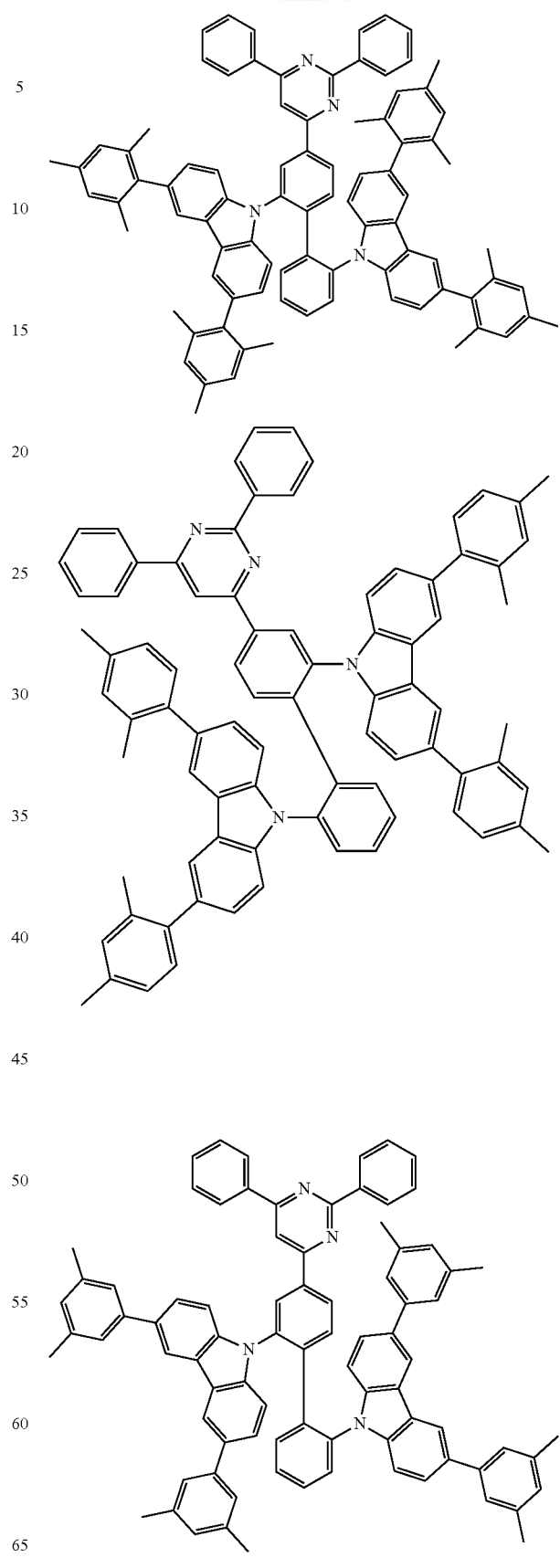

87
-continued
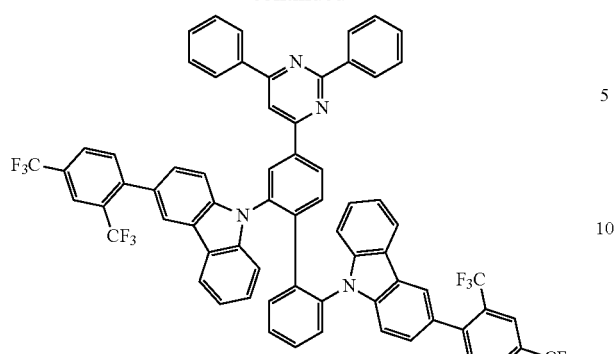
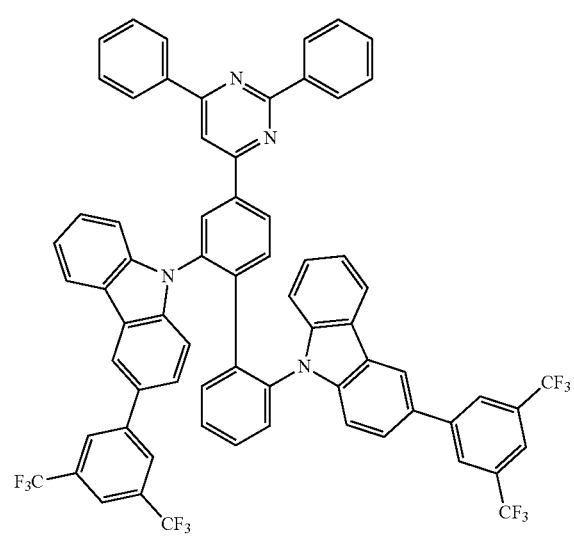
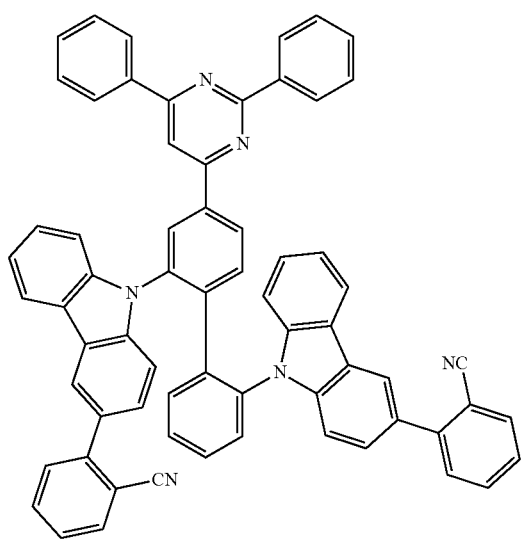
88
-continued
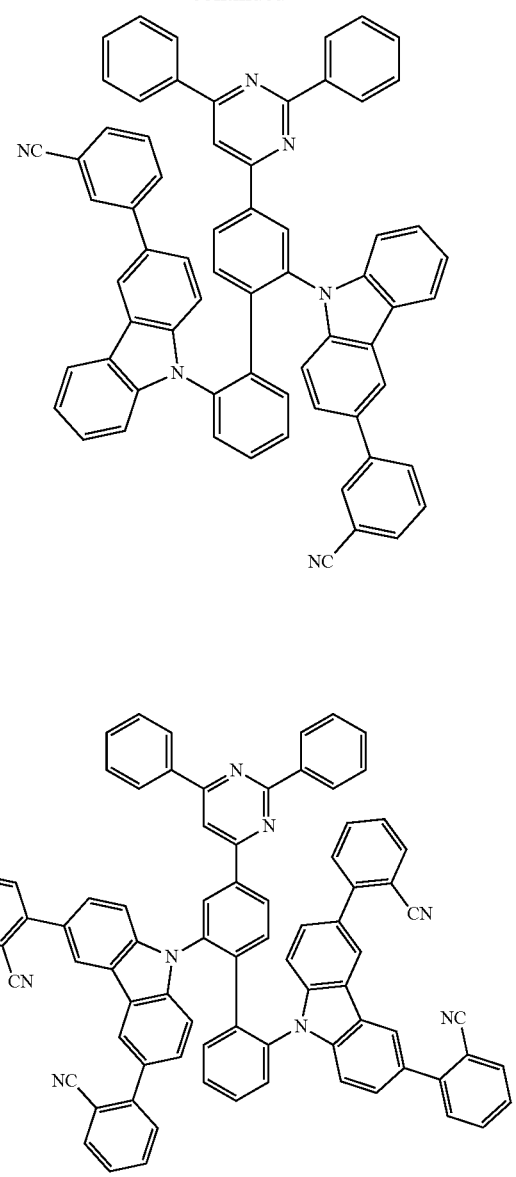
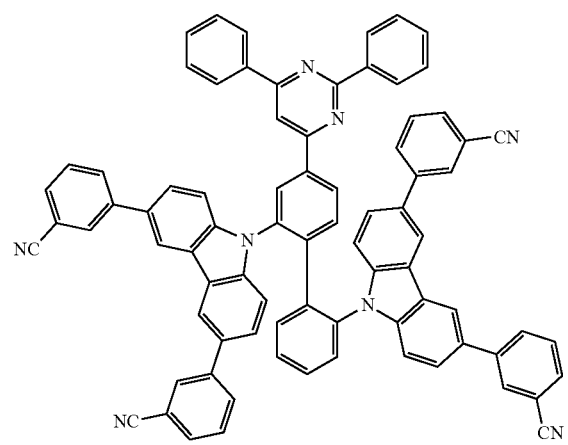

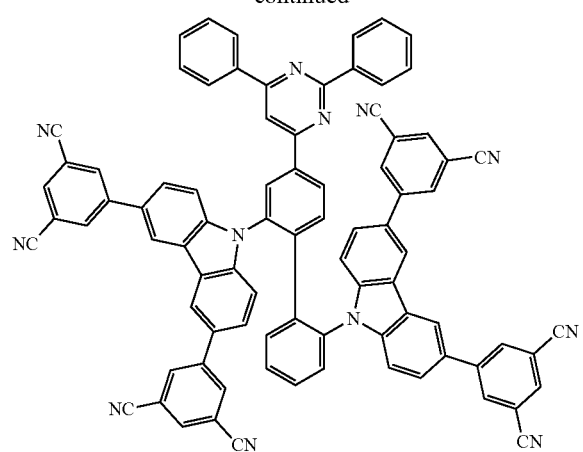
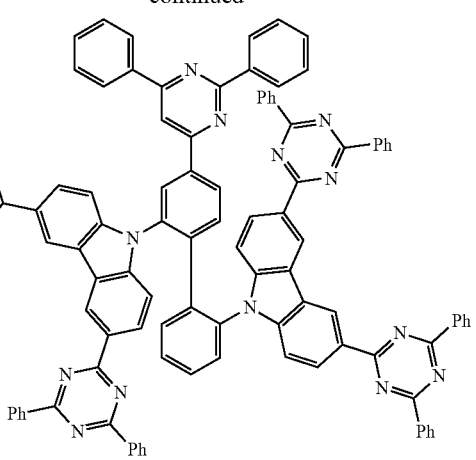
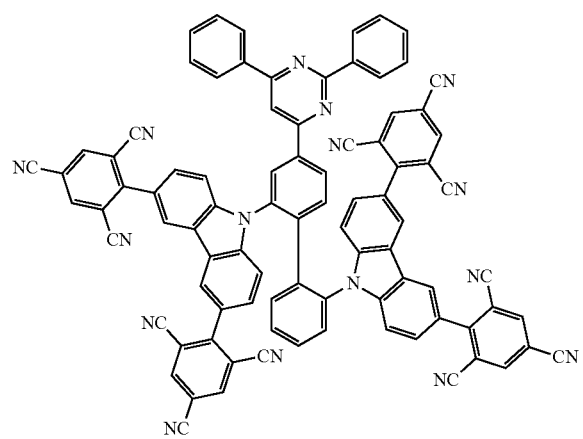
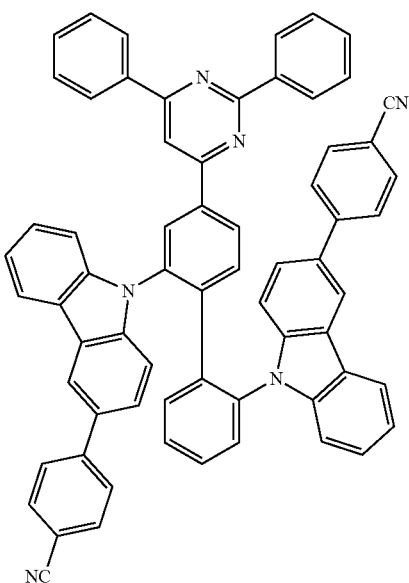
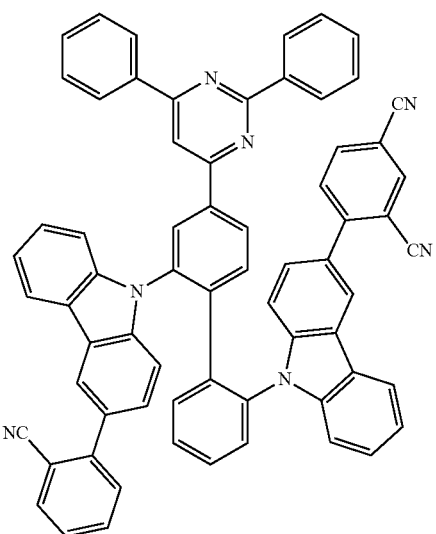

-continued
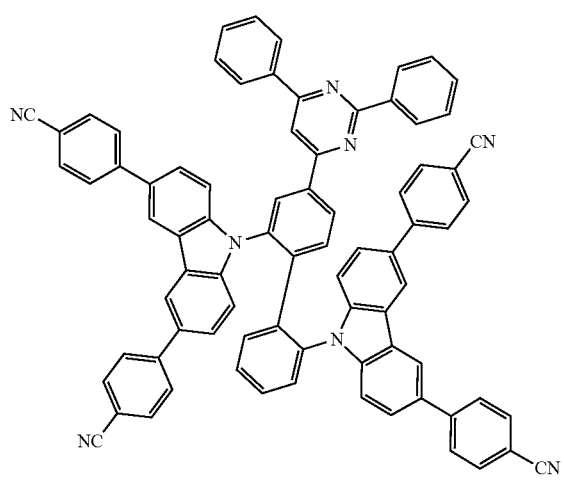
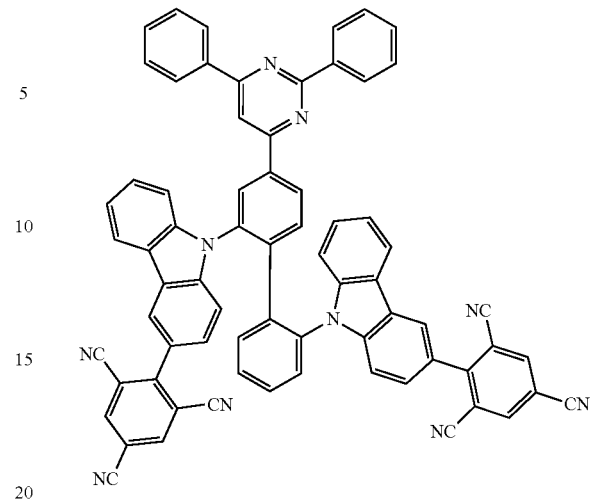
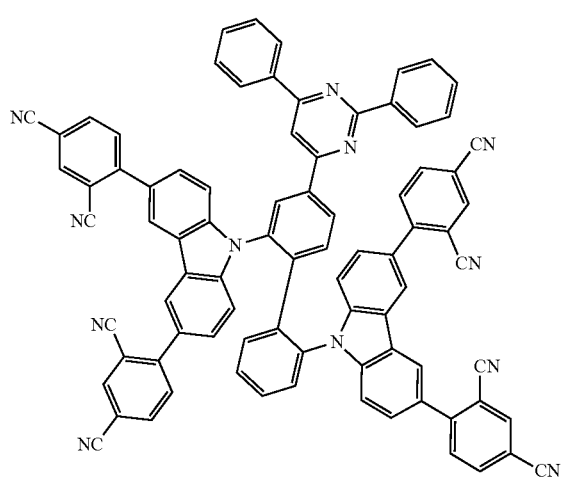
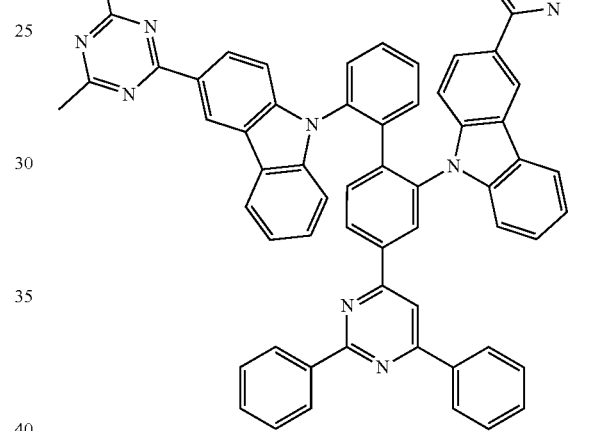
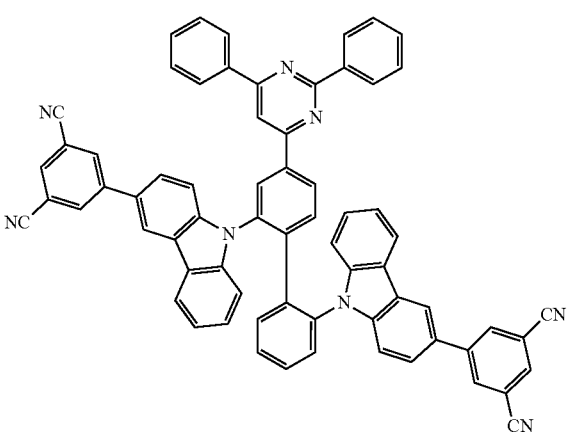
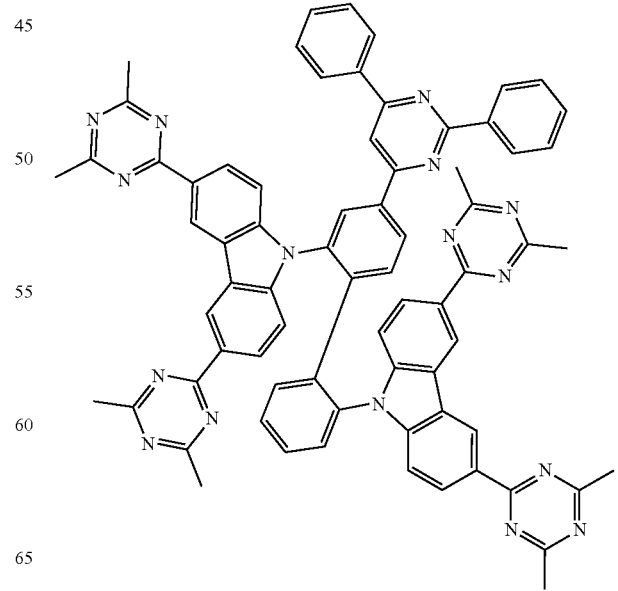

93
-continued
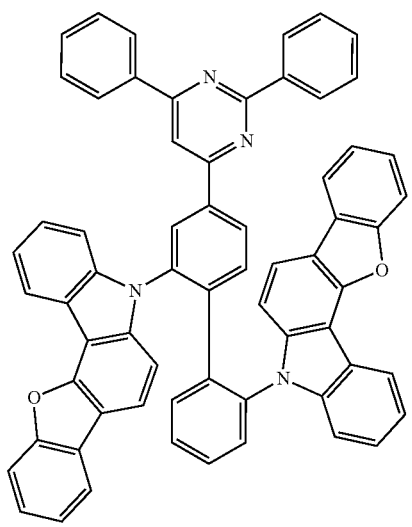
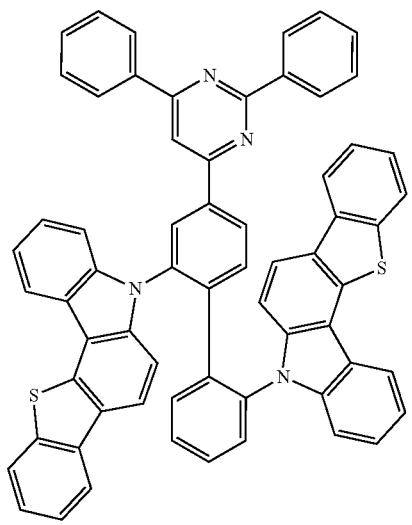
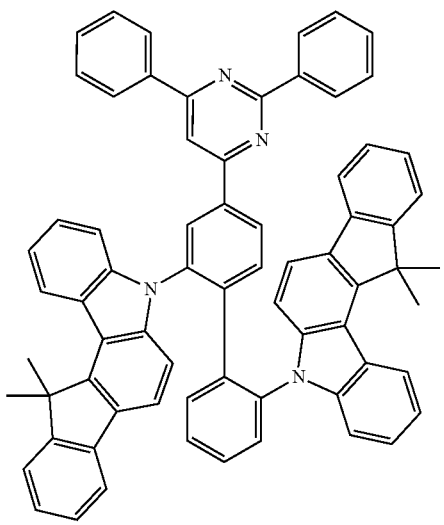
94
-continued
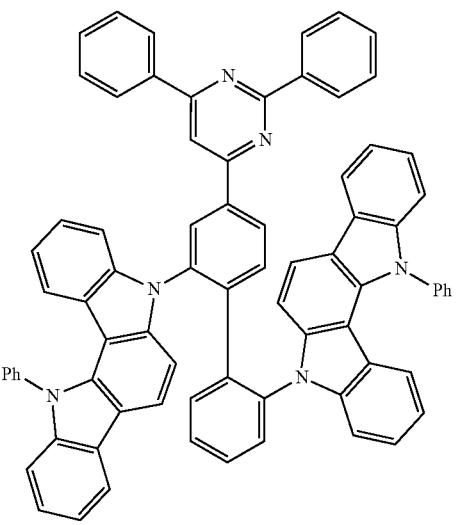
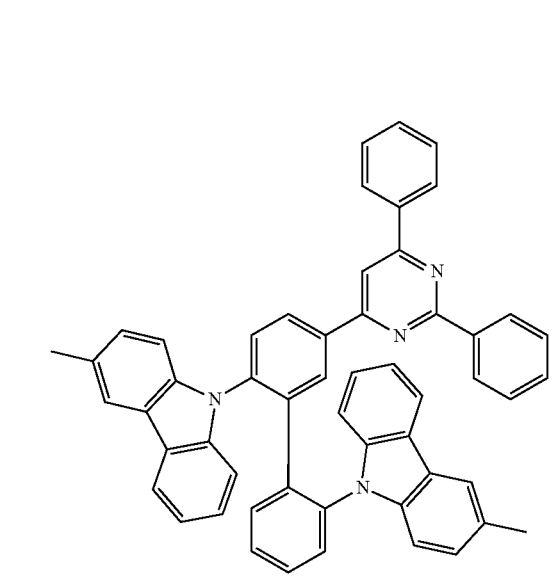

95
-continued
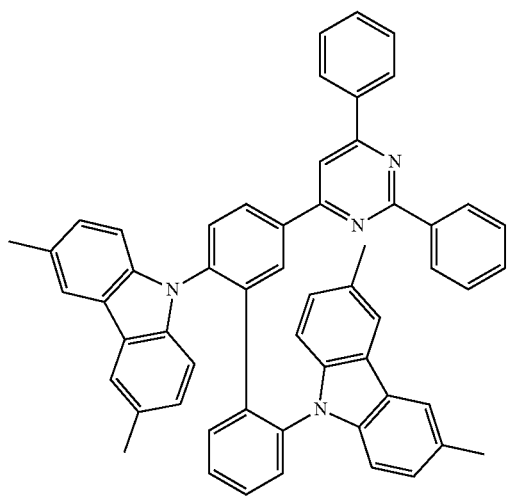
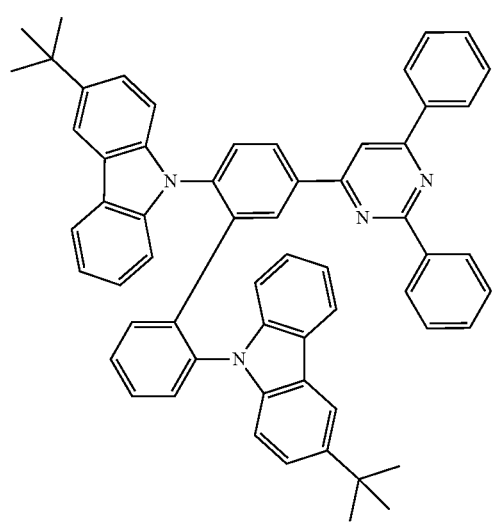
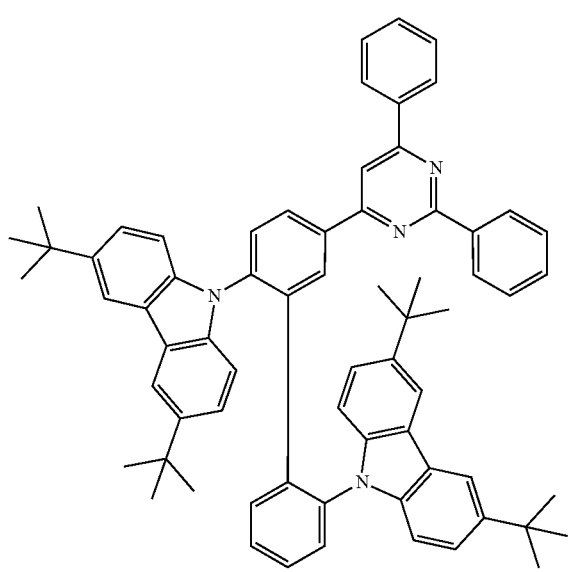
96
-continued
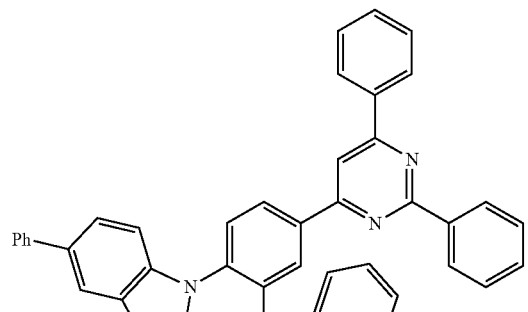
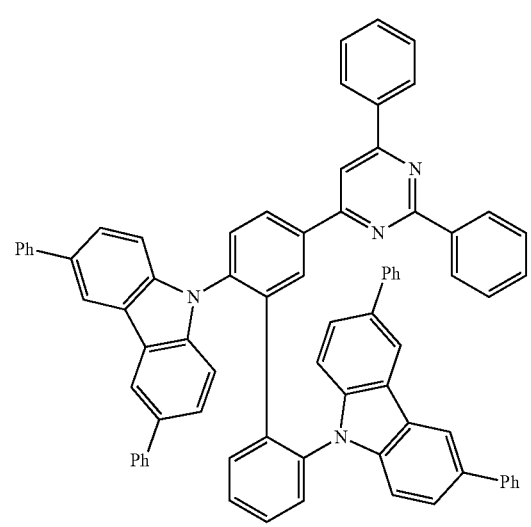
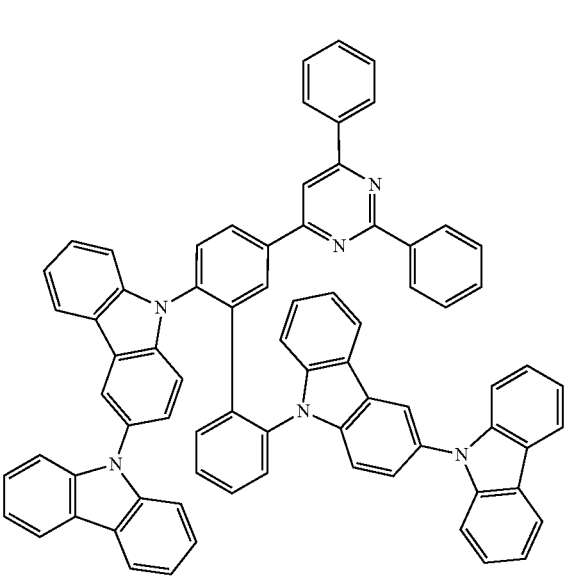

97
-continued
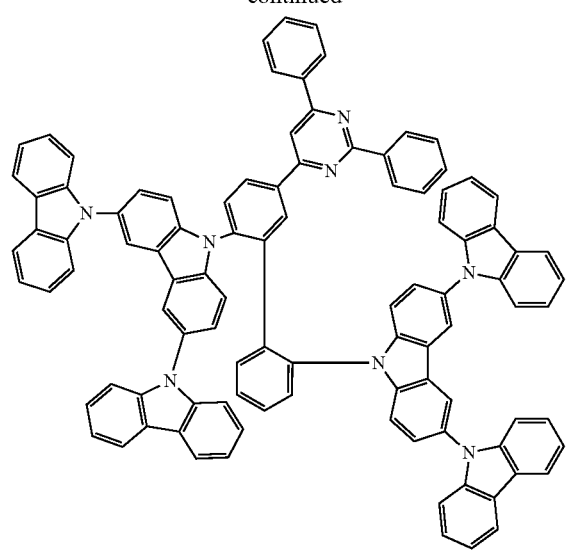
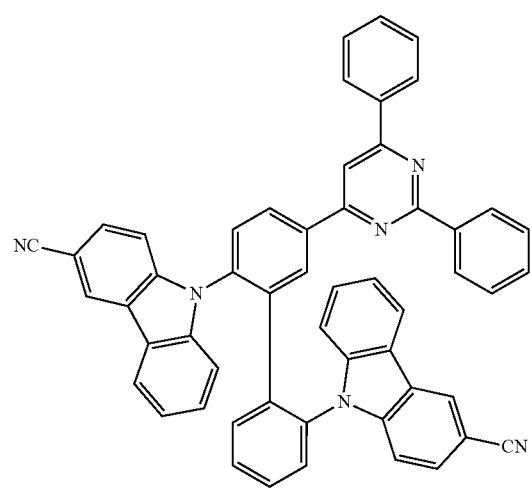
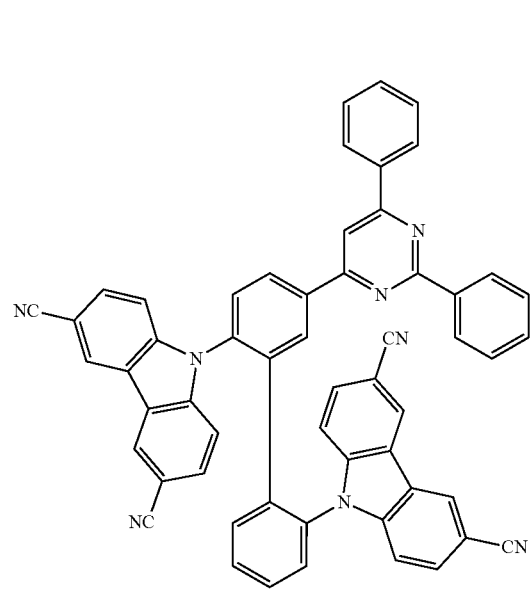
98
-continued
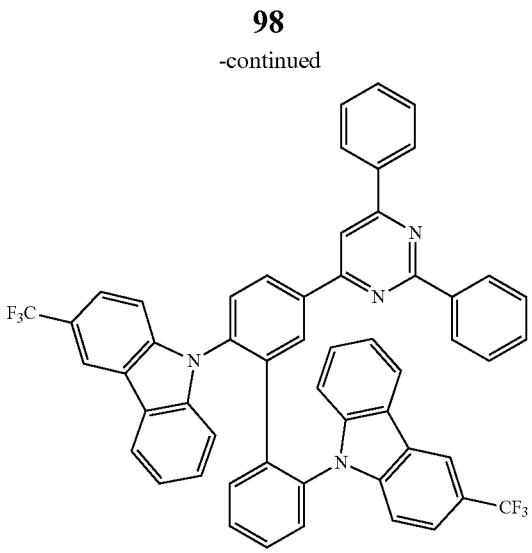
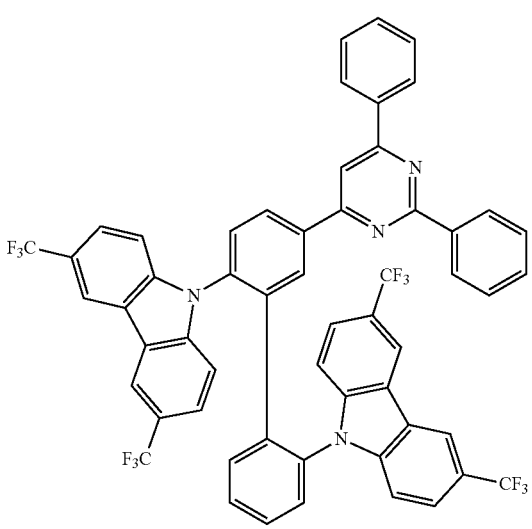
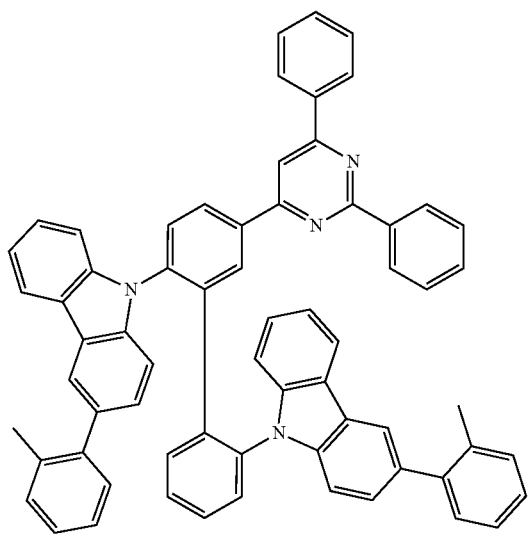

99
-continued
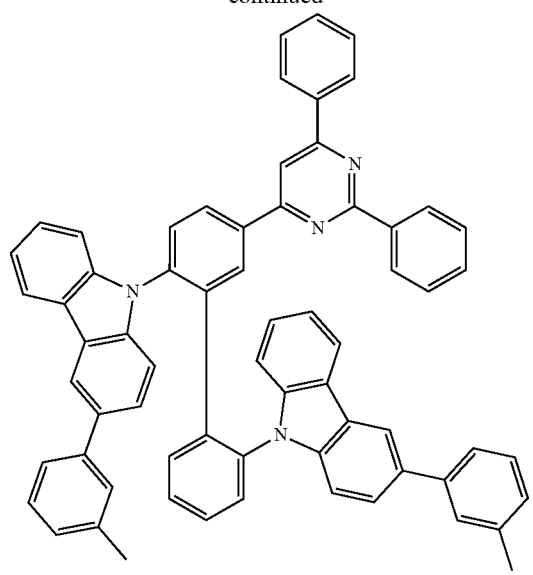
100
-continued
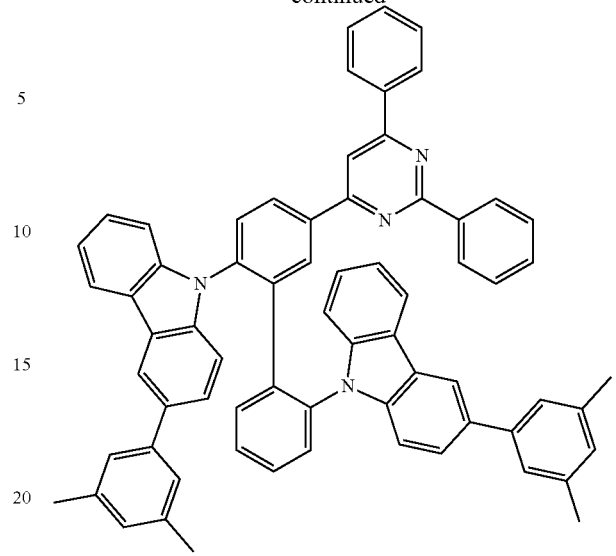
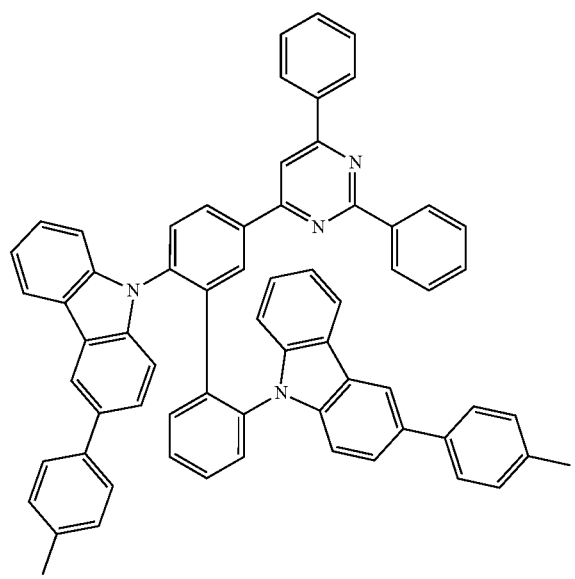
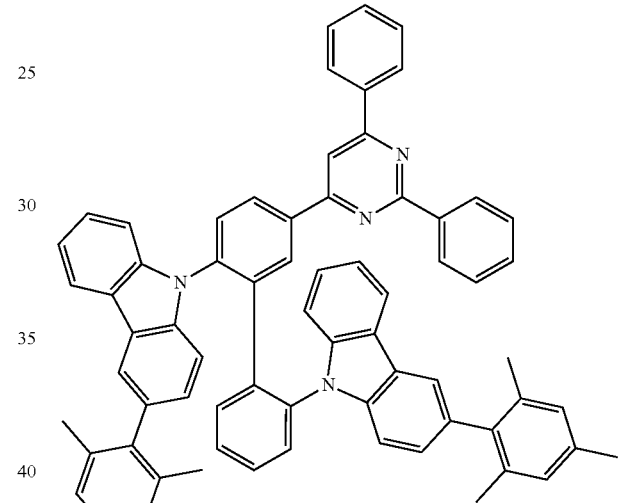
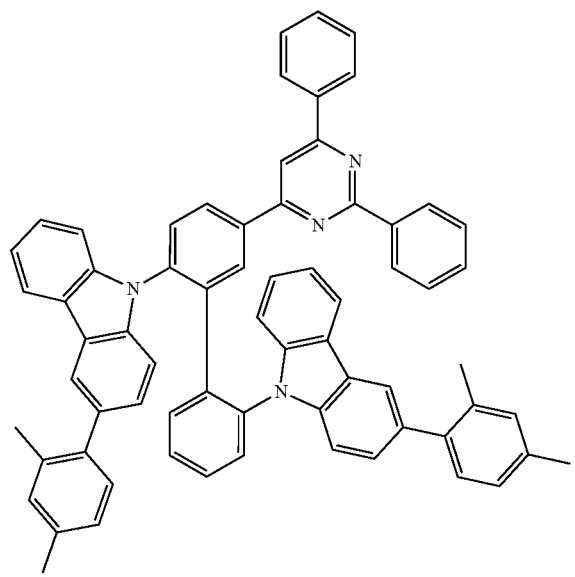
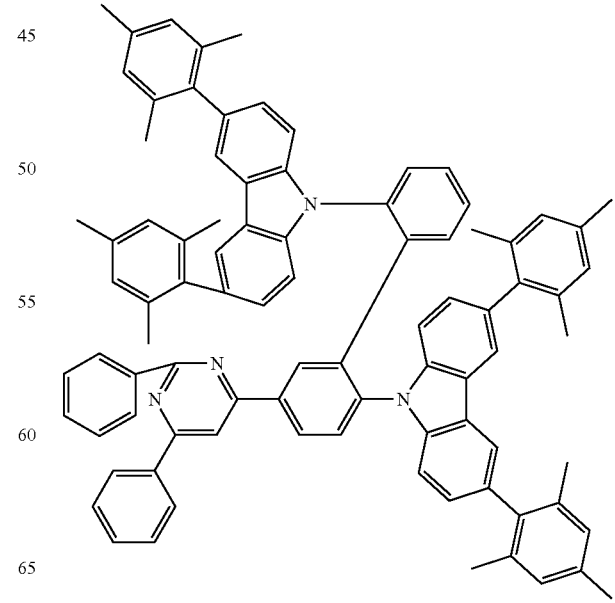

101
-continued
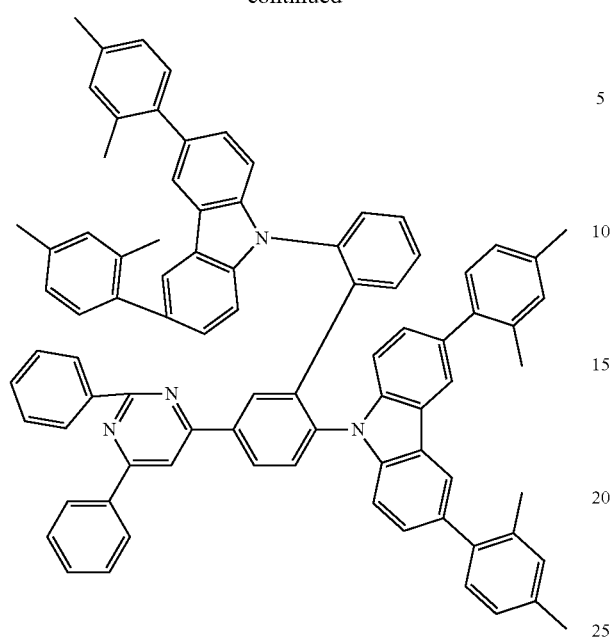
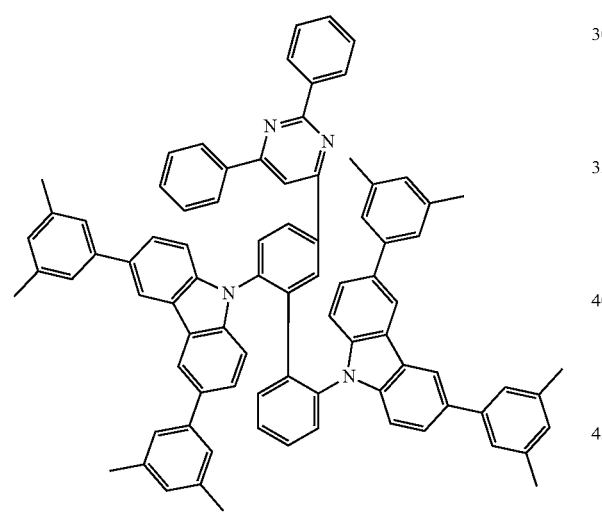
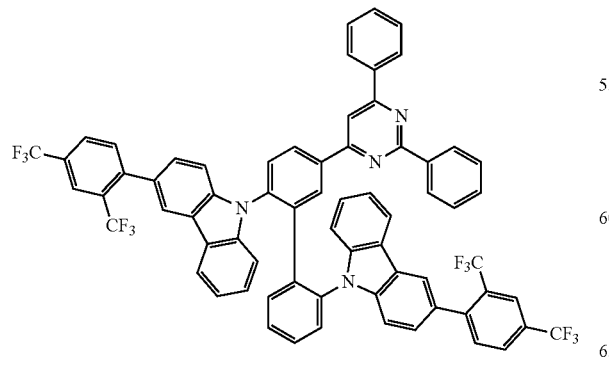
102
-continued
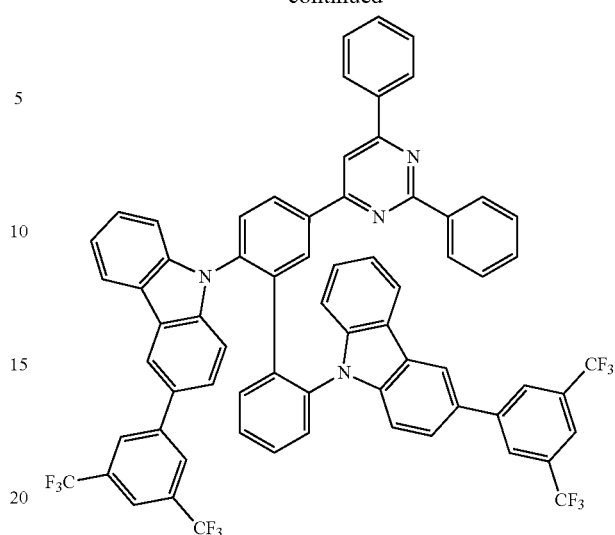
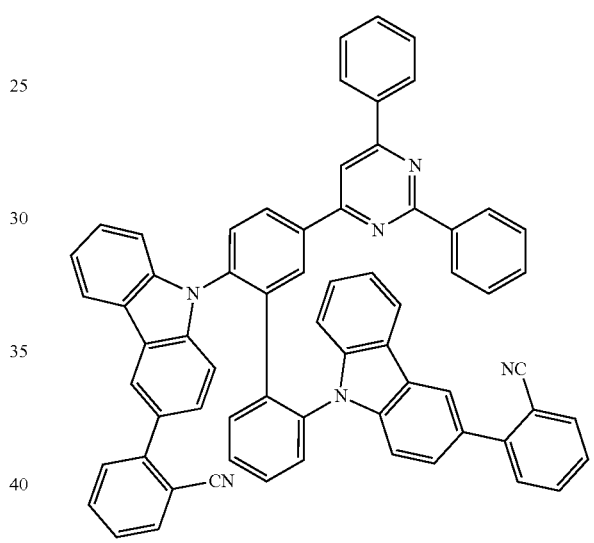
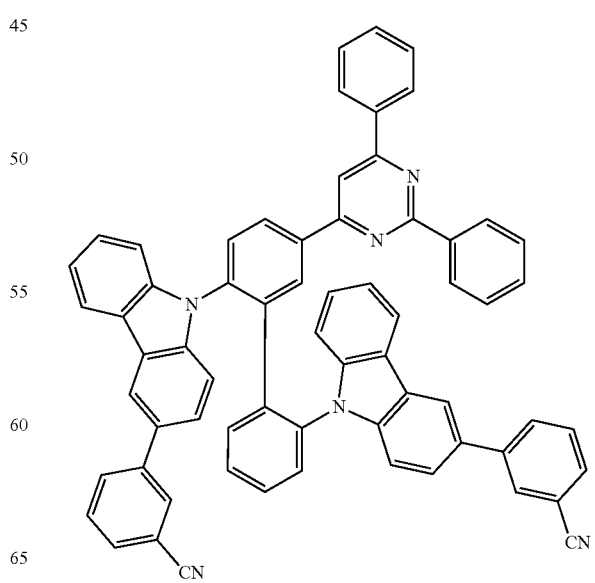

103
-continued
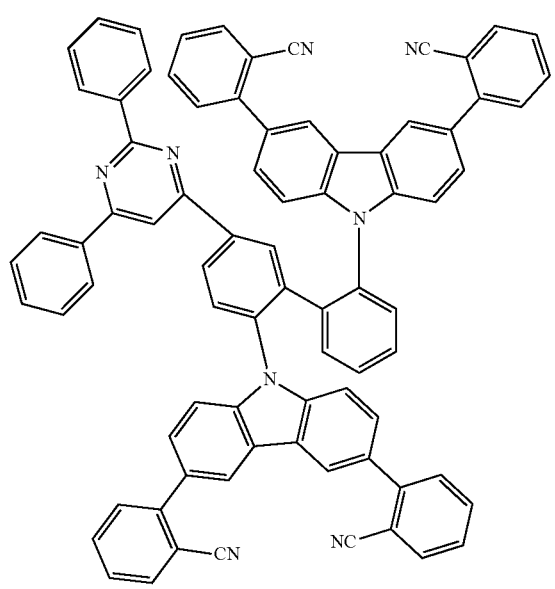
104
-continued
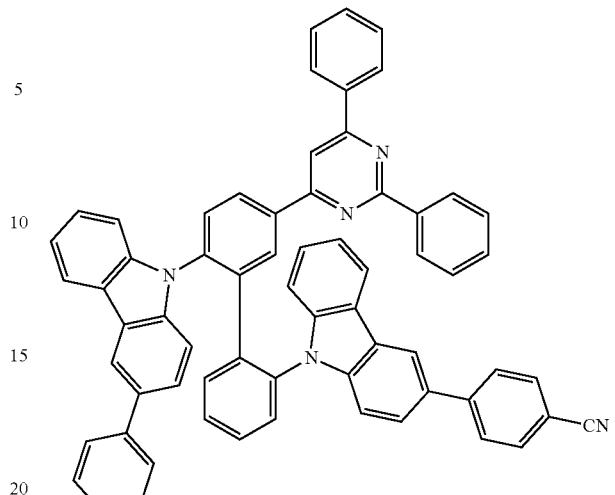
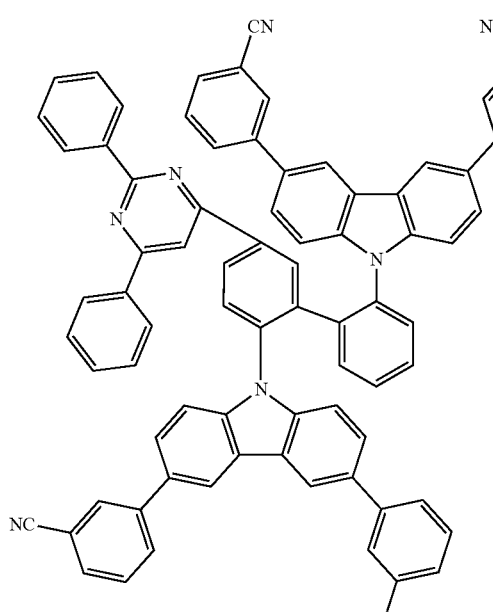
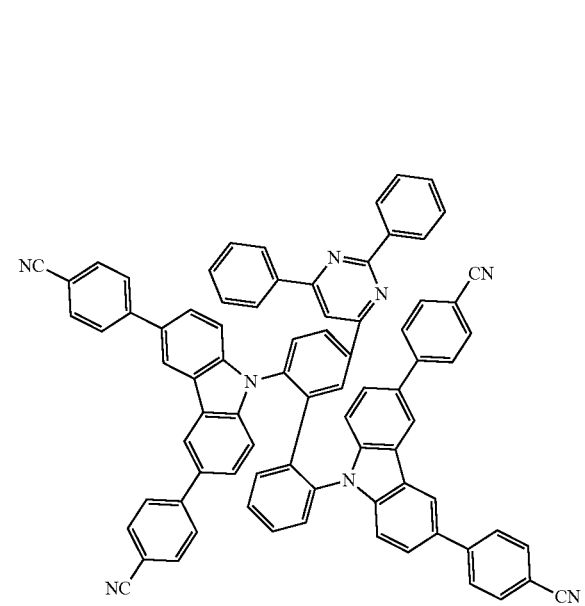

105
-continued
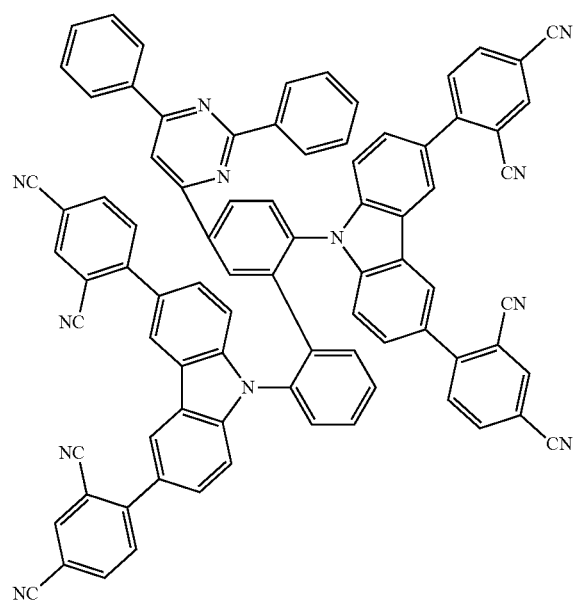
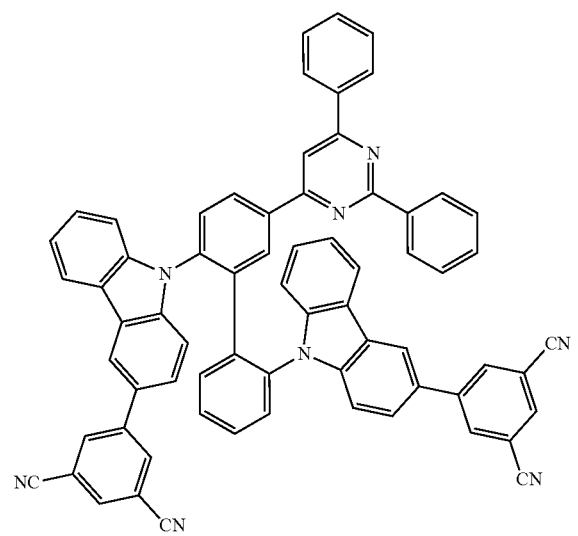
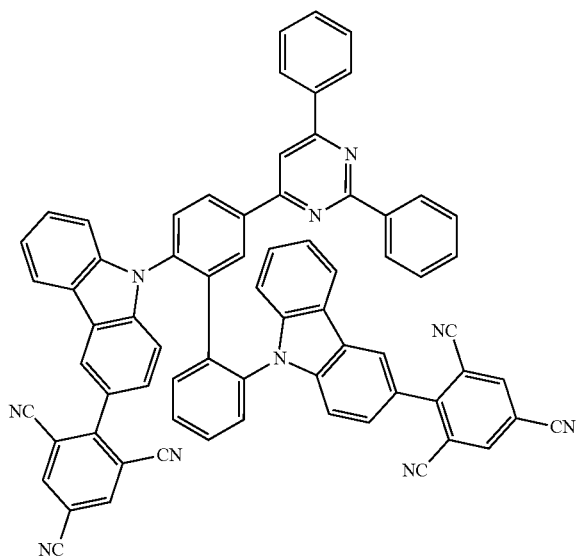
106
-continued
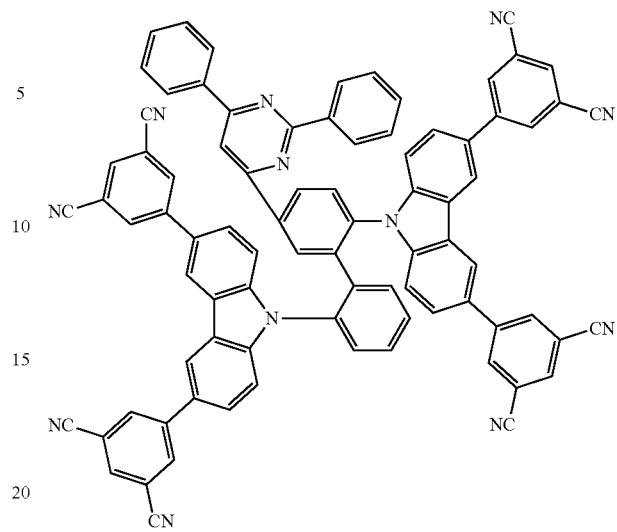
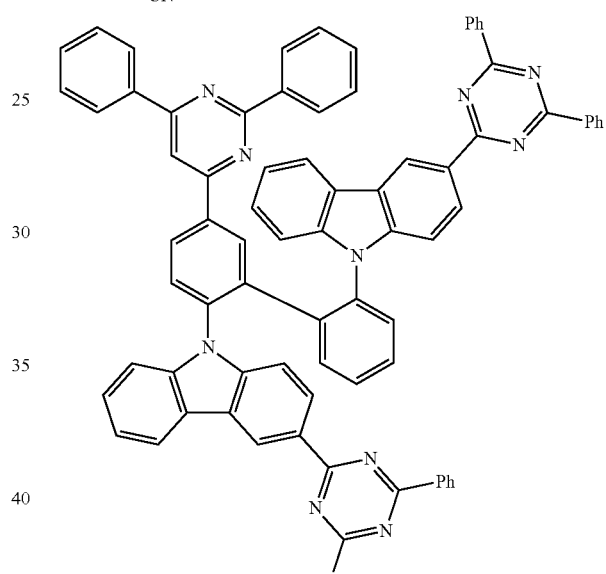
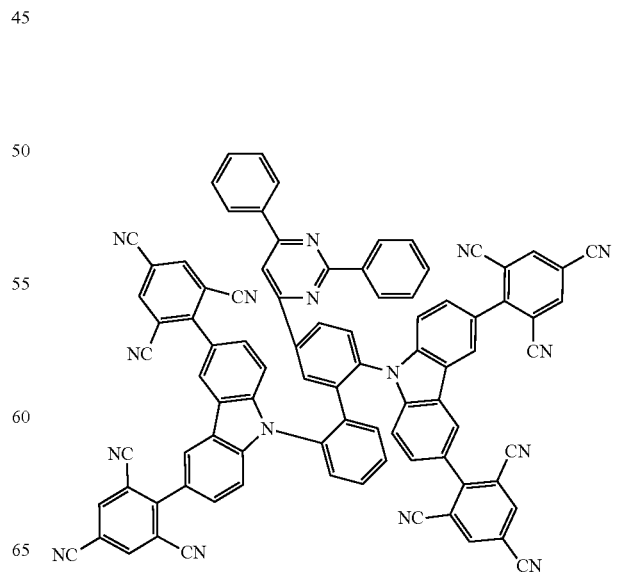

107
-continued
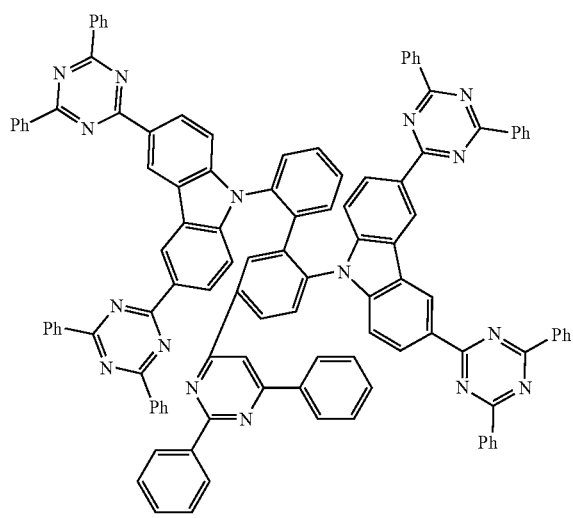
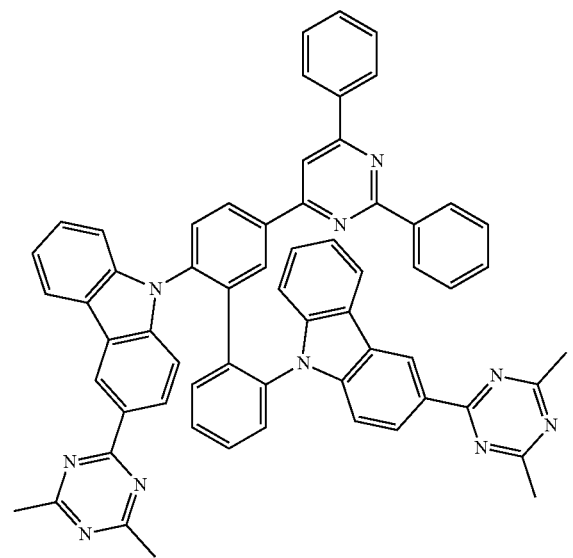
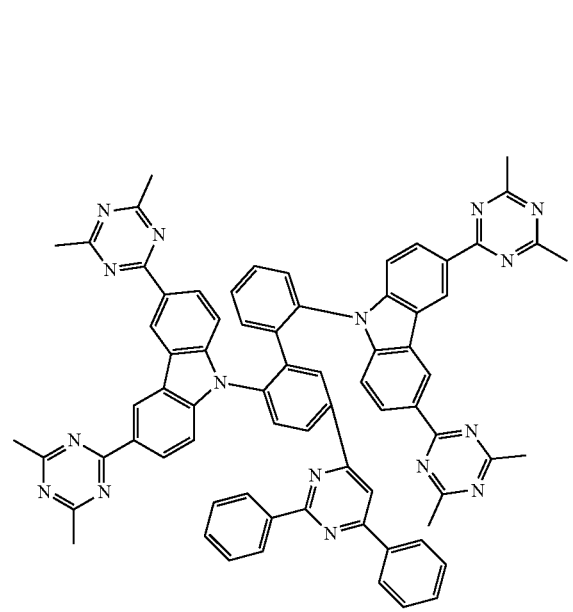
108
-continued
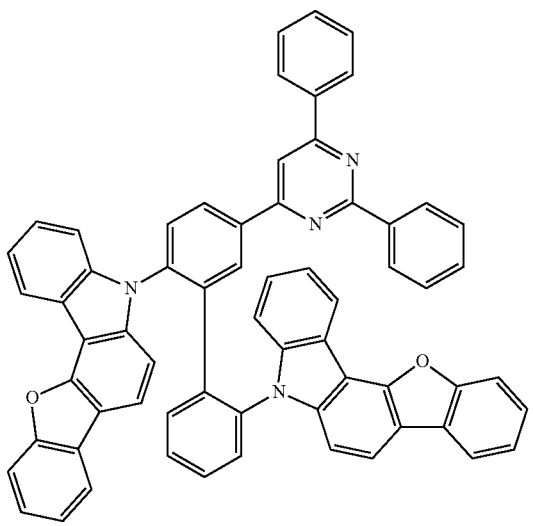
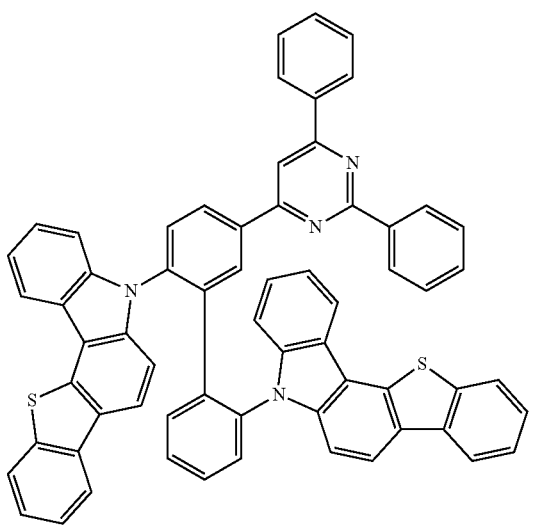
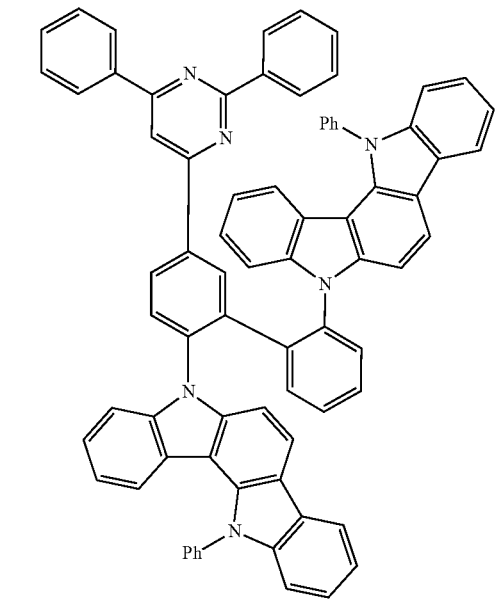

109
-continued
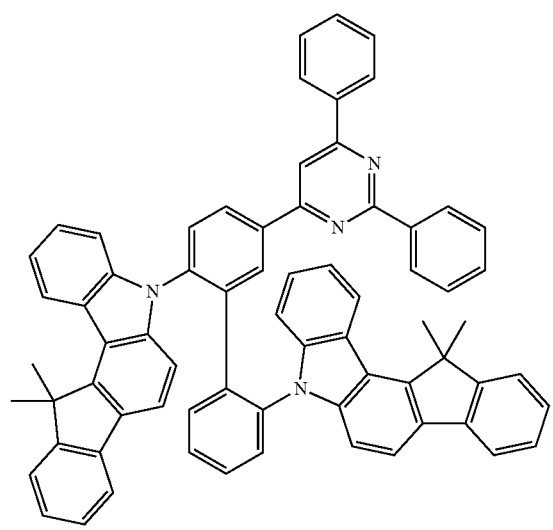
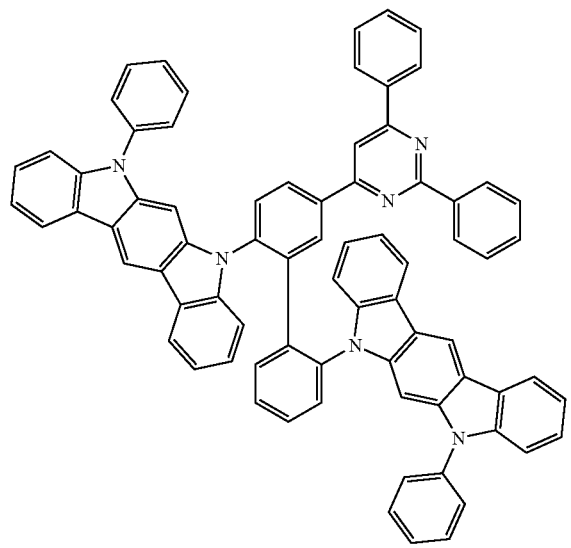
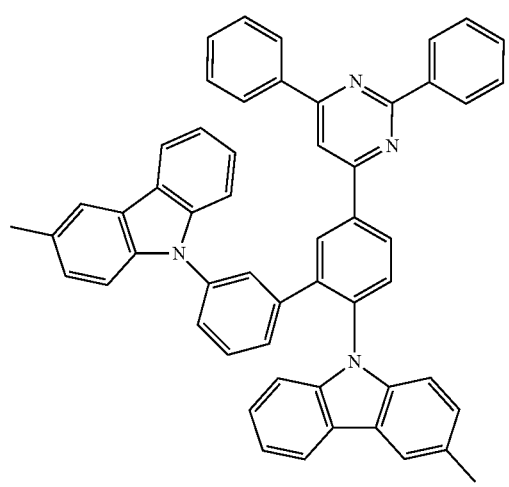
110
-continued
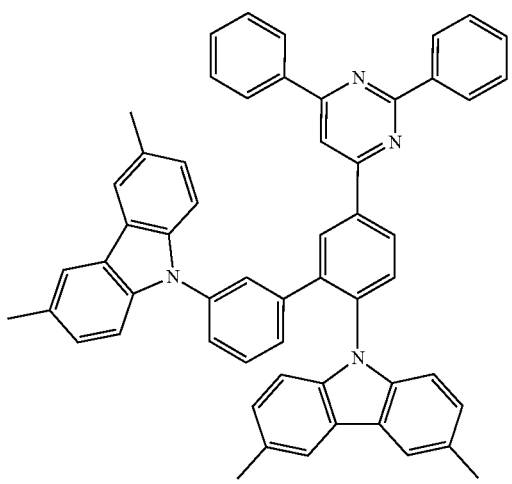
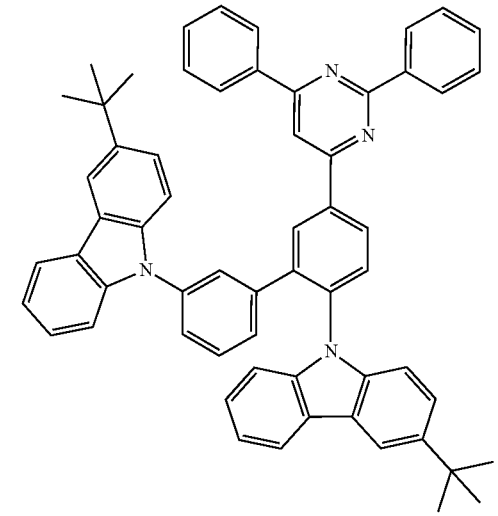
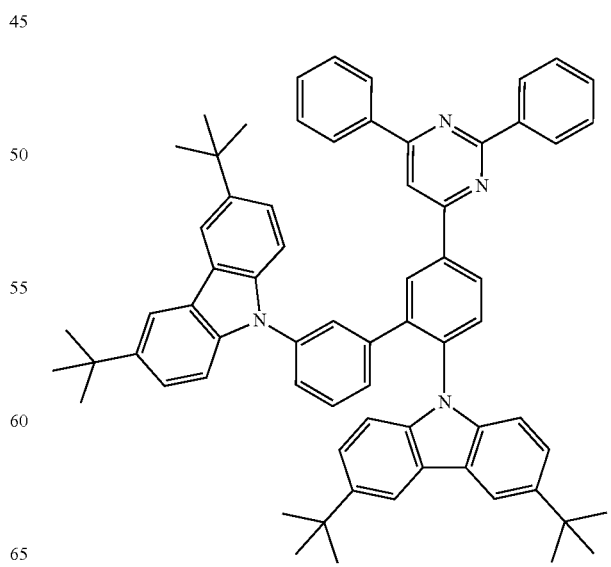

111
-continued
112
-continued
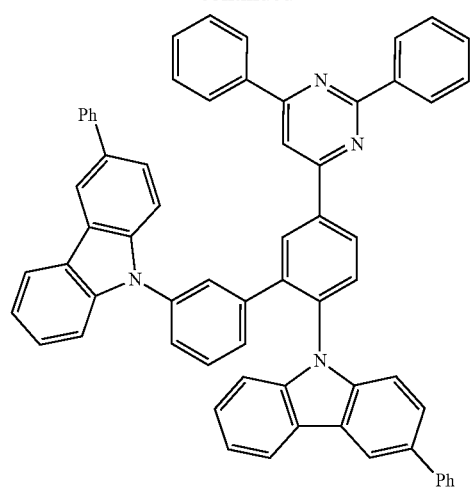
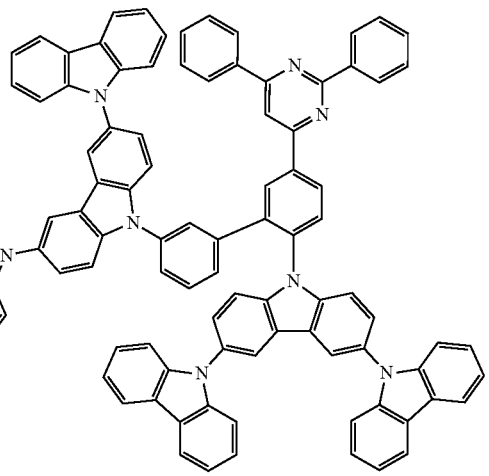
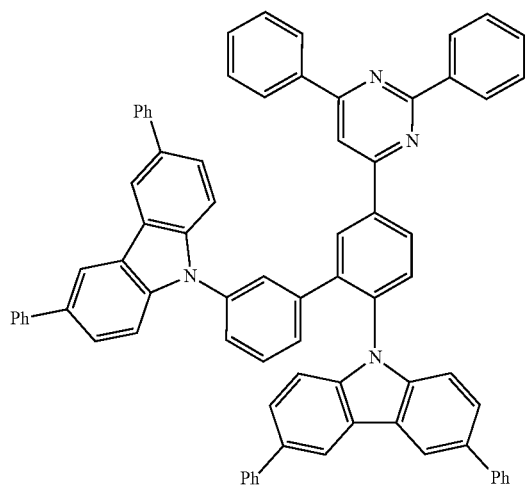
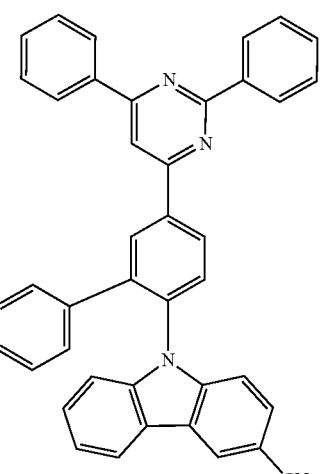
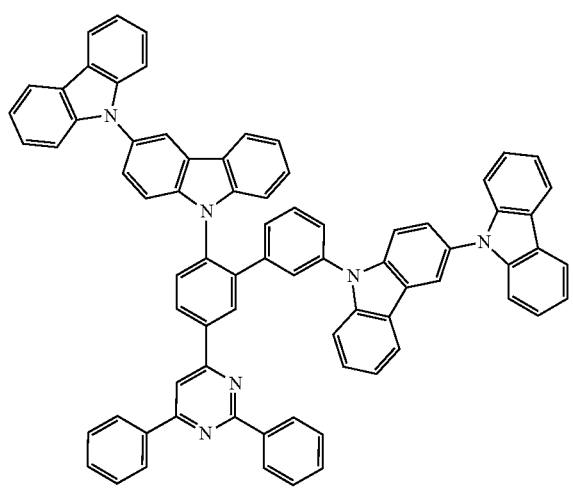
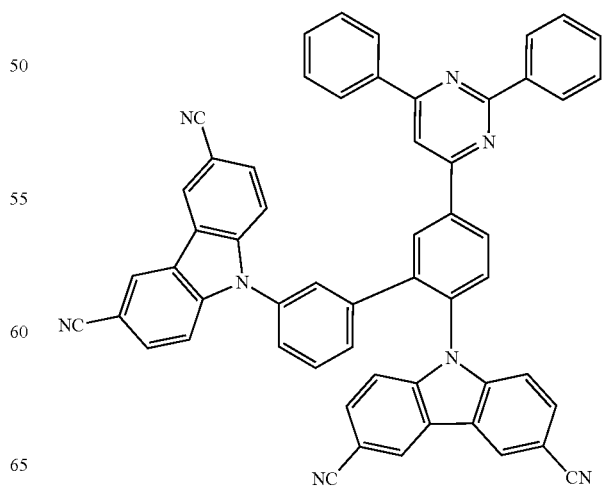

113
-continued
114
-continued
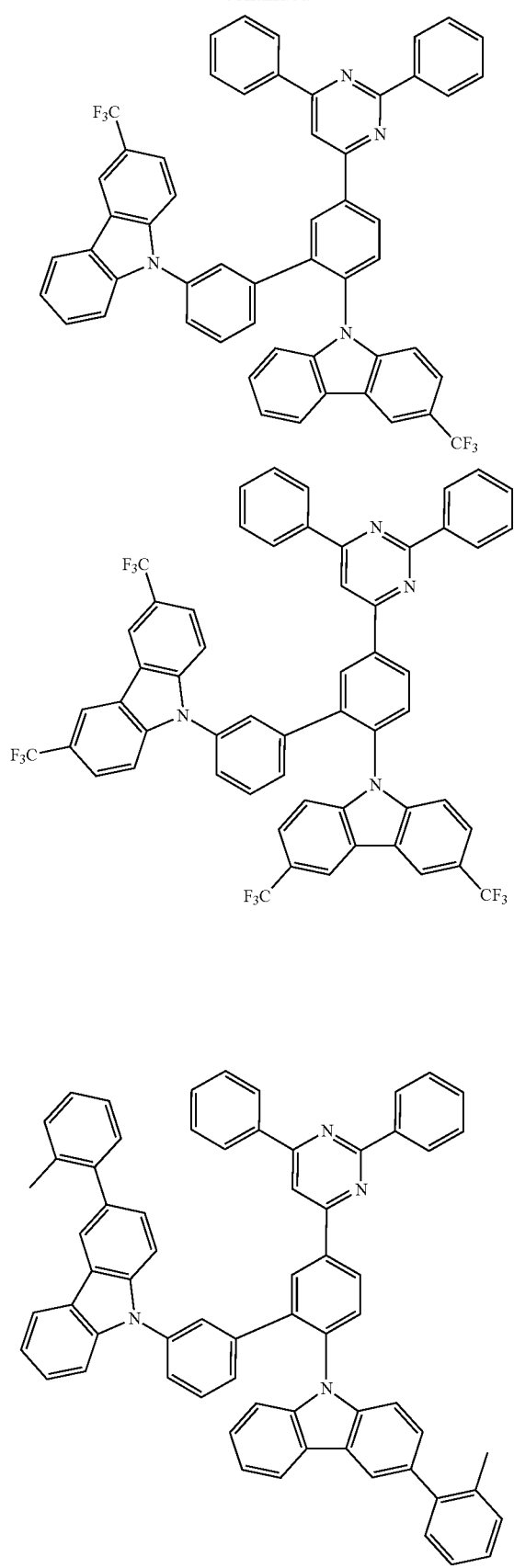
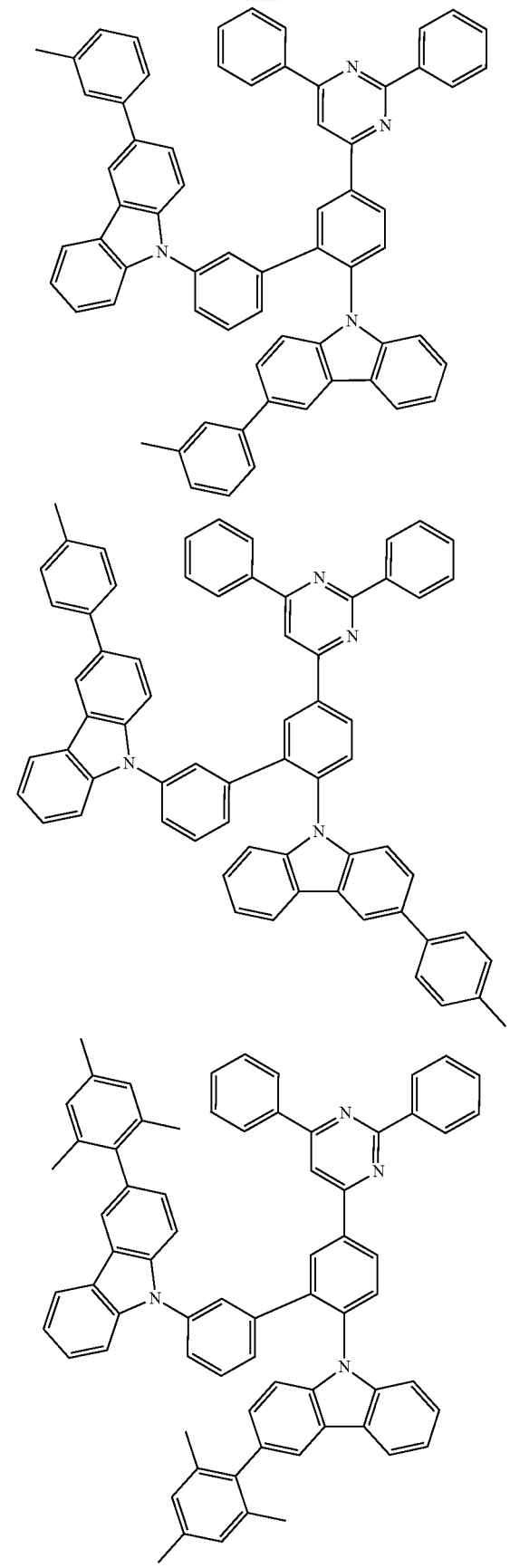

115
-continued
116
-continued
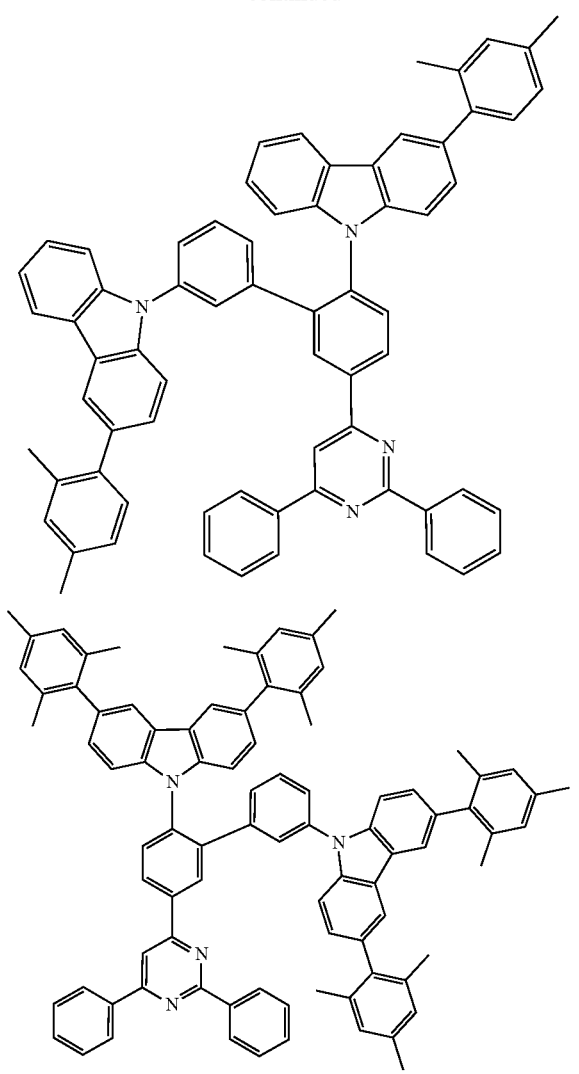
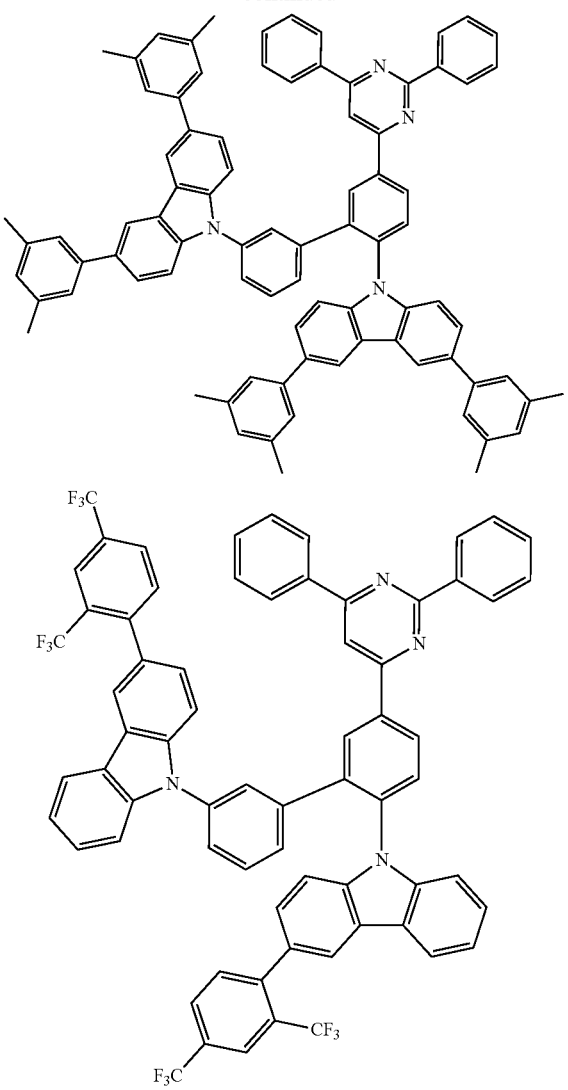
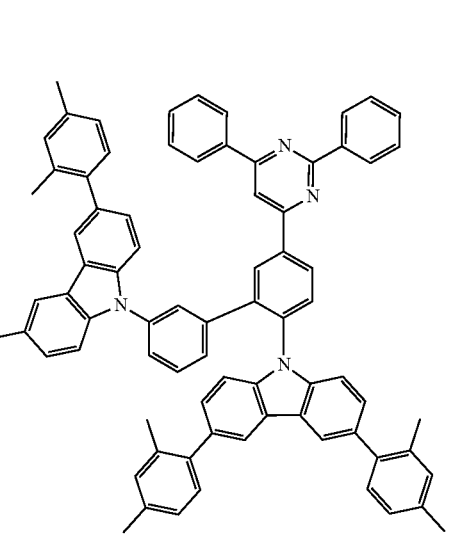

117
-continued
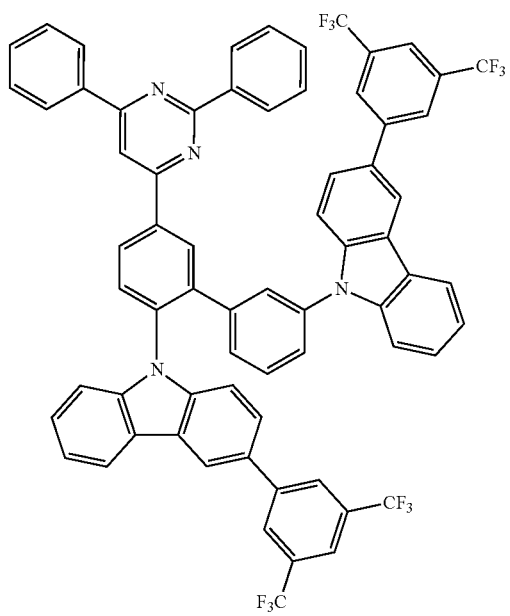
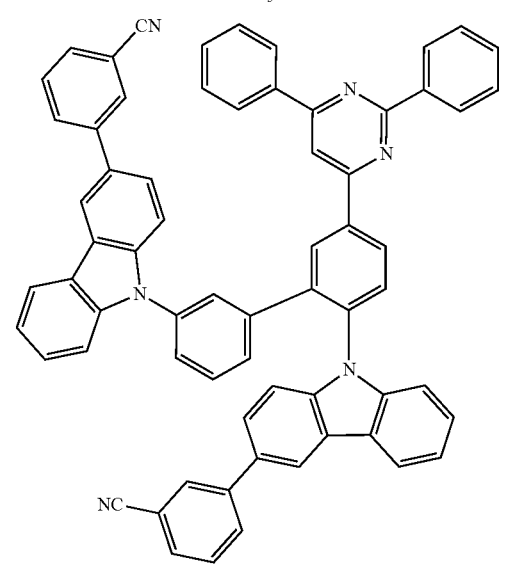
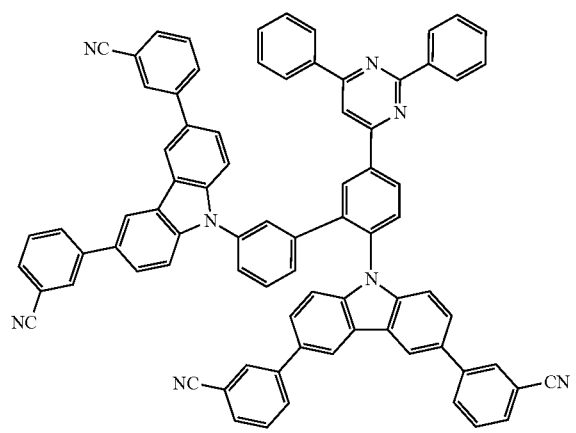
118
-continued
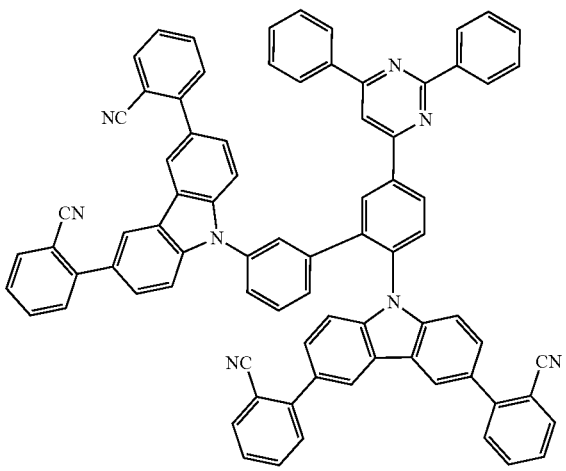
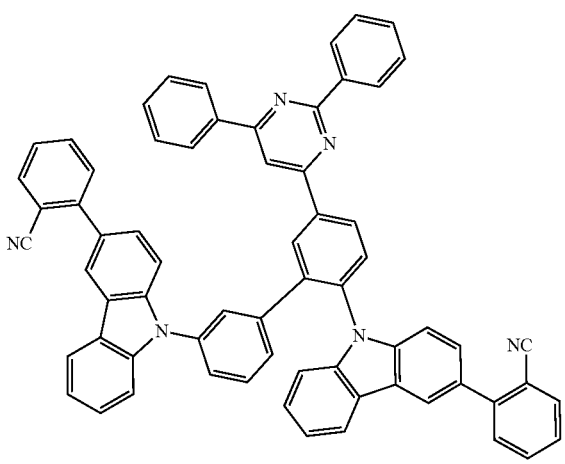

119
-continued
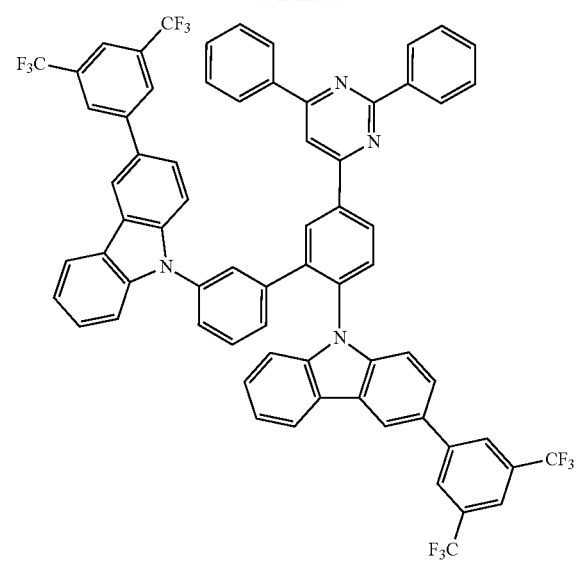
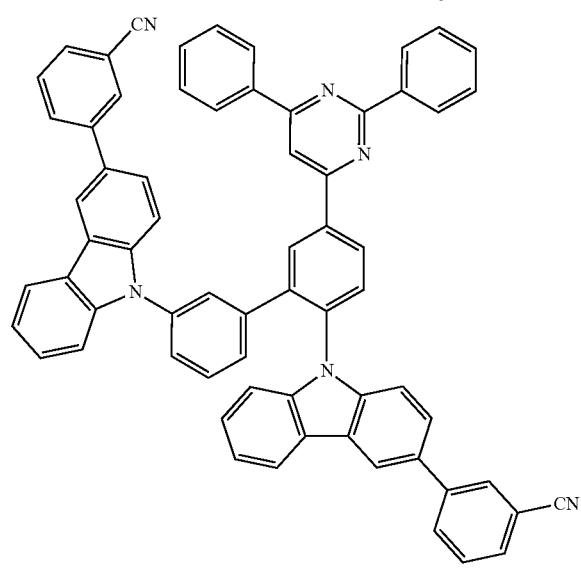
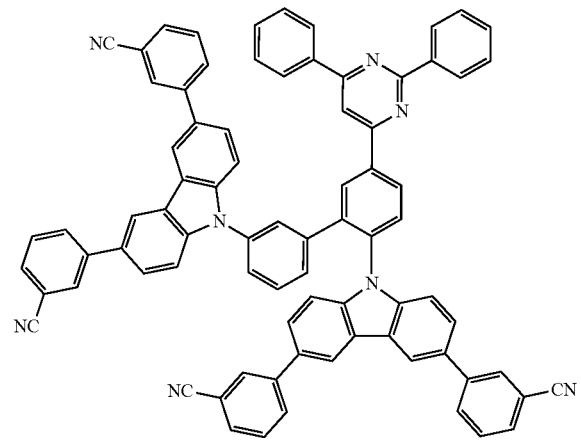
120
-continued
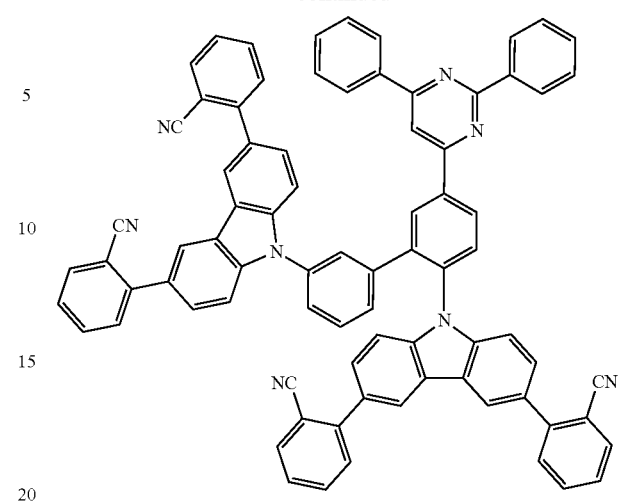
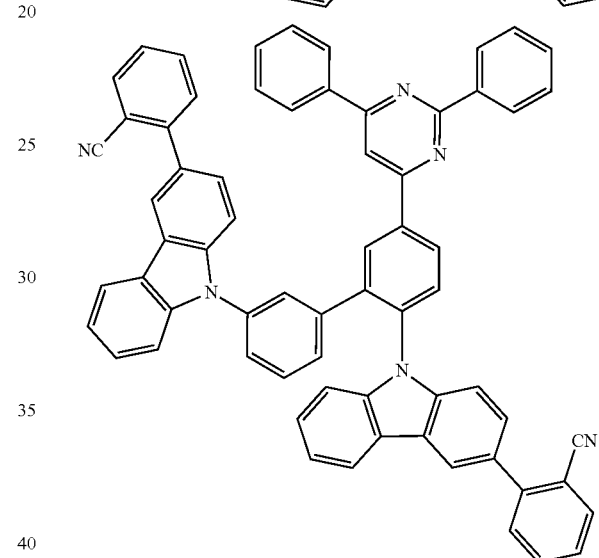
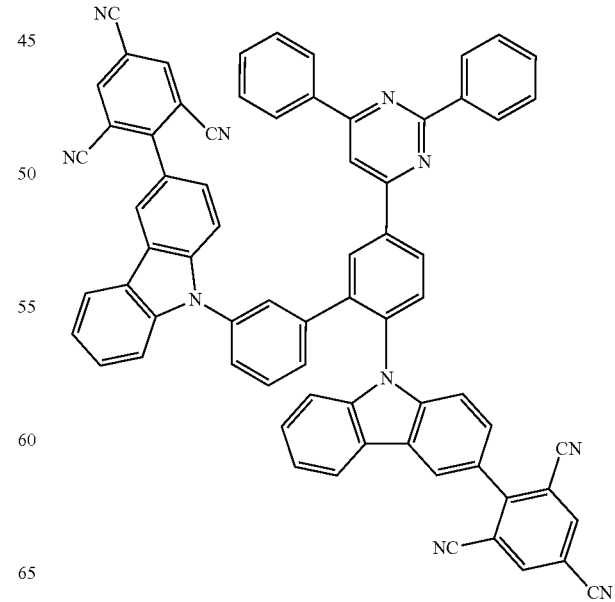

121
-continued
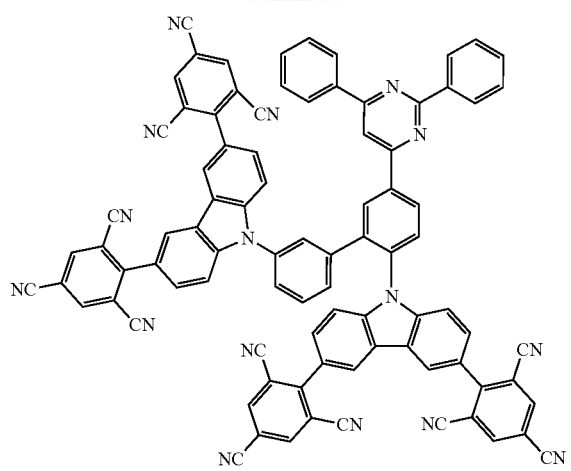
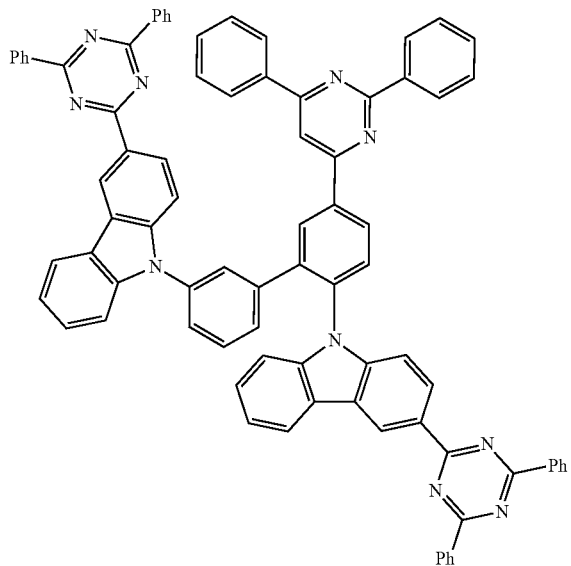
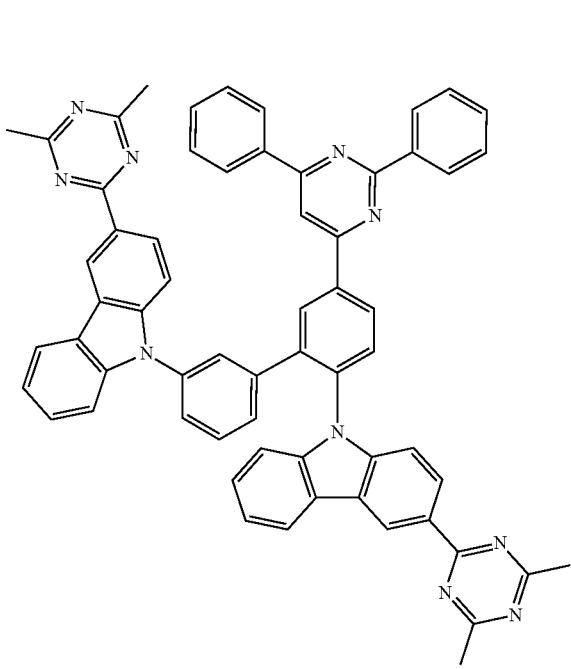
122
-continued
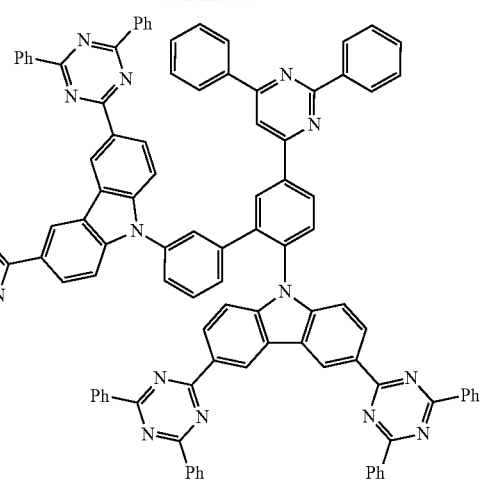
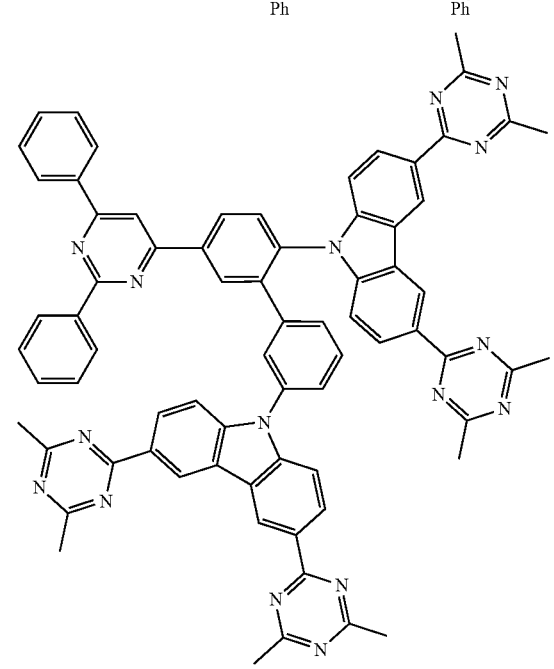

-continued
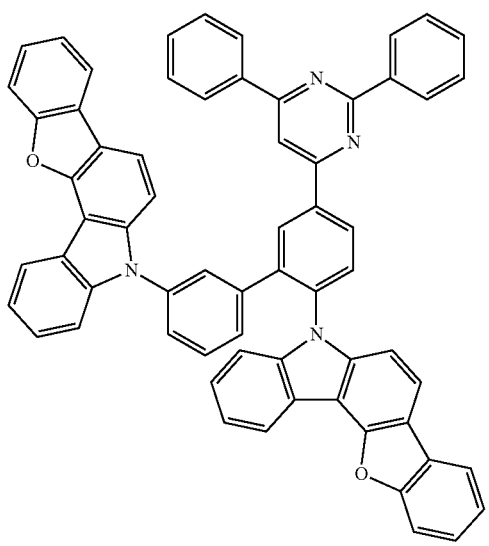
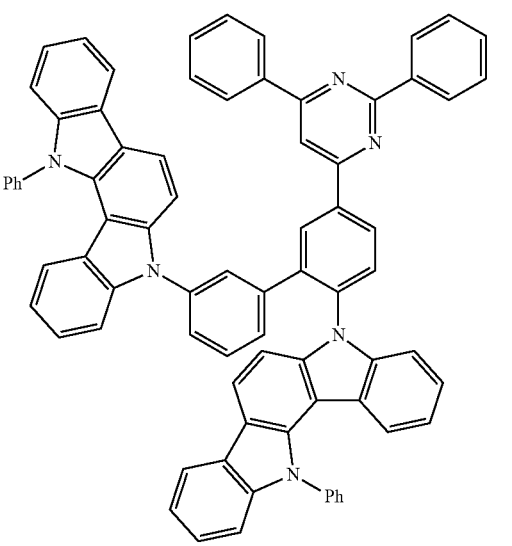
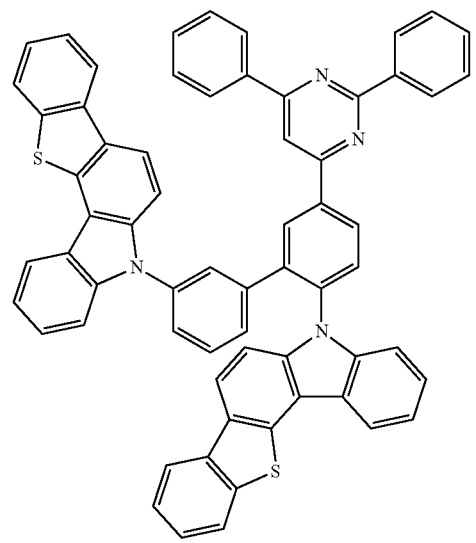
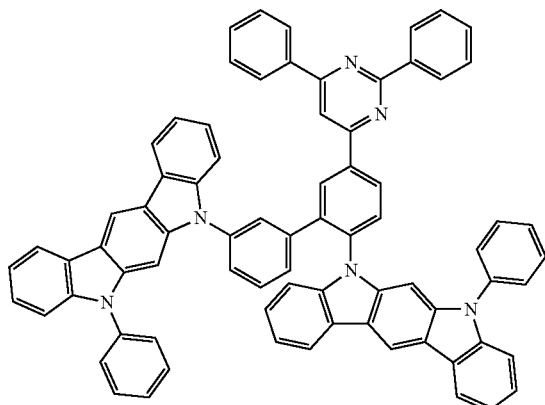
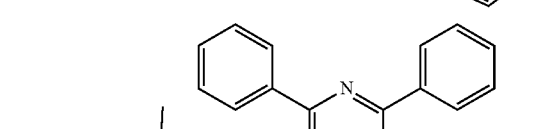
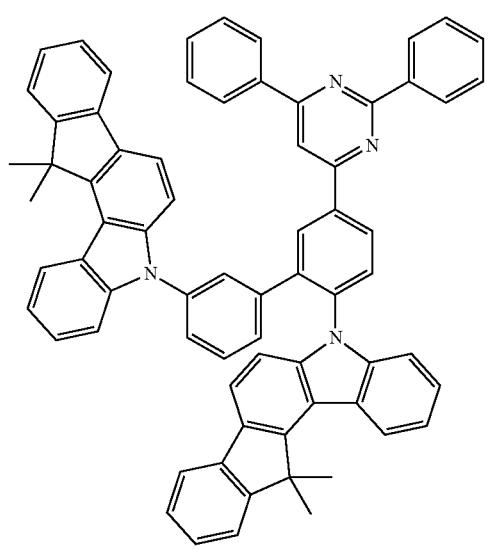
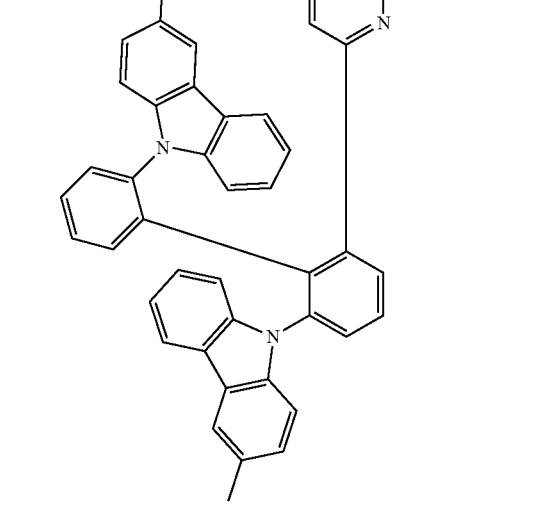

125
-continued
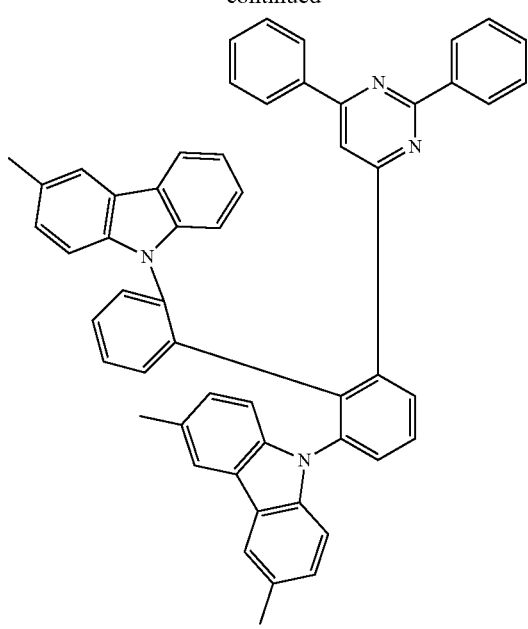
126
-continued
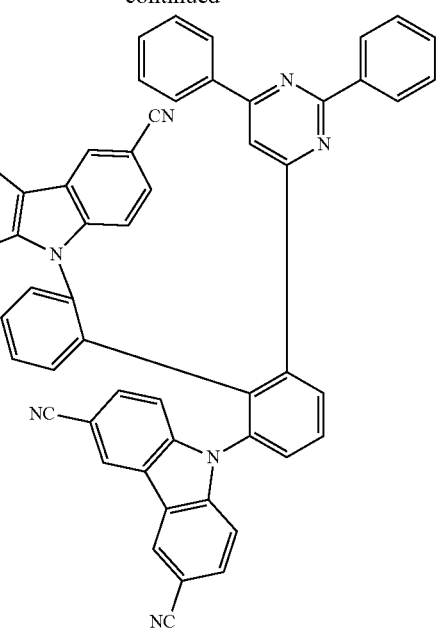
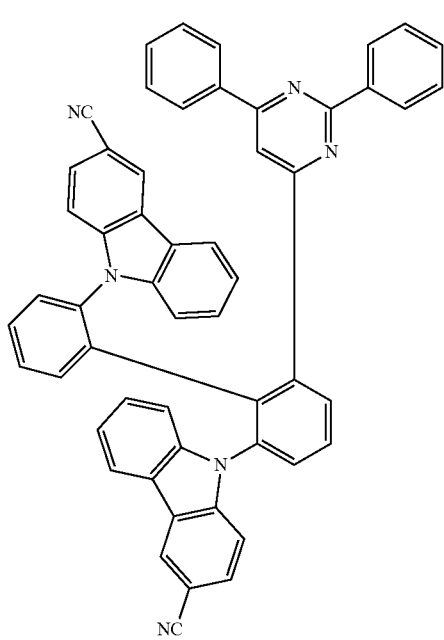
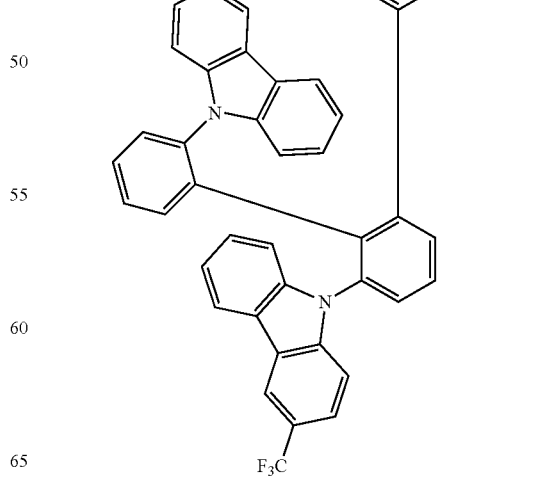

127
-continued
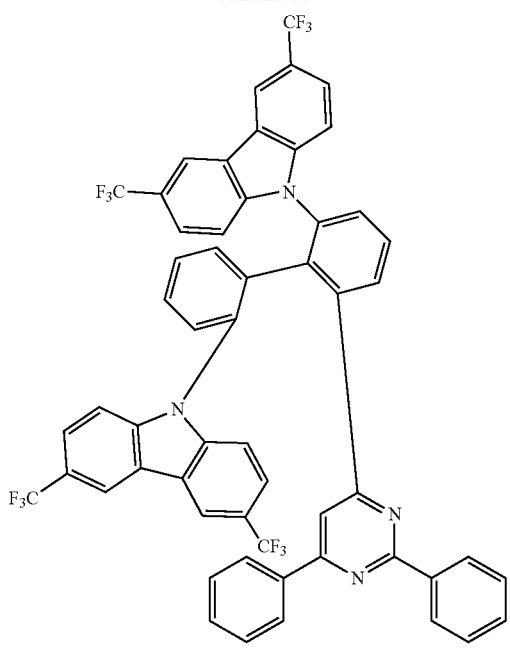
128
-continued
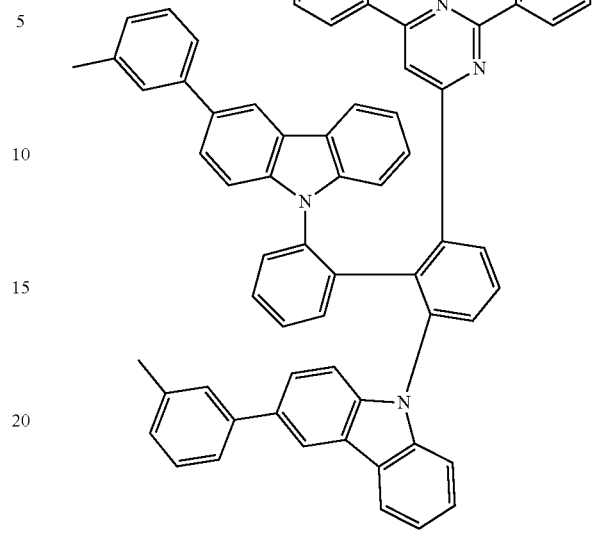
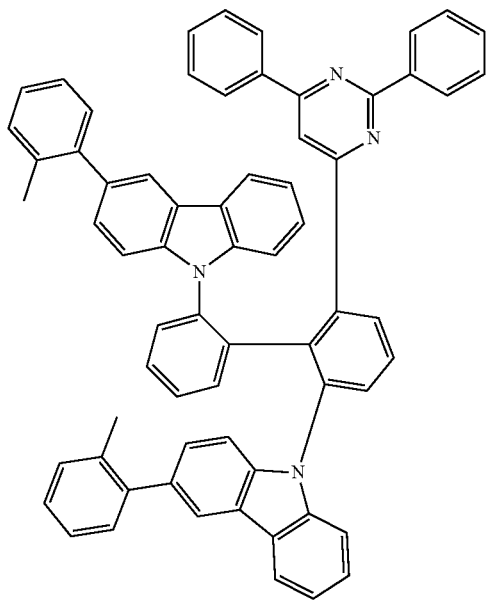
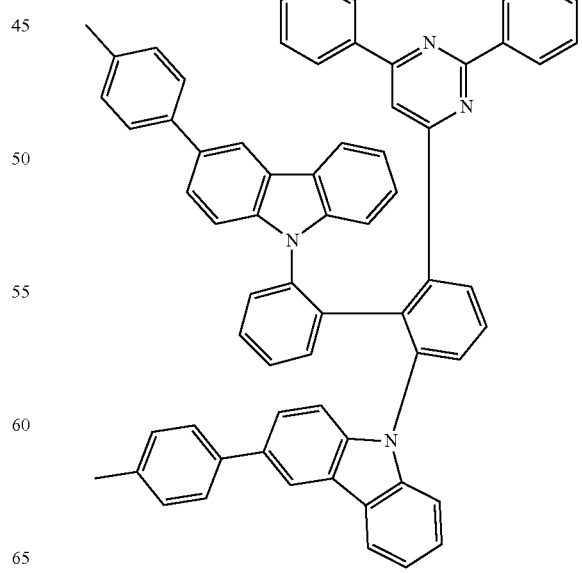

129
-continued
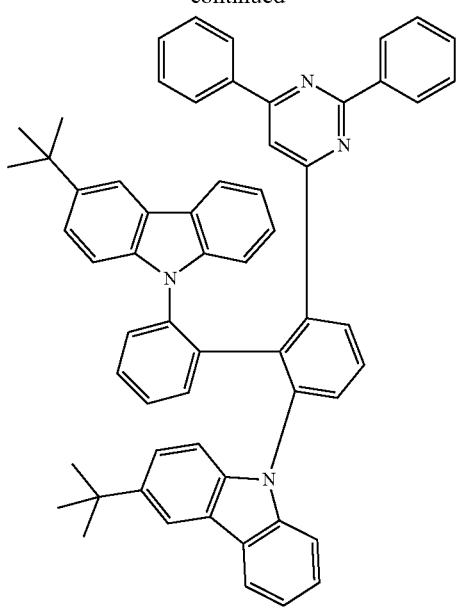
130
-continued
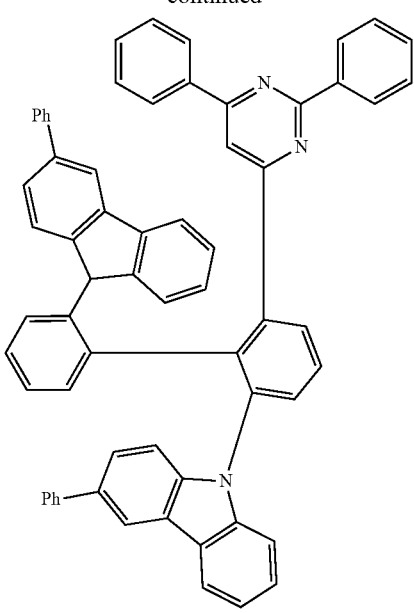
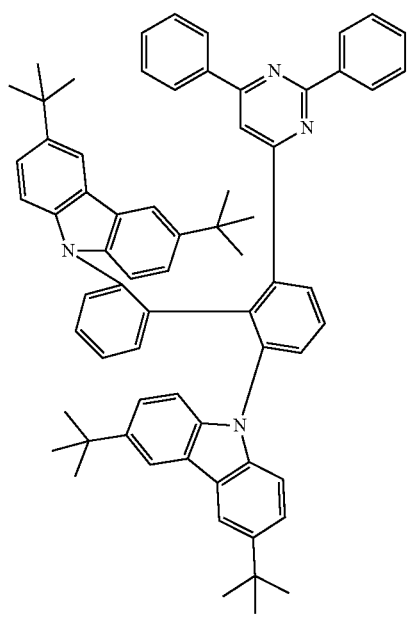
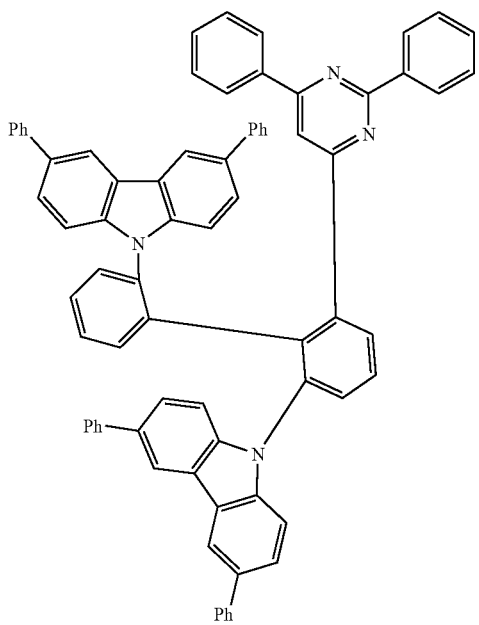

131
-continued
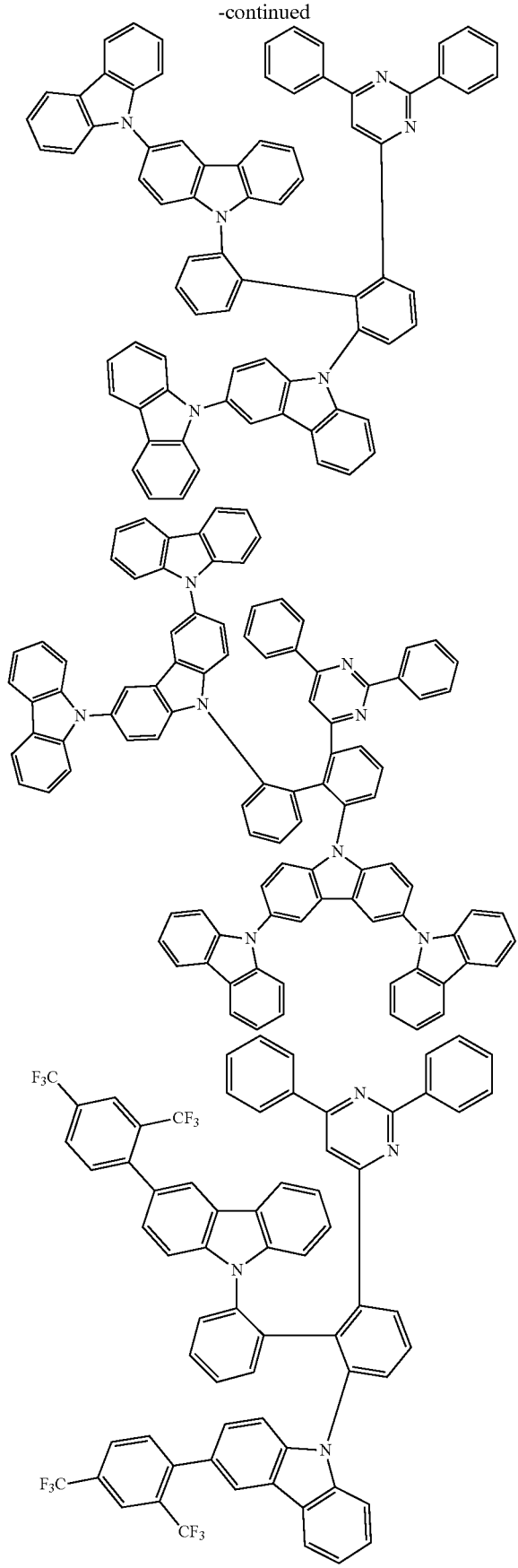
132
-continued
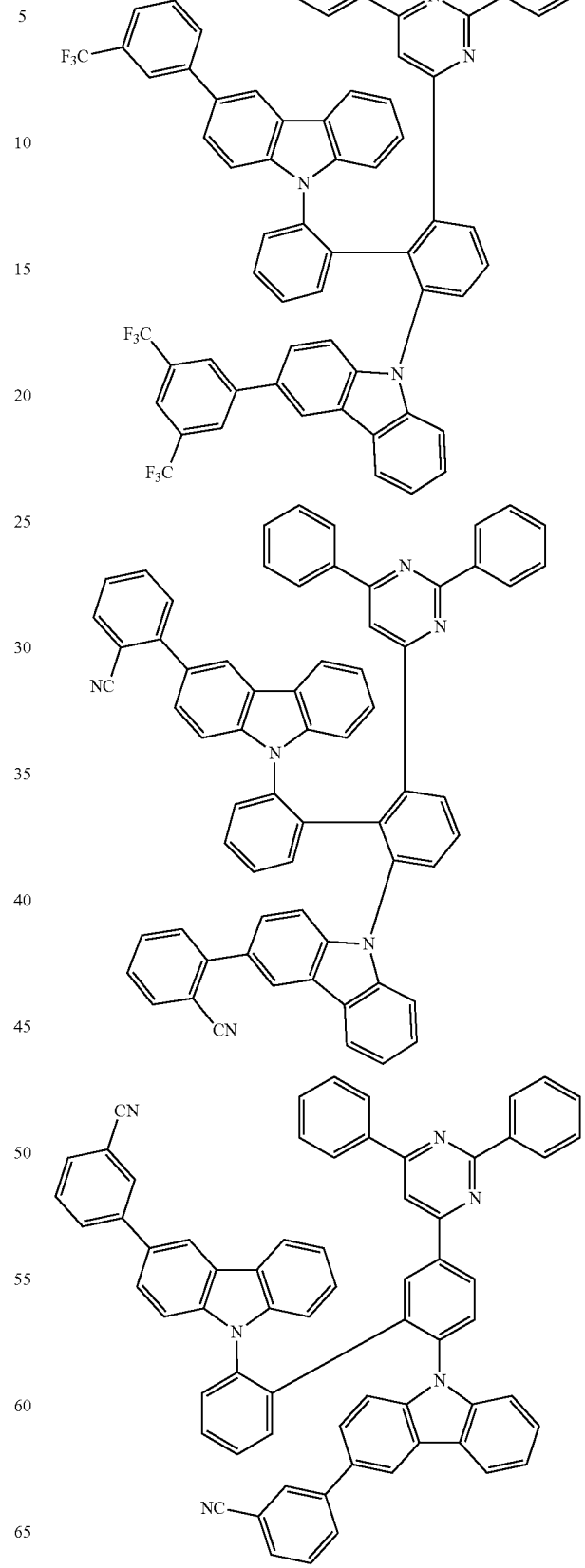

133
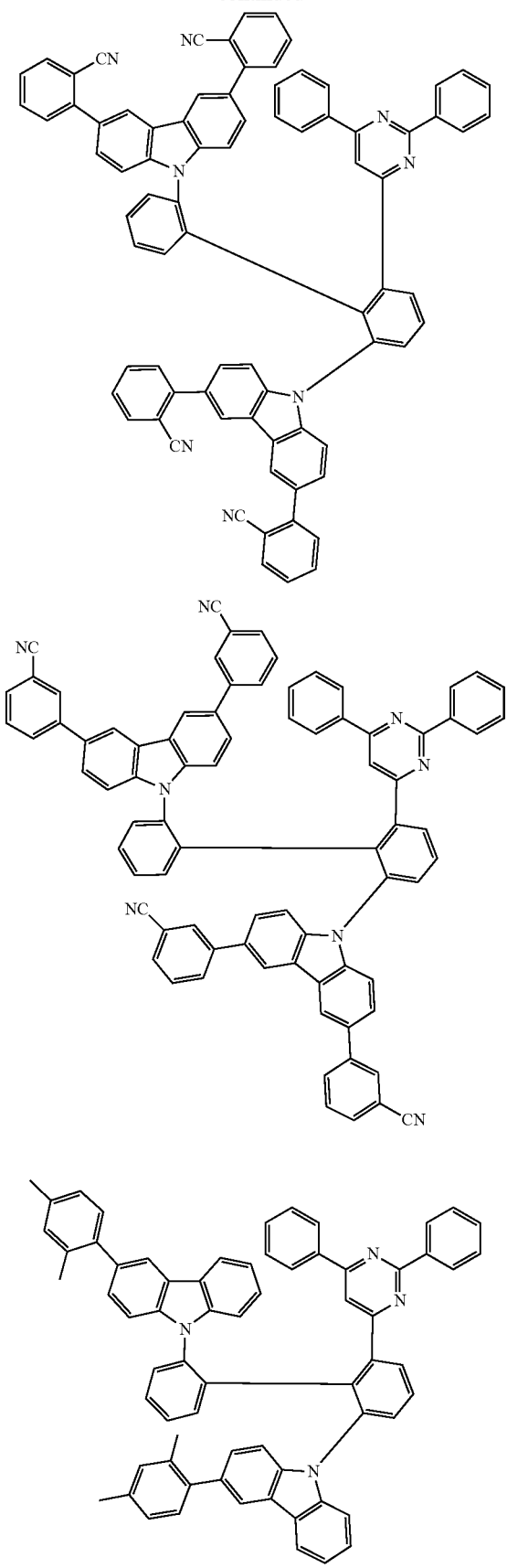
134
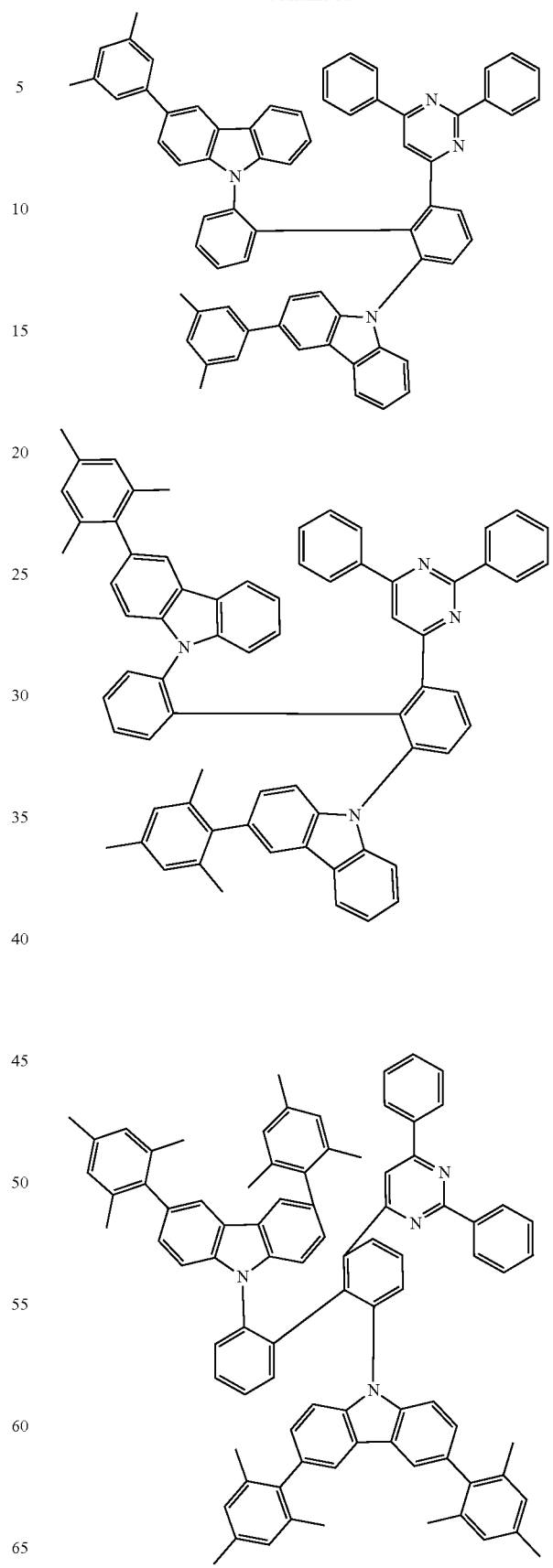

135
-continued
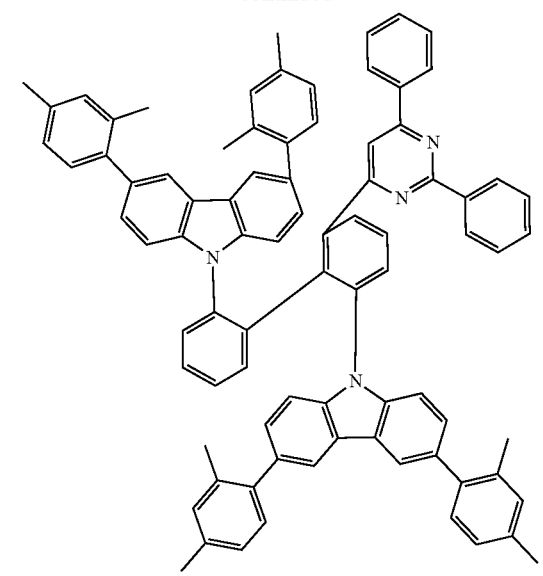
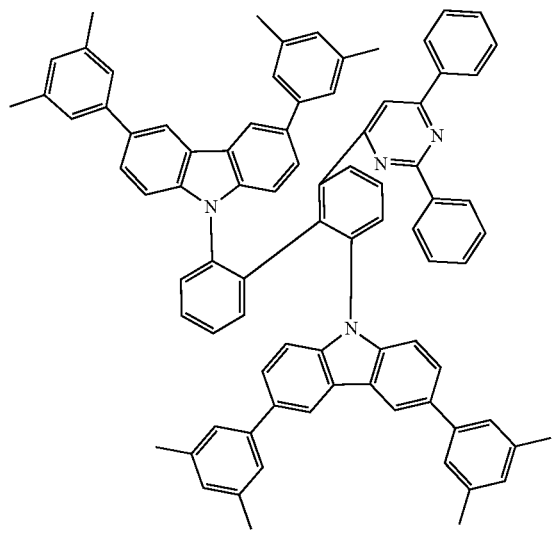
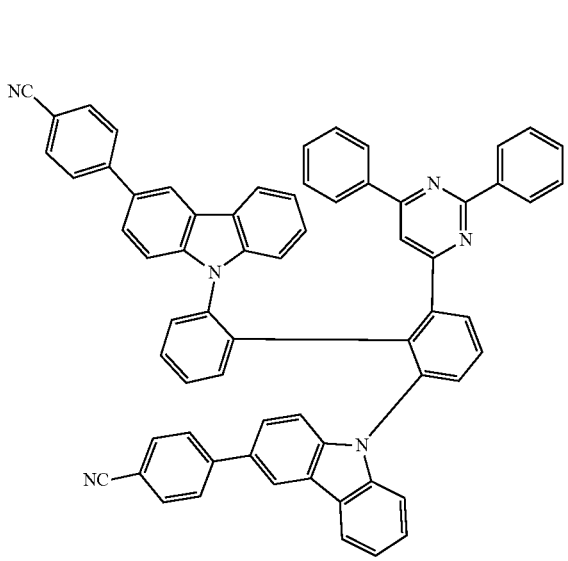
136
-continued
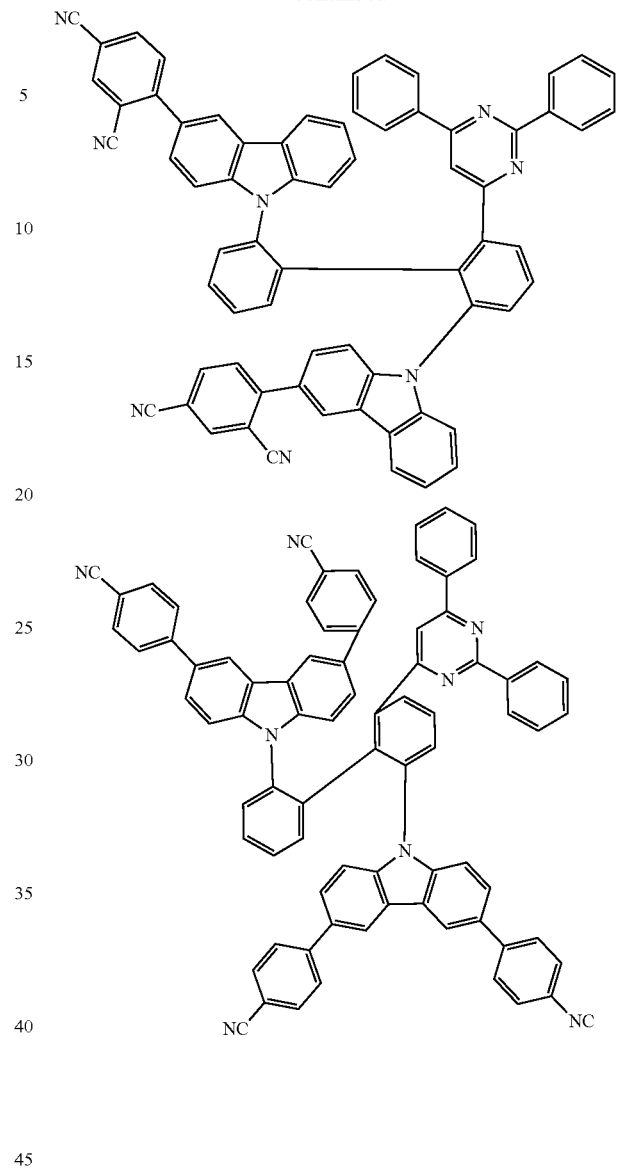
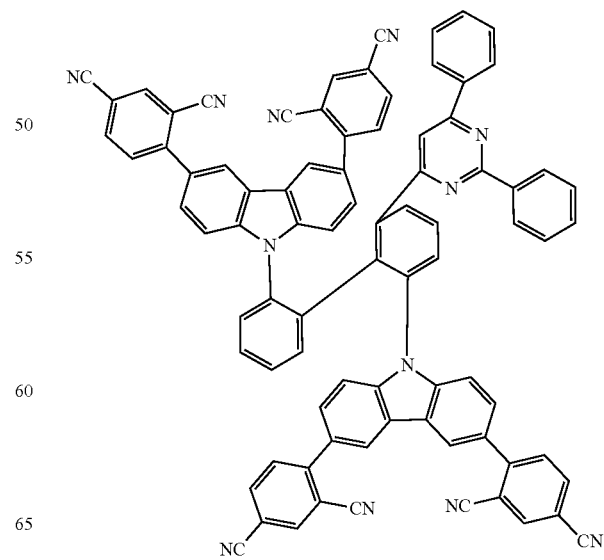

137
-continued
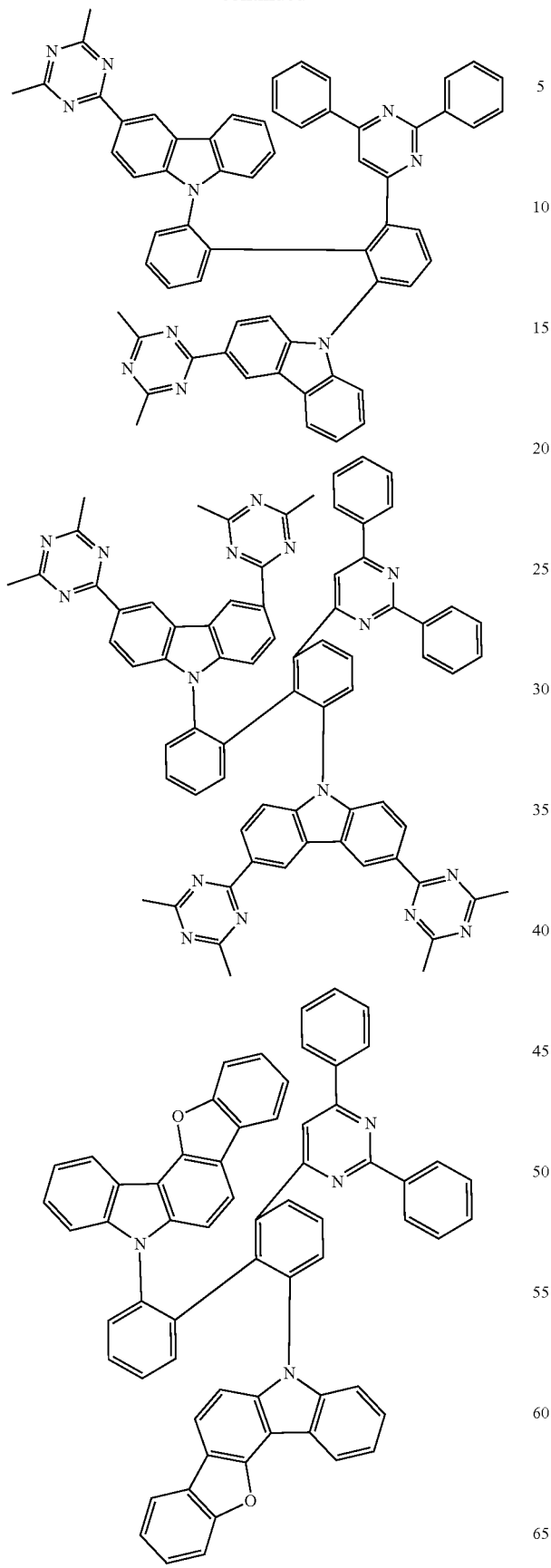
138
-continued
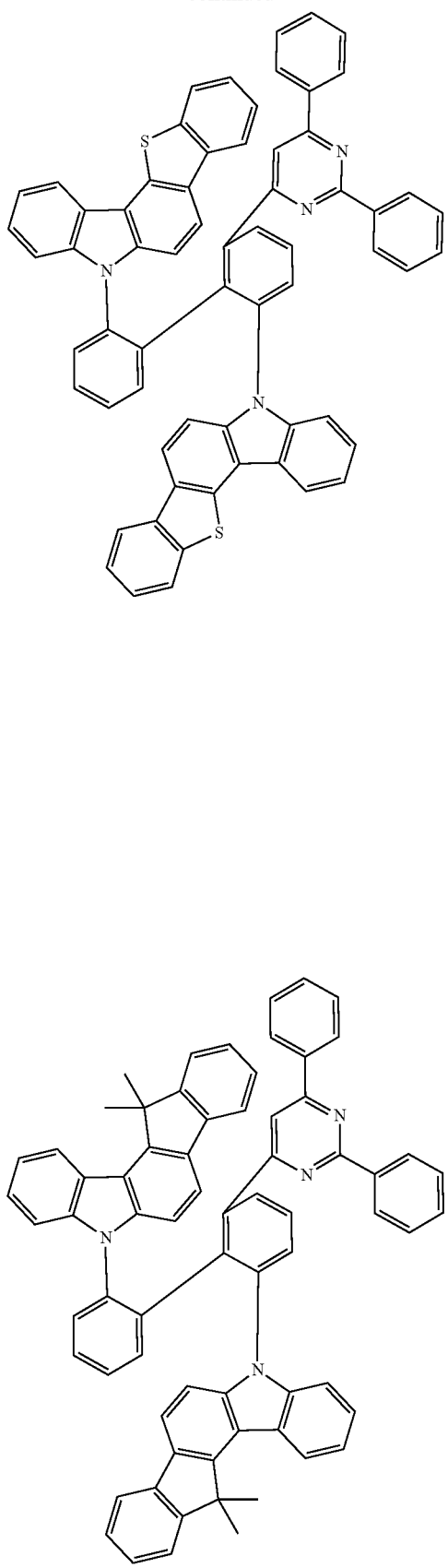

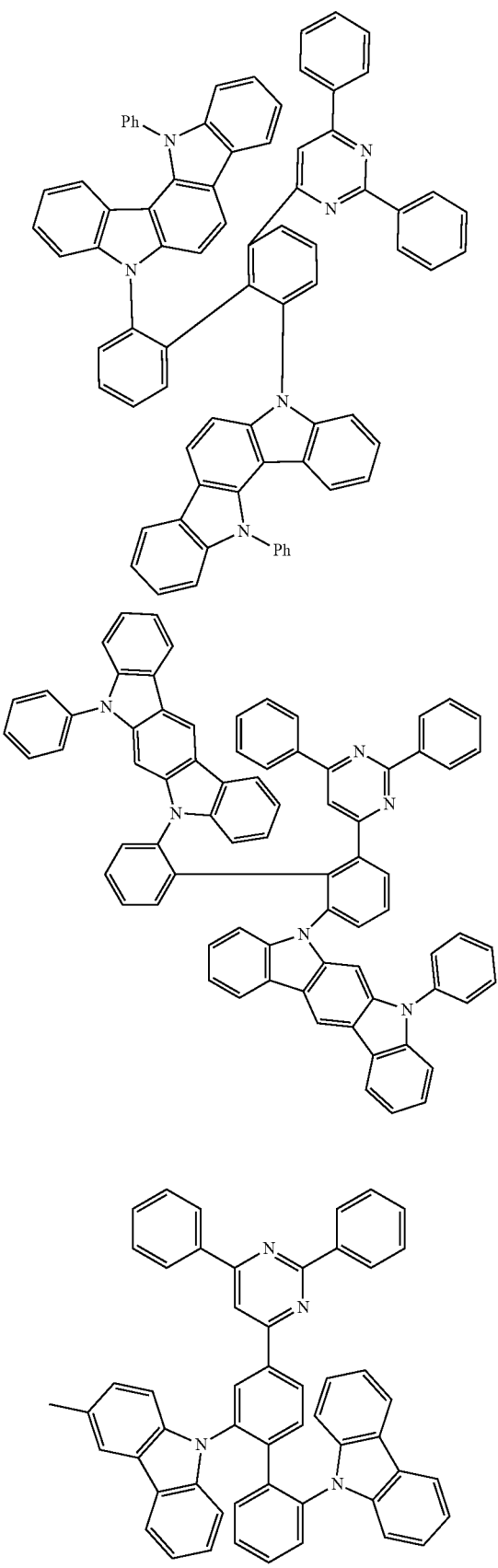
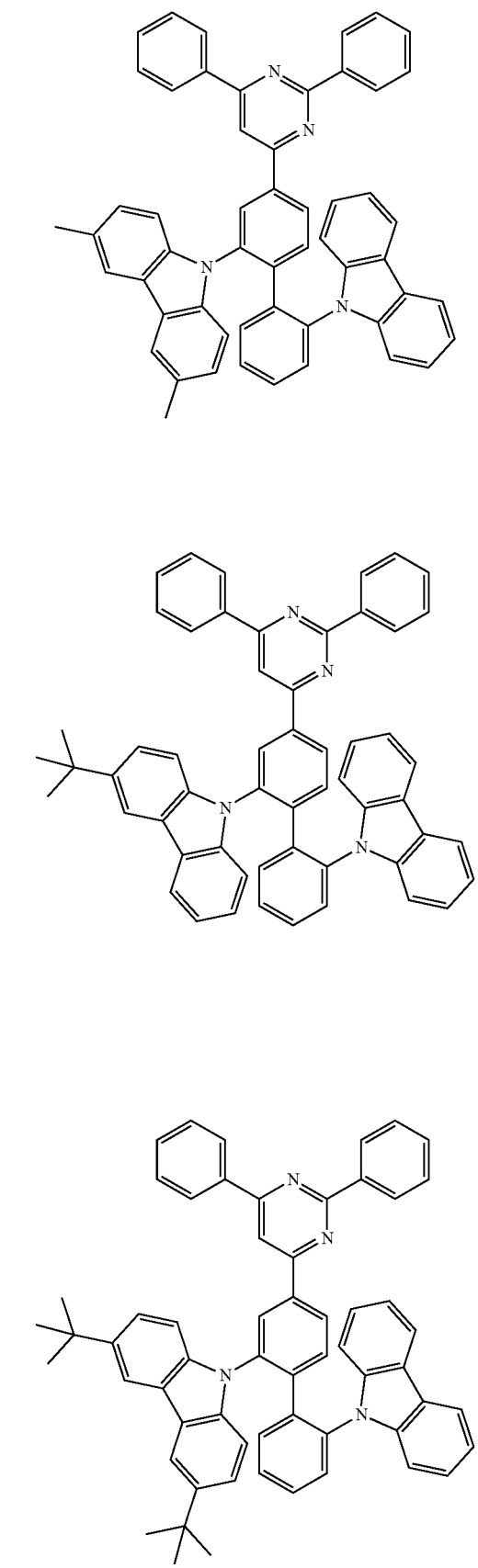

141
-continued
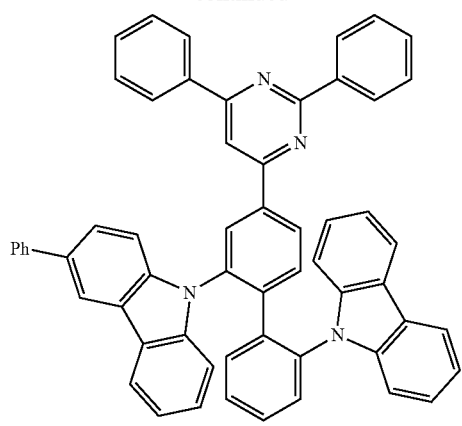
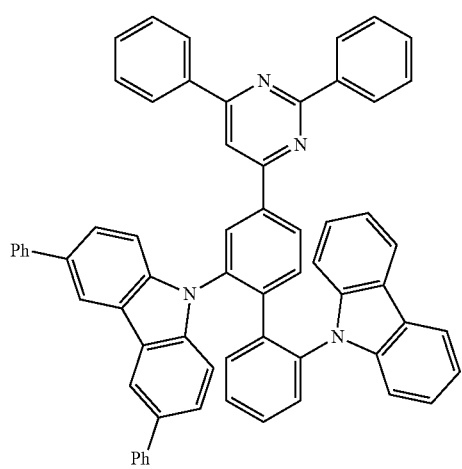
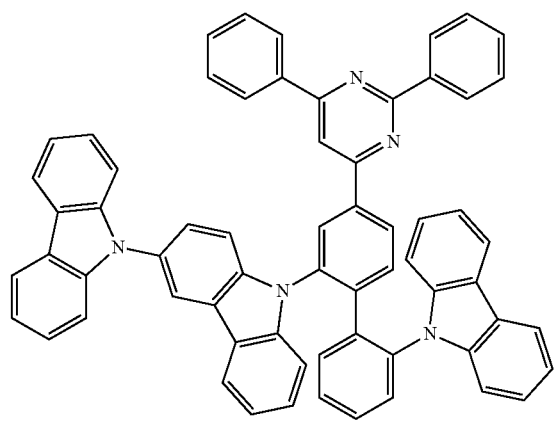
142
-continued
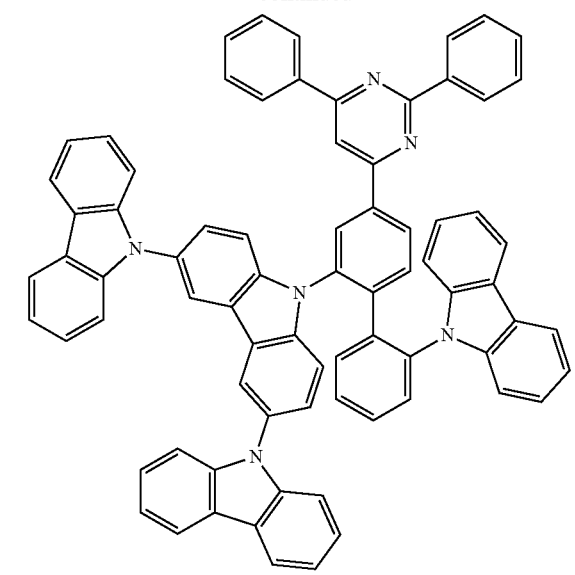
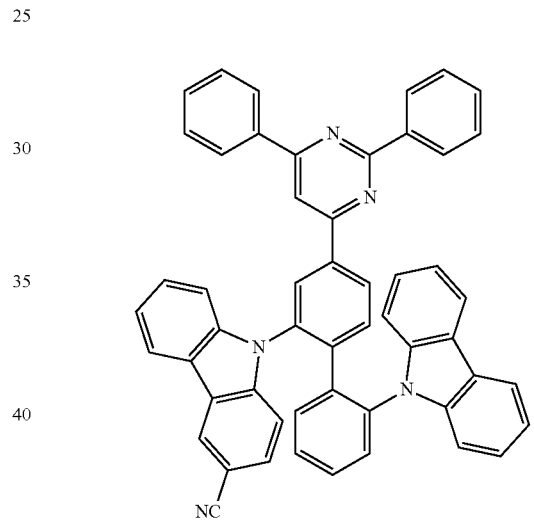
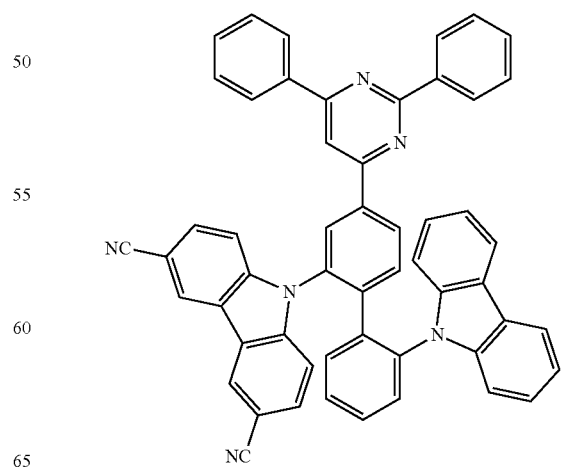

143
-continued
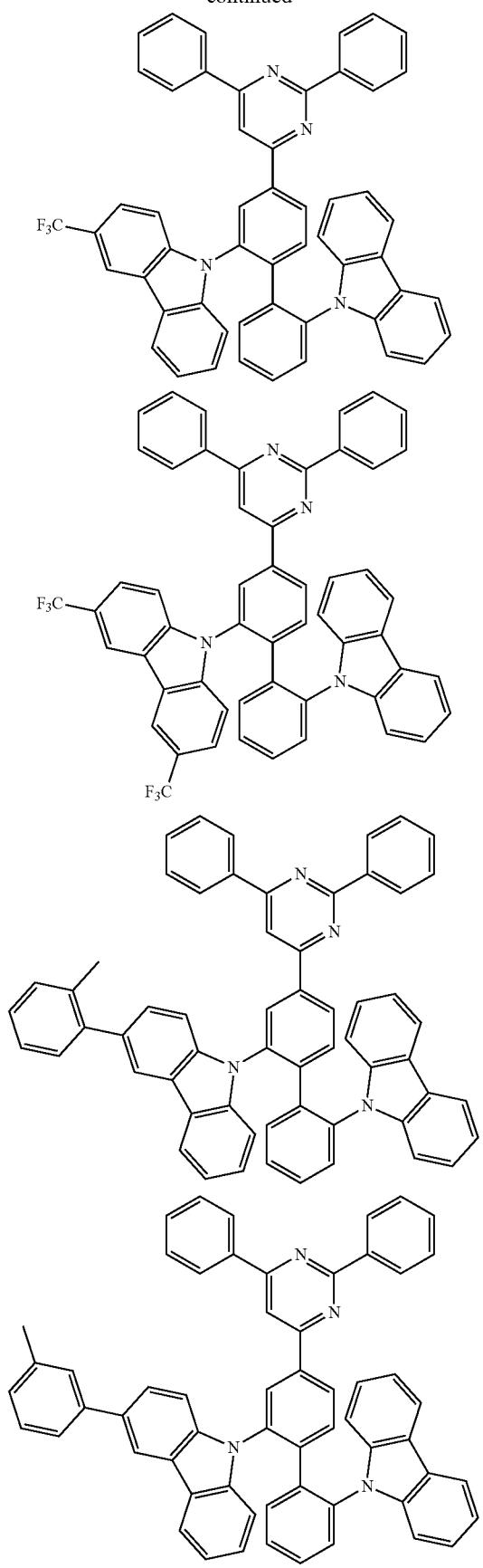
144
-continued
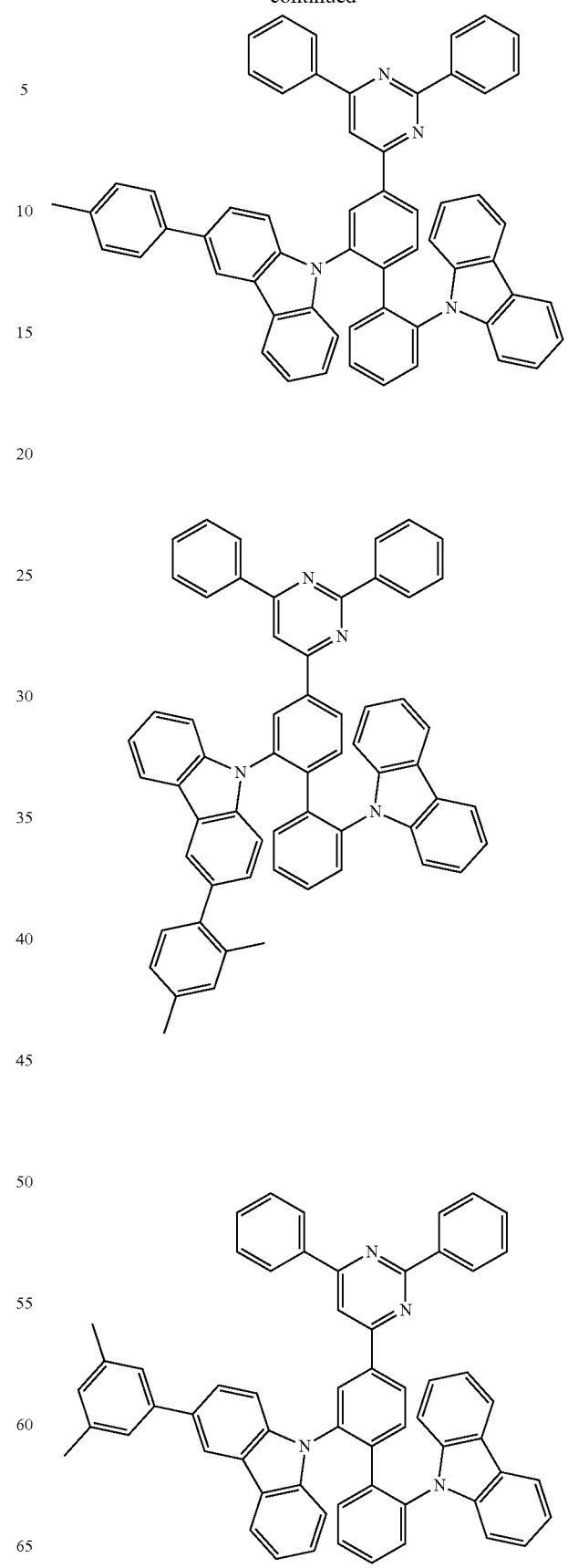

145
-continued
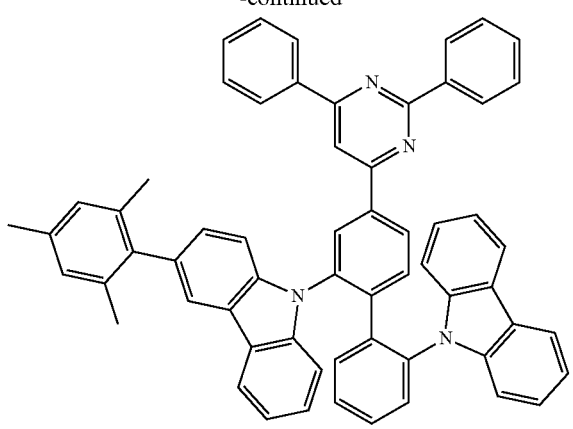
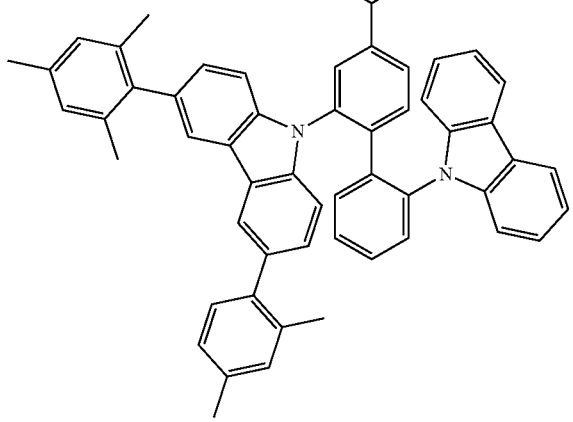
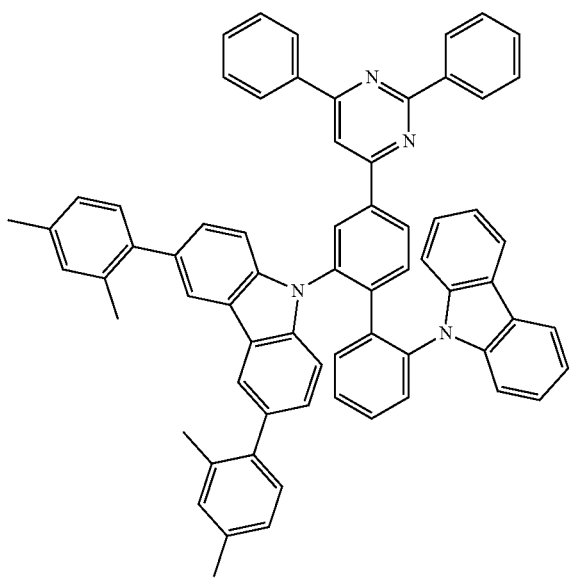
146
-continued
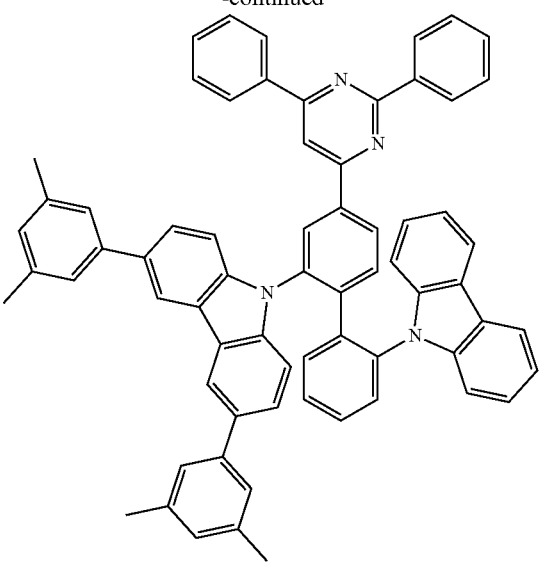
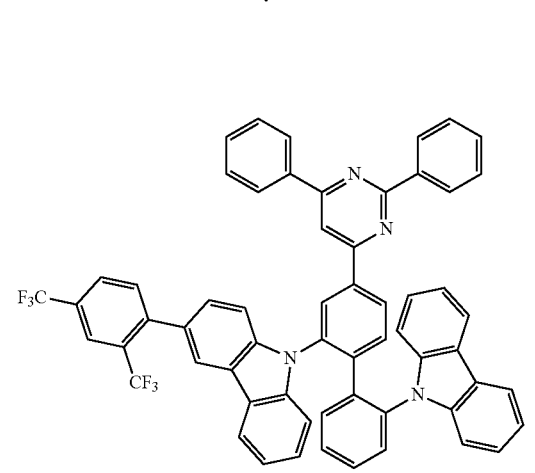
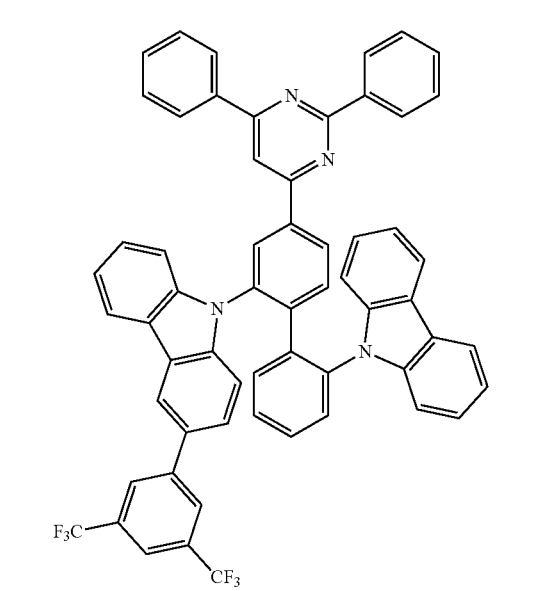

147
-continued
148
-continued
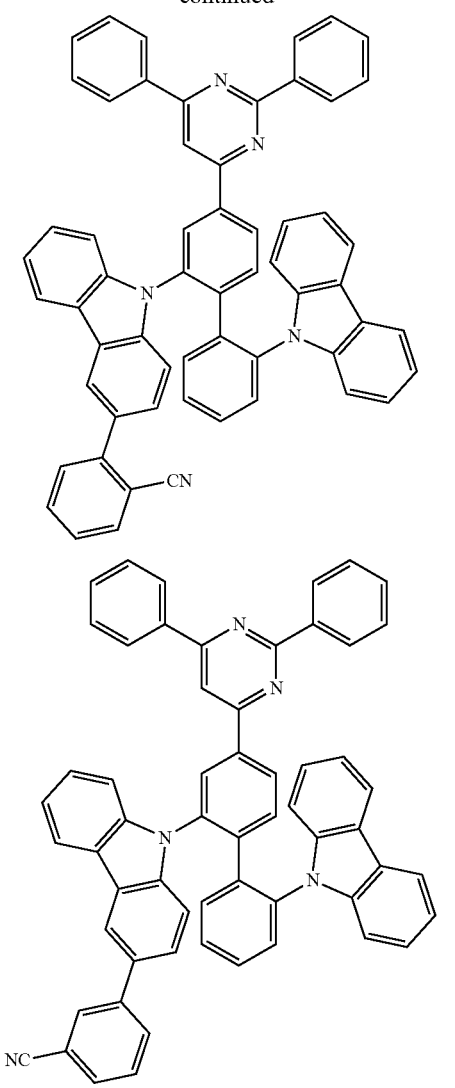
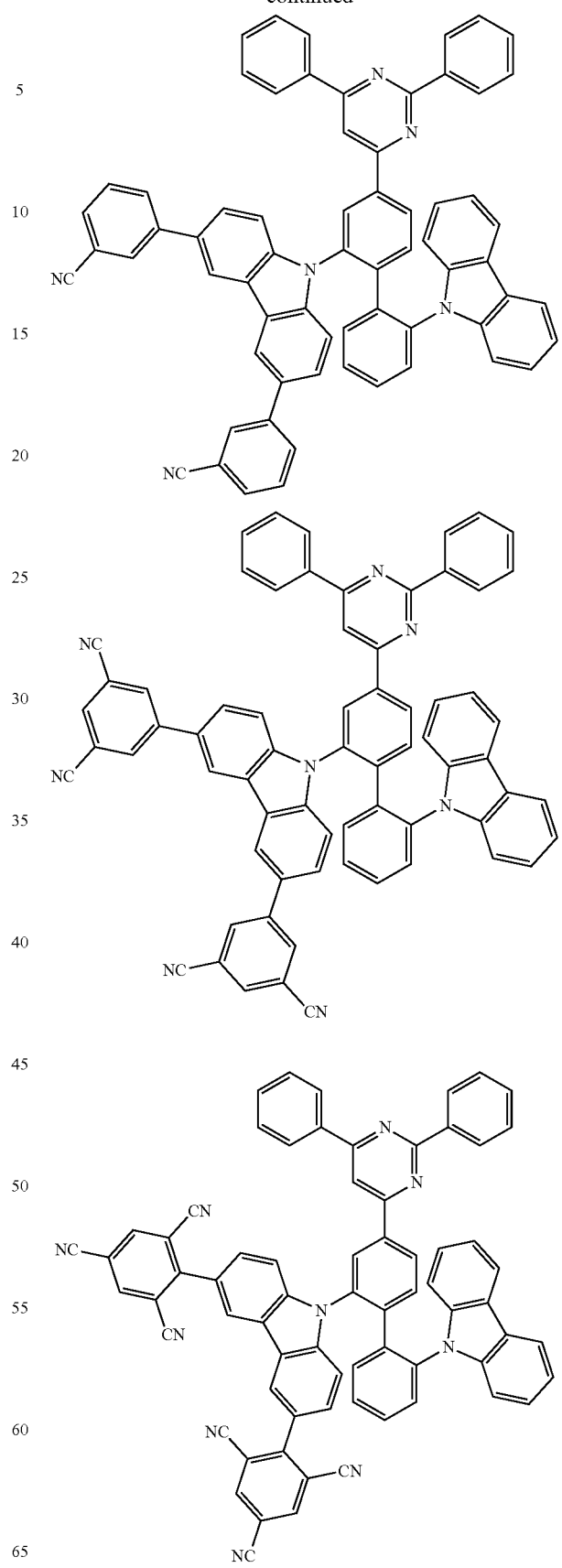

149
-continued
150
-continued
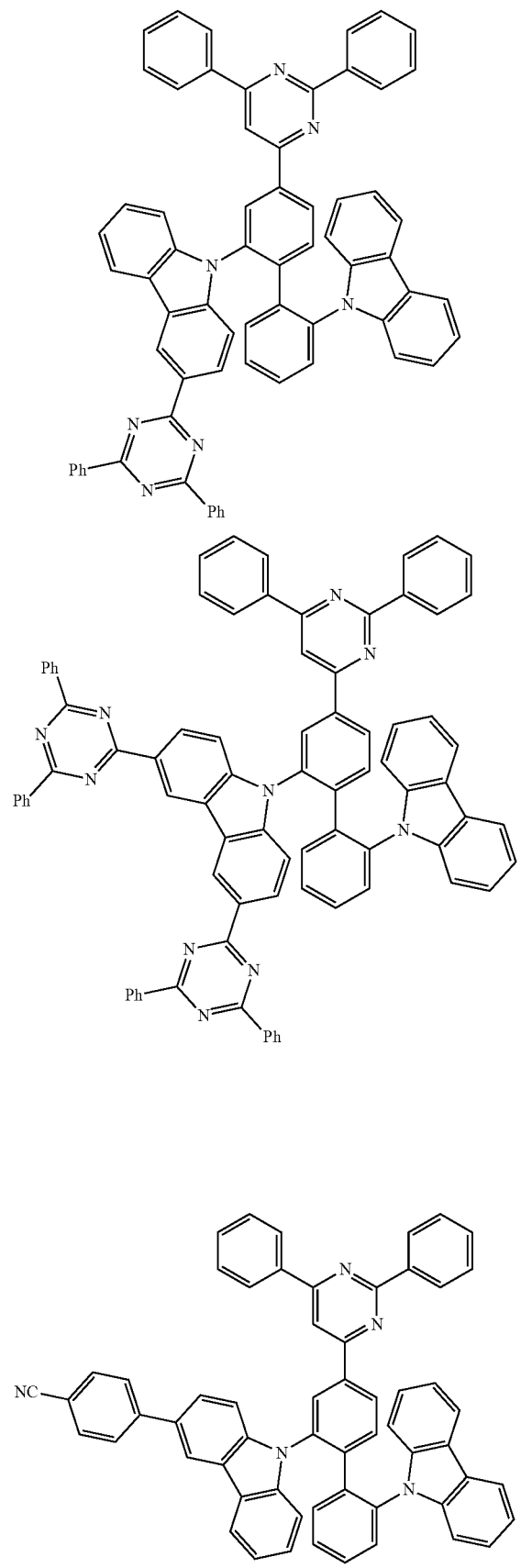
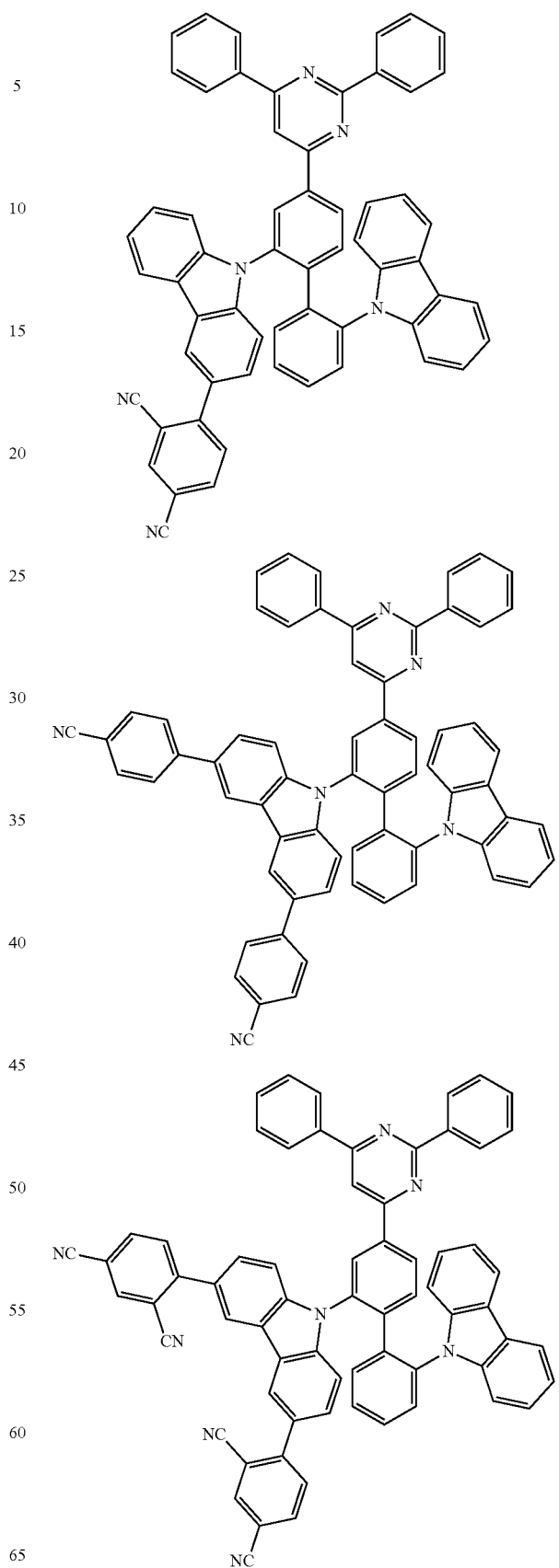

| 151 -continued | 152 -continued |
|---|---|
| 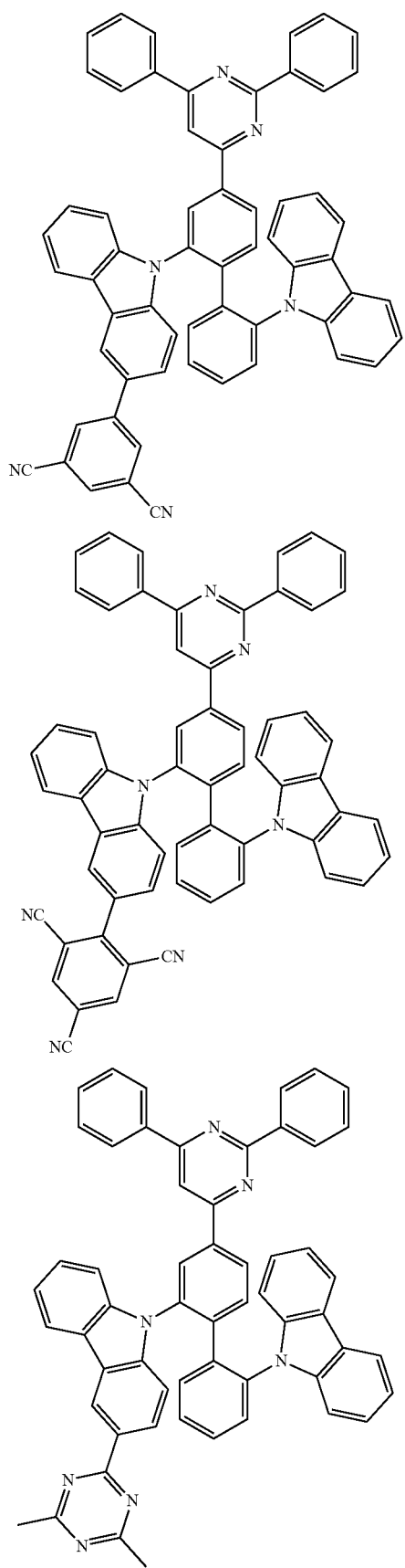 | 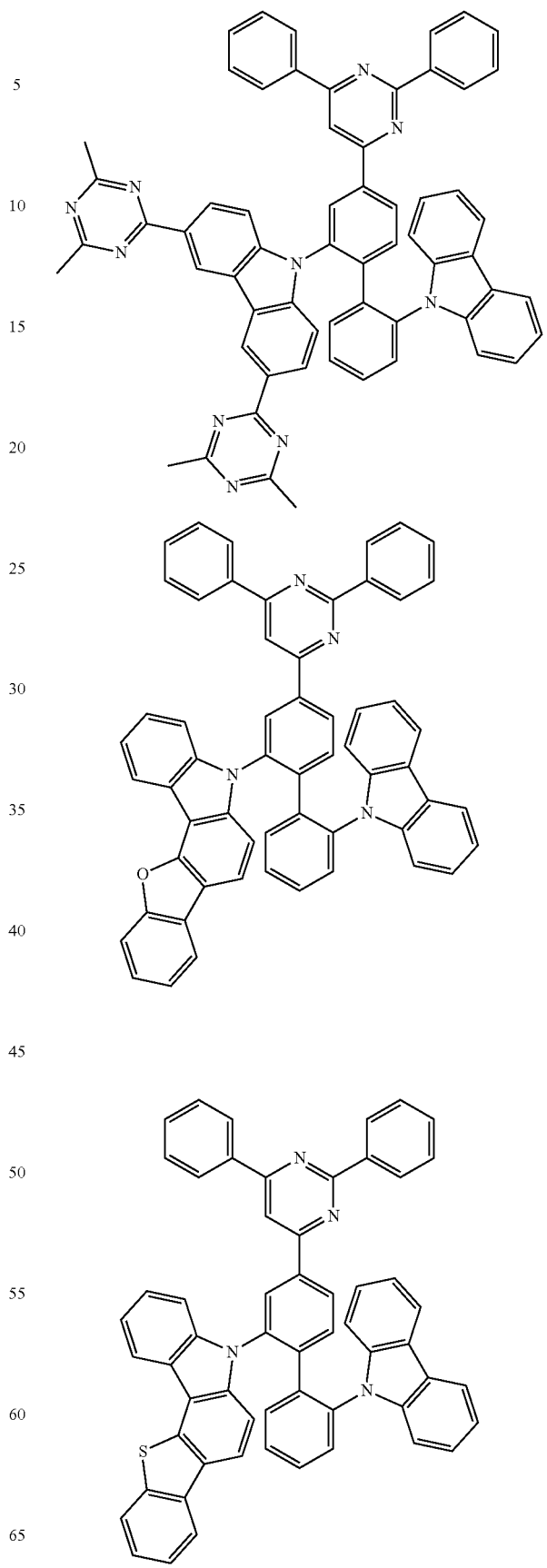 |

-continued
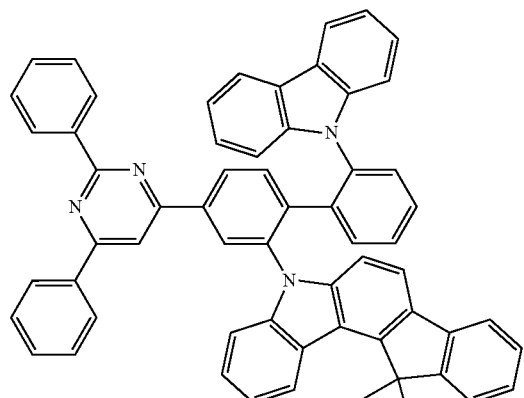
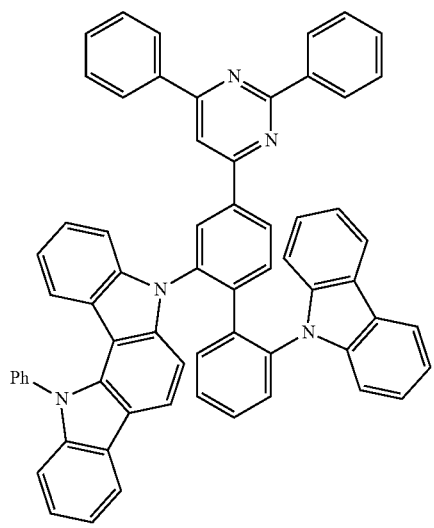
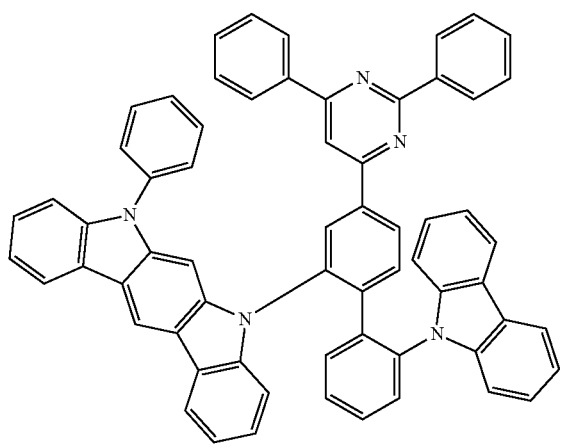
-continued
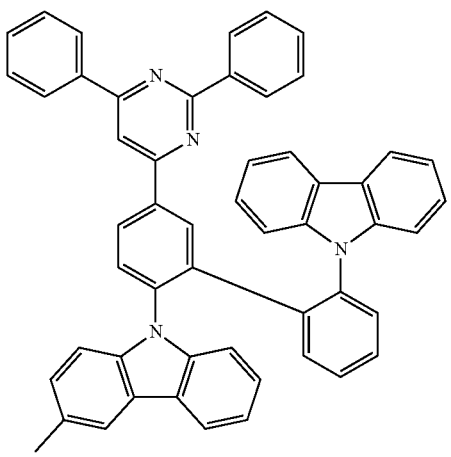
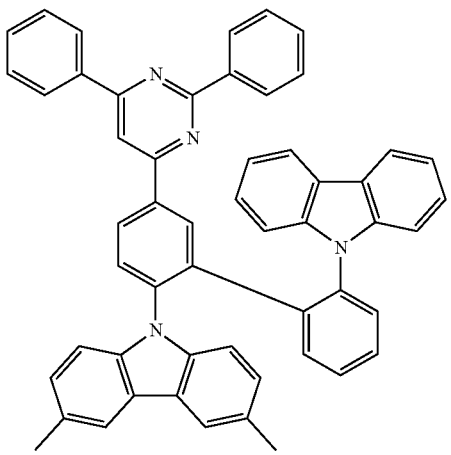
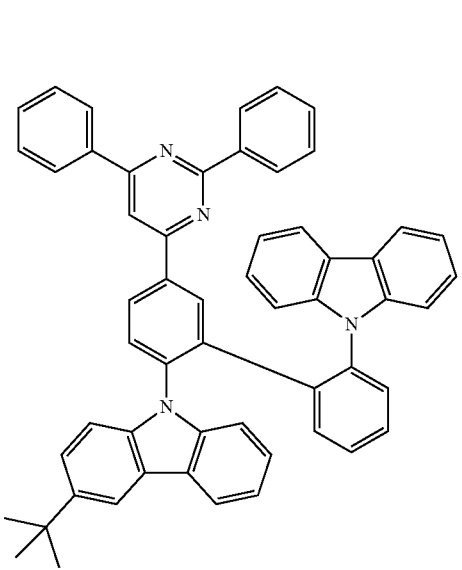

155
-continued
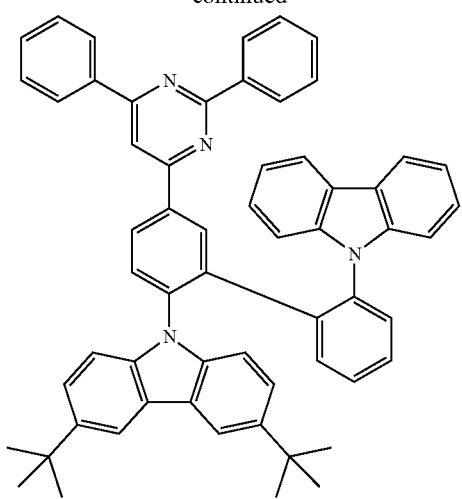
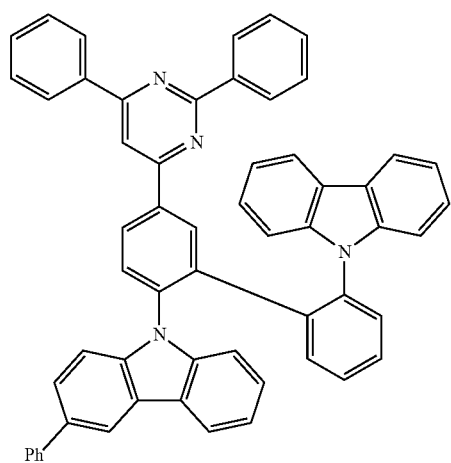
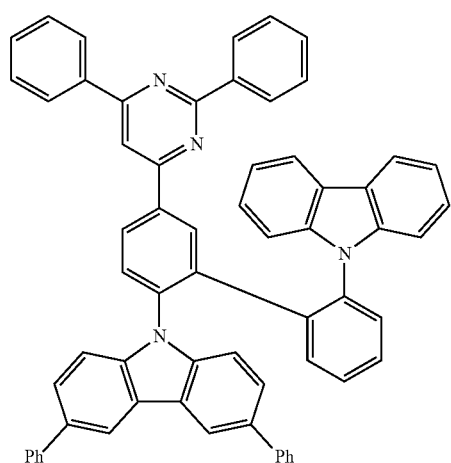
156
-continued
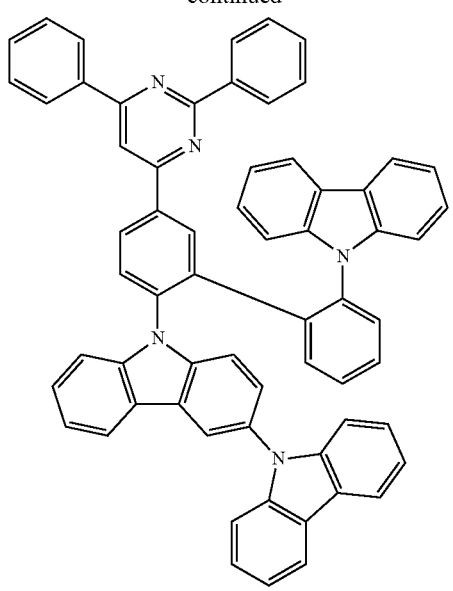
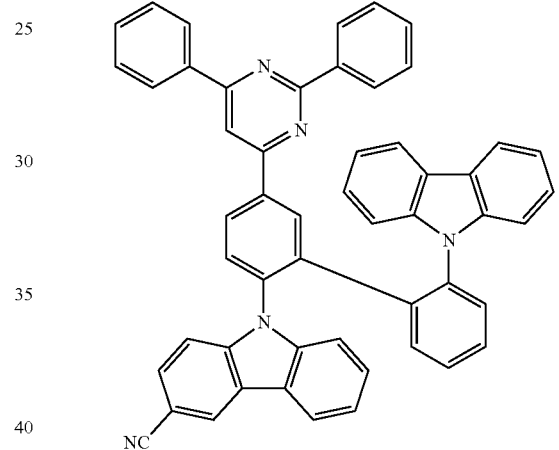
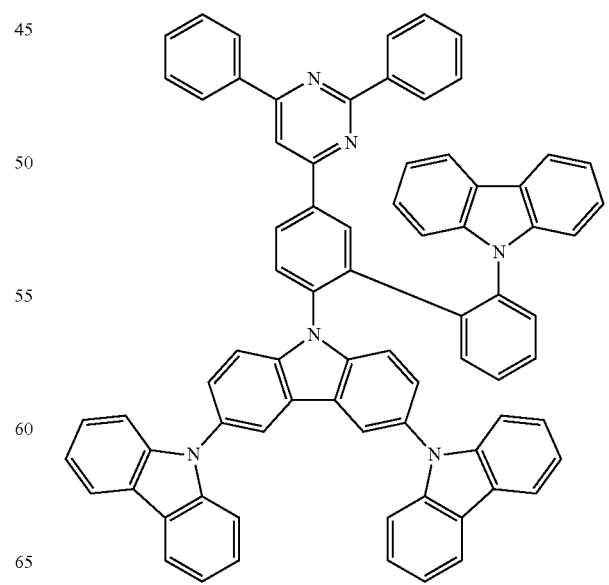

157
-continued
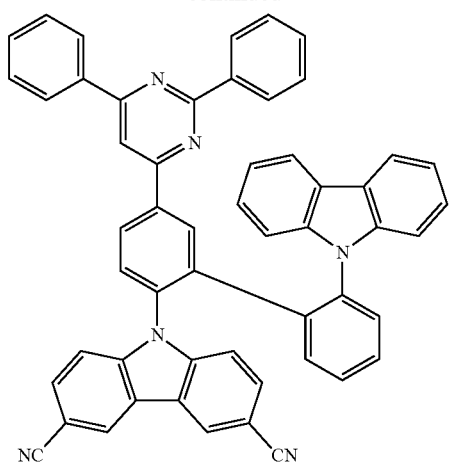
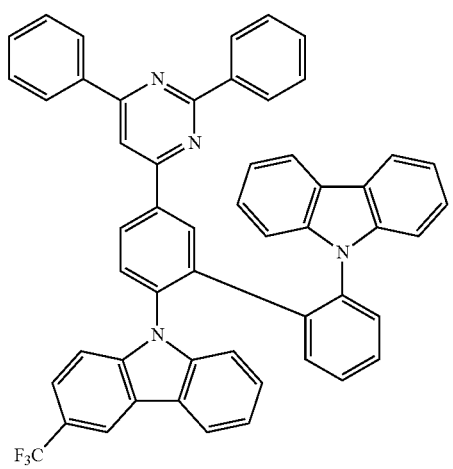
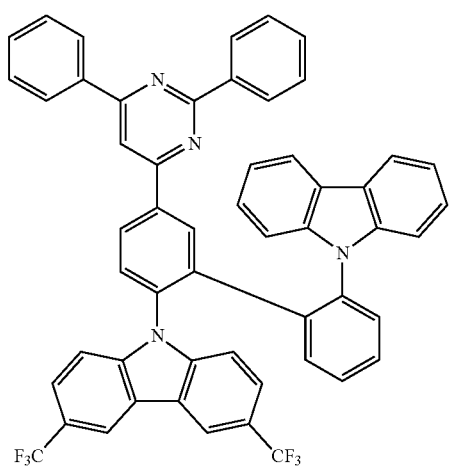
158
-continued
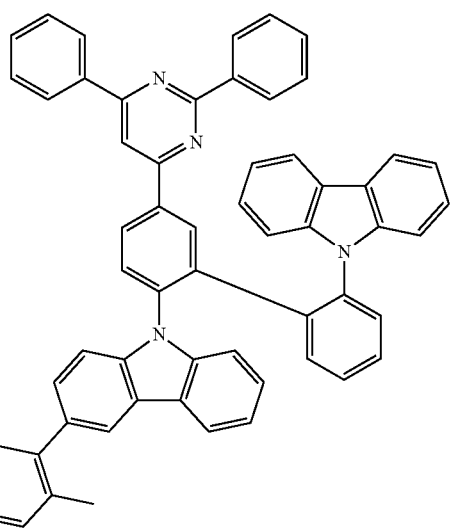
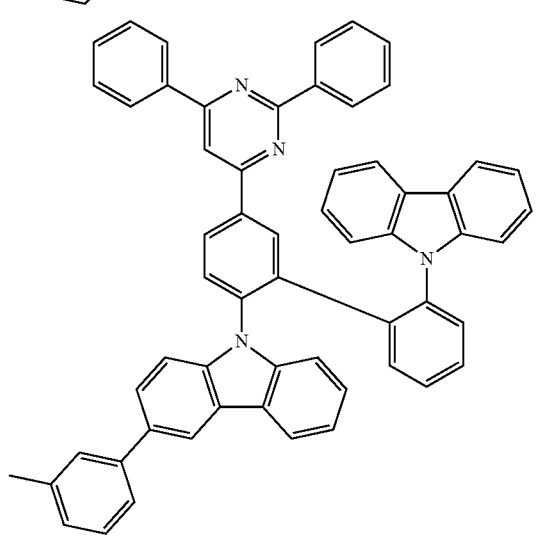
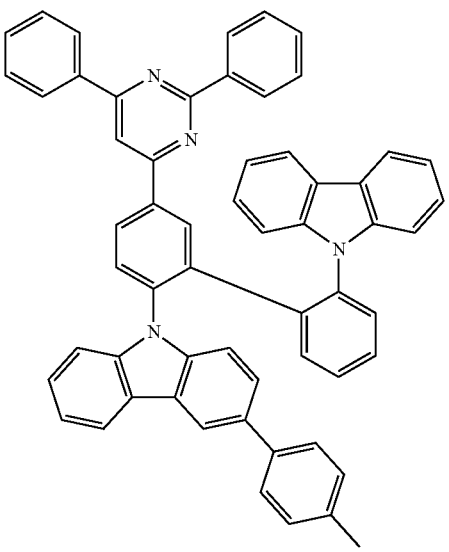

159
-continued
160
-continued
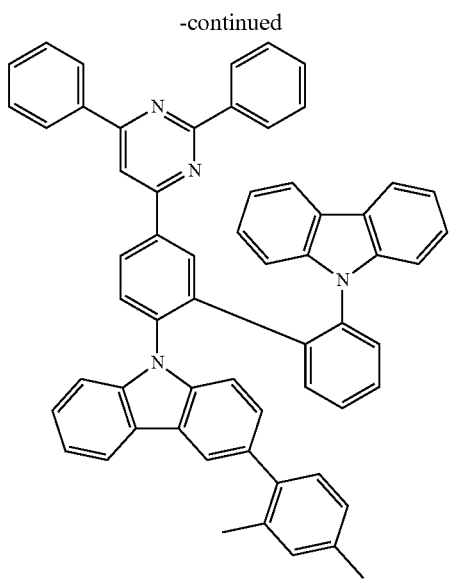
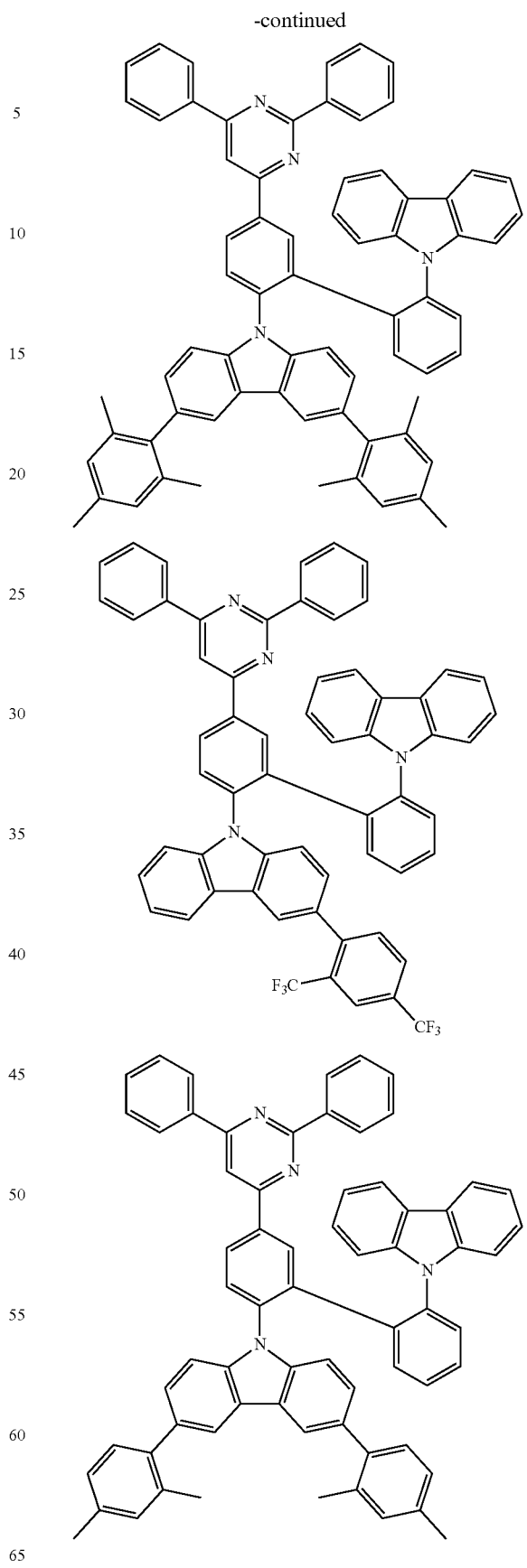

161
-continued
162
-continued
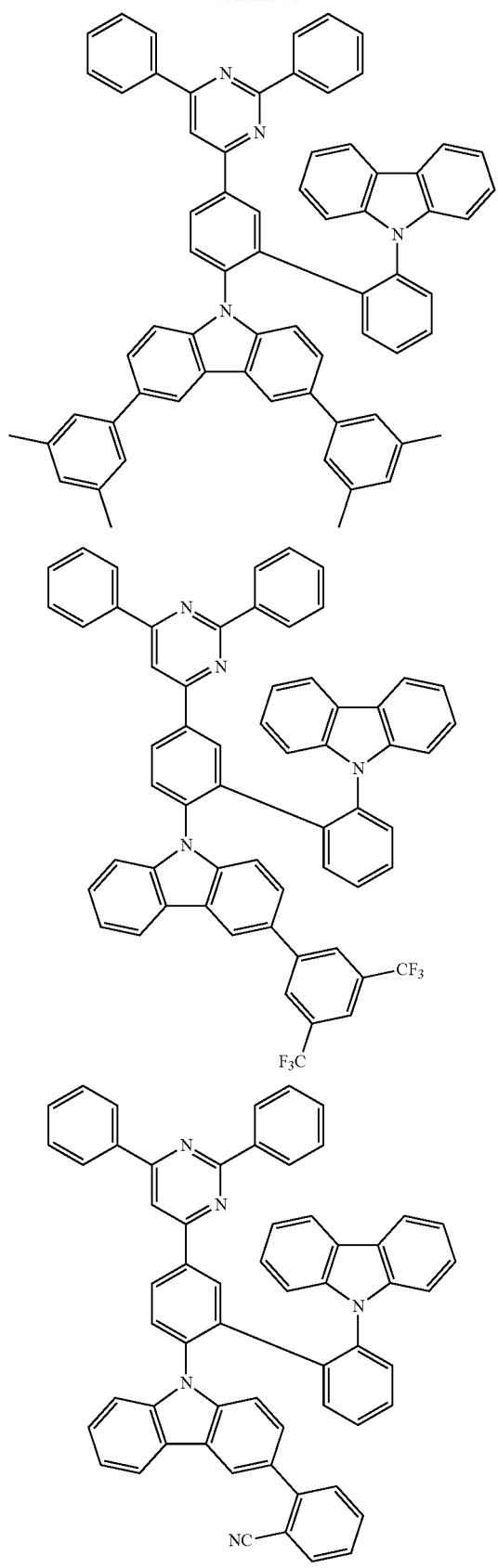
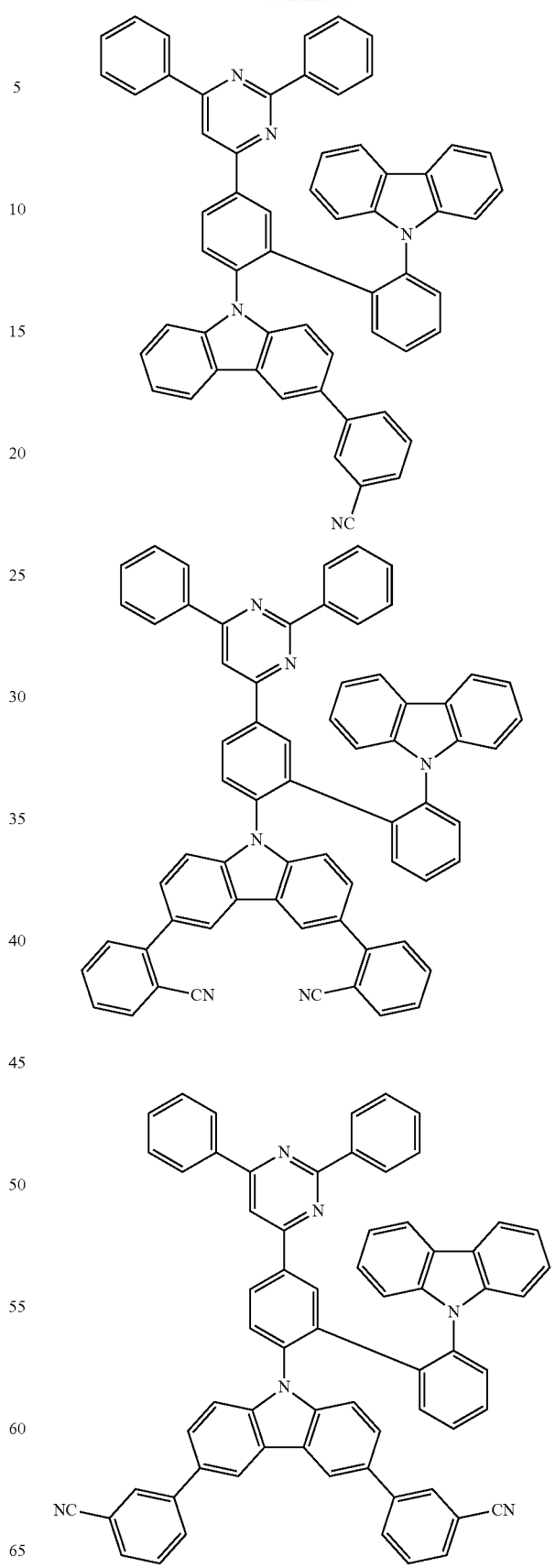

163
-continued
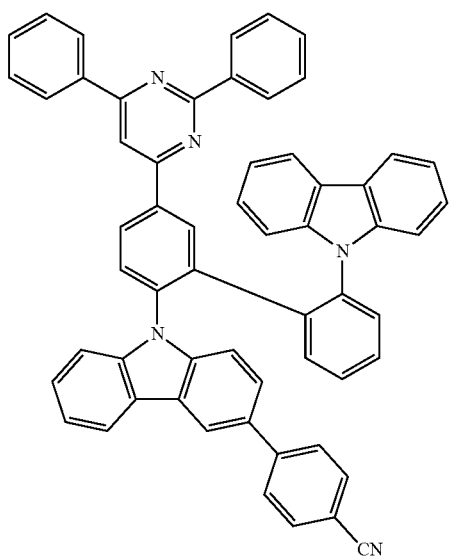
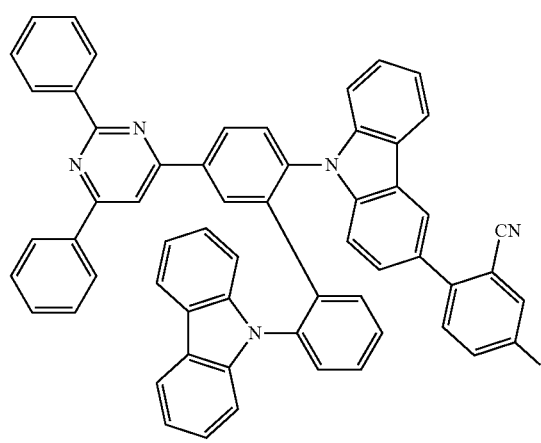
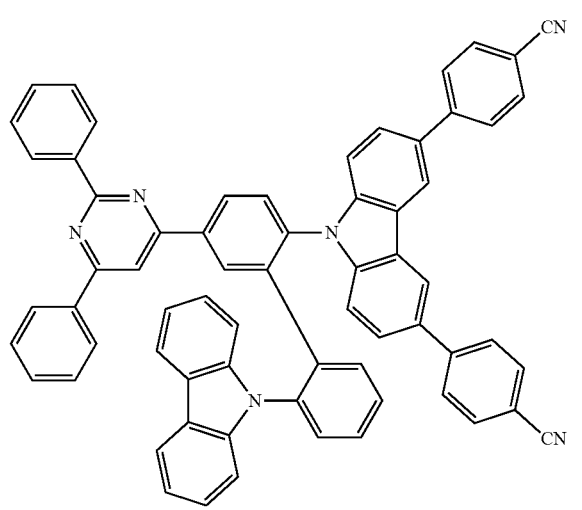
164
-continued
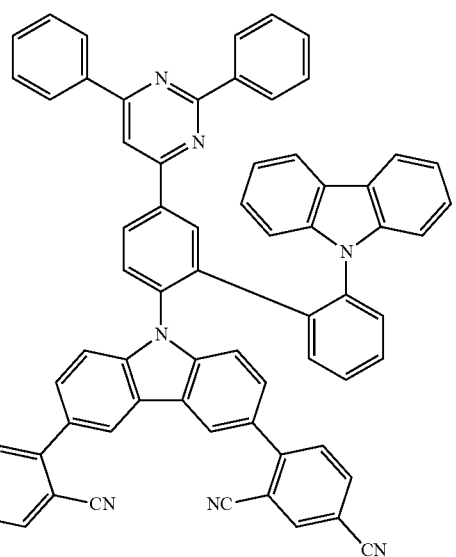
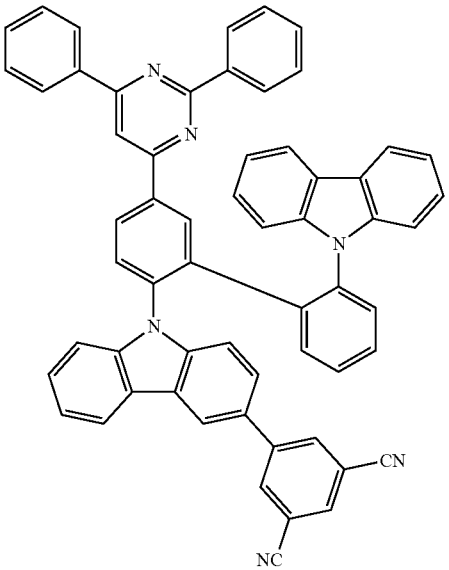
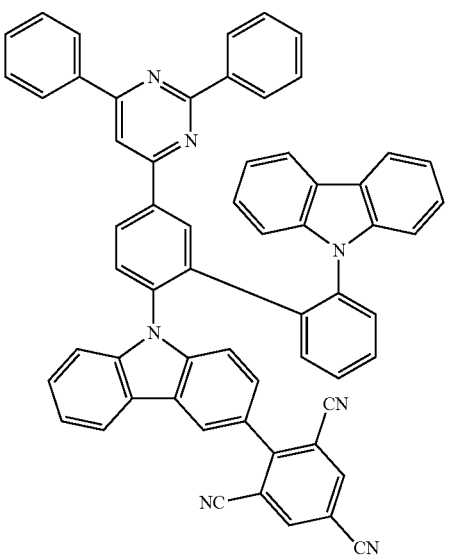

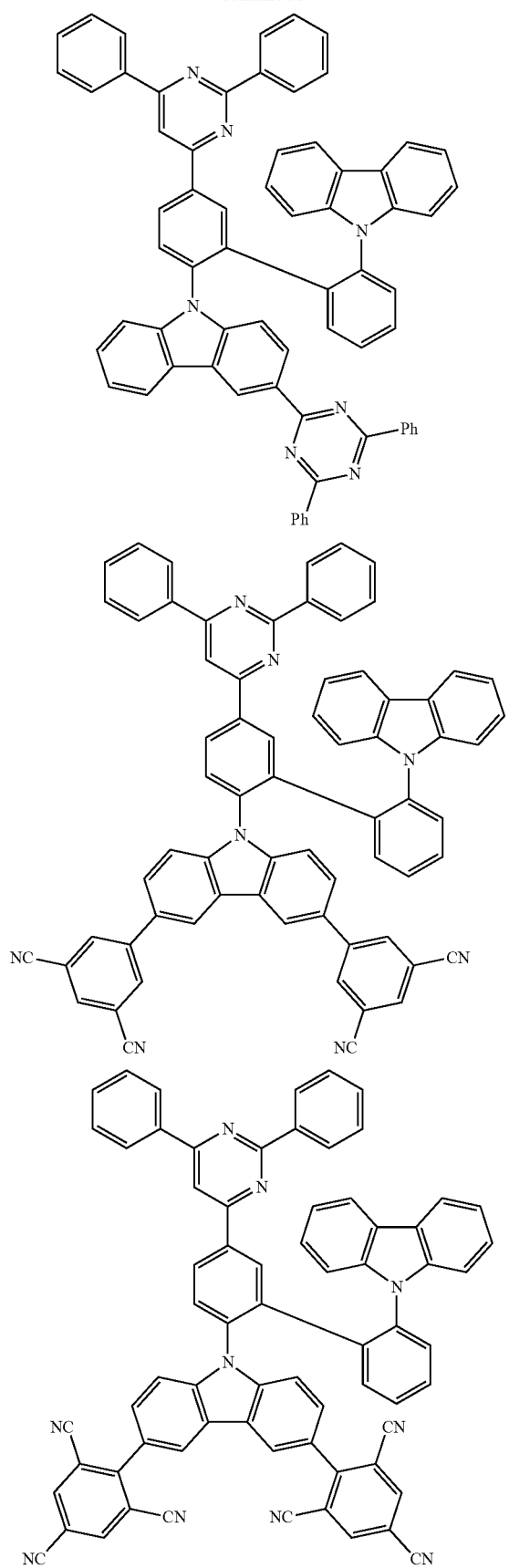
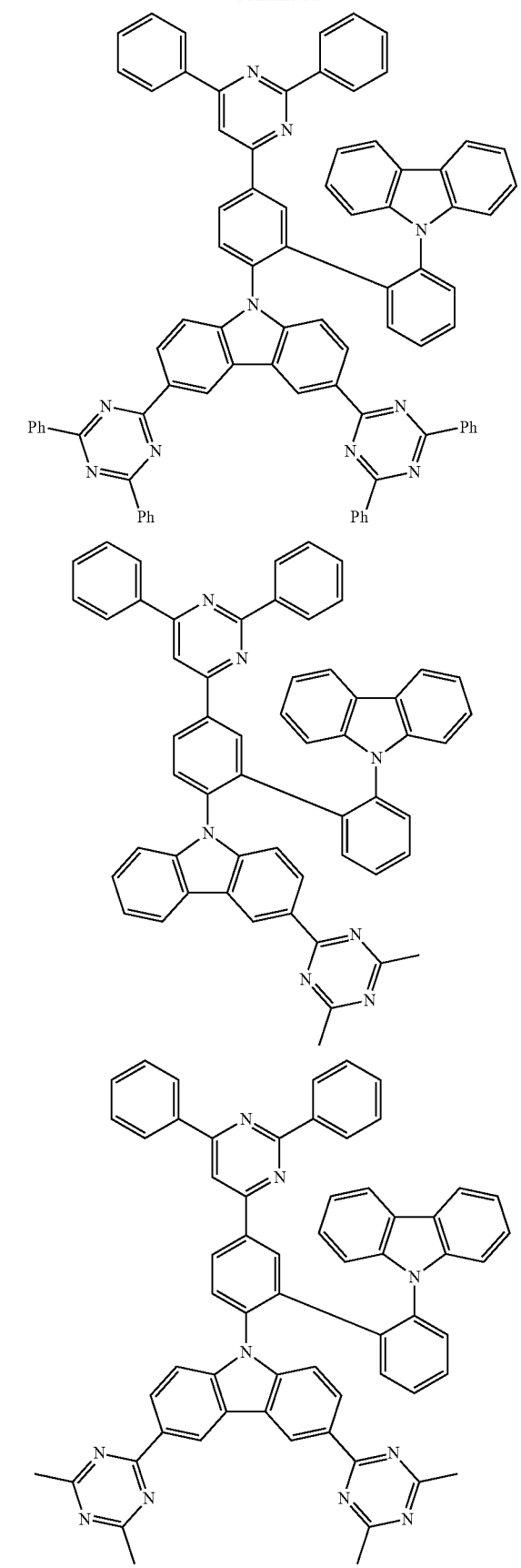

167
-continued
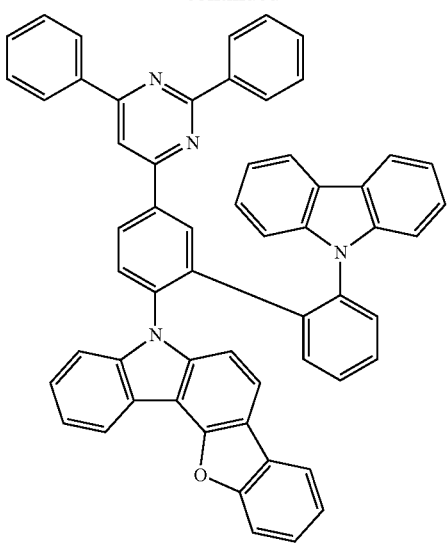
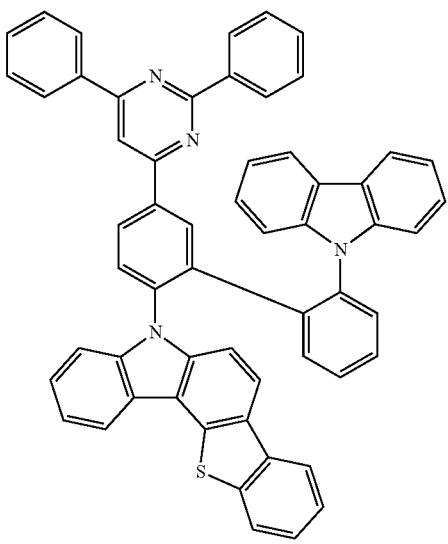
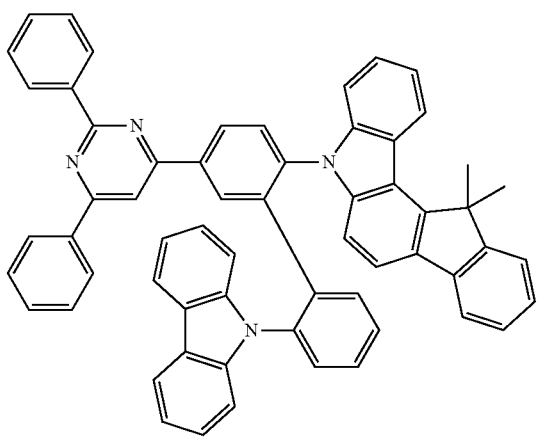
168
-continued
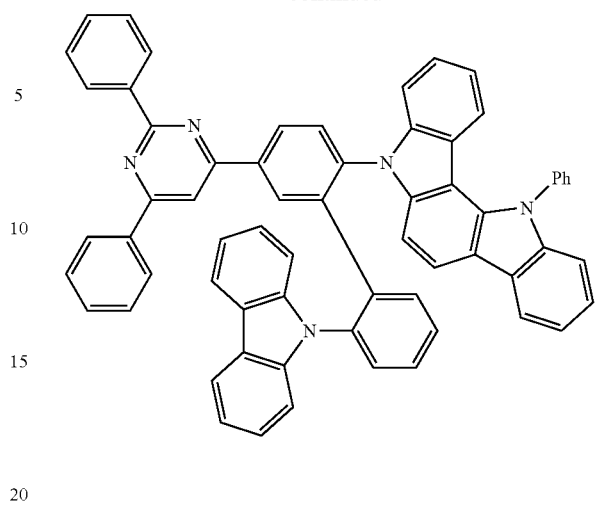
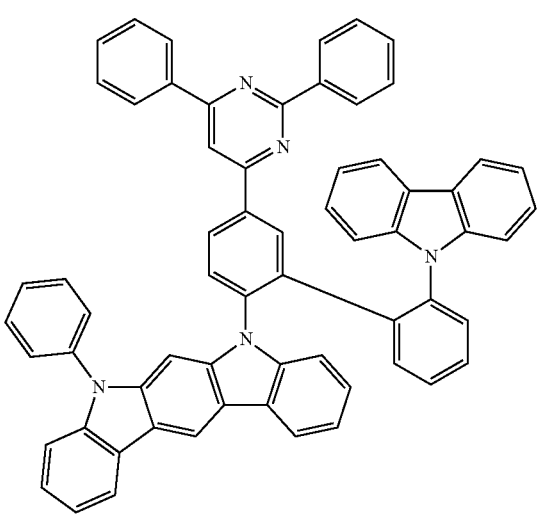
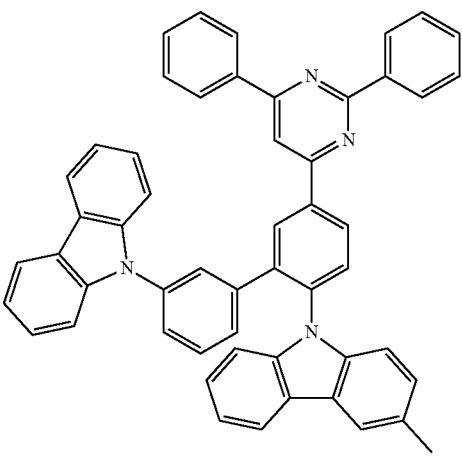

169
-continued
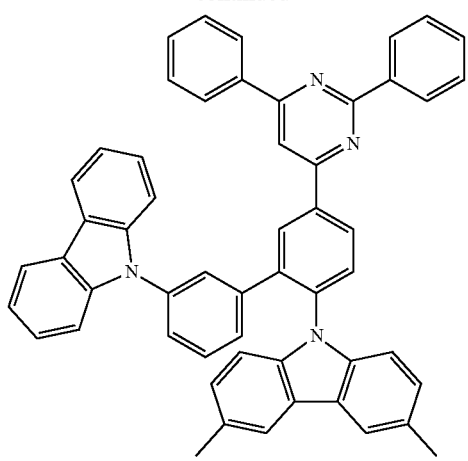
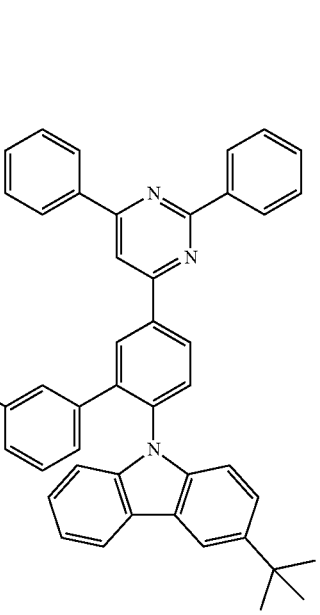
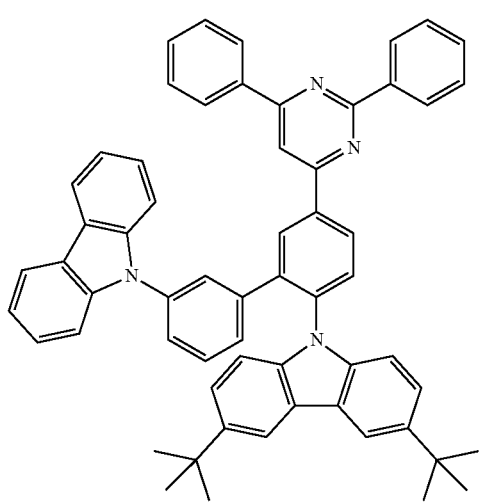
170
-continued
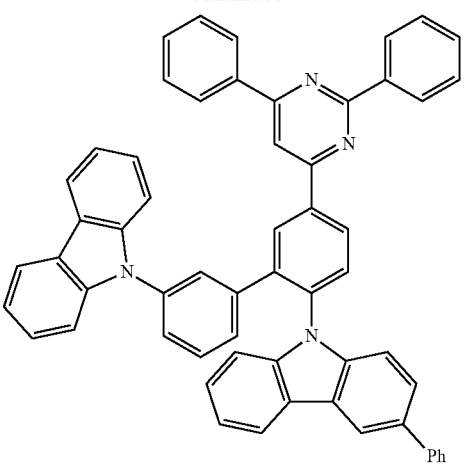
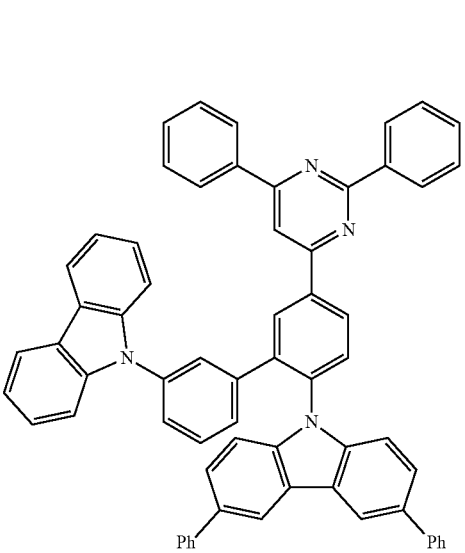
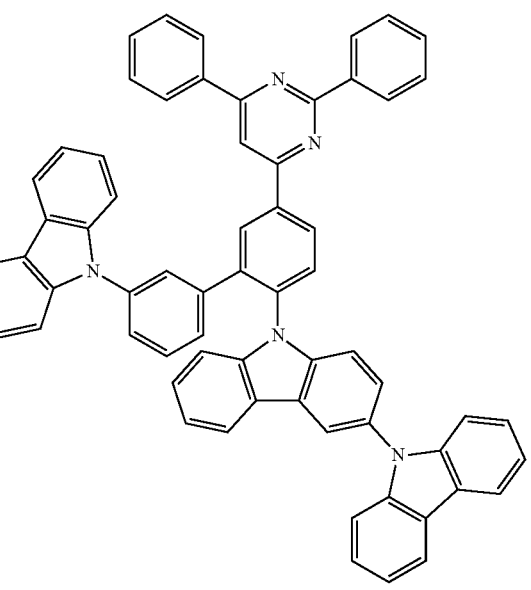

171
-continued
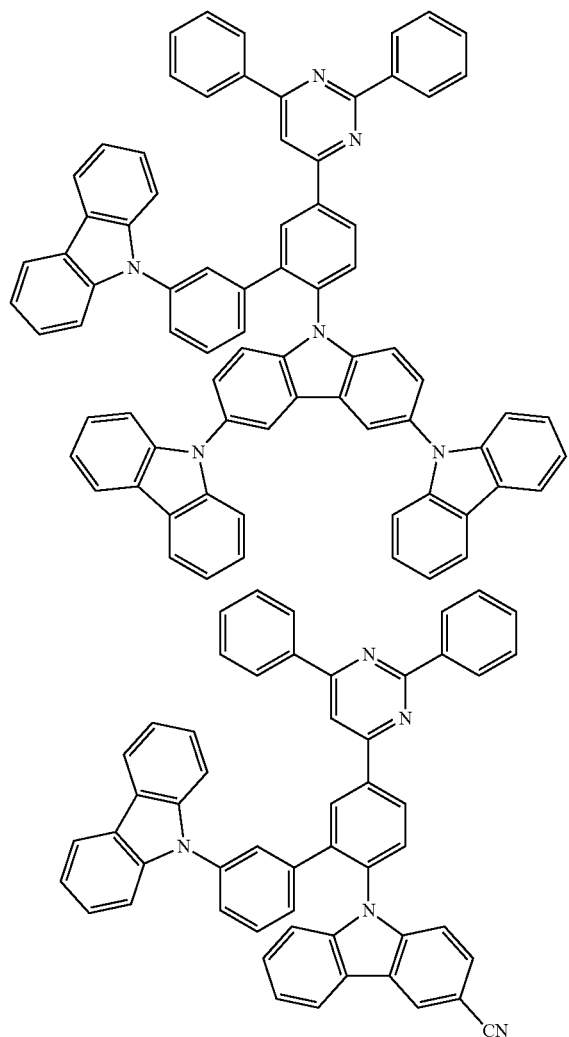
172
-continued
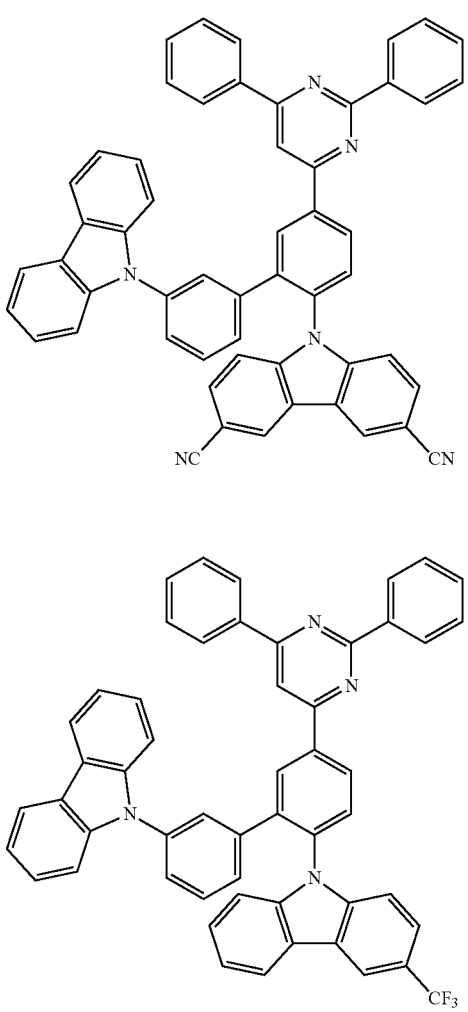
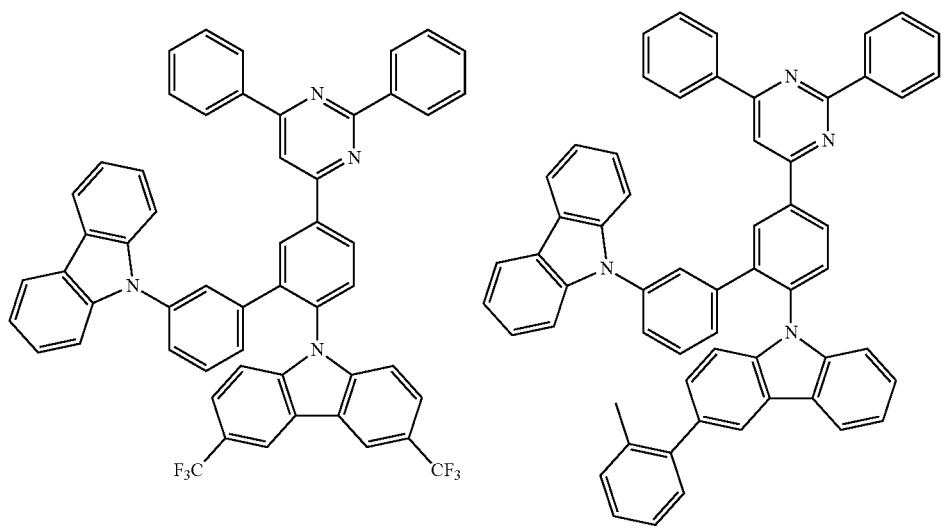

-continued
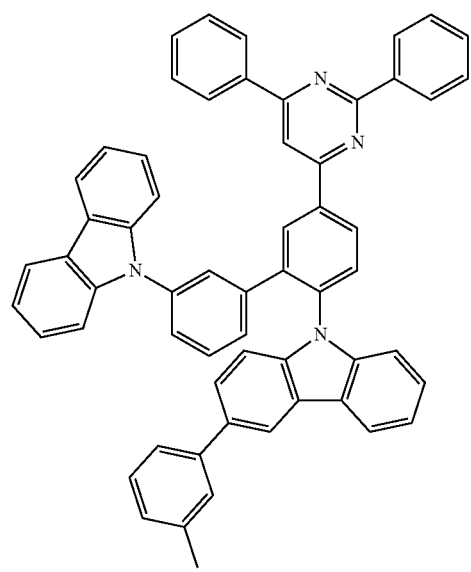
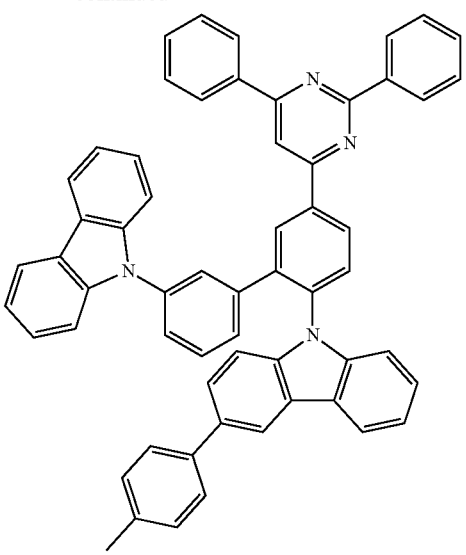
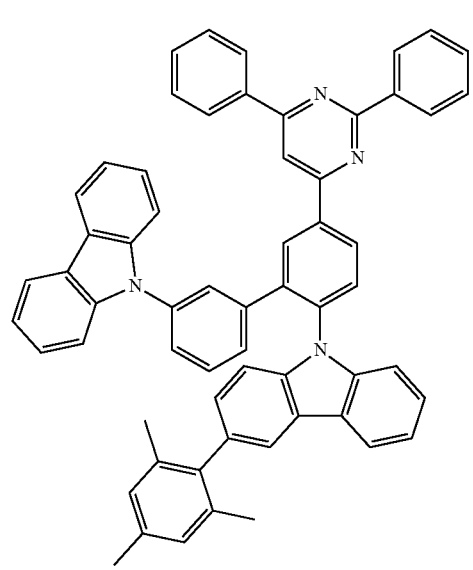
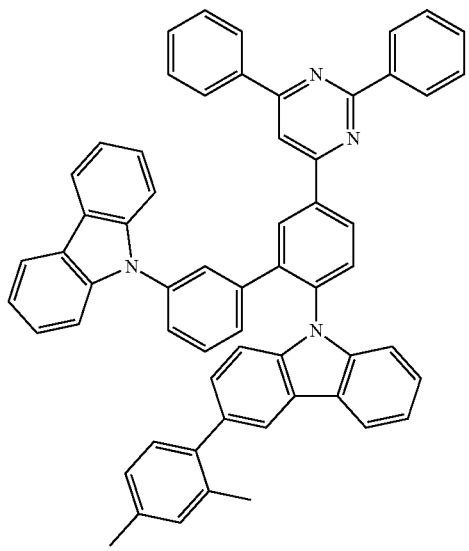
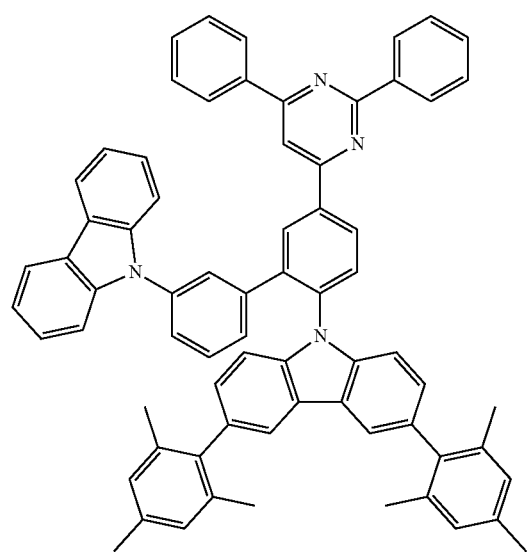
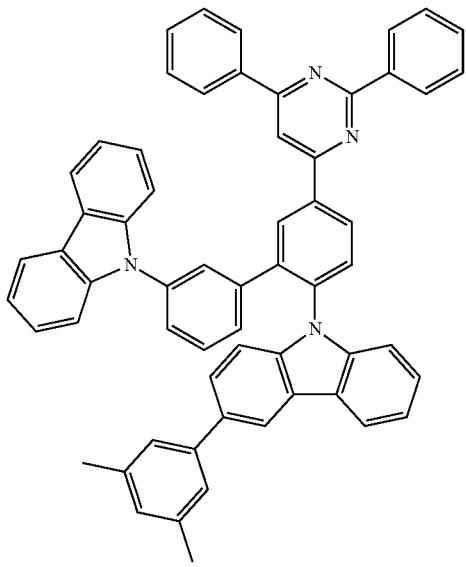

-continued
175
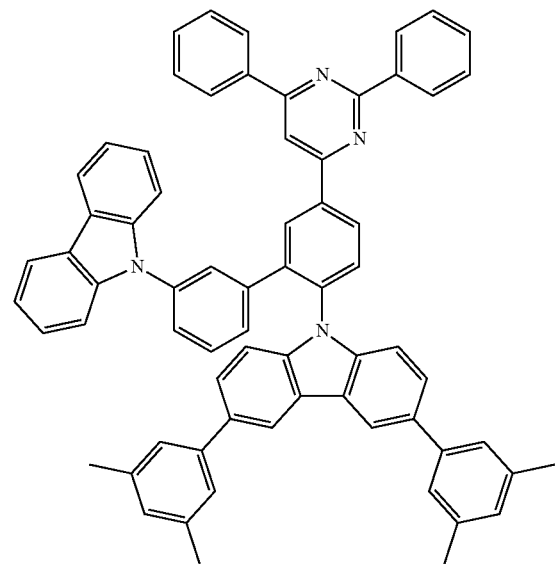
176
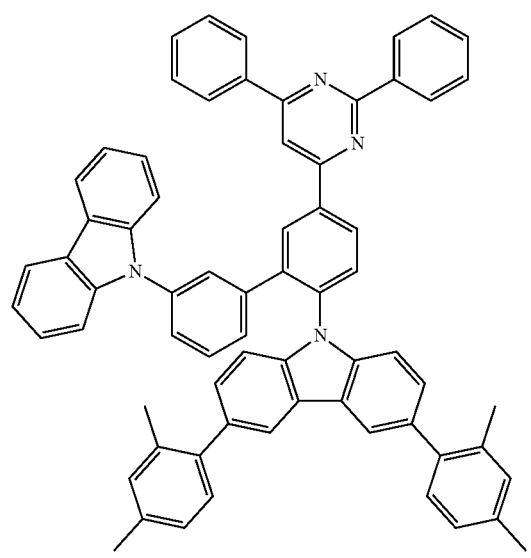
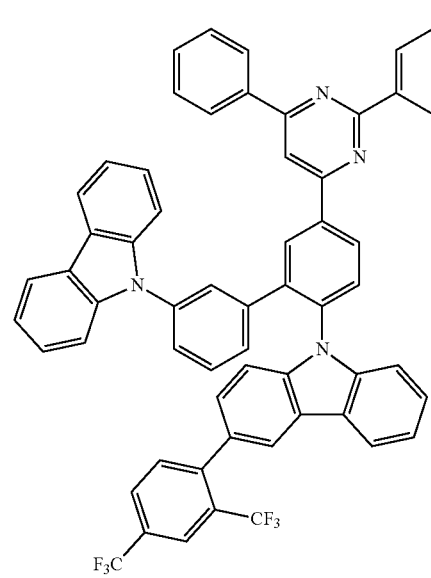
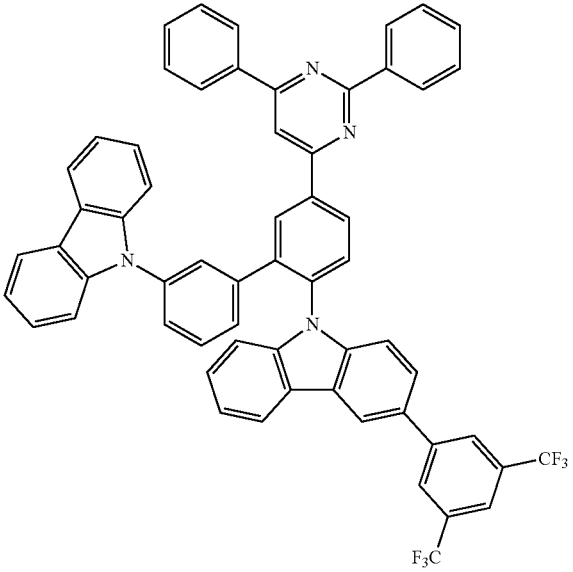
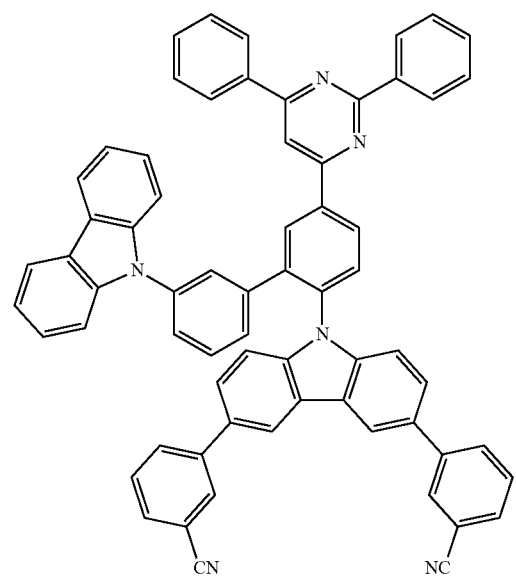
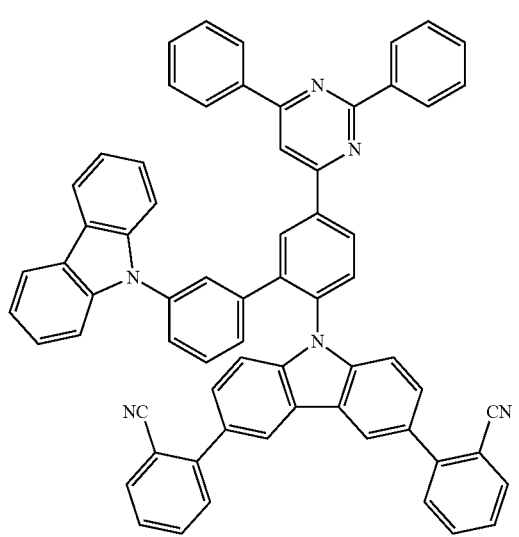

177
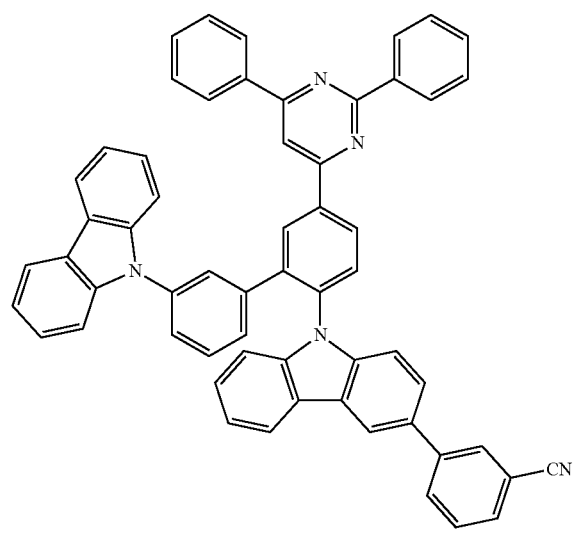
178
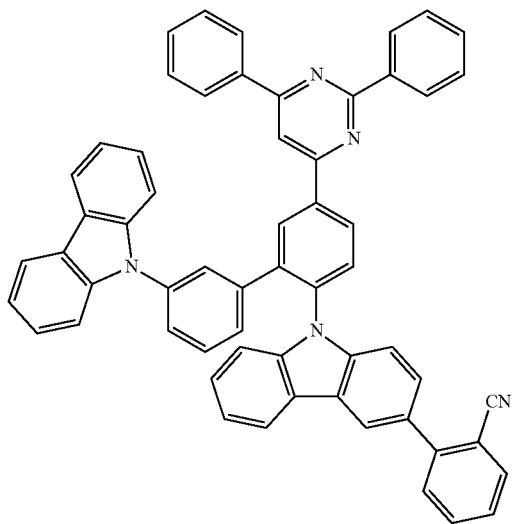
-continued
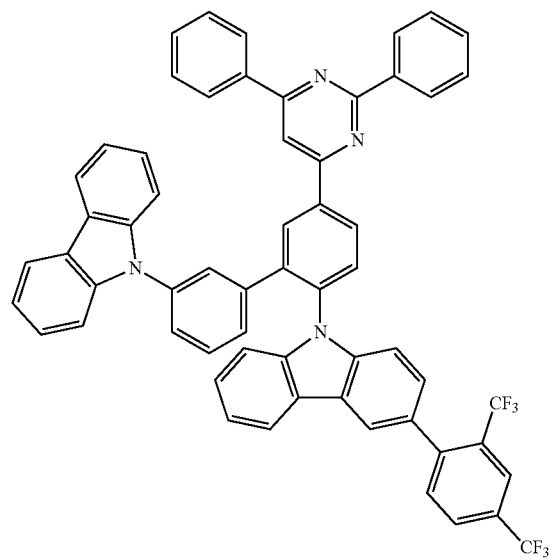
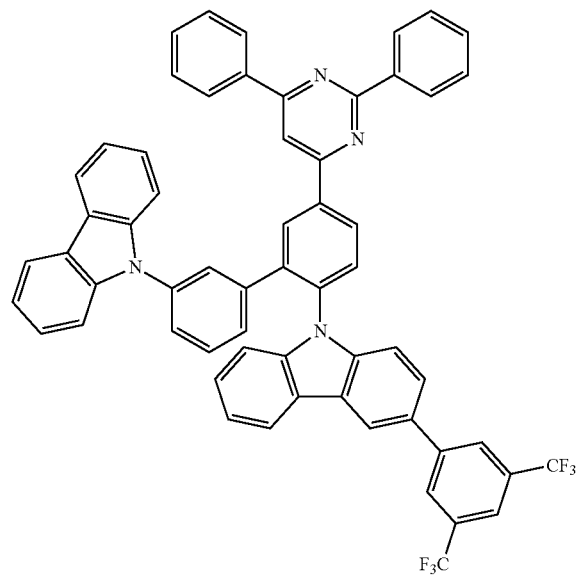
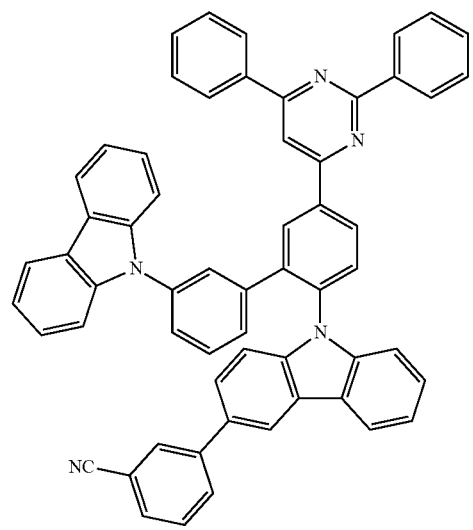

-continued
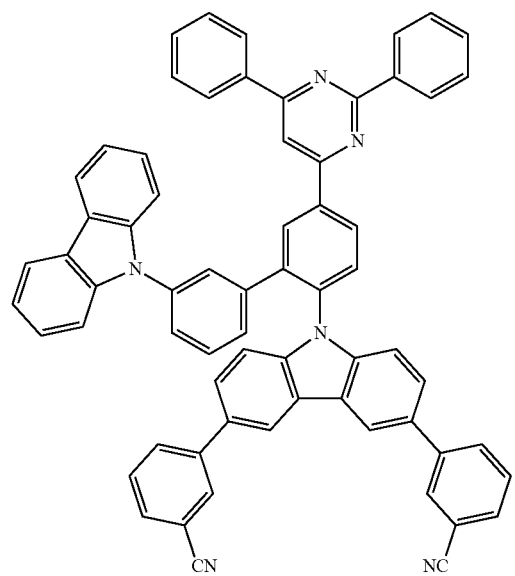
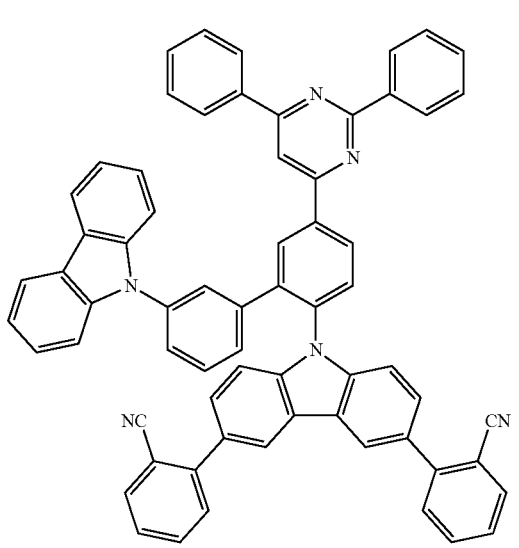
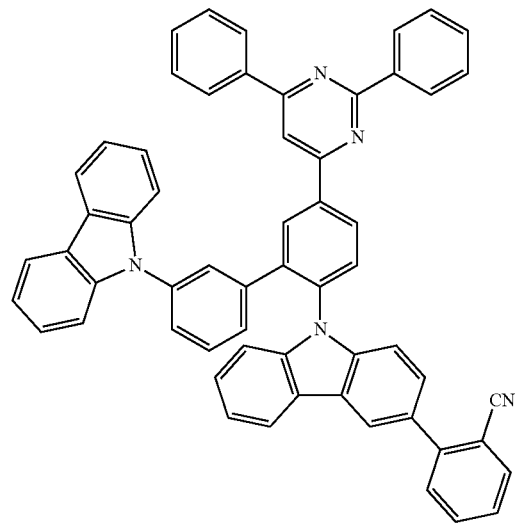
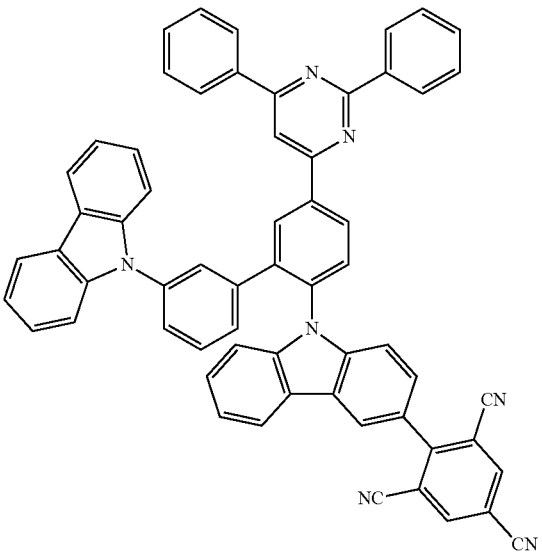
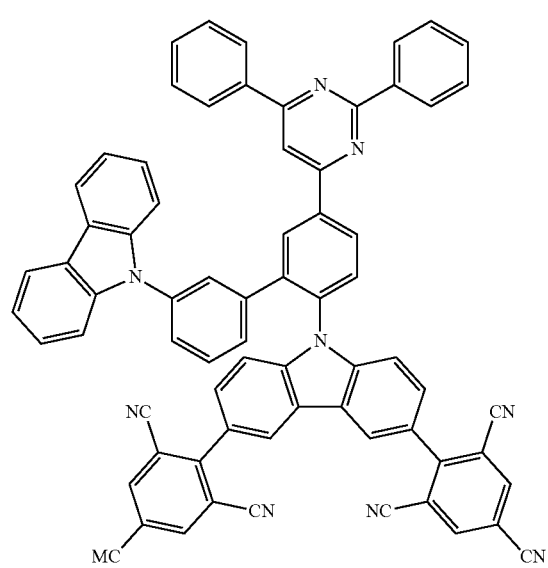

-continued
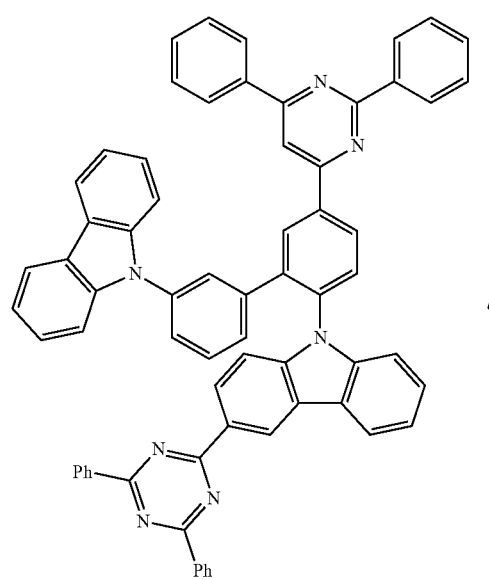
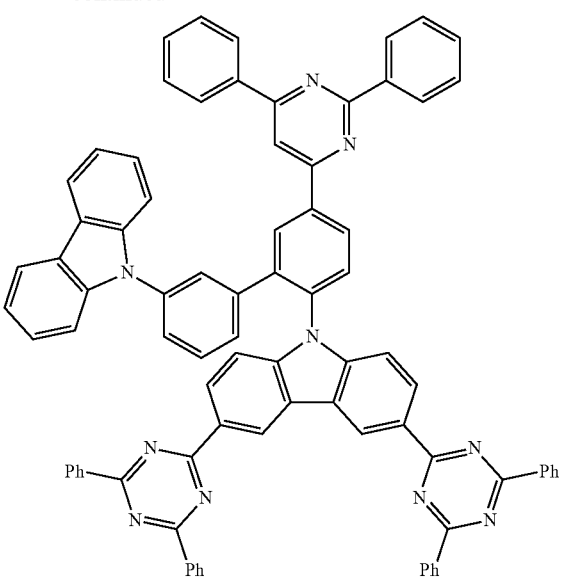
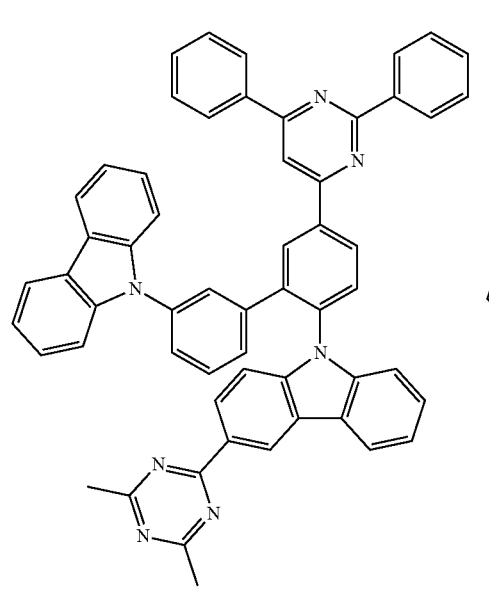
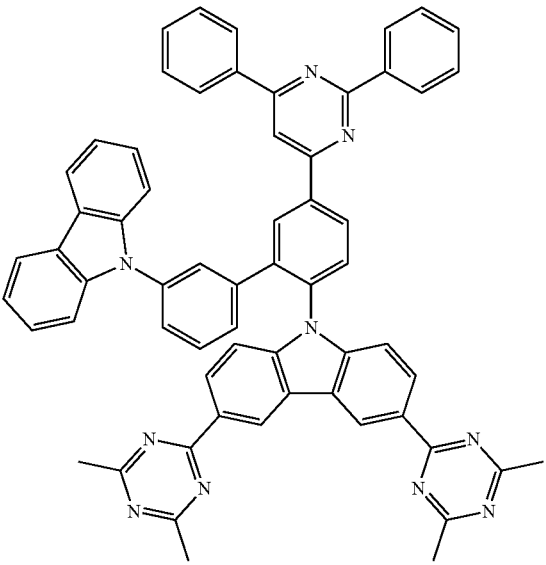
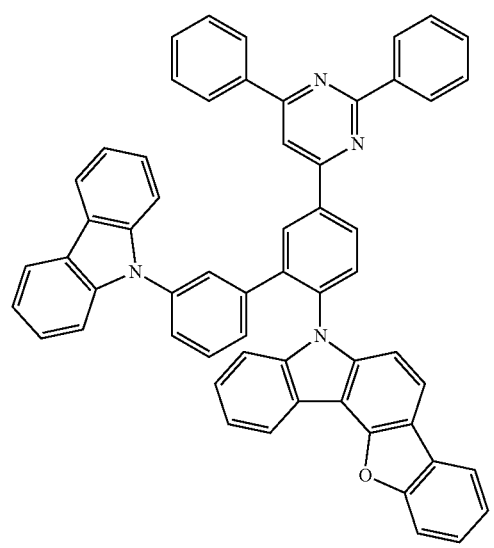
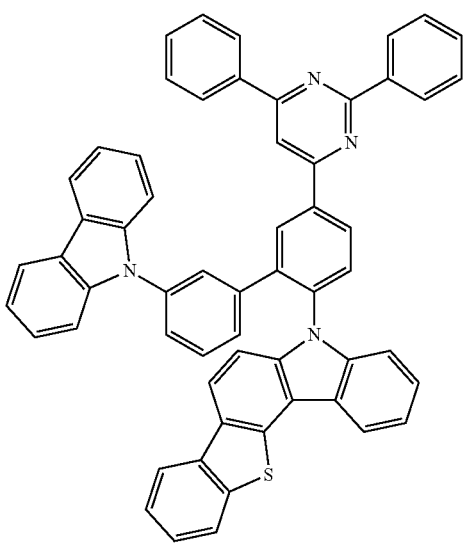

-continued
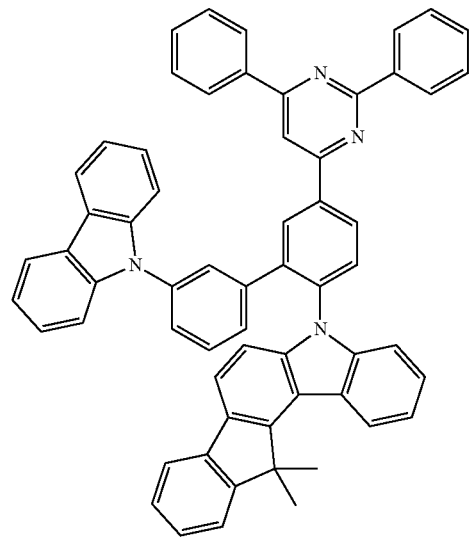
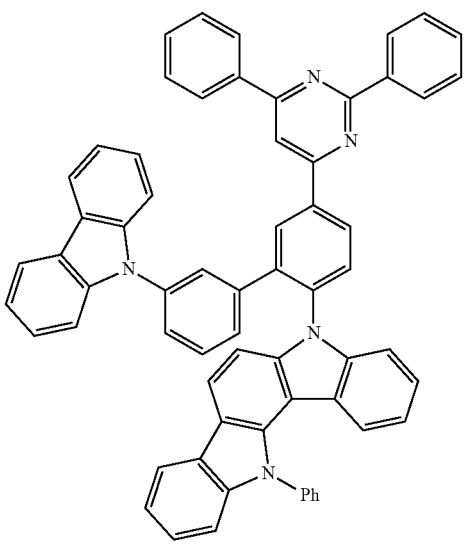
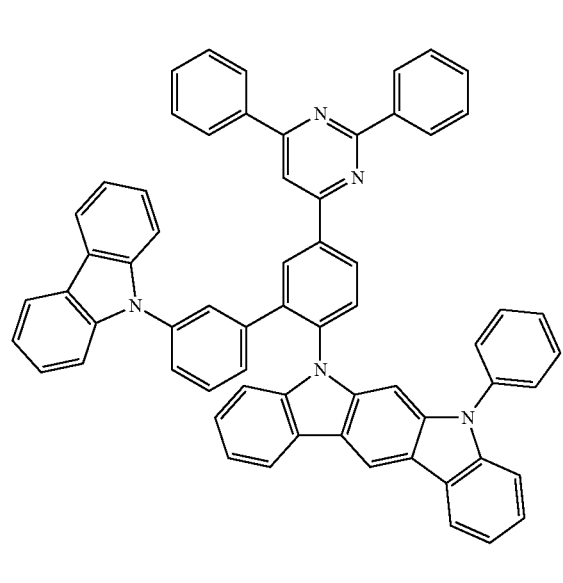
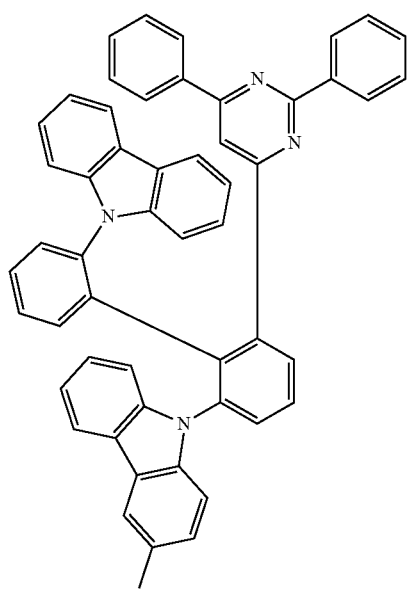

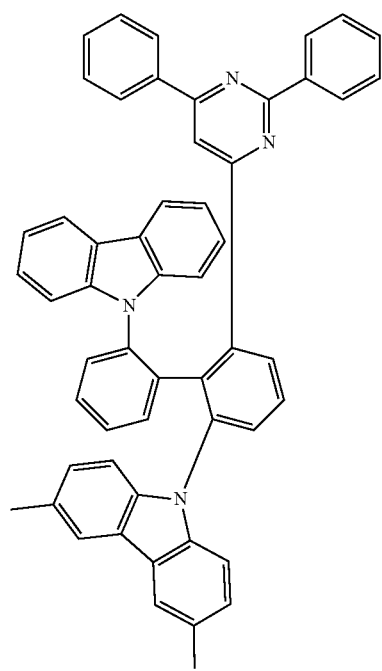
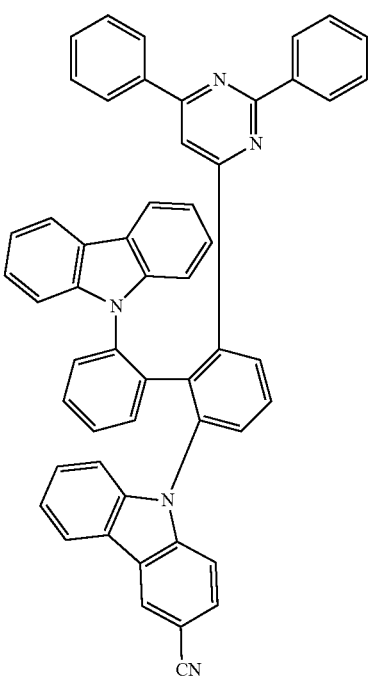
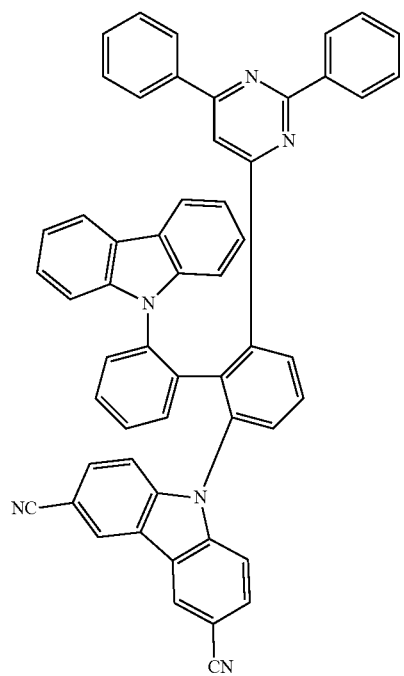
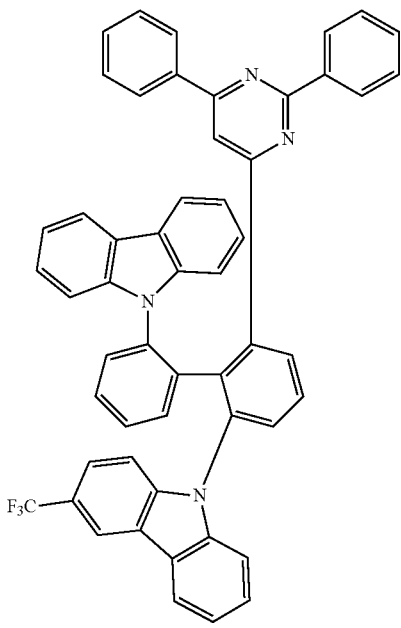

-continued
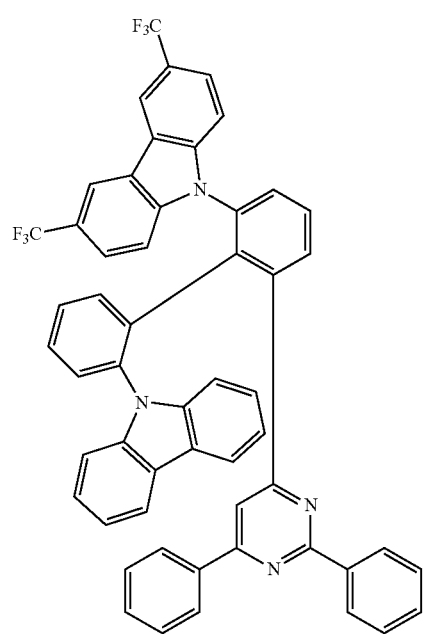
187
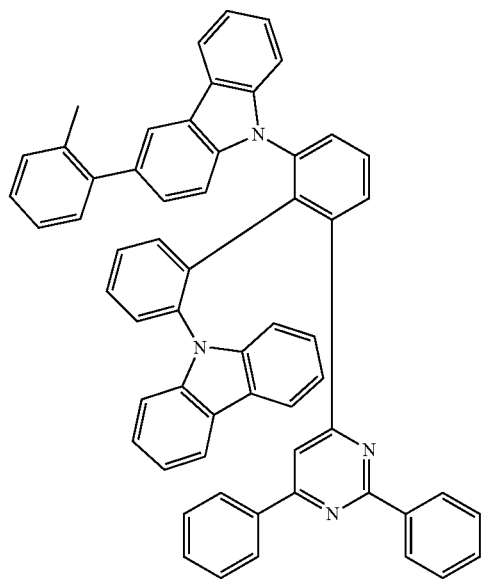
188
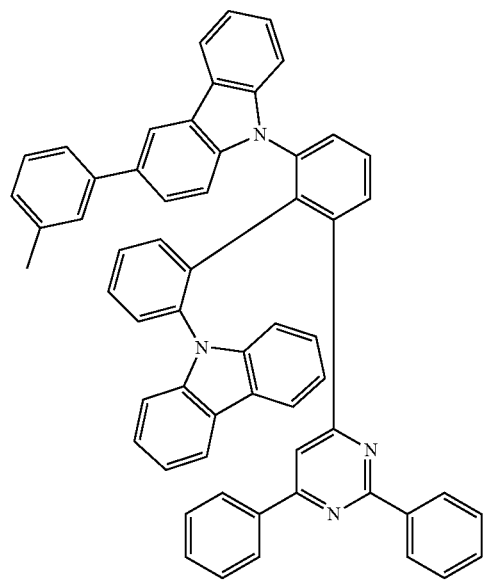
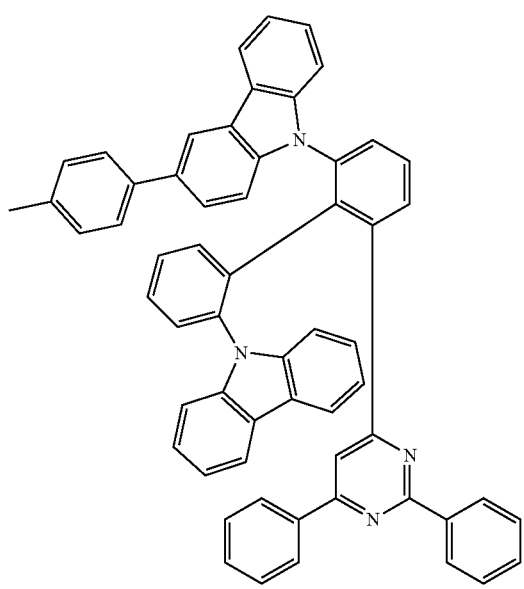

-continued
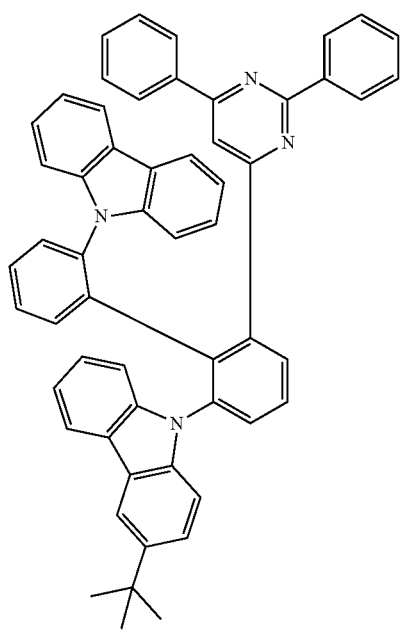
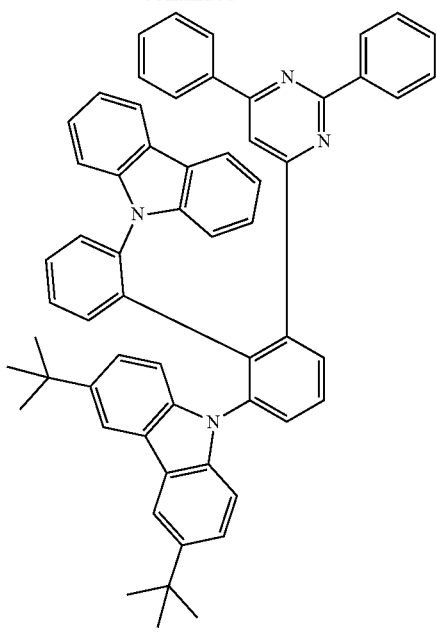
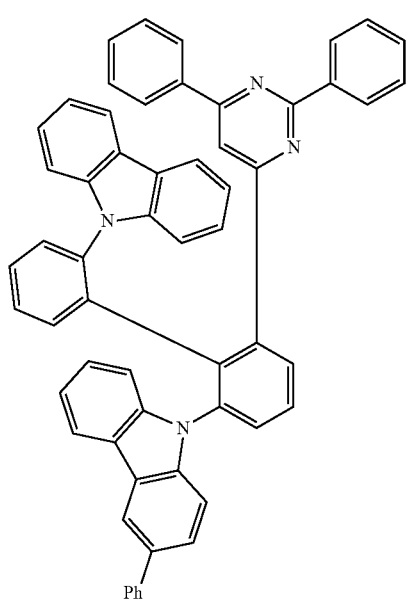
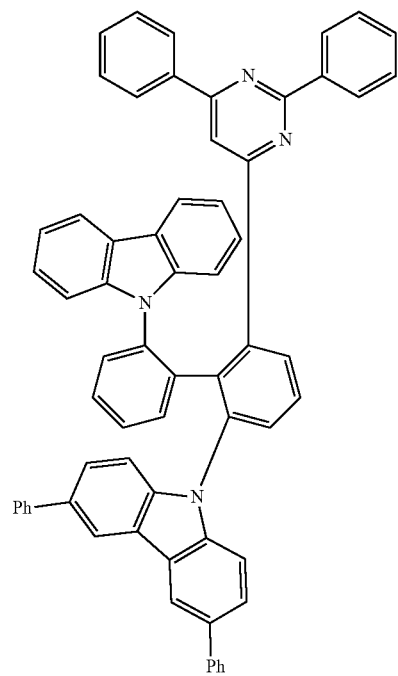

-continued
191
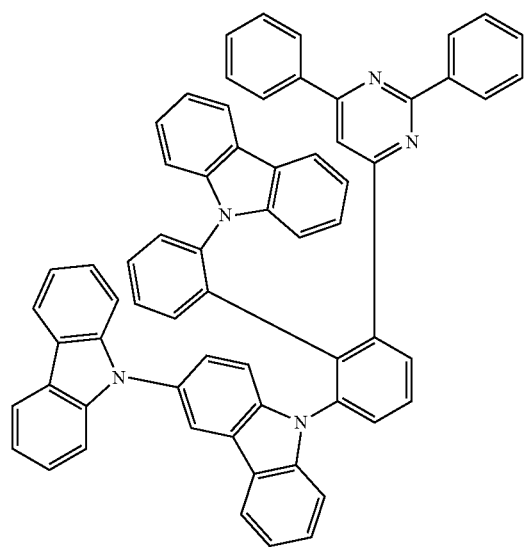
192
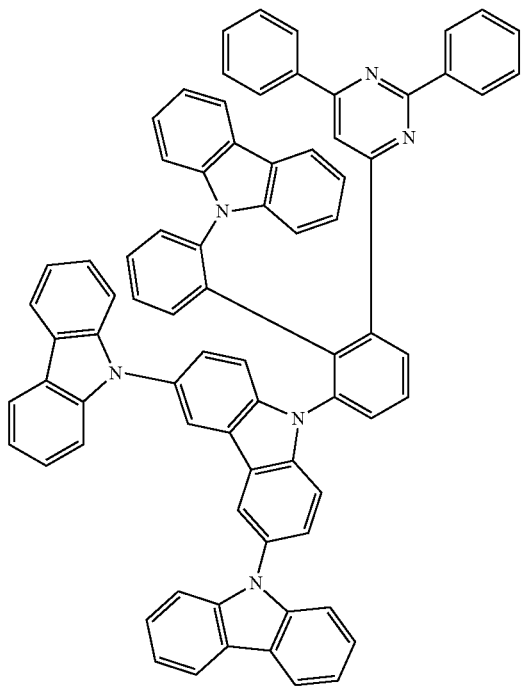
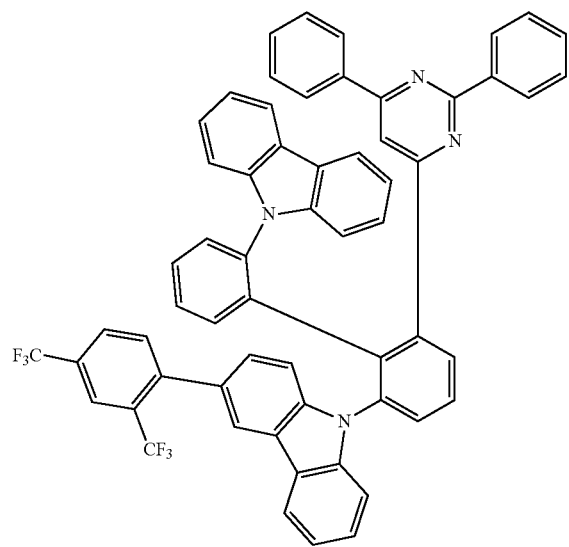

193
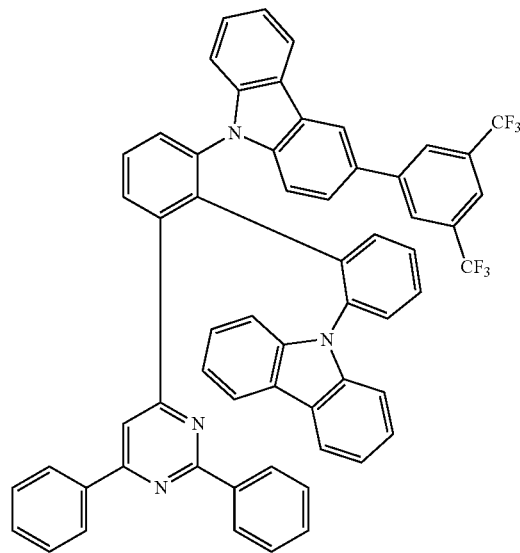
194
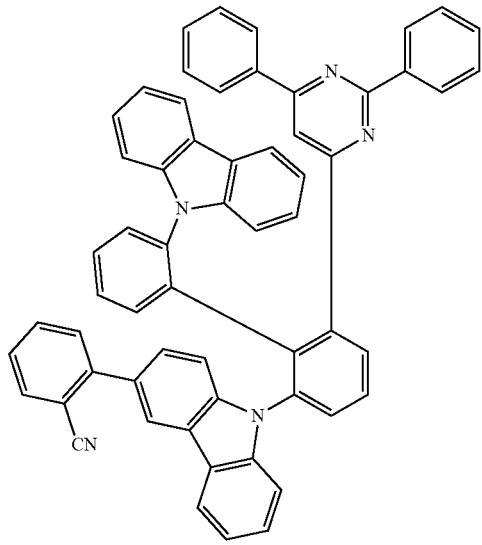
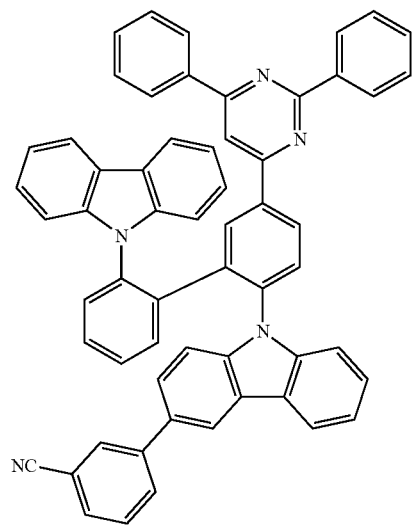

-continued
195
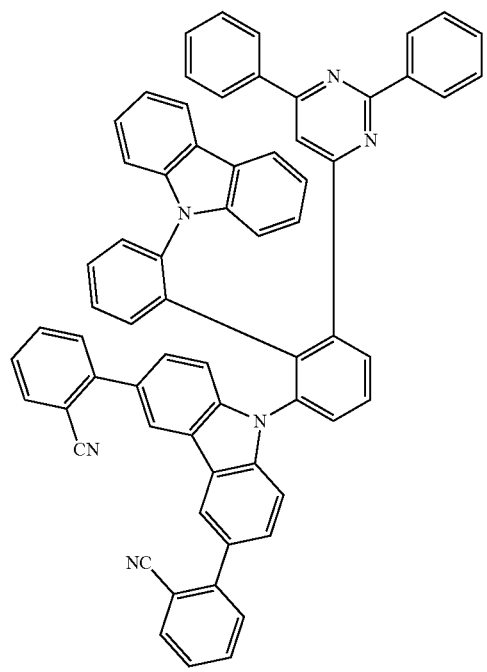
196
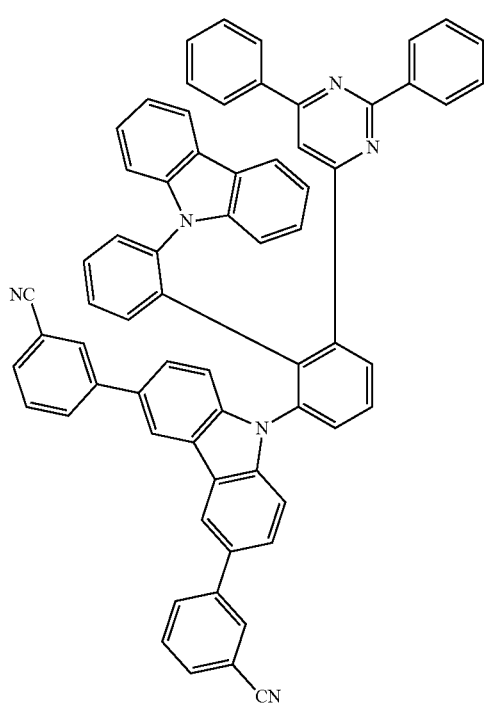
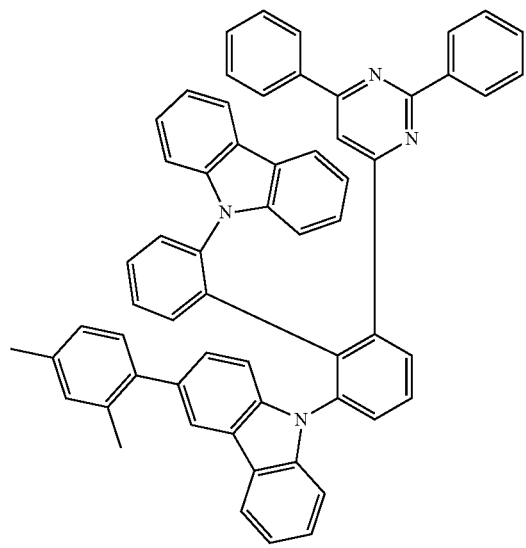
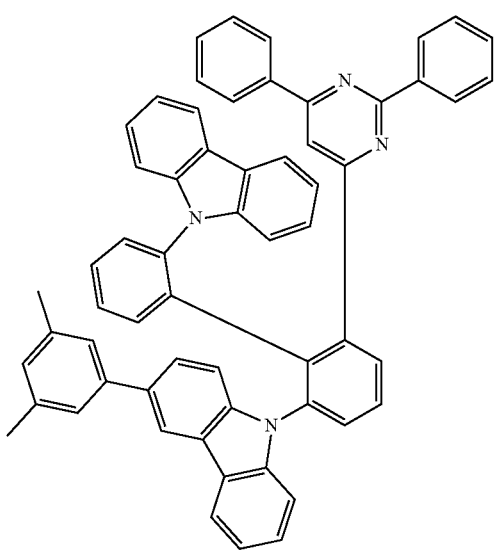

197 198
-continued
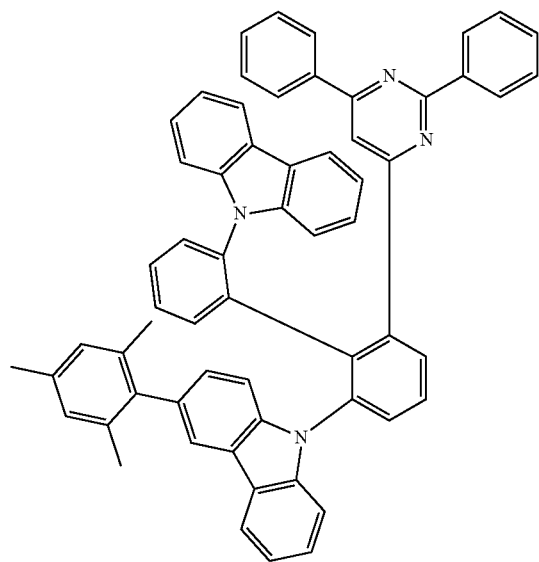
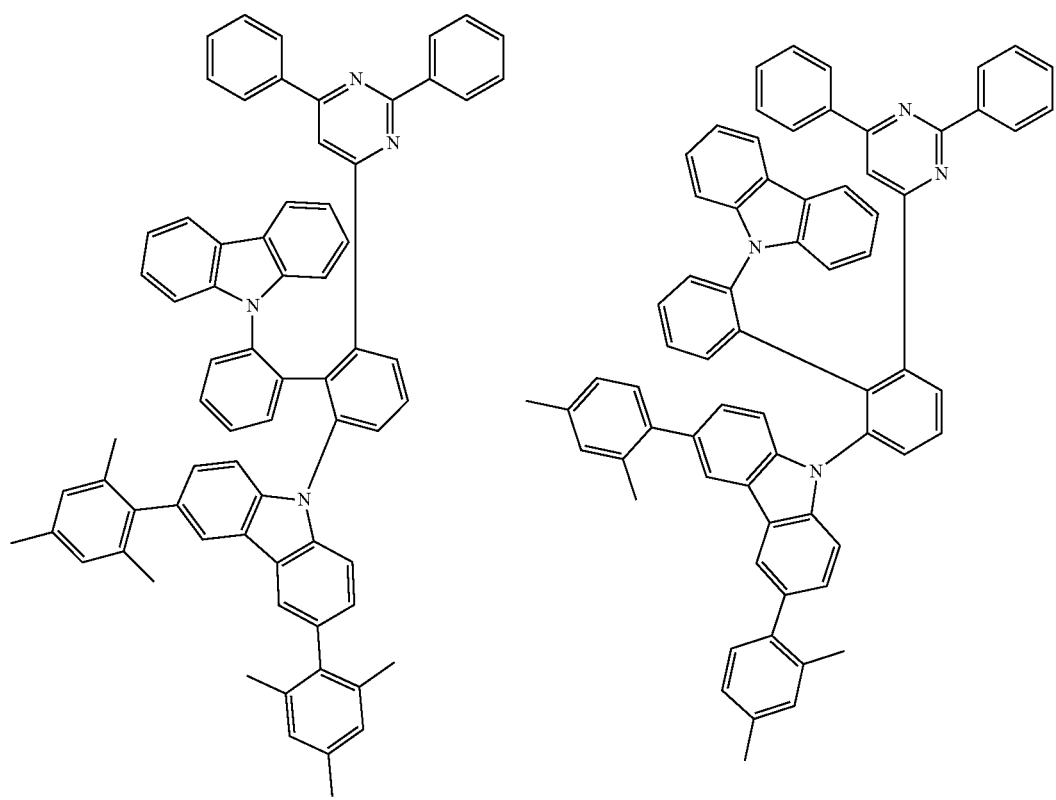

199
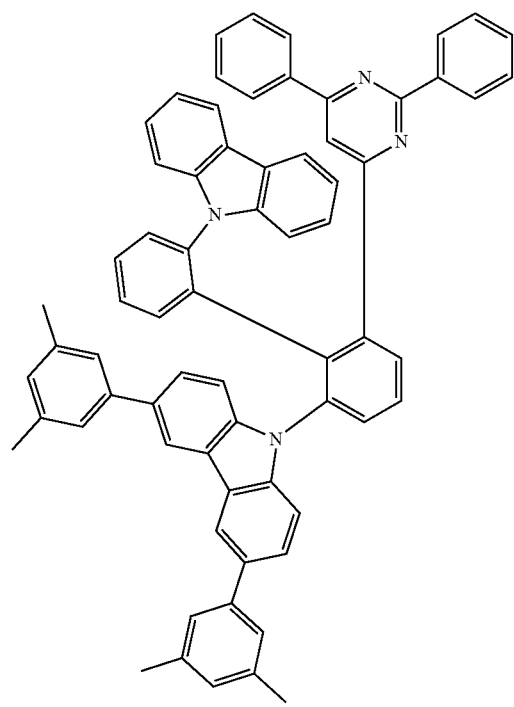
200
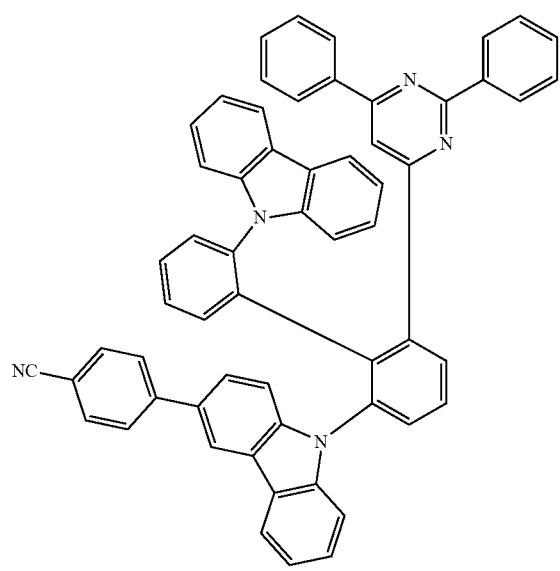
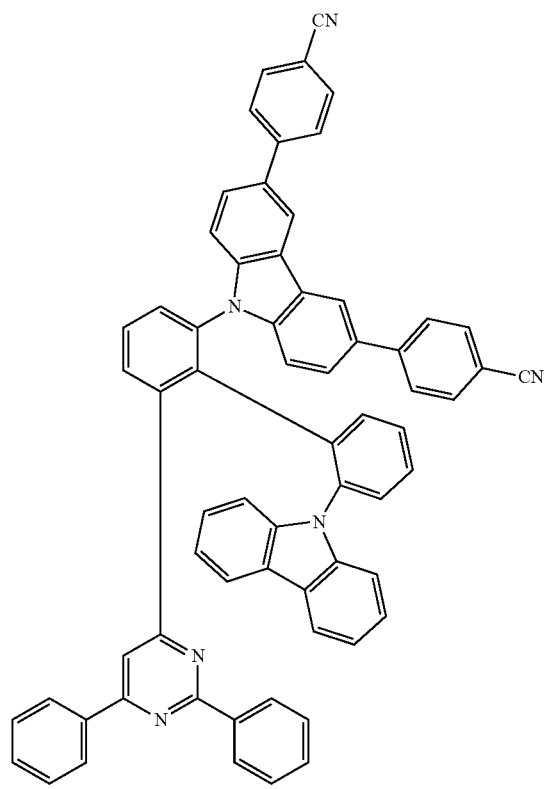
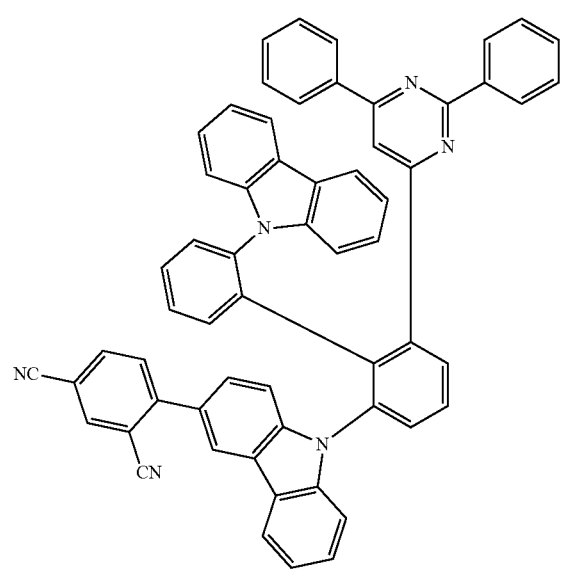

-continued
201
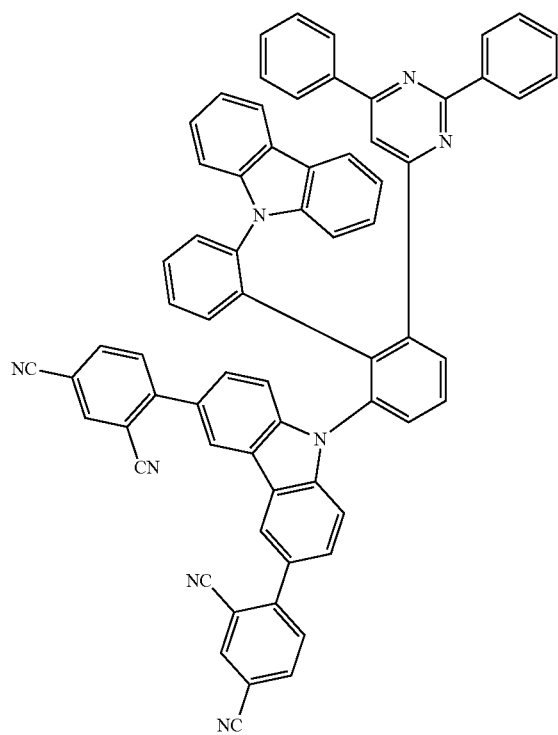
202
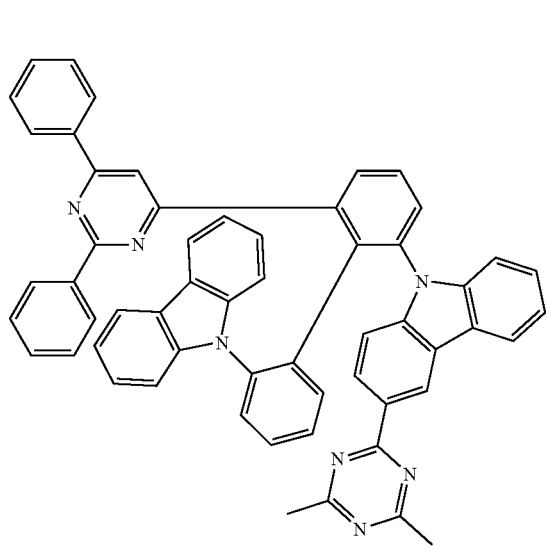
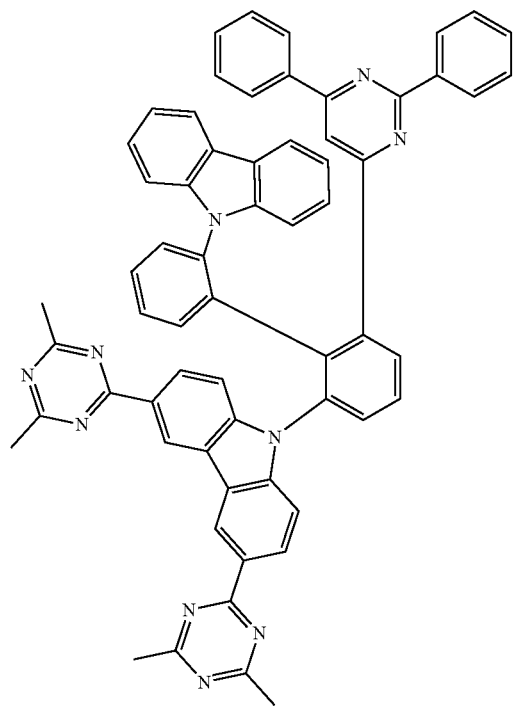
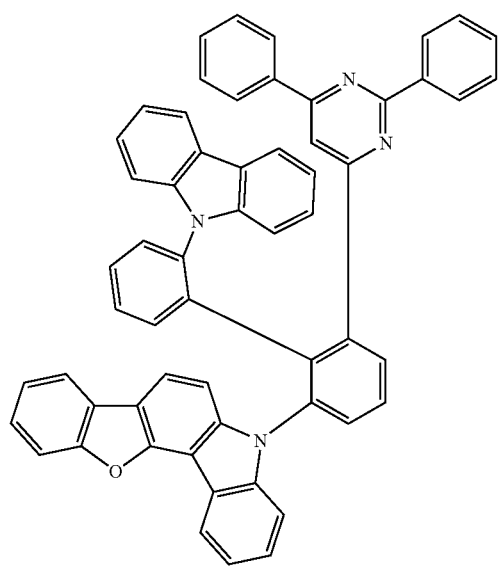

203
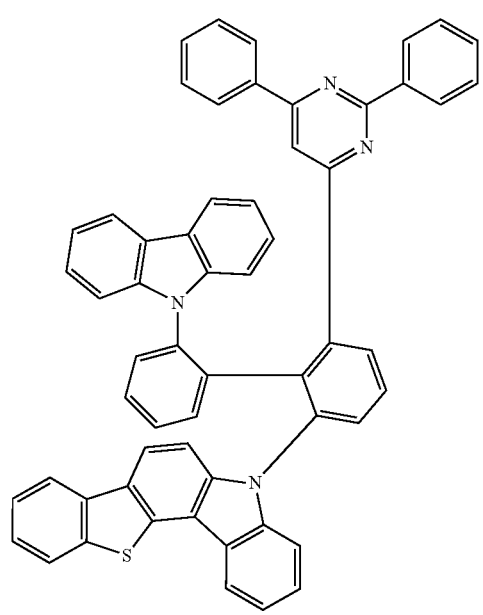
204
-continued
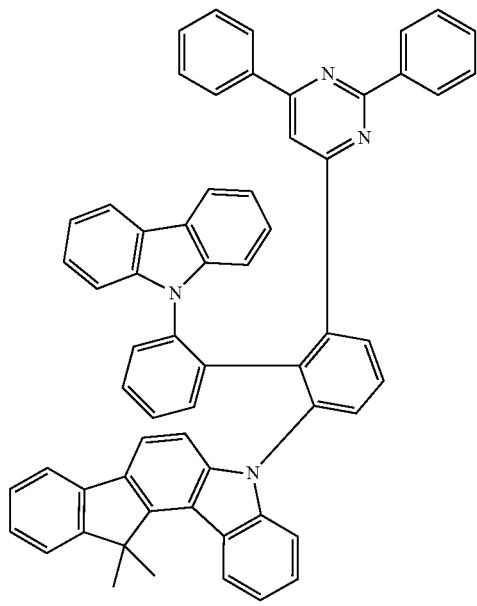
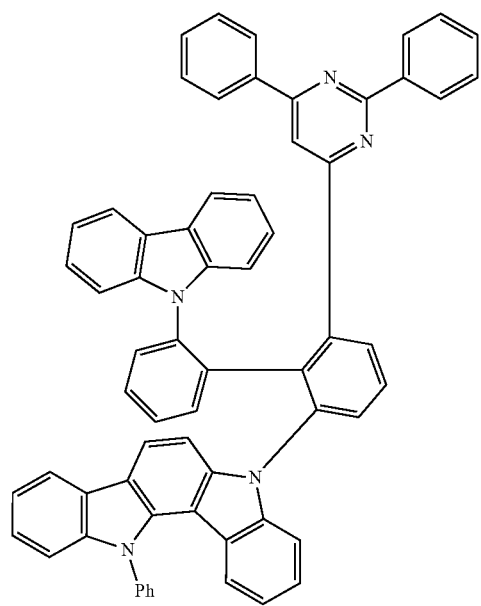

205
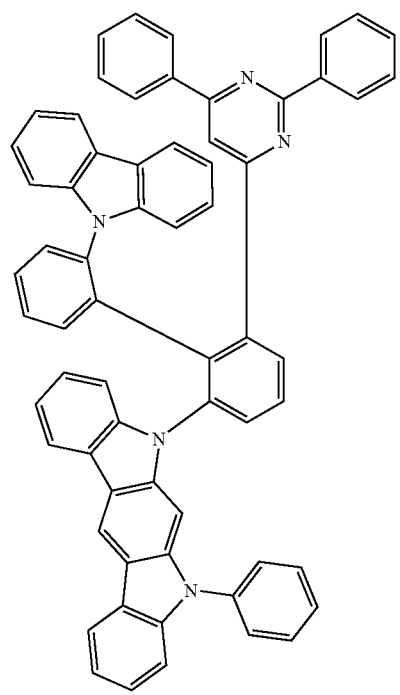
206
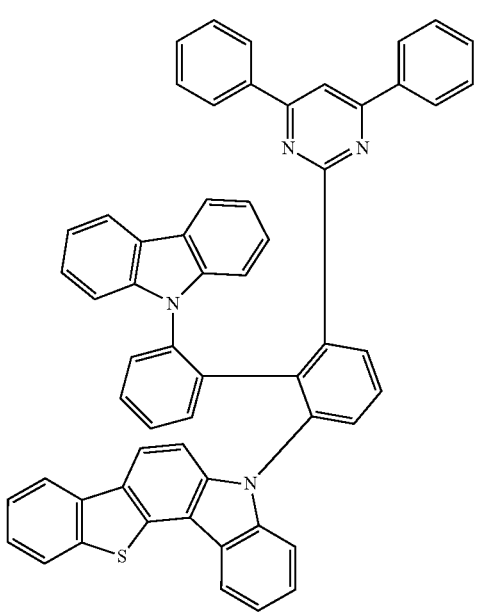
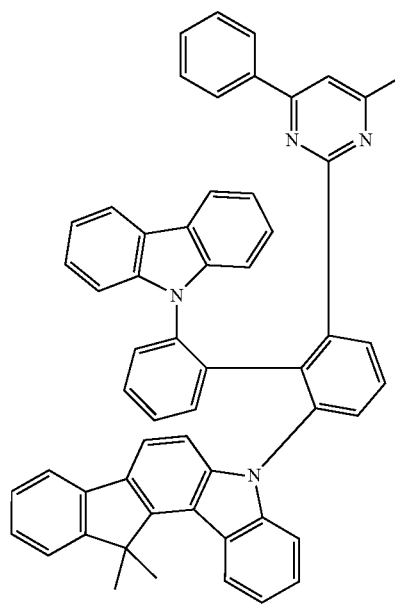
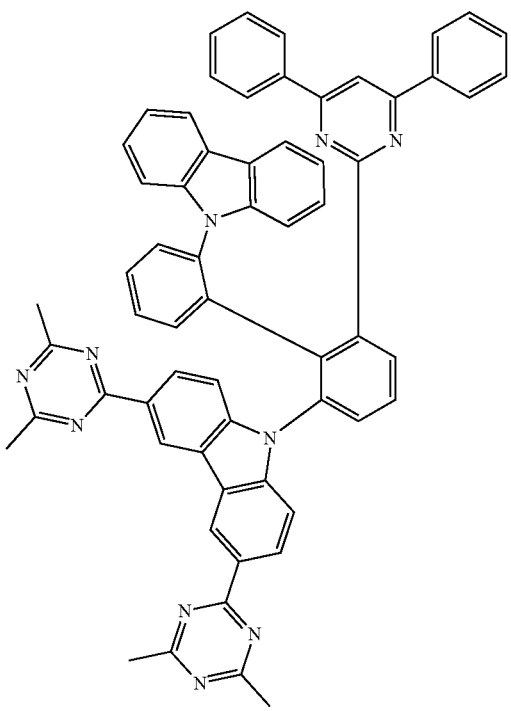

207
-continued
208
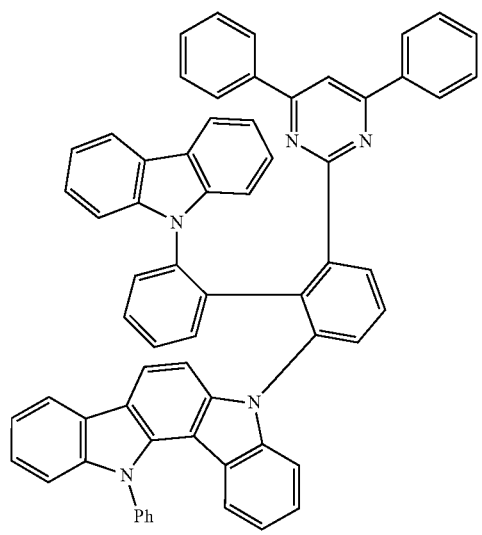
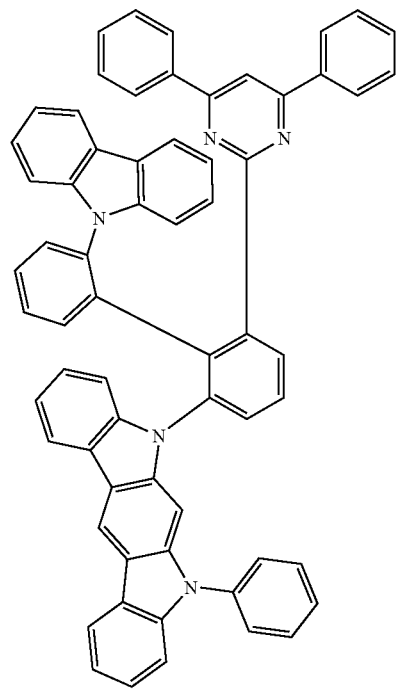
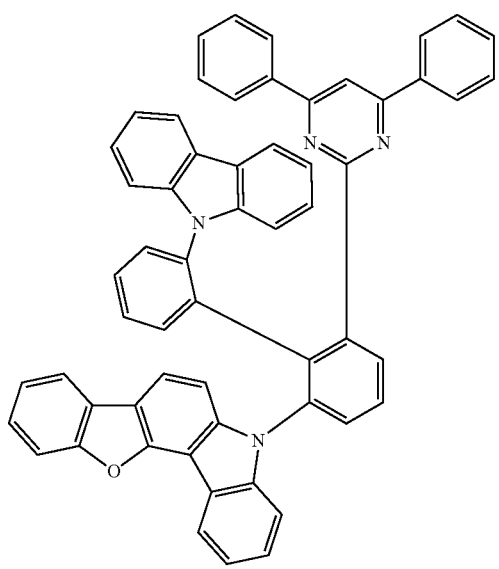
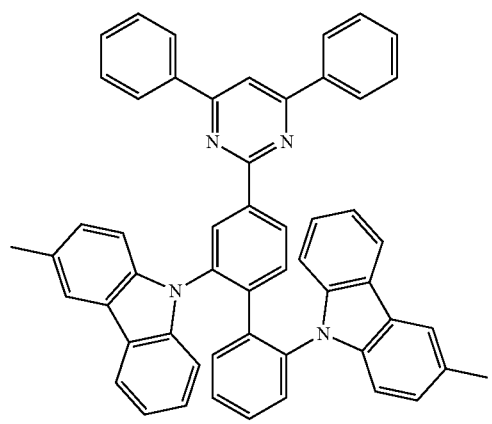
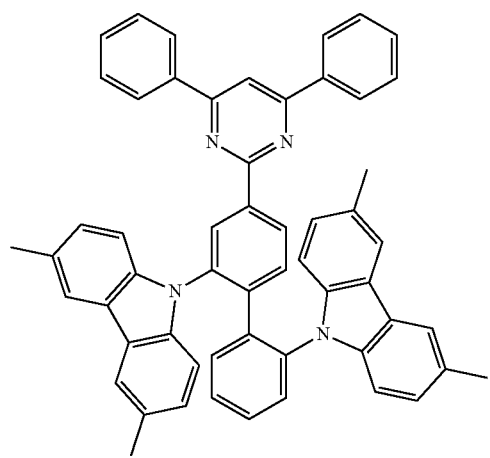

209
210
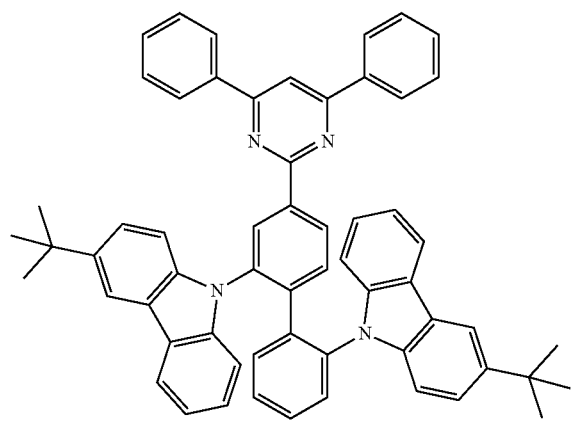
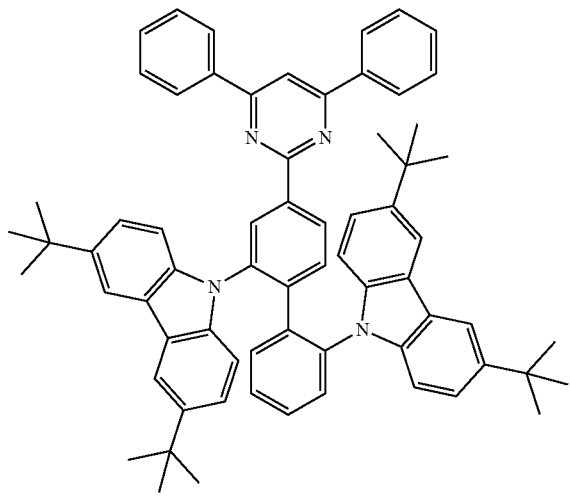
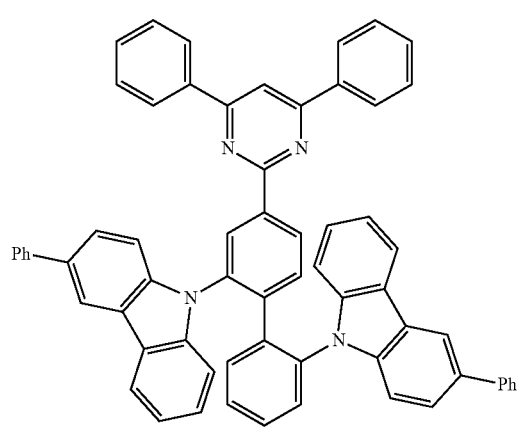
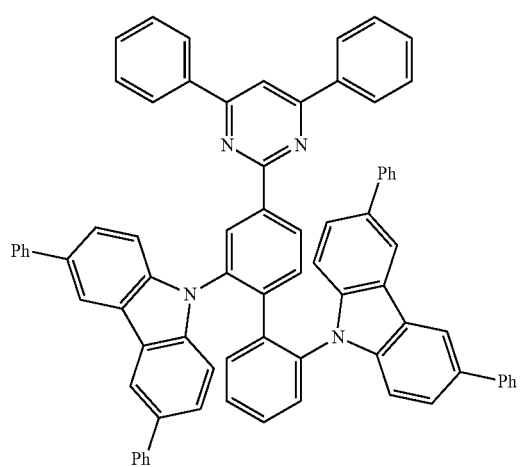
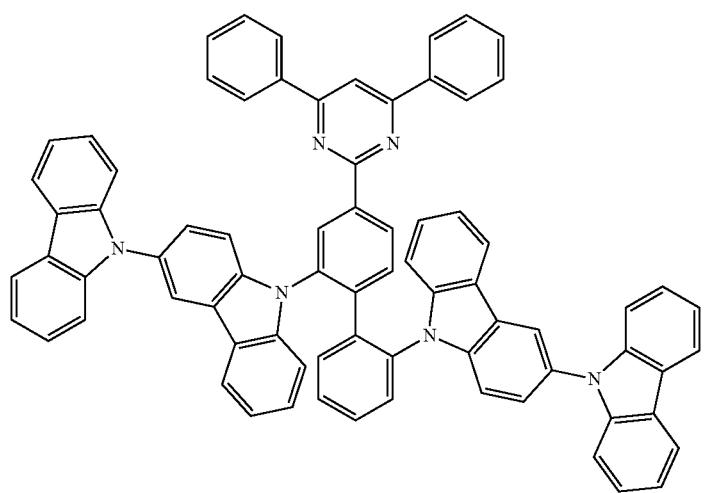

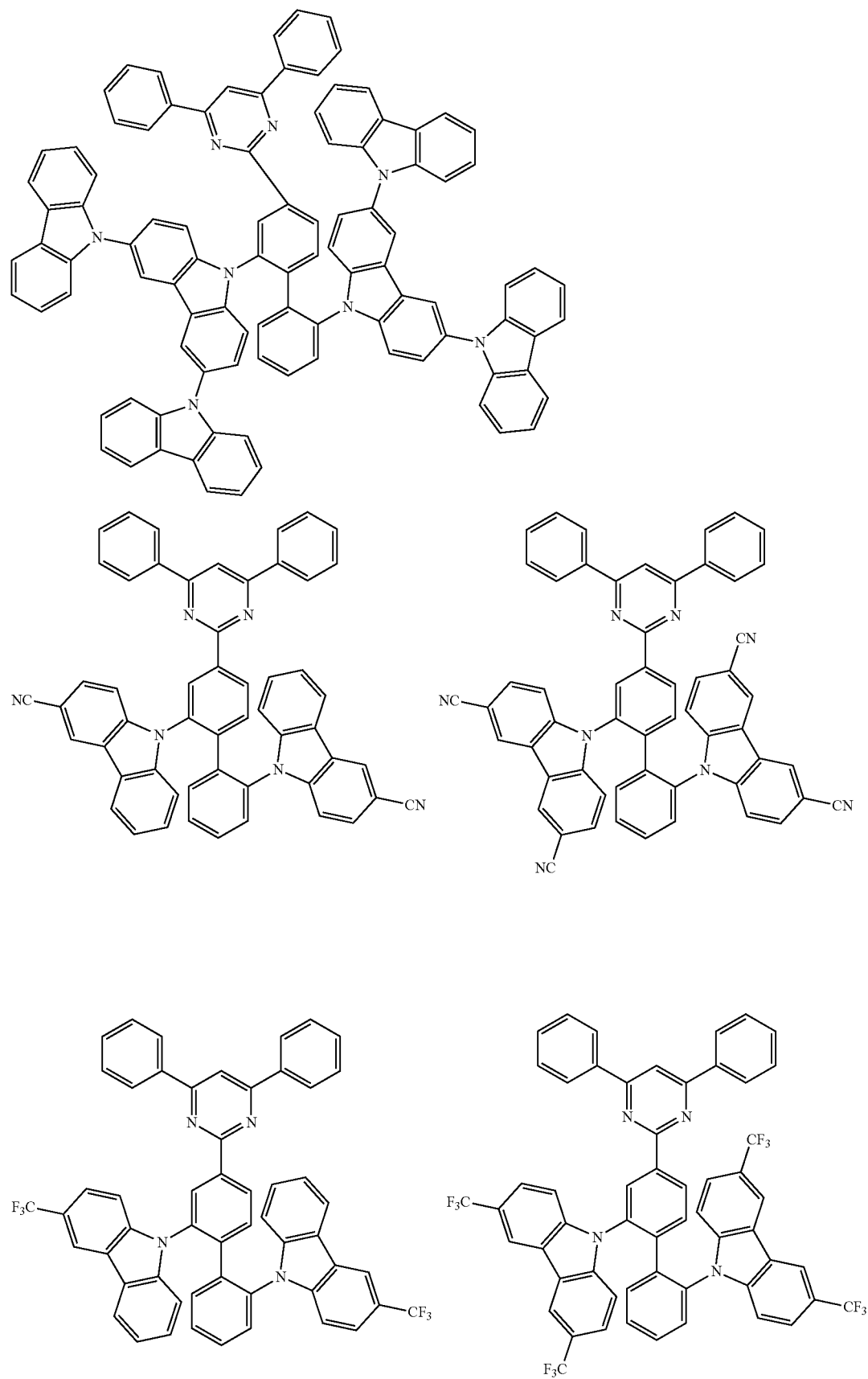

-continued
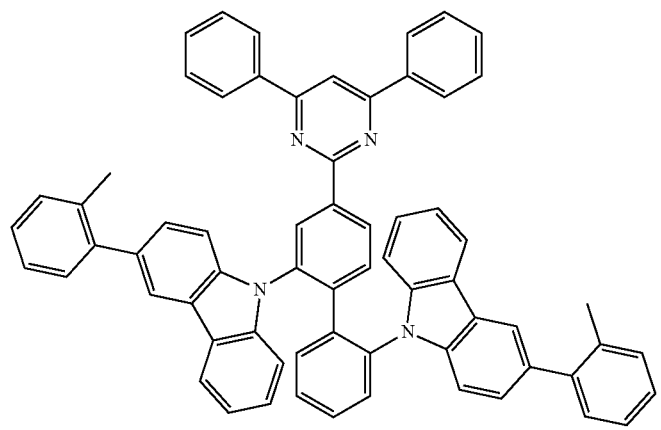
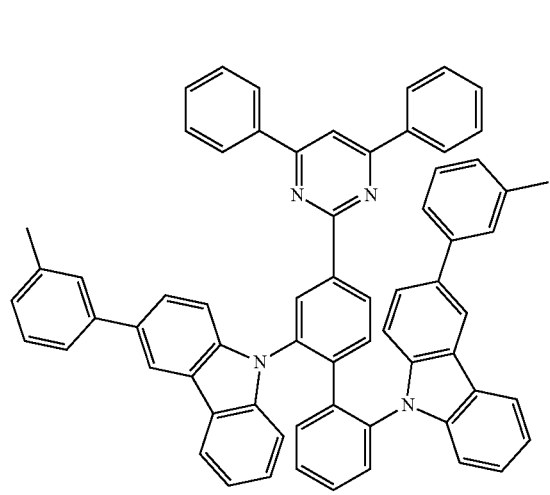
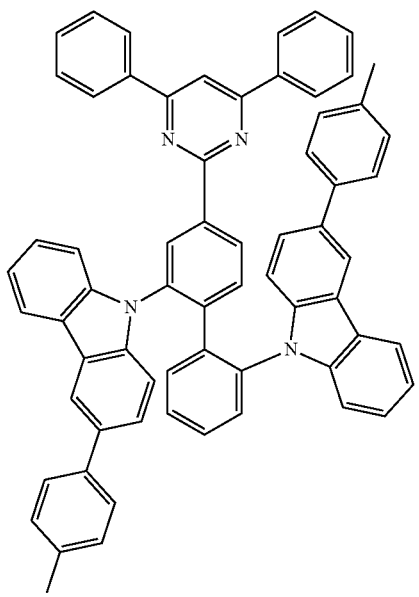
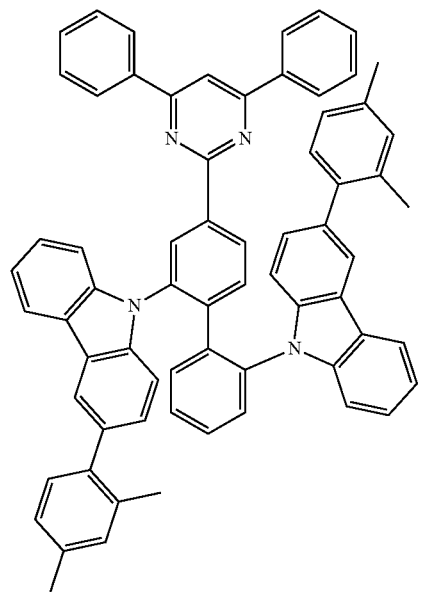
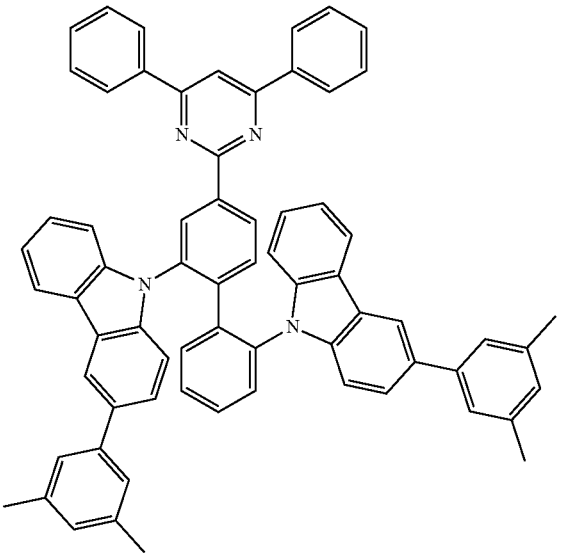

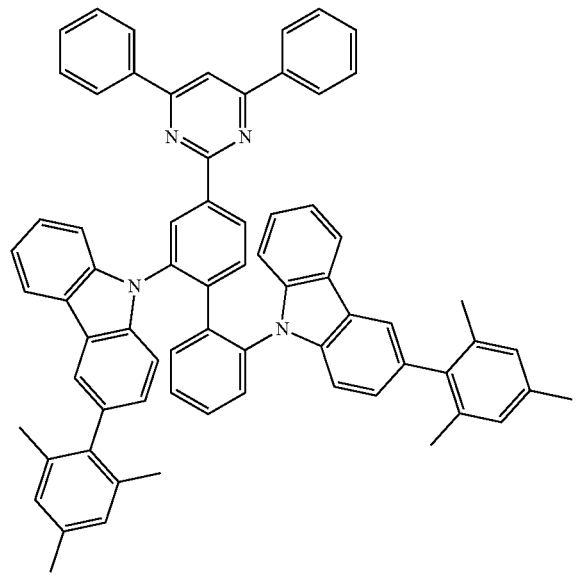
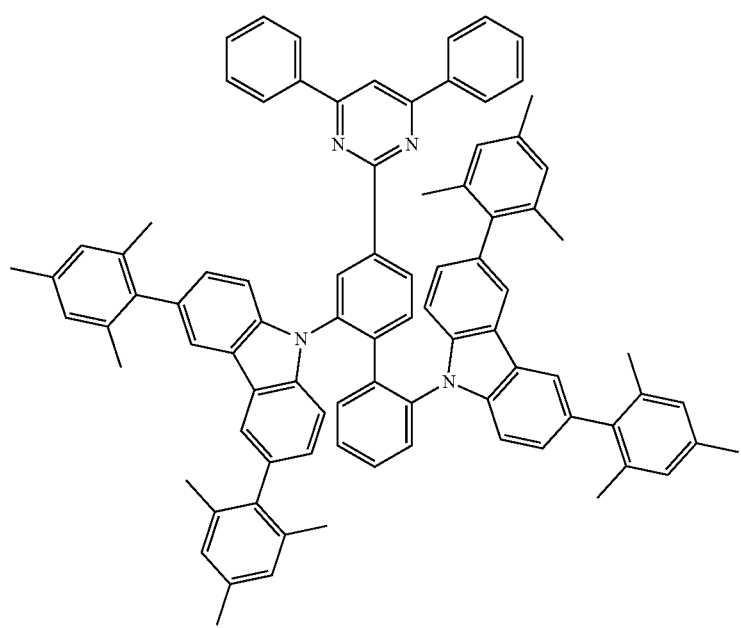

-continued
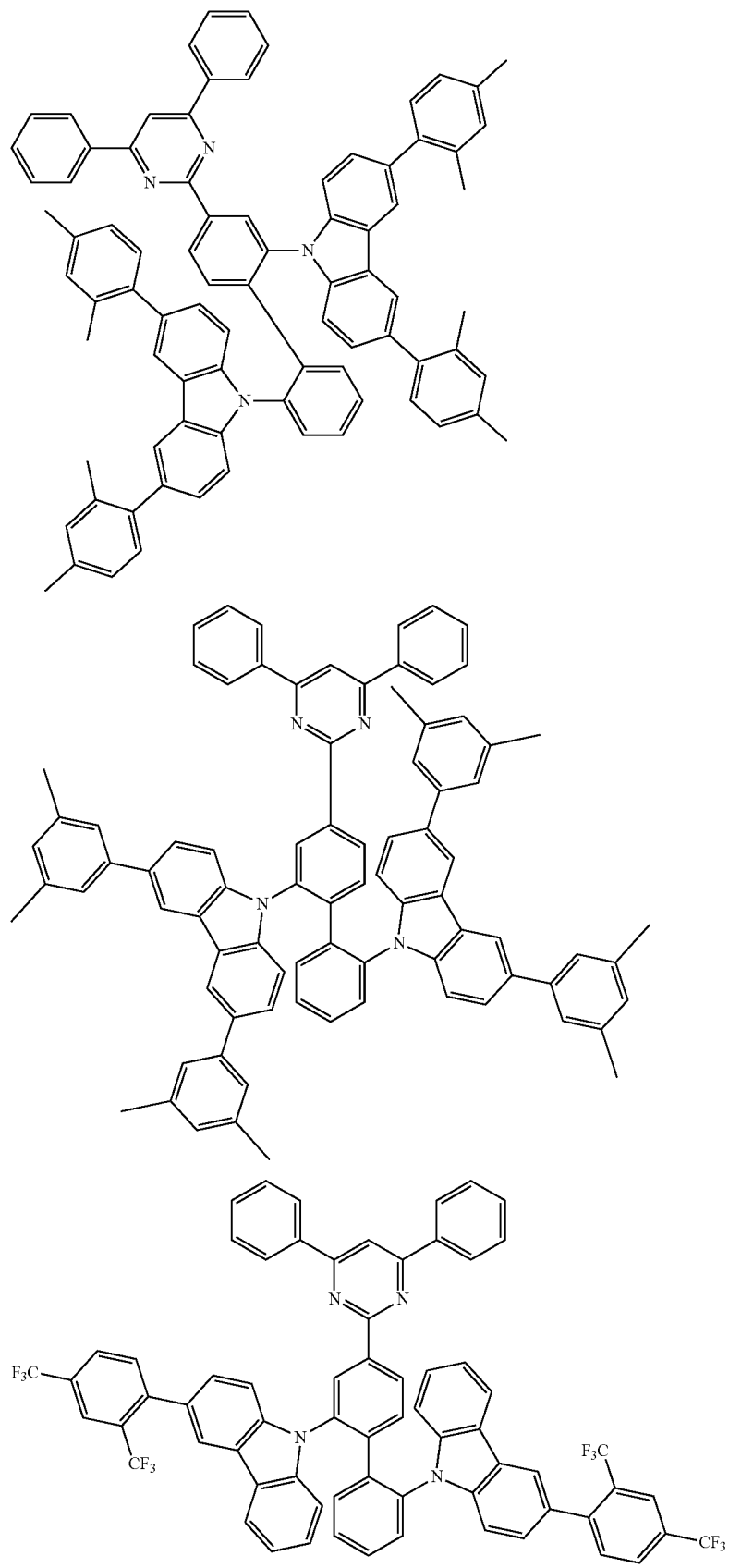

219 220
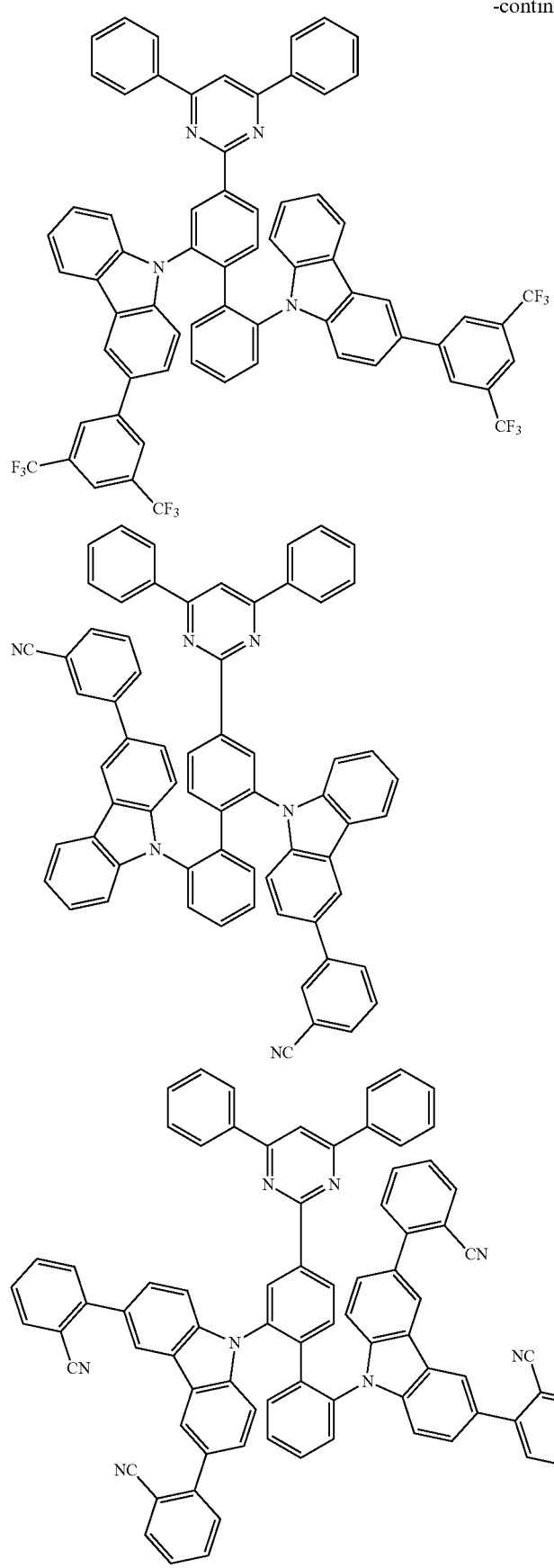
-continued

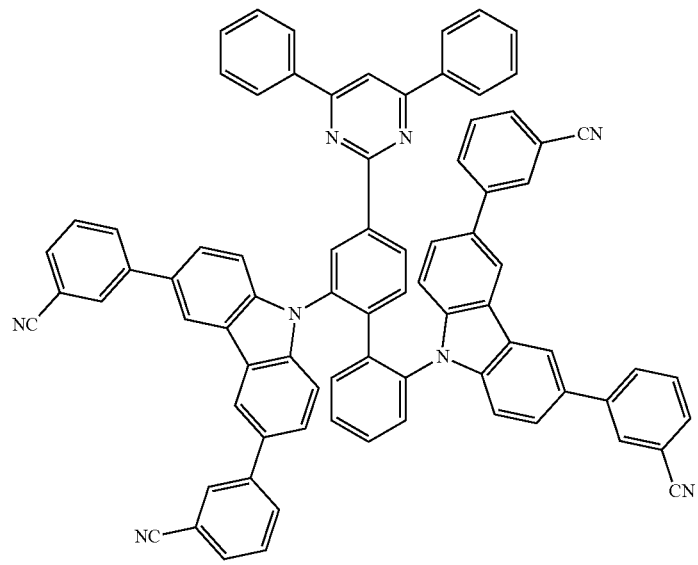
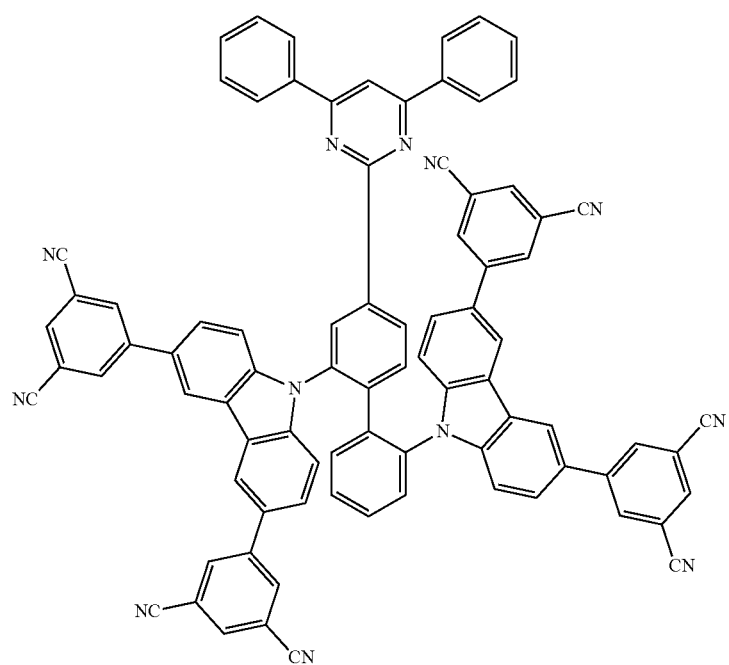

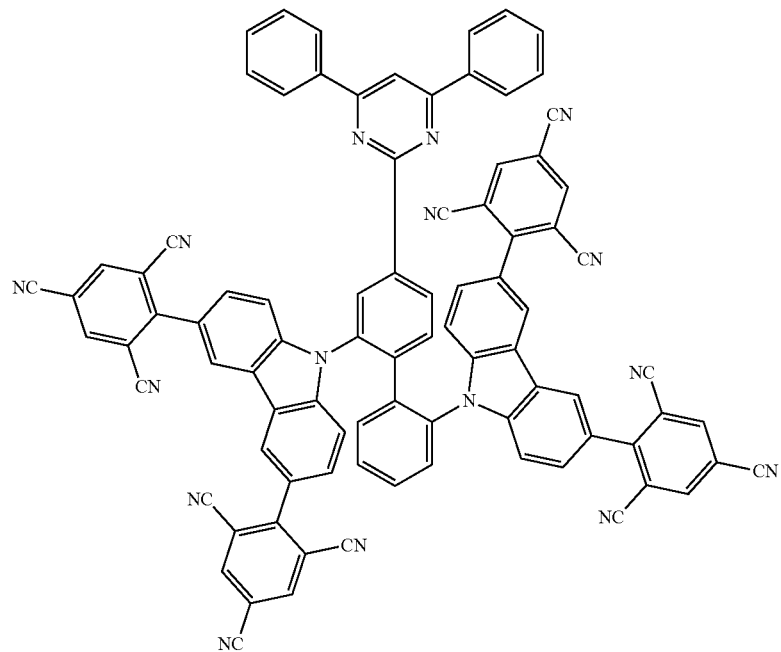
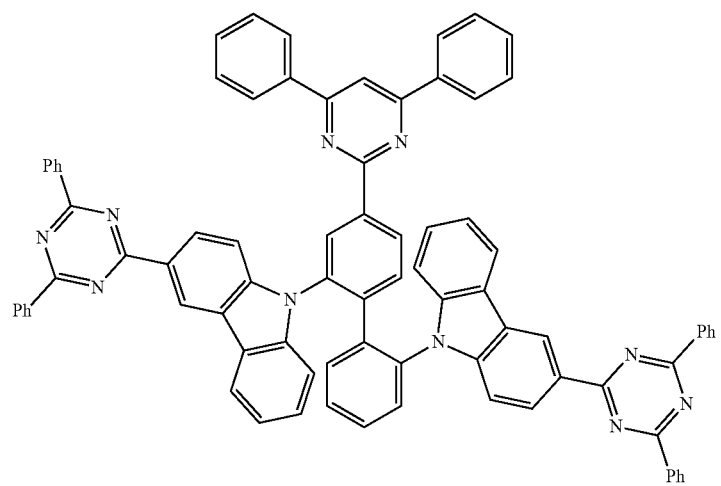

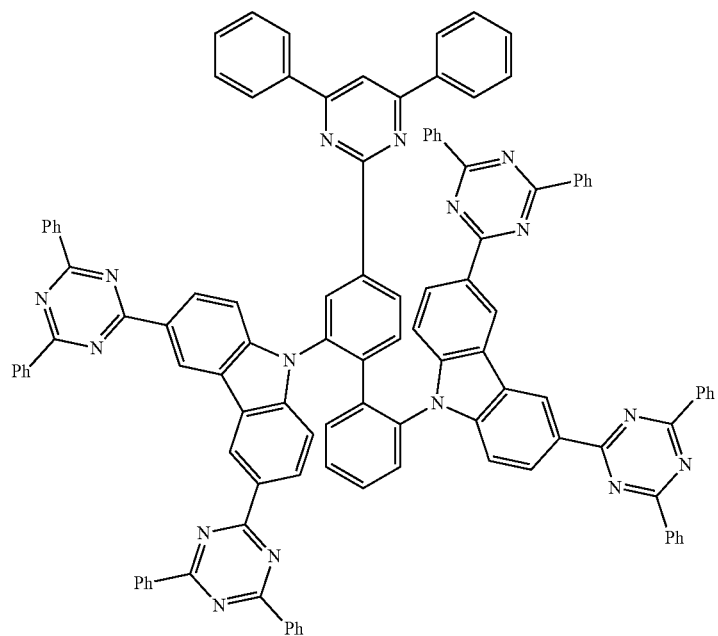
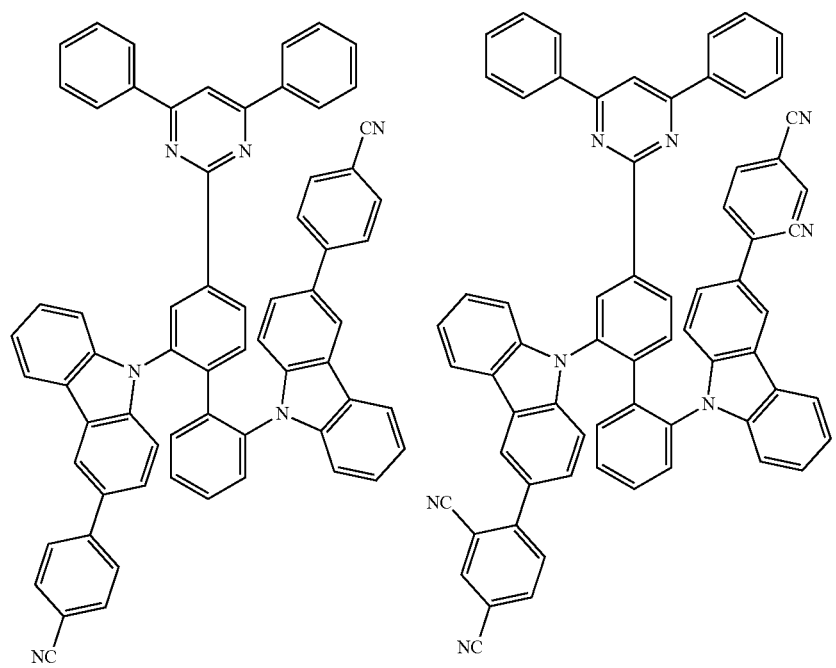

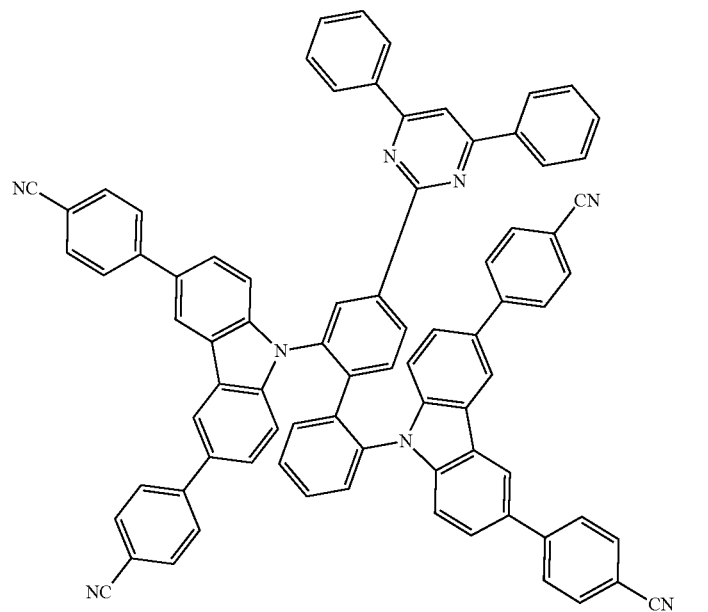
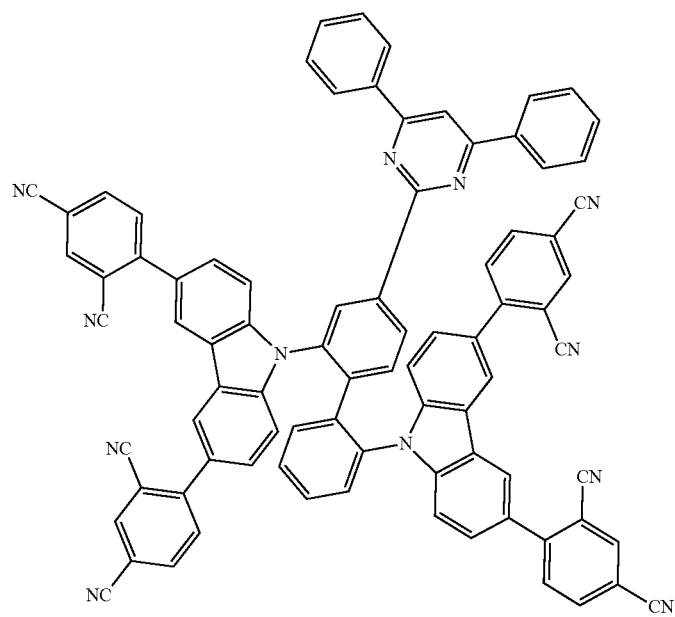
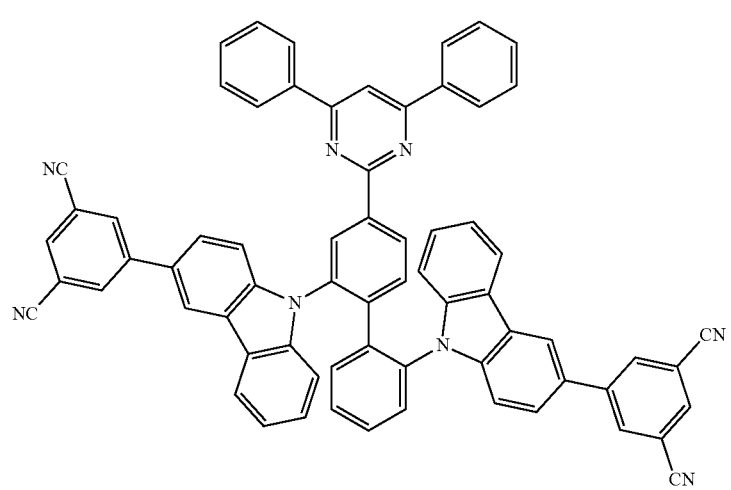

229 230
-continued
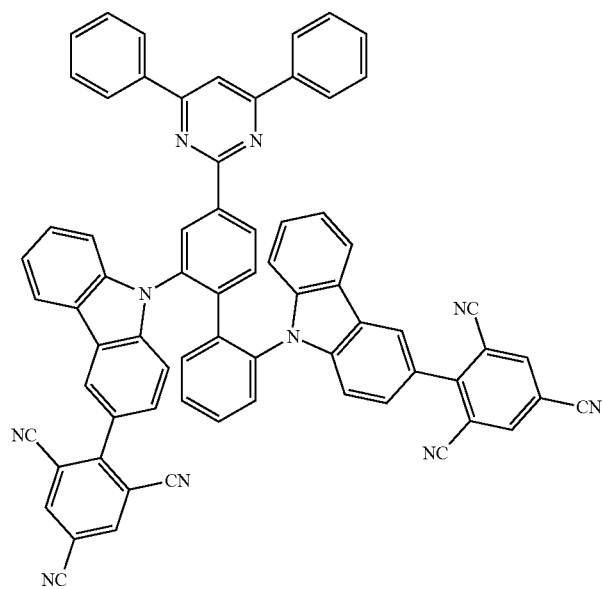 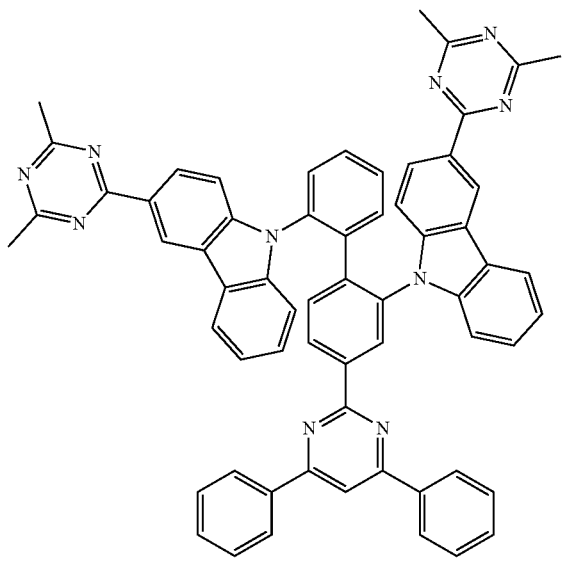
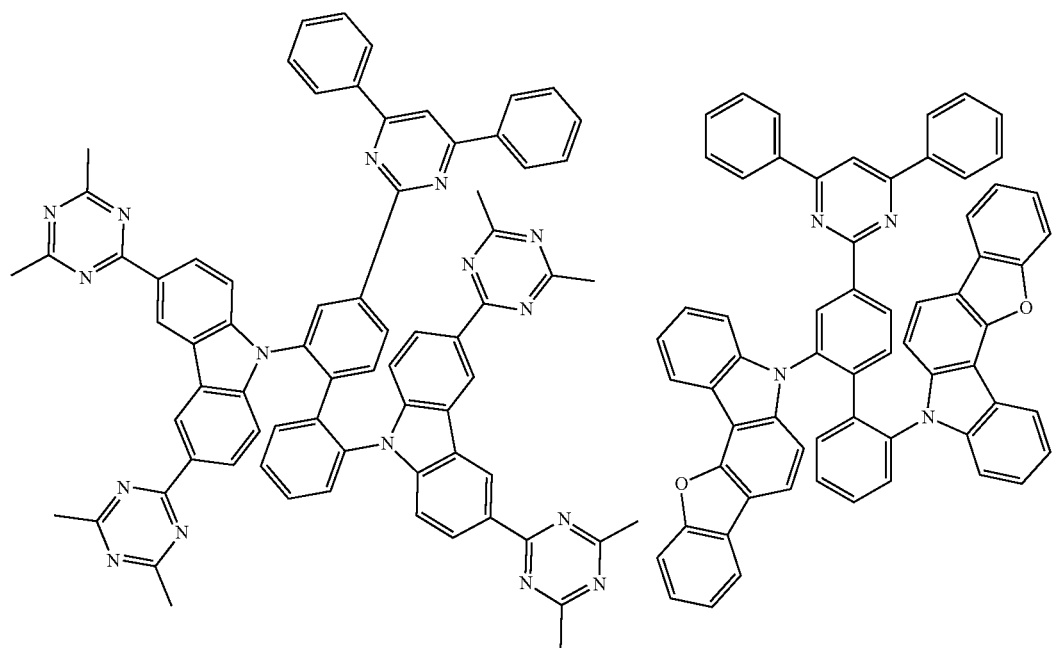

231
232
-continued
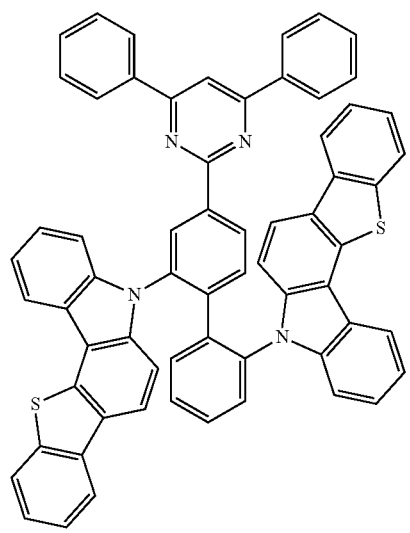
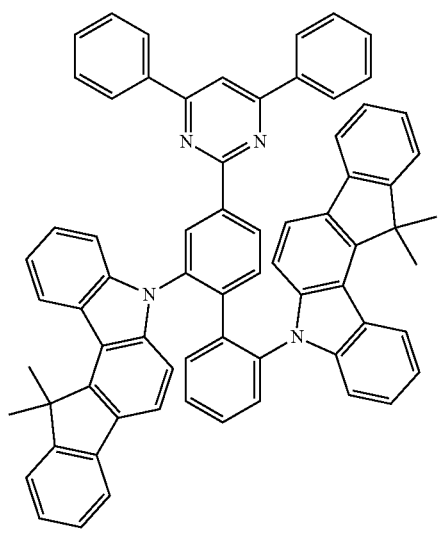
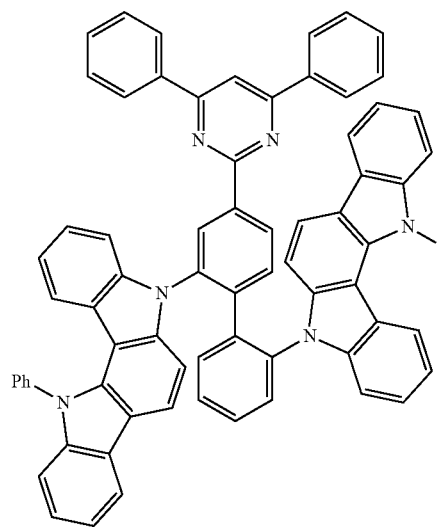
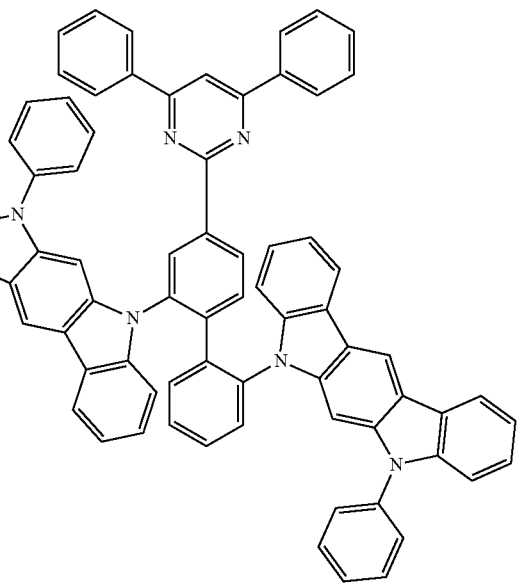
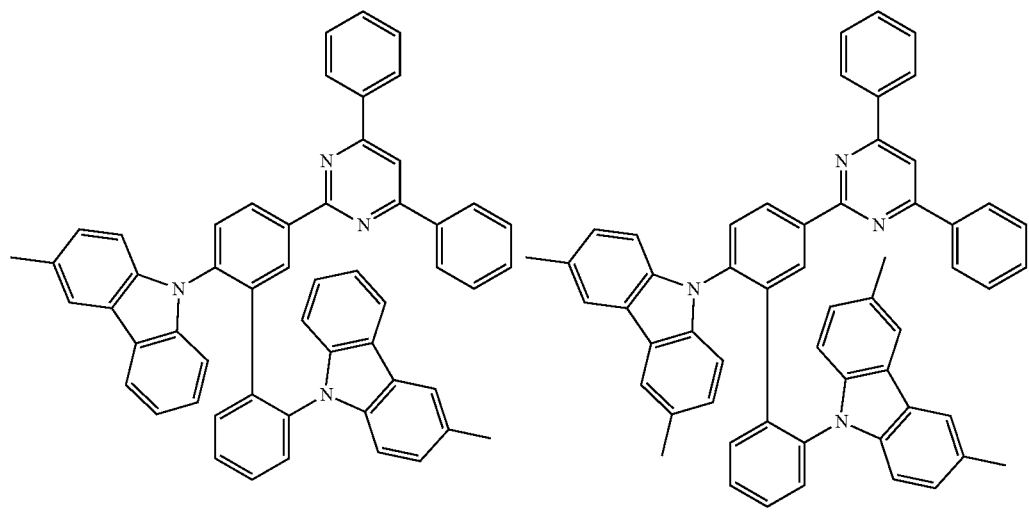

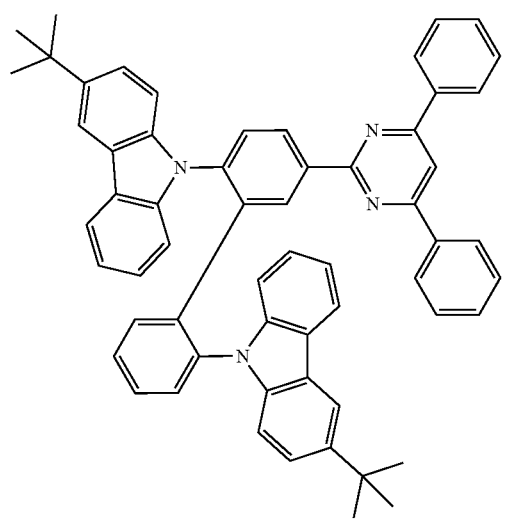
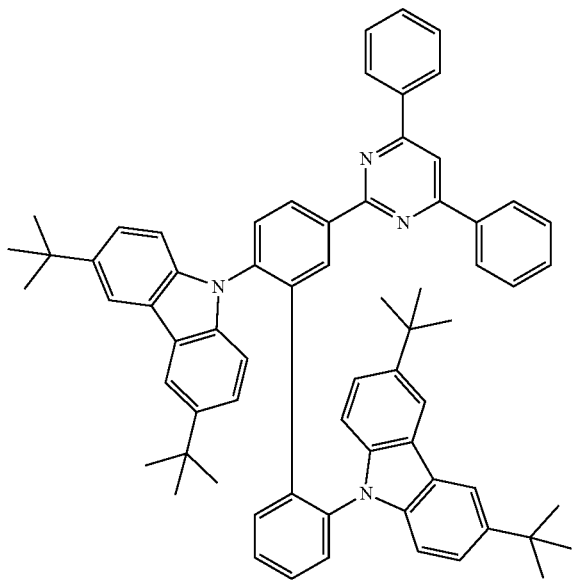
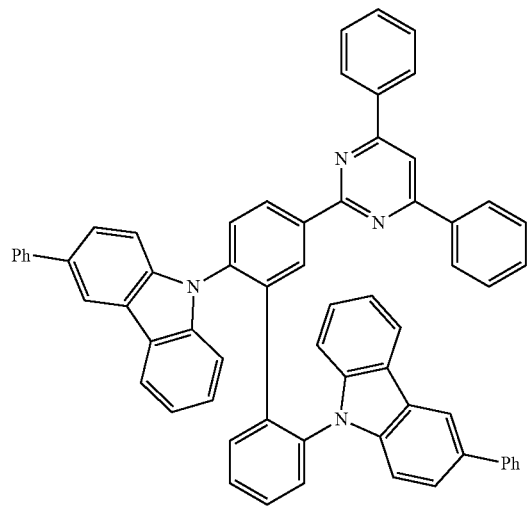
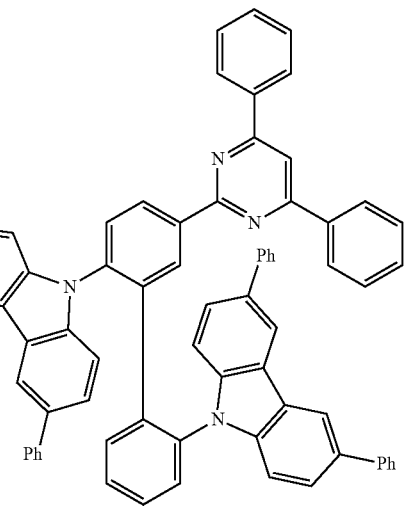
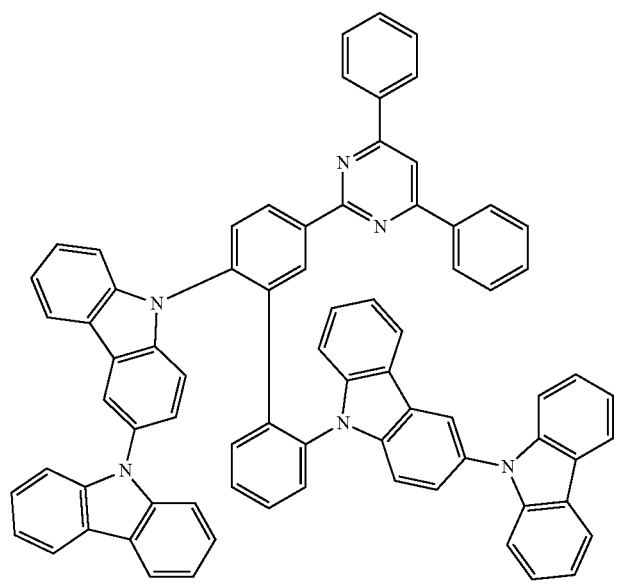

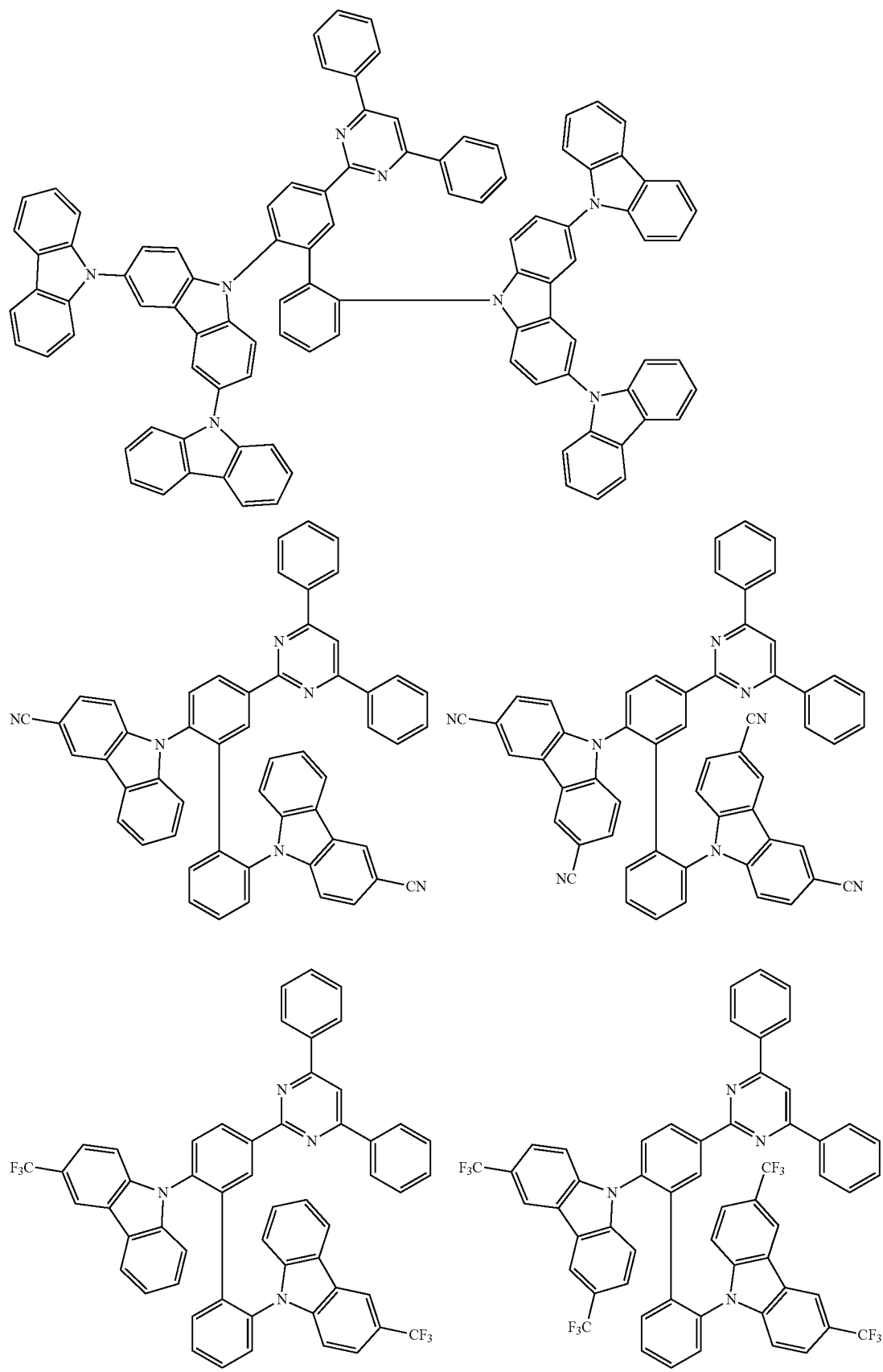

237 238
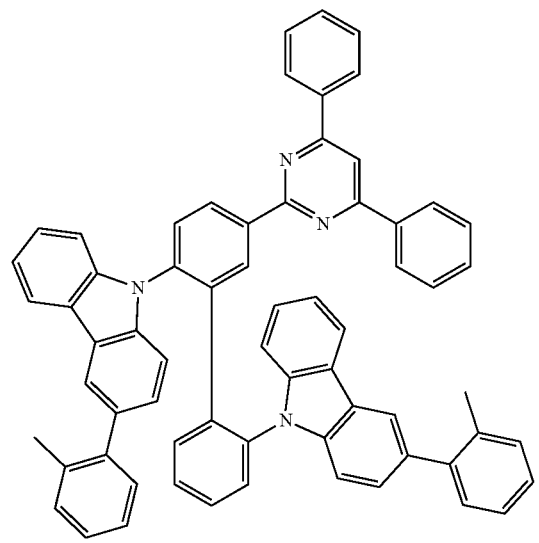 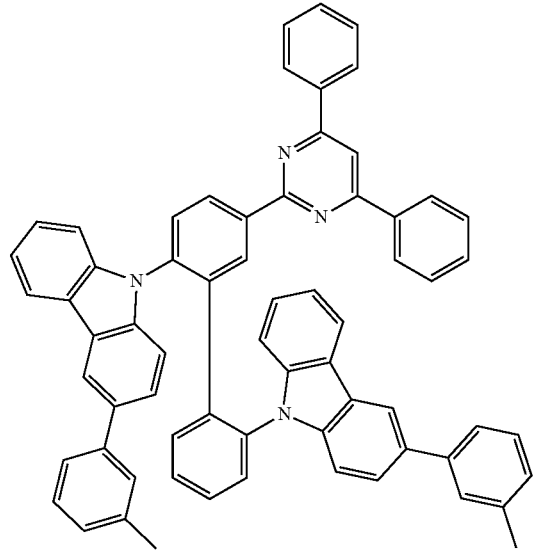
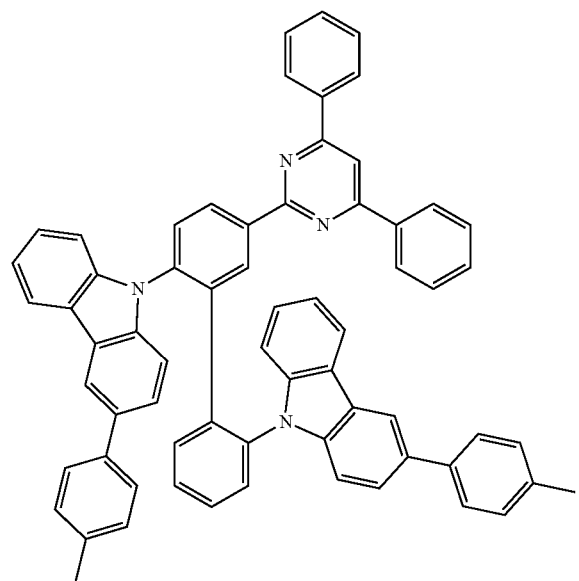 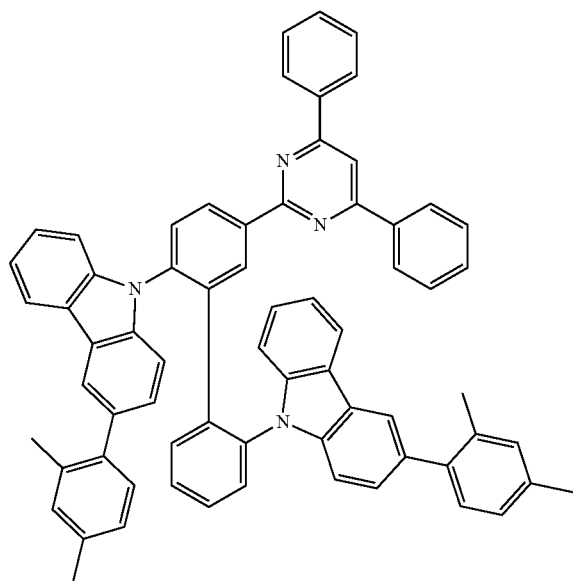

239 240
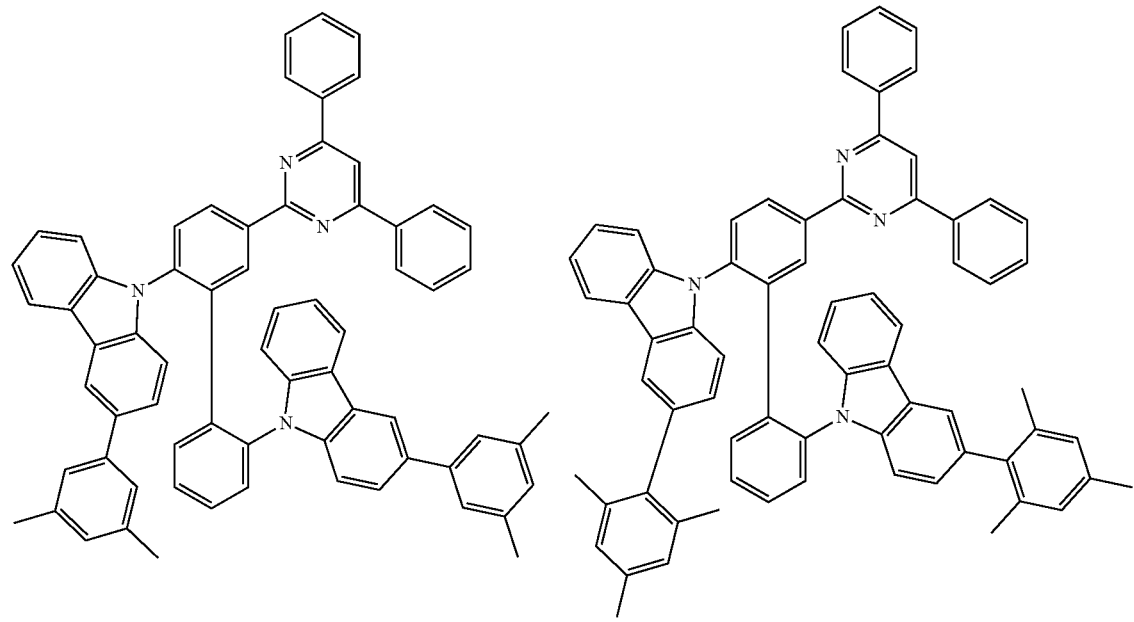
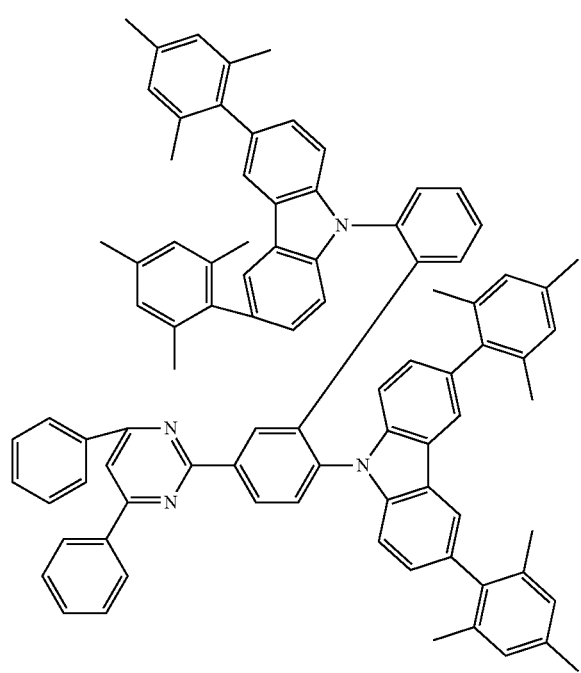

-continued
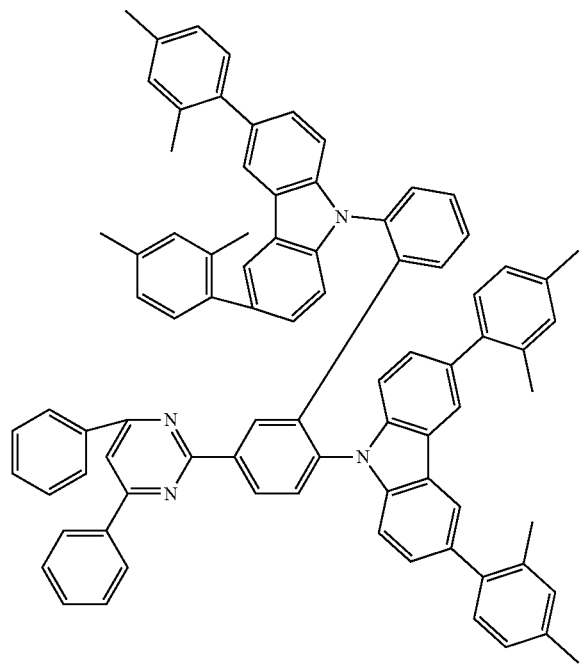
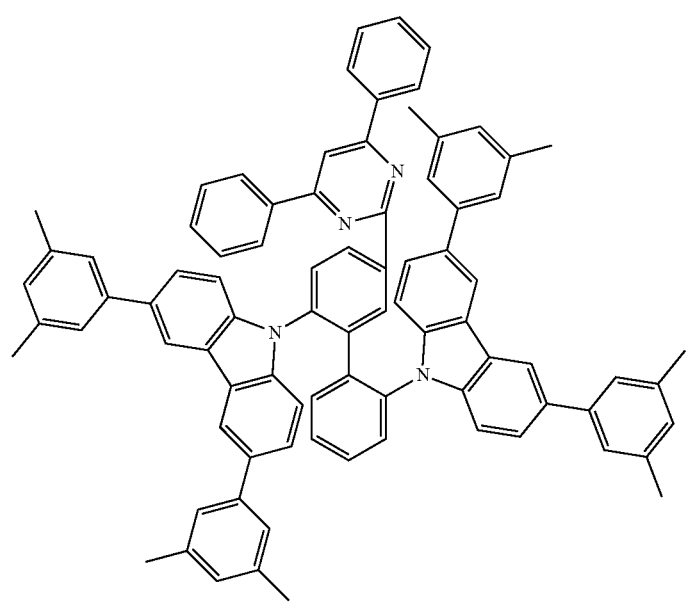

-continued
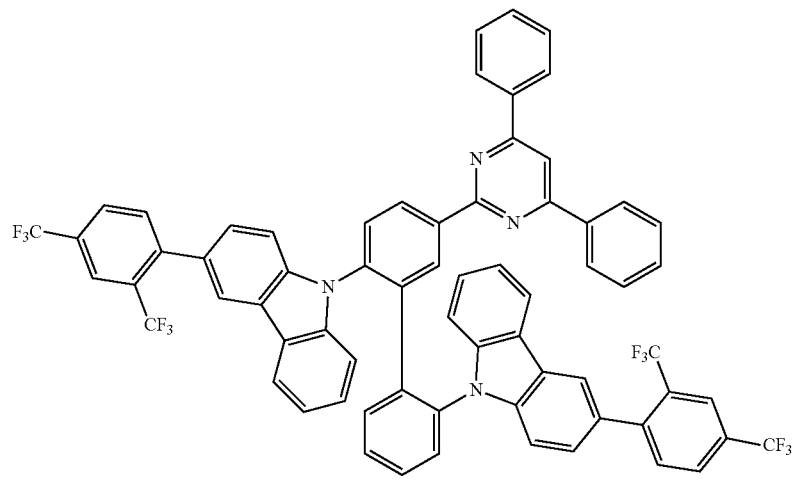
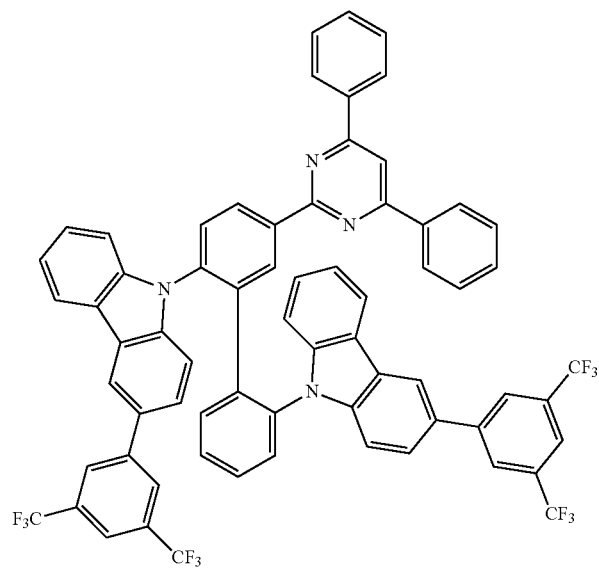
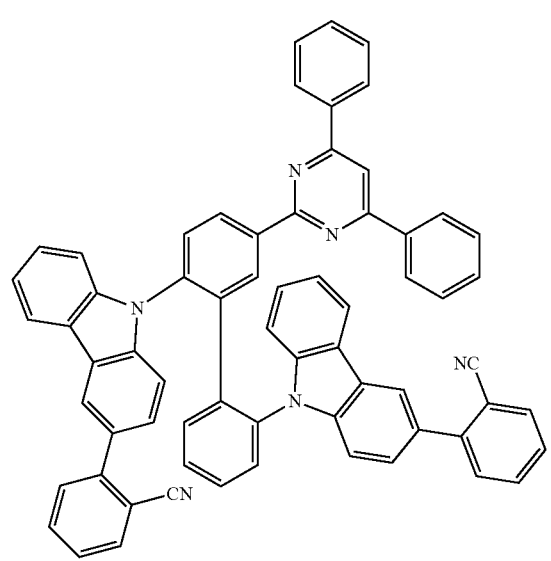
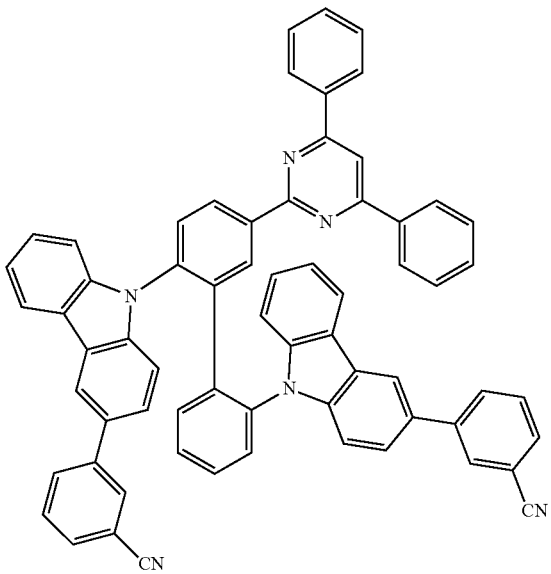

-continued
245
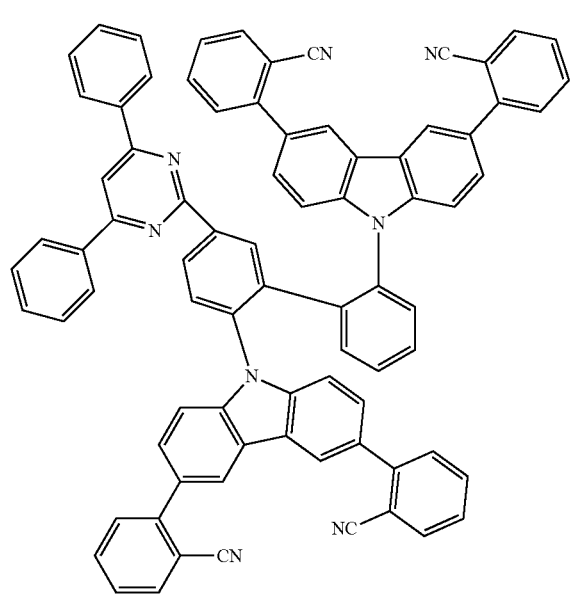
246
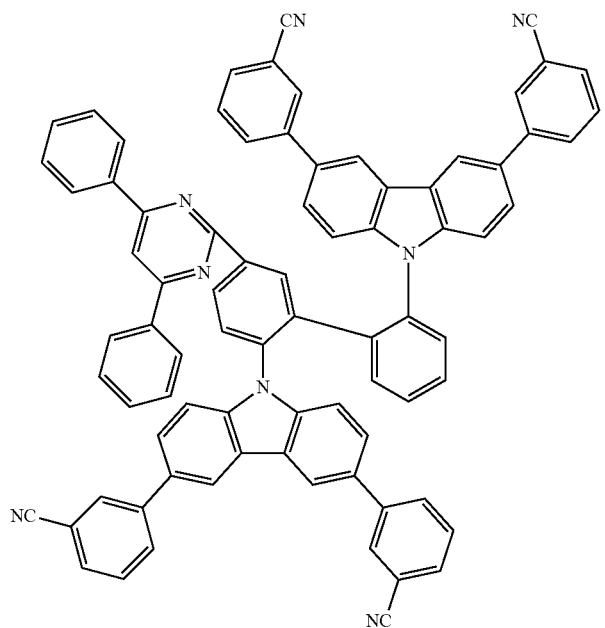
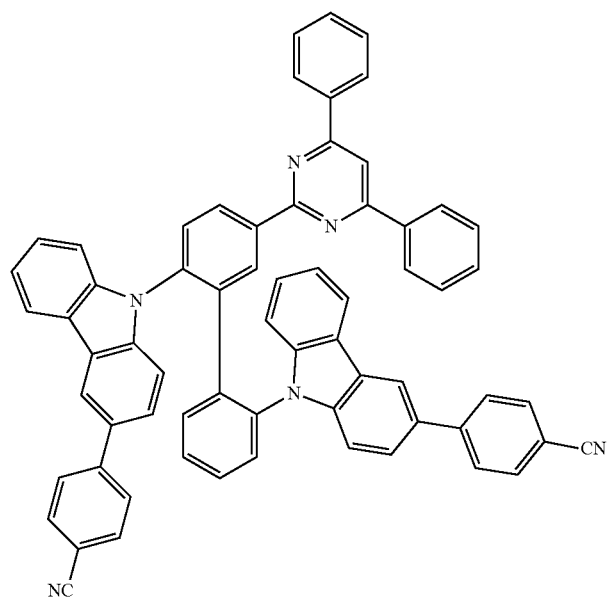

-continued
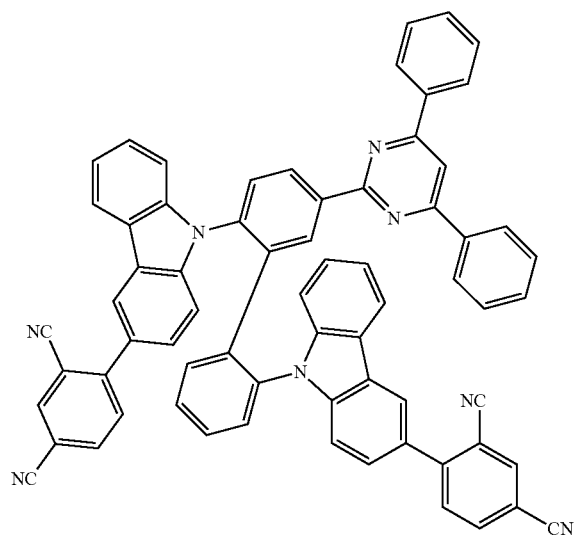
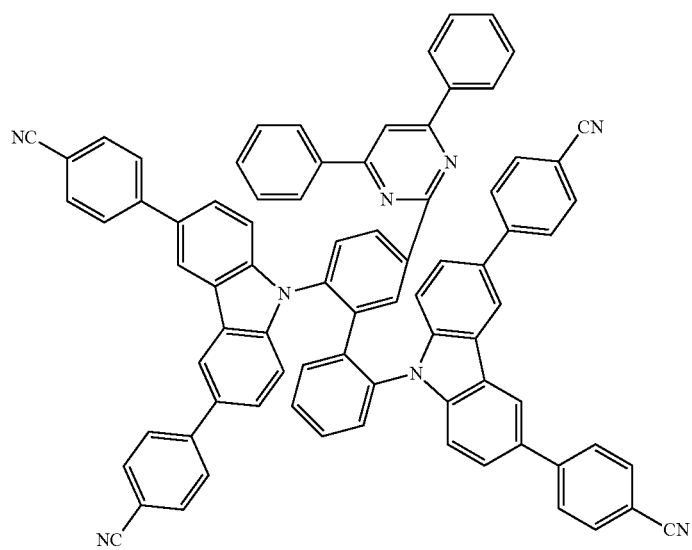
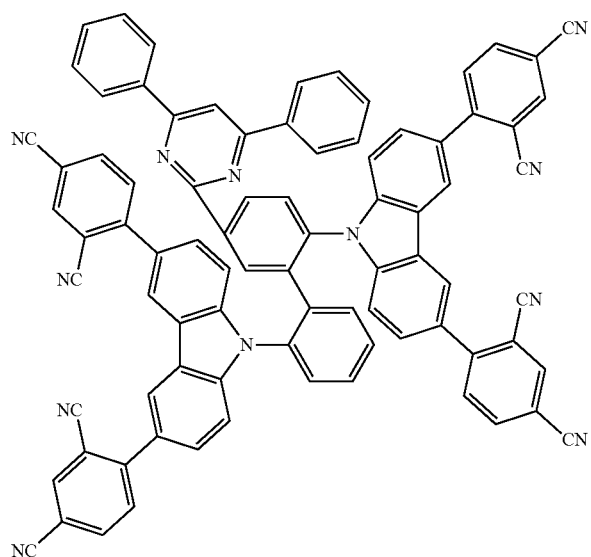

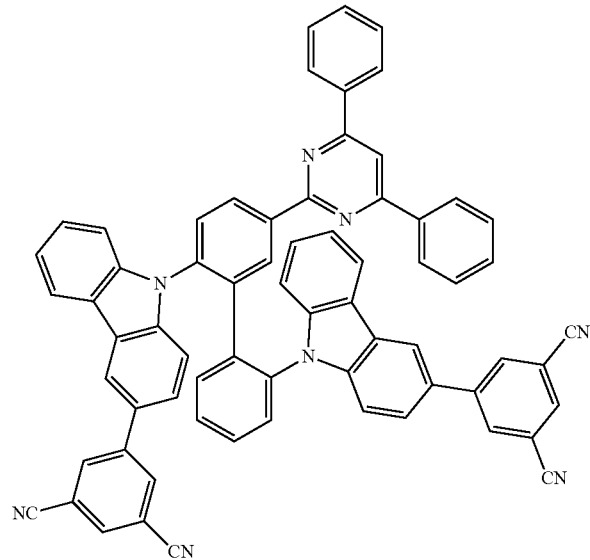
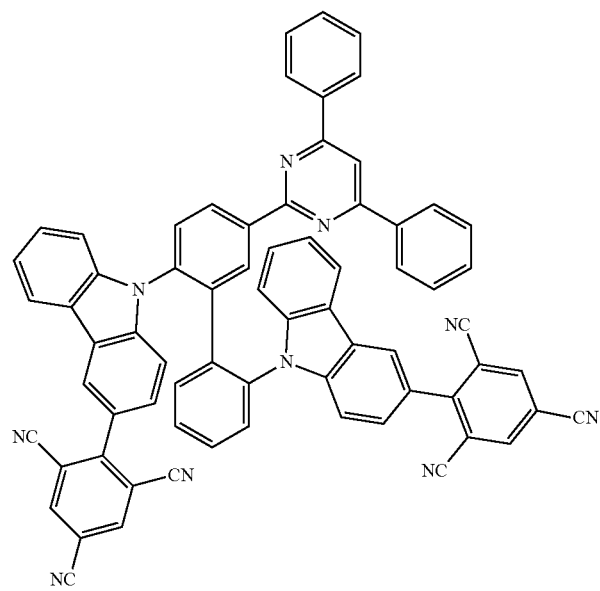

-continued
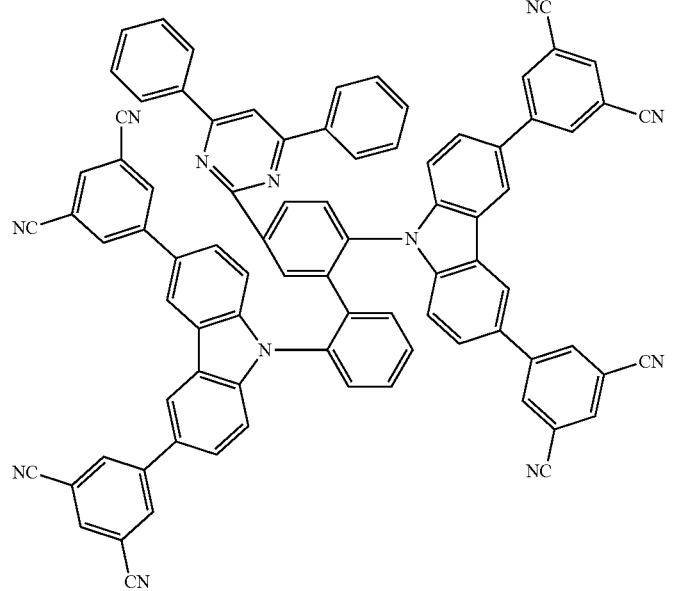
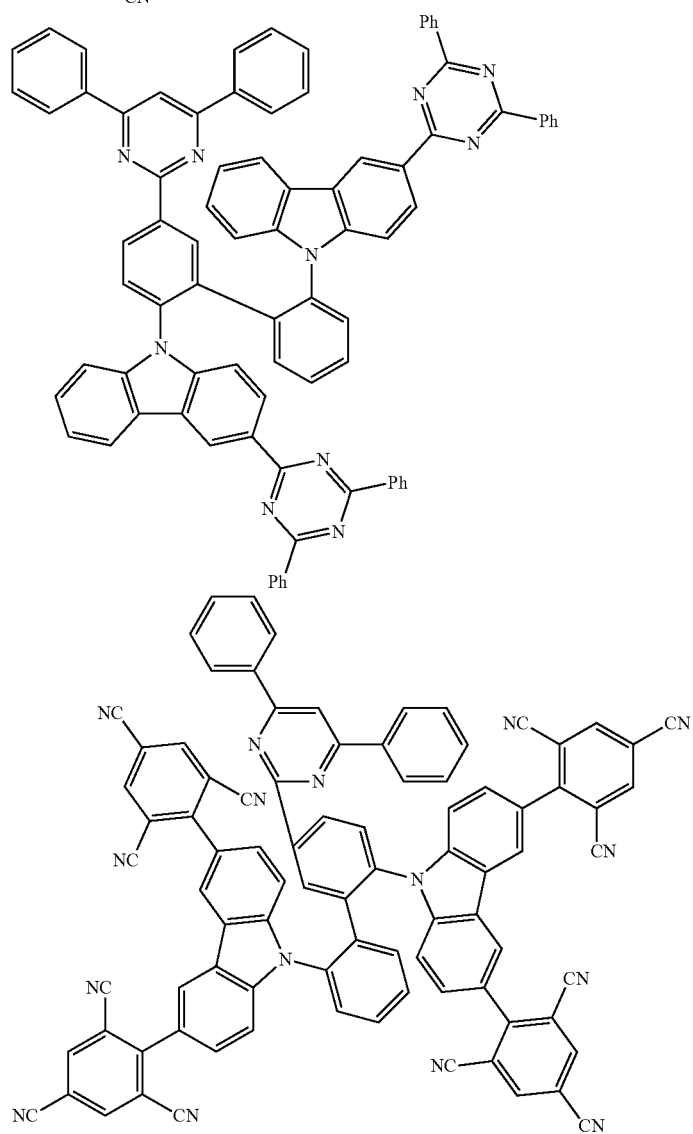

-continued
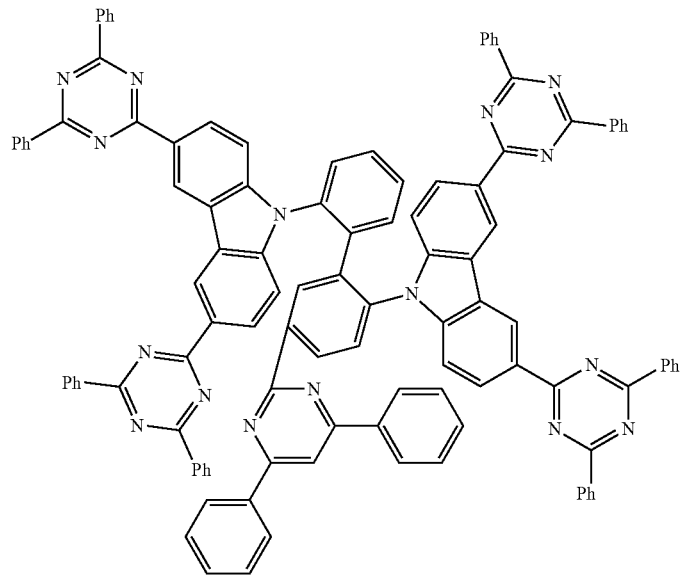
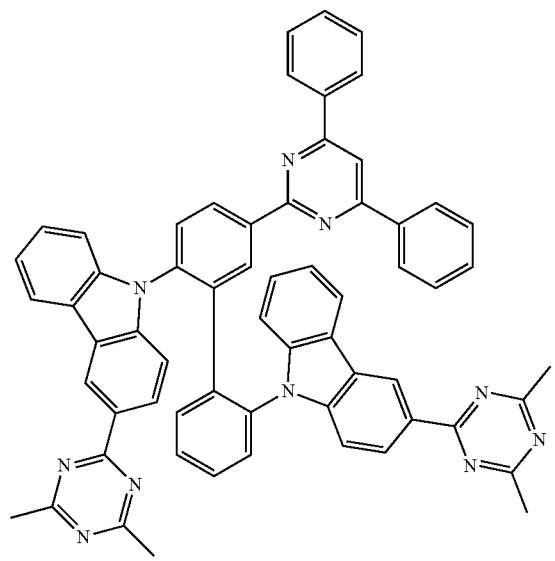
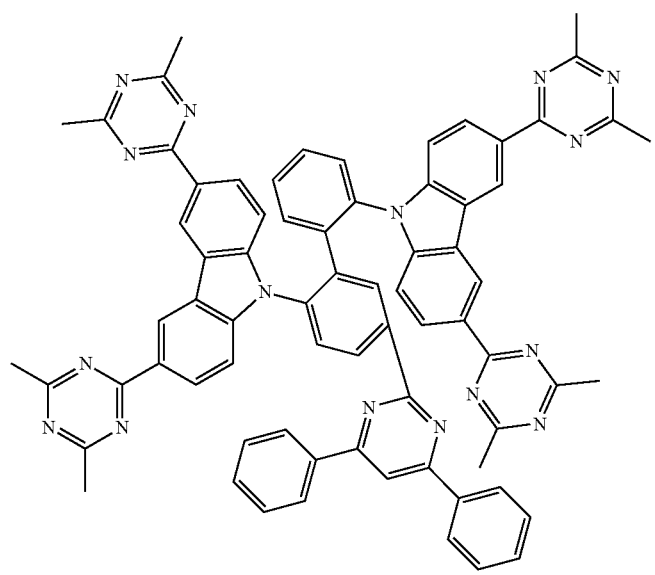

255
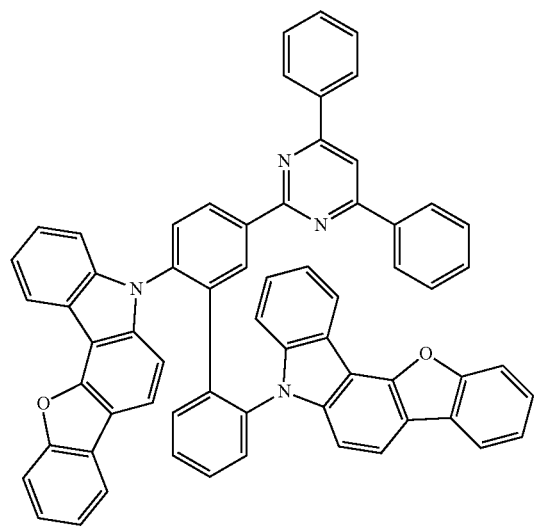
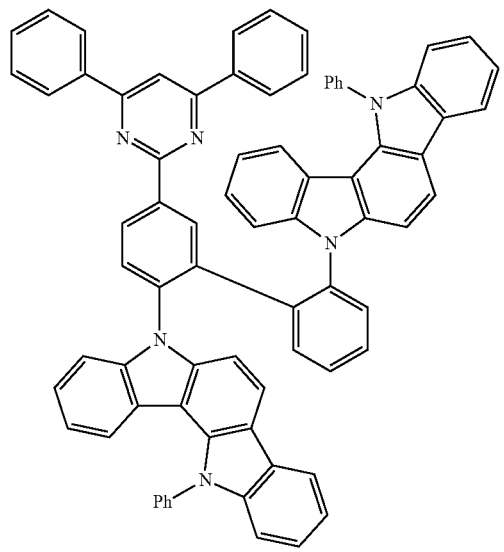
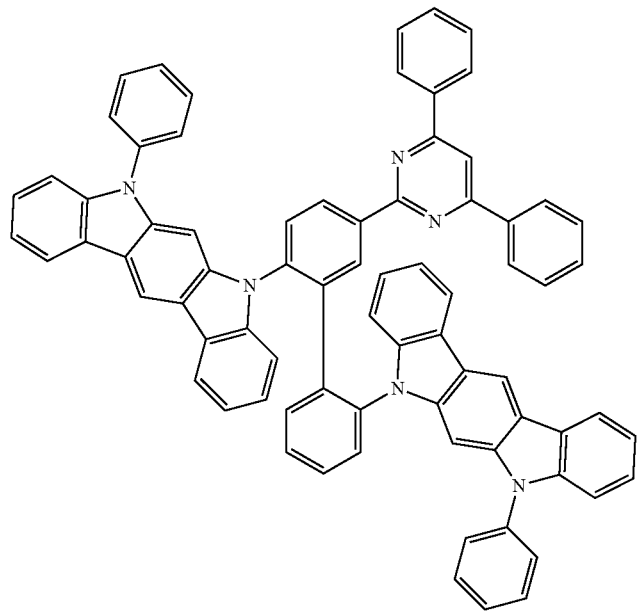
256
-continued
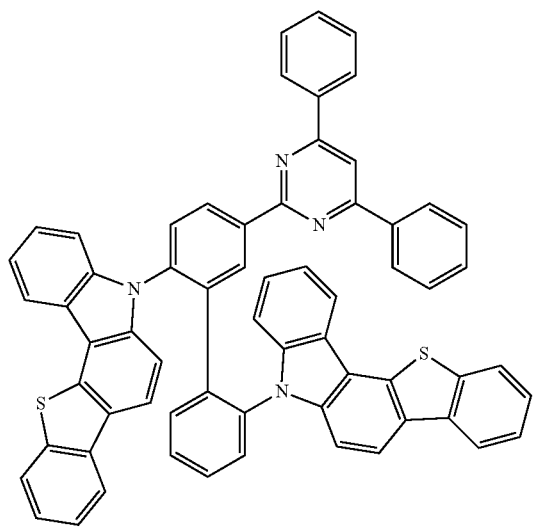
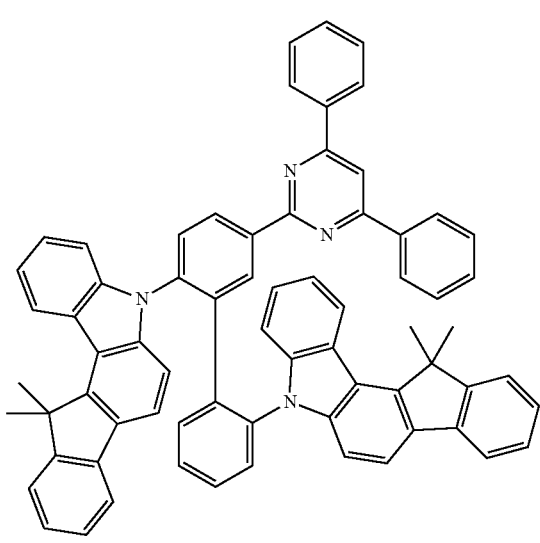
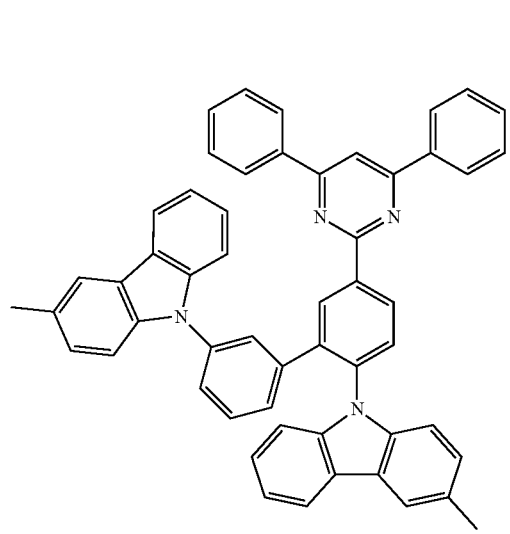

257
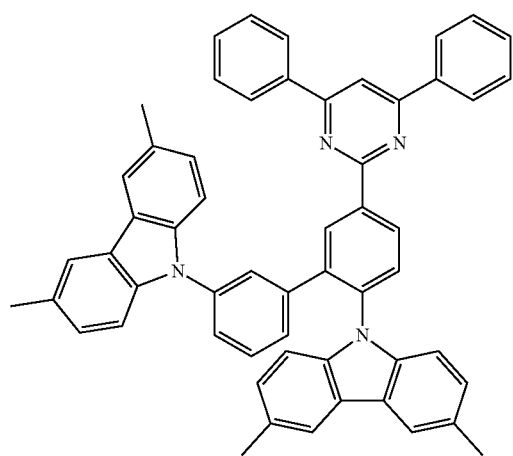
258
-continued
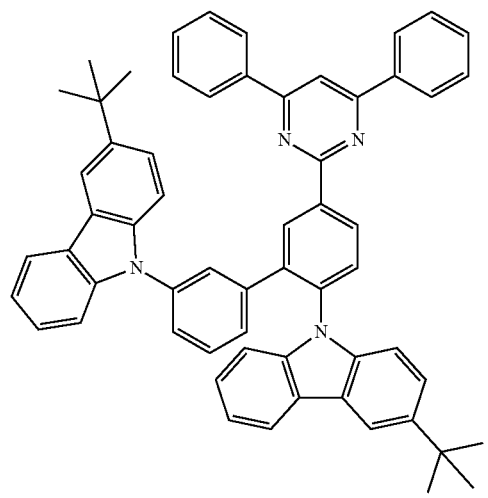
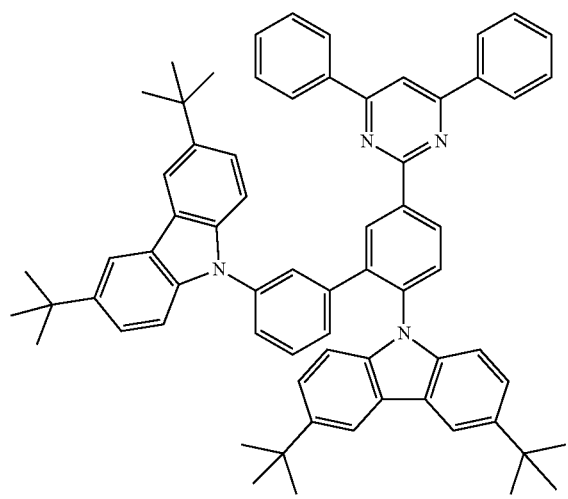
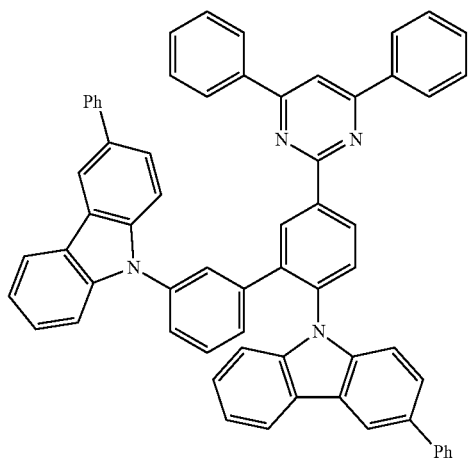
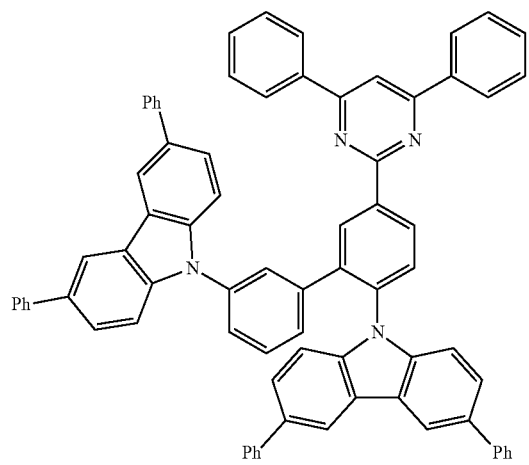

-continued
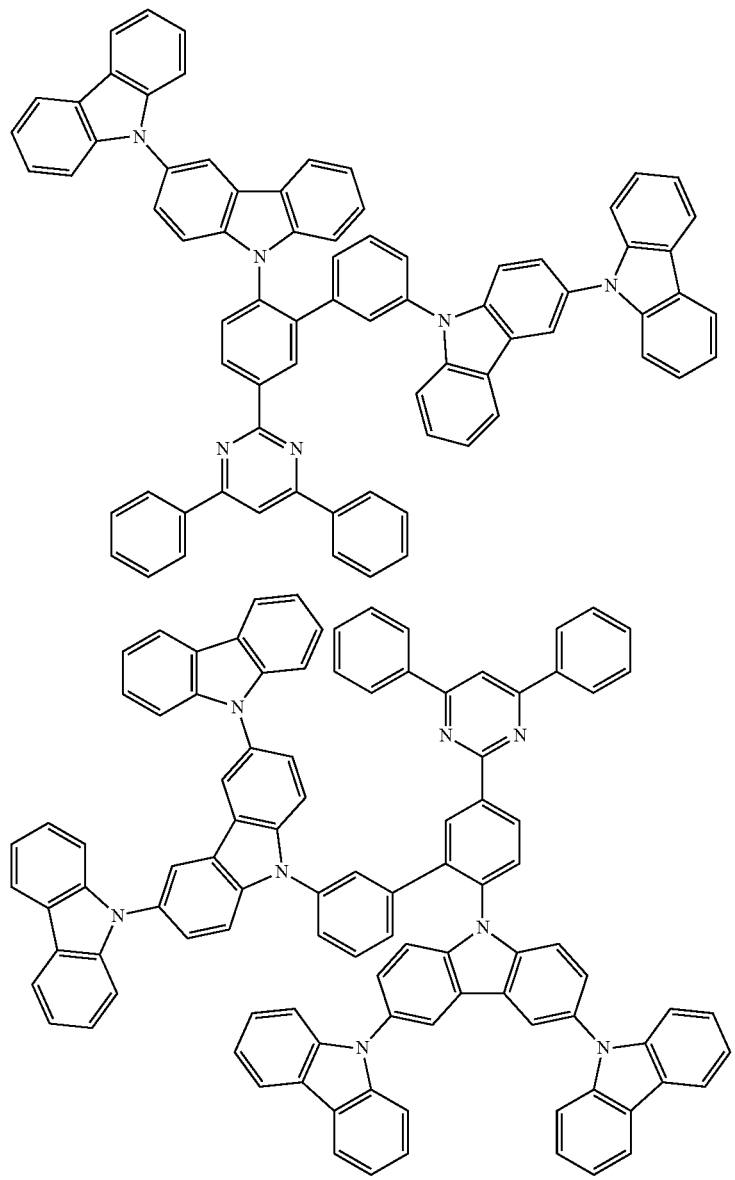
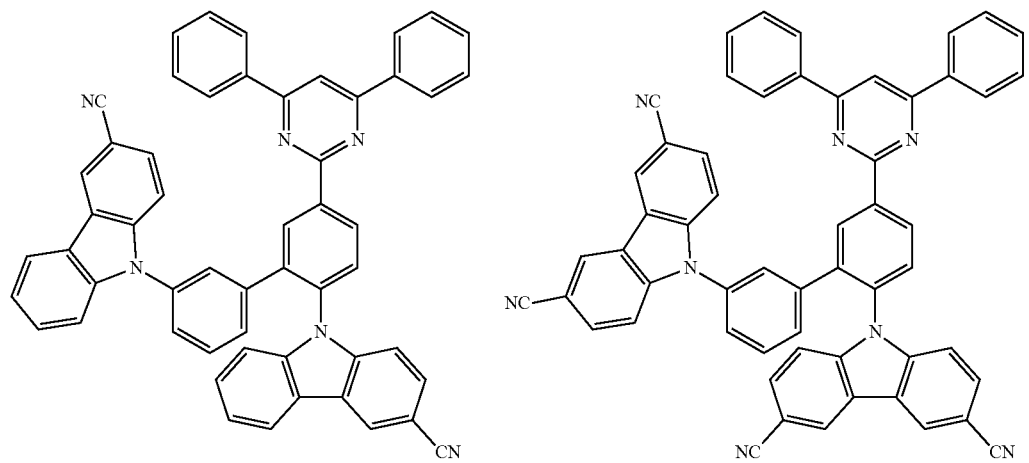

261
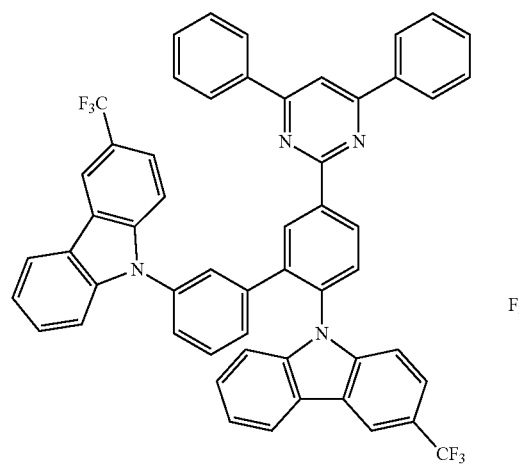
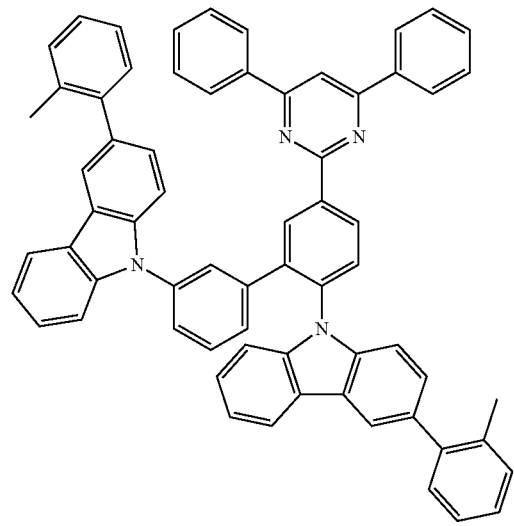
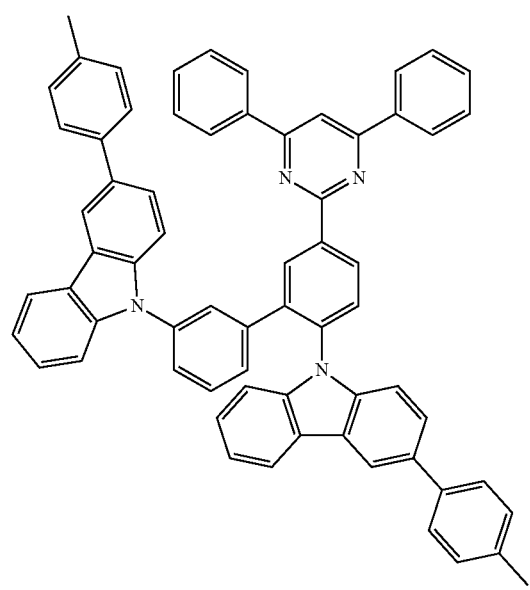
-continued
262
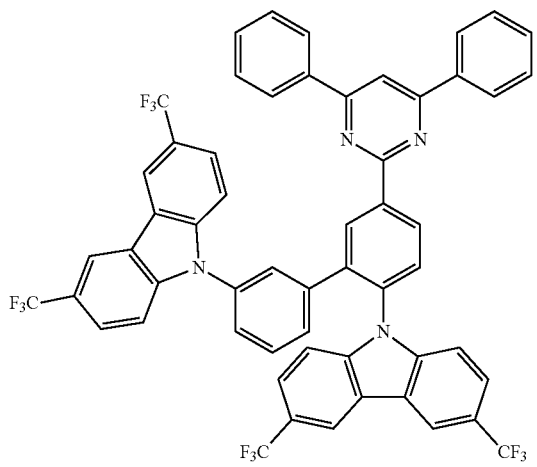
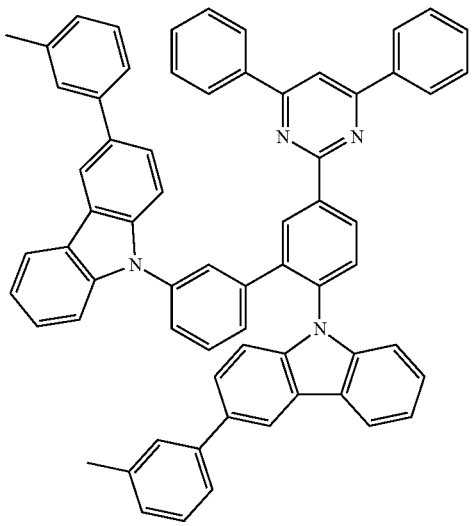
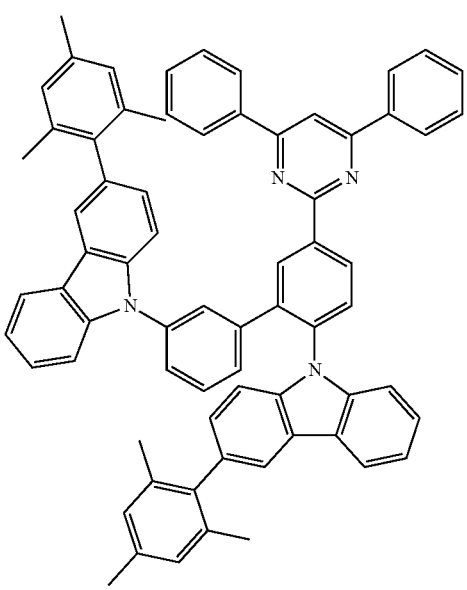

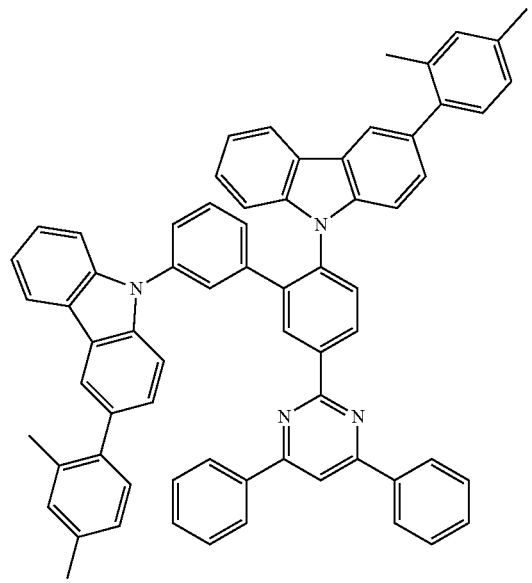
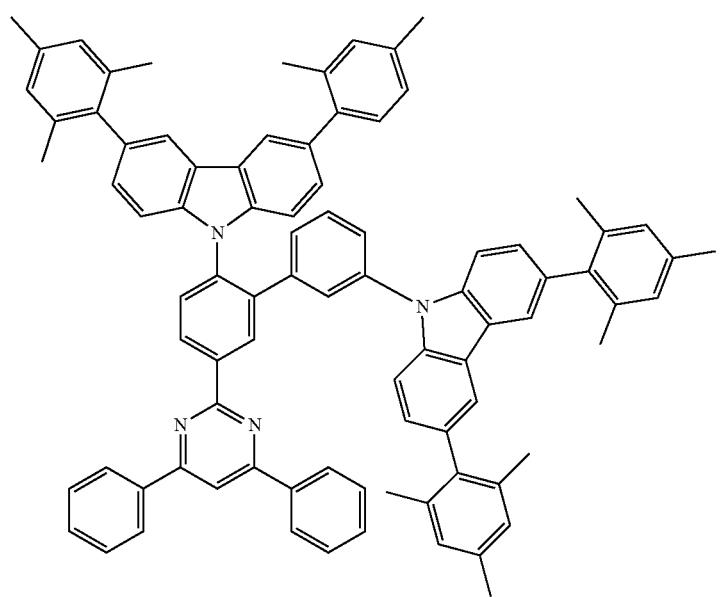

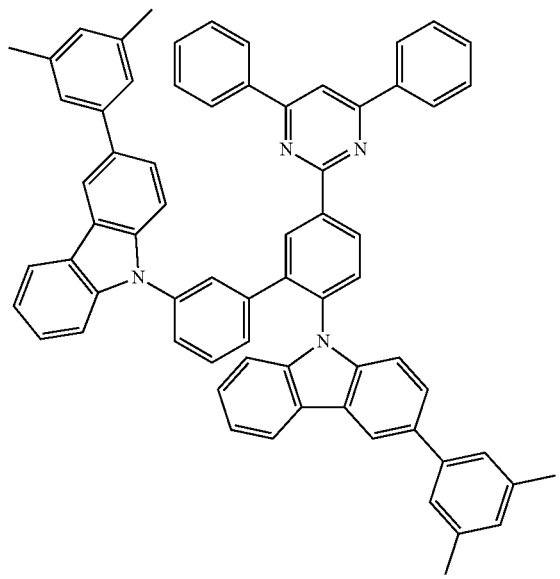
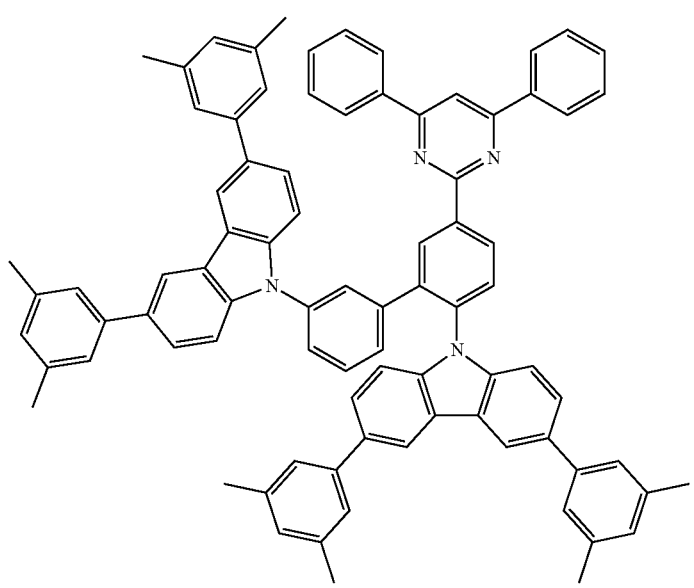

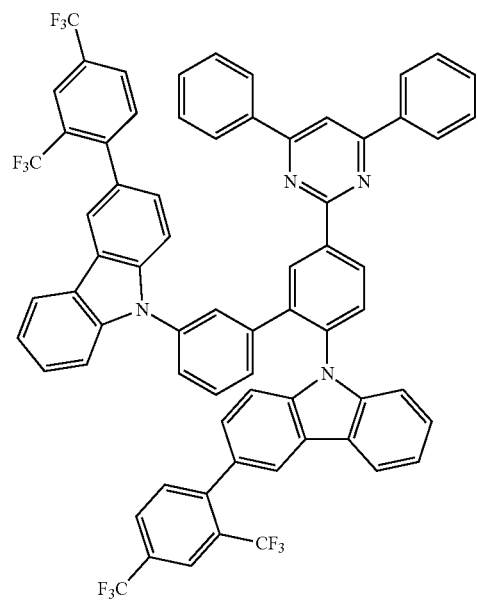
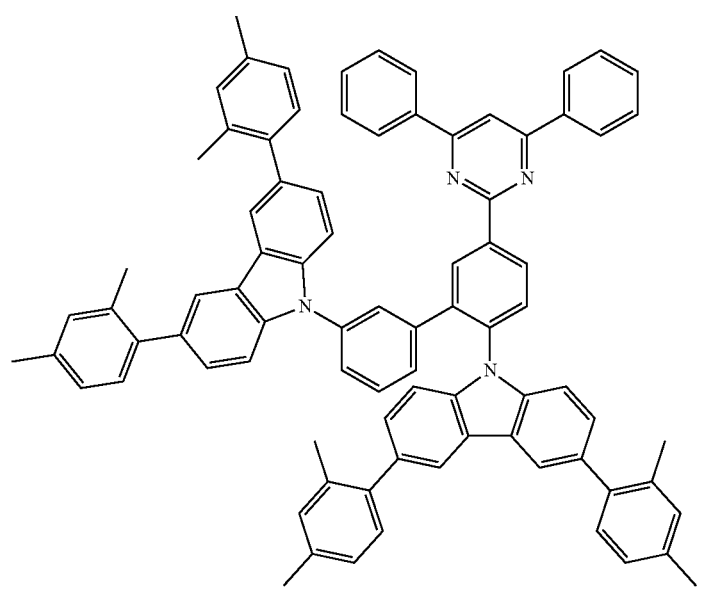

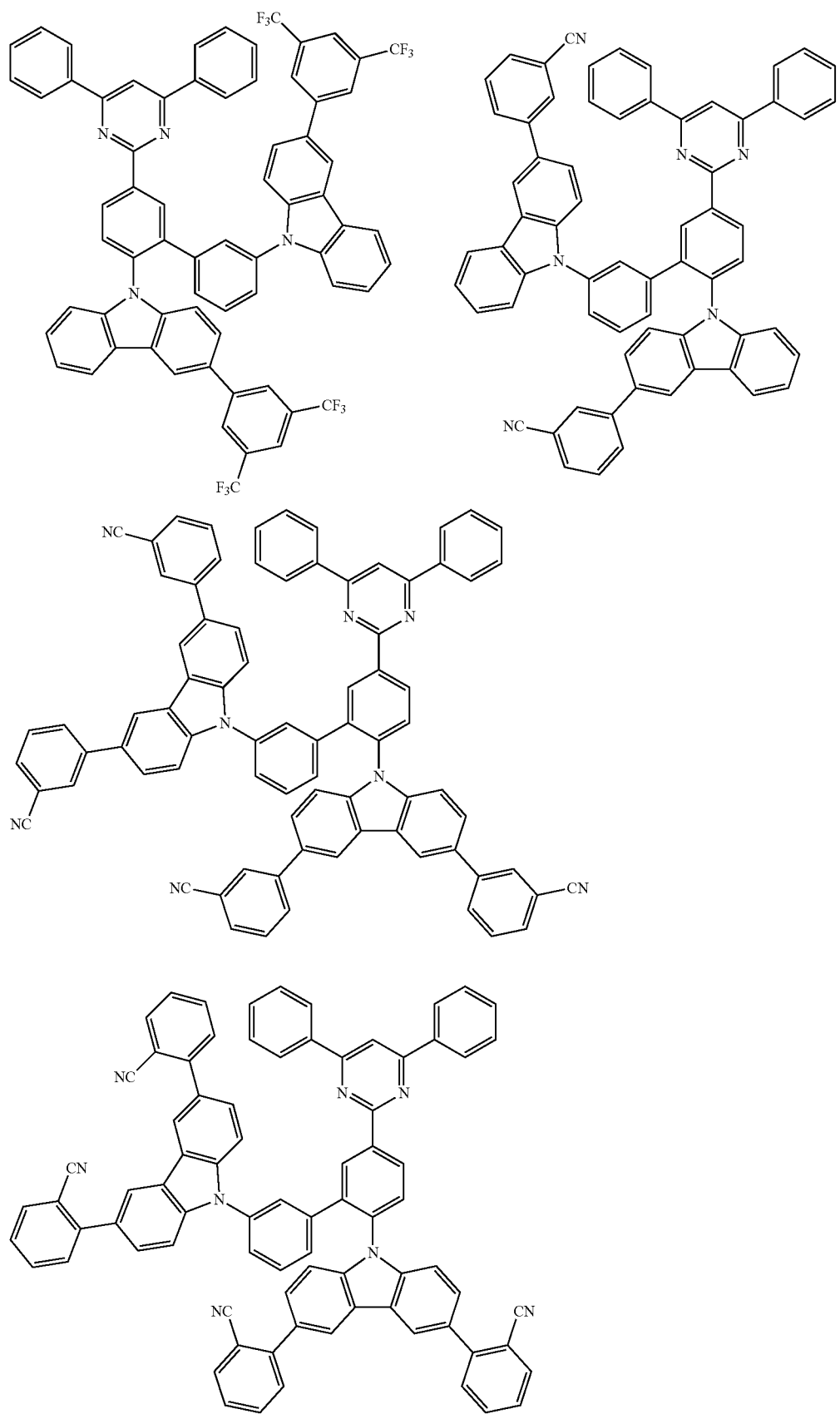

-continued
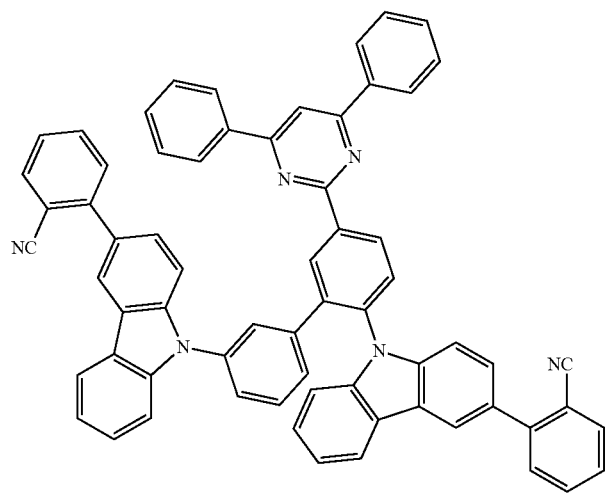
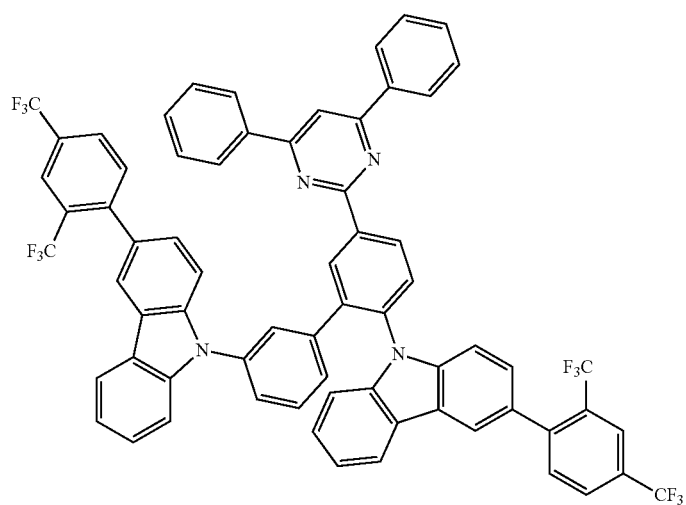
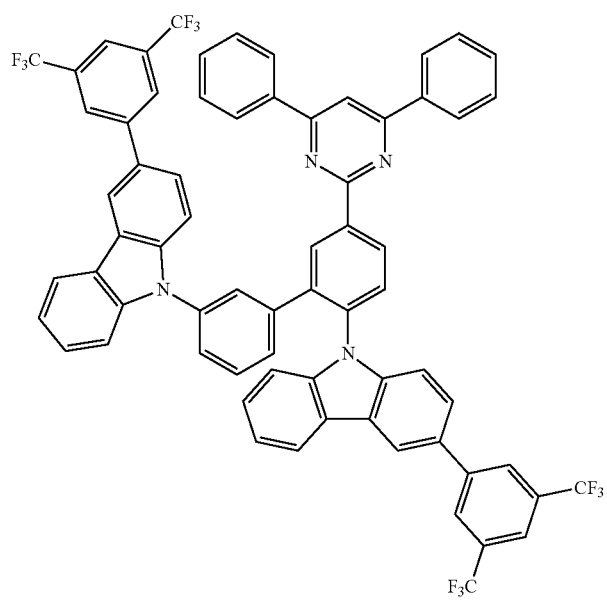

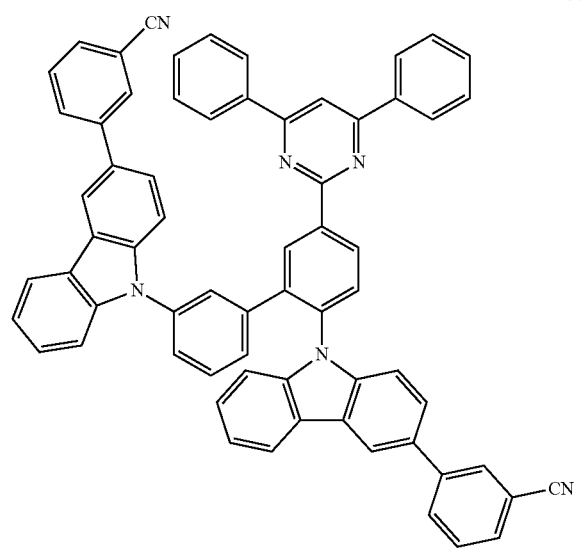
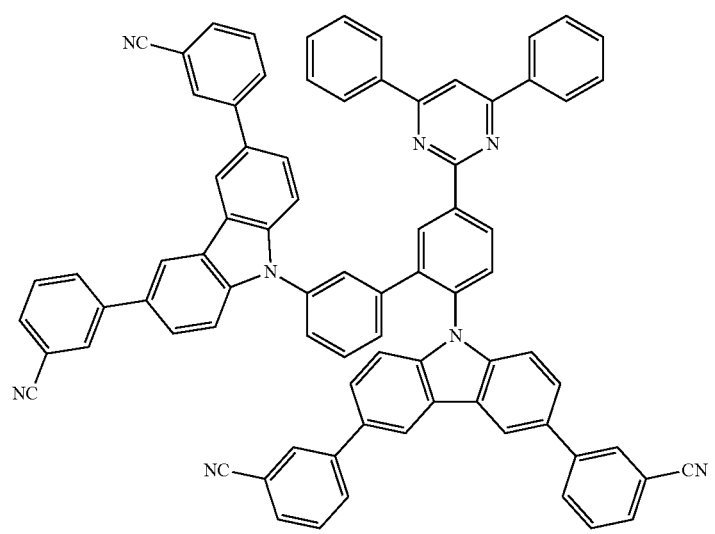
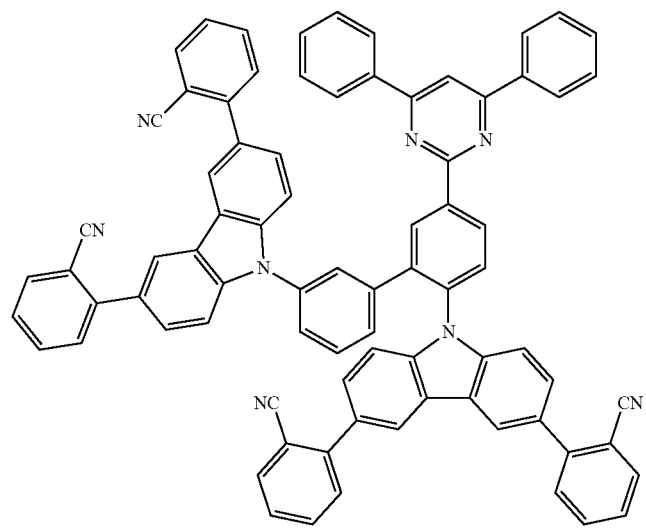

275
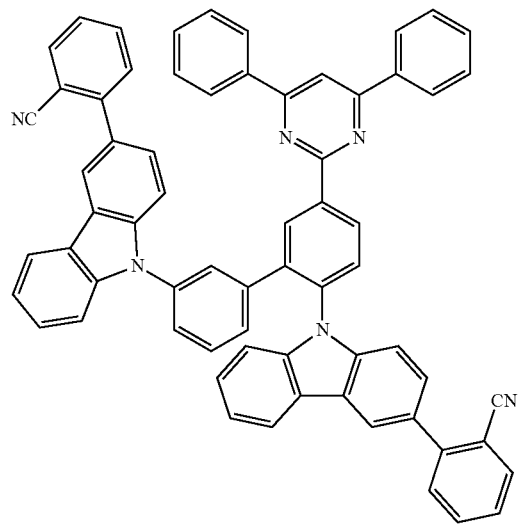
276
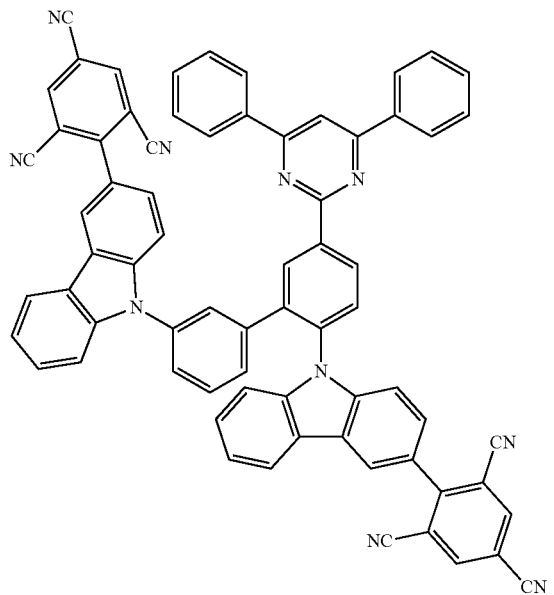
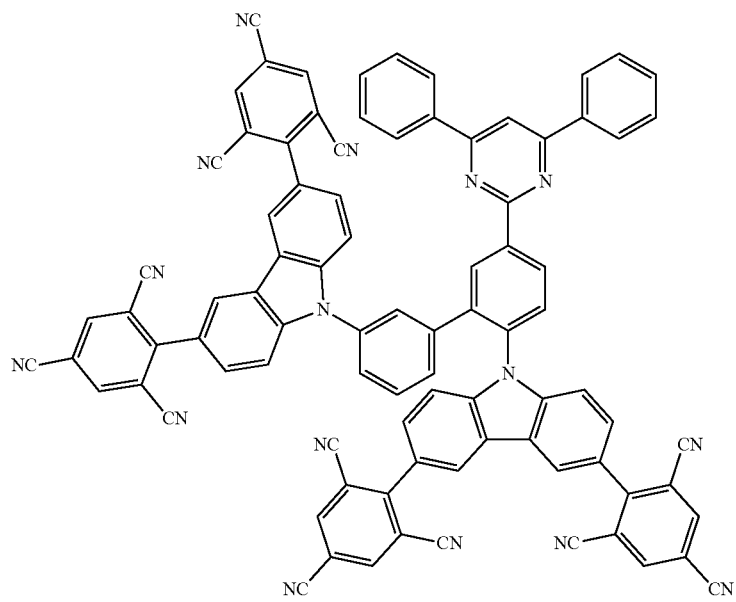

-continued
277 278
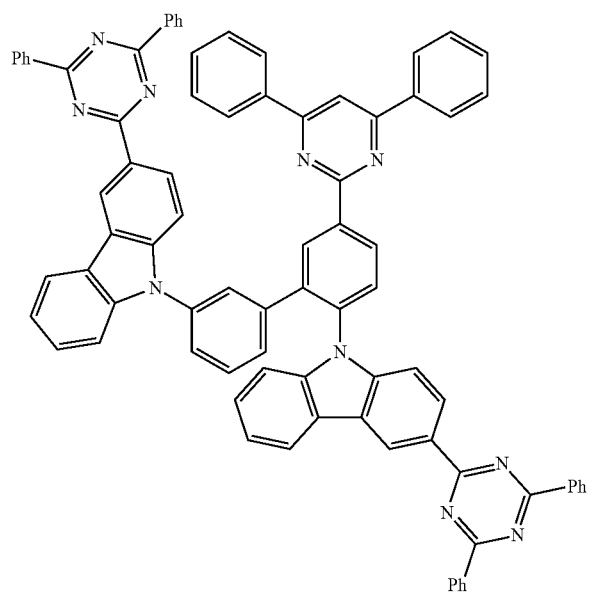 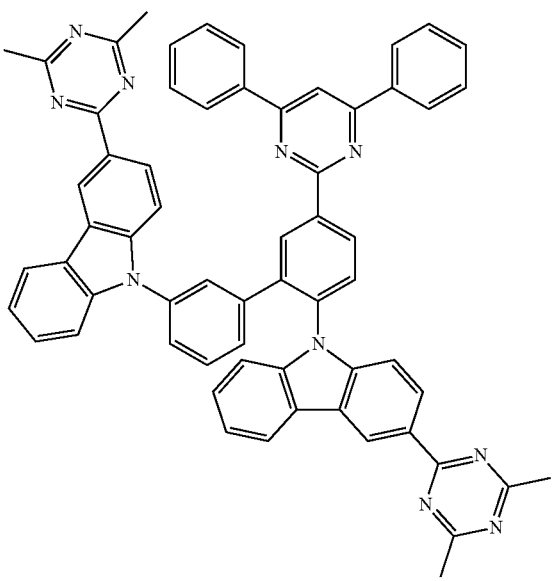
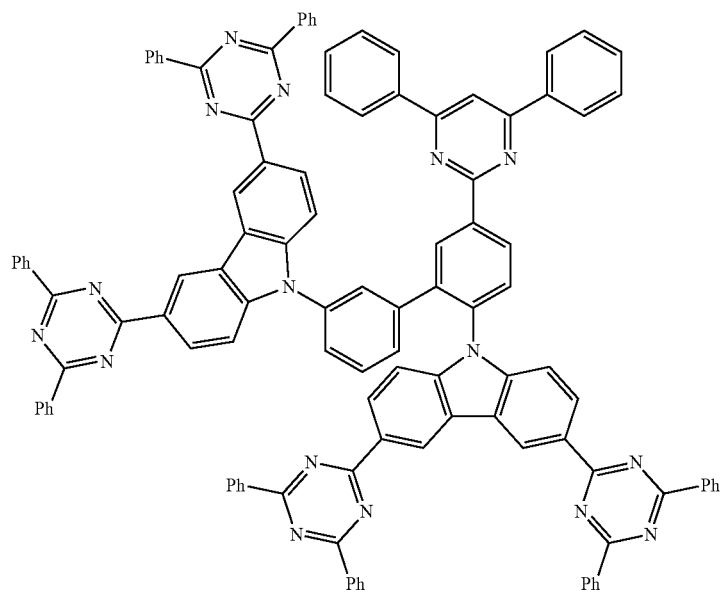

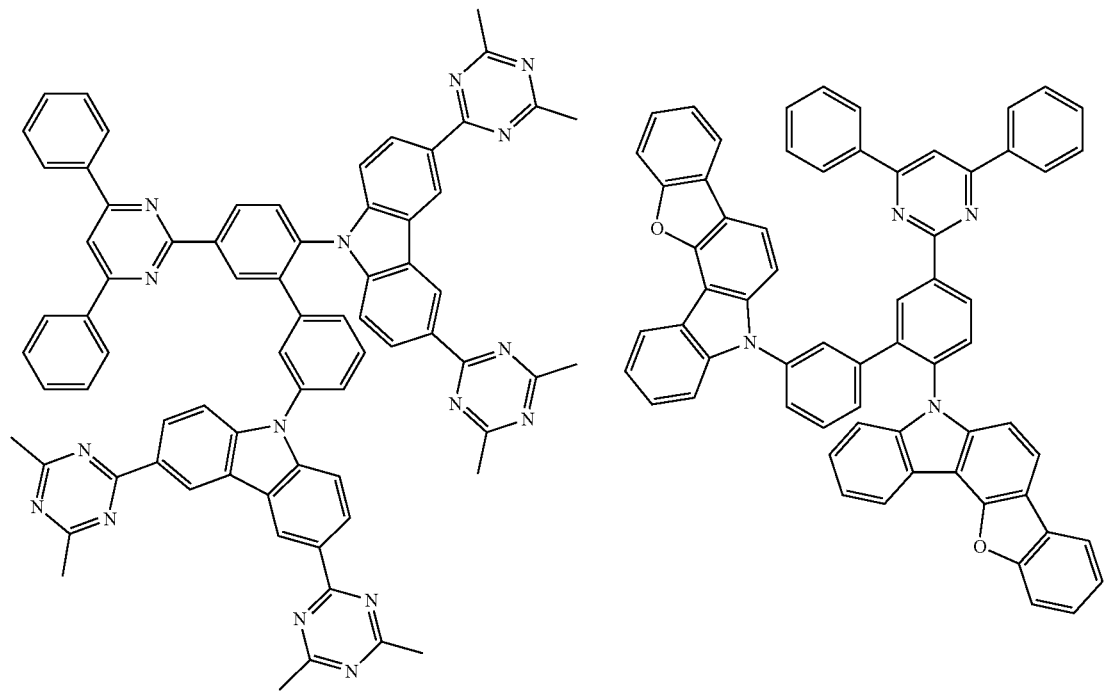
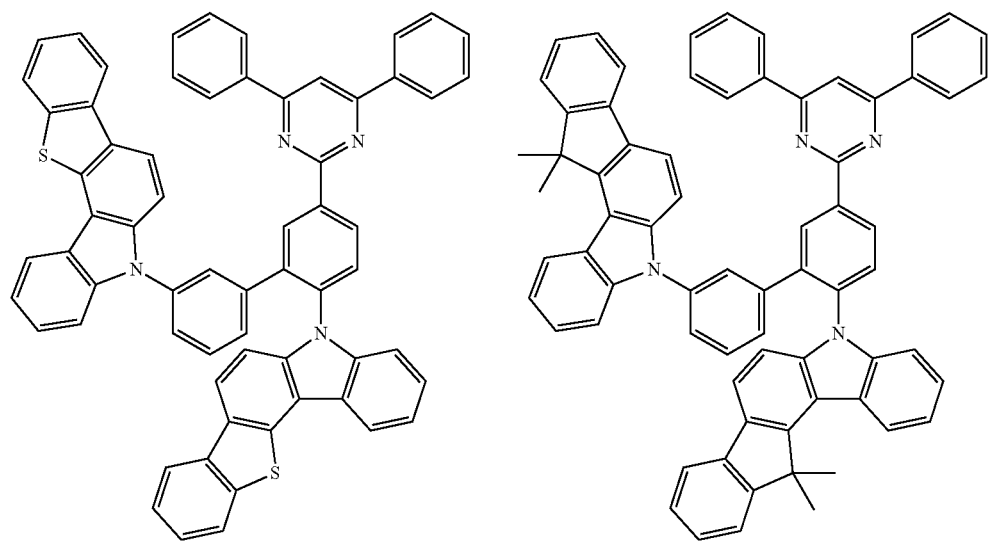

281
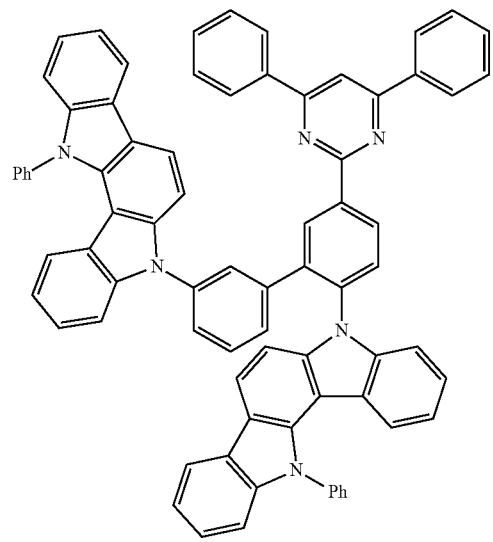
282
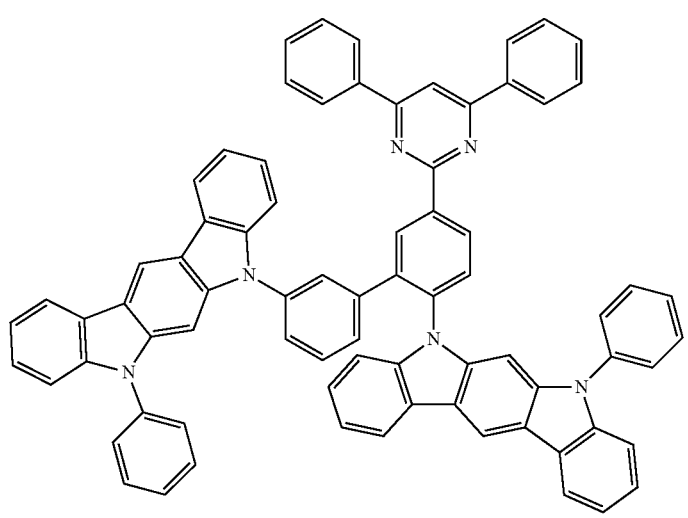
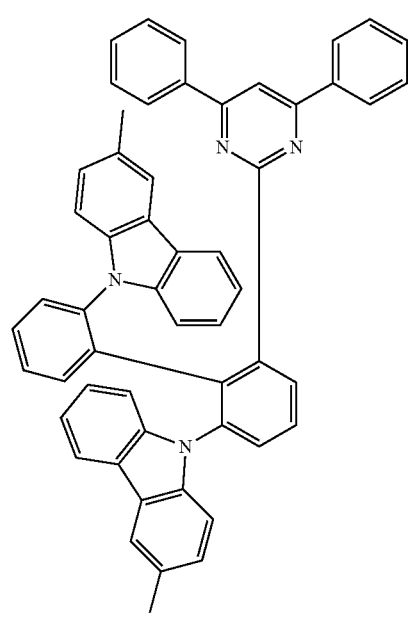
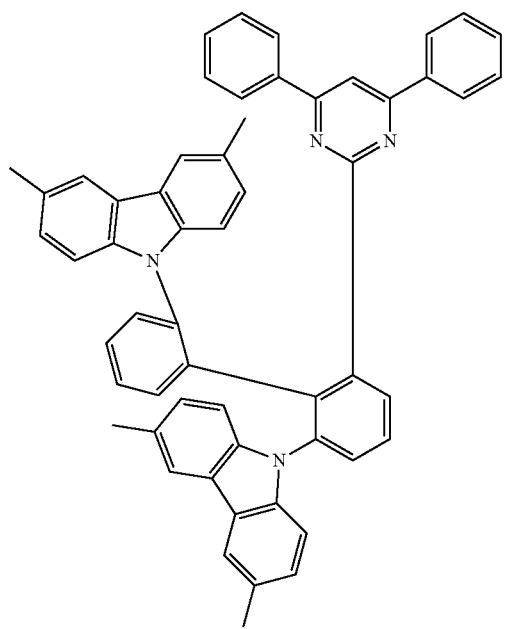

283
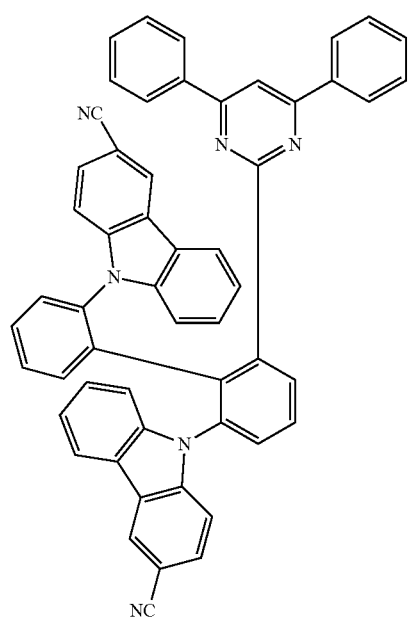
284
-continued
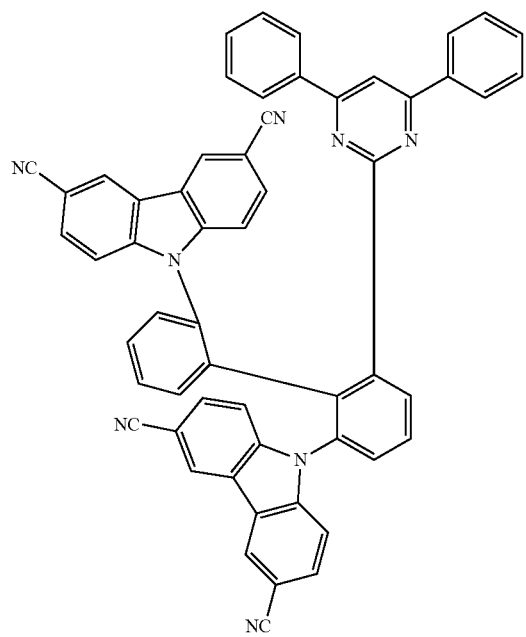
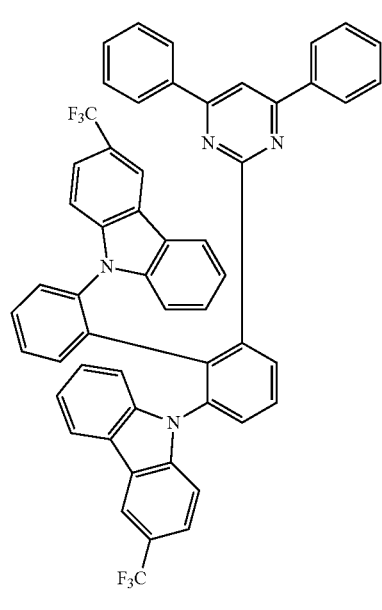
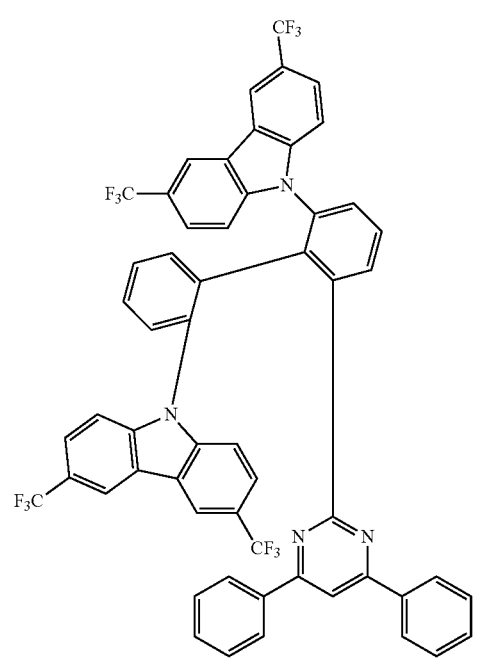

-continued
285
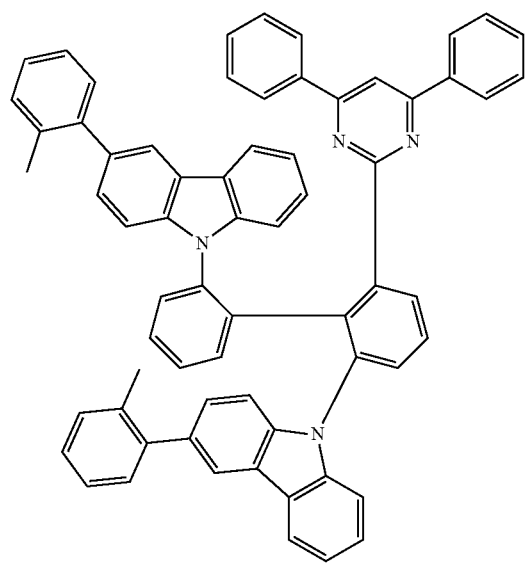
286
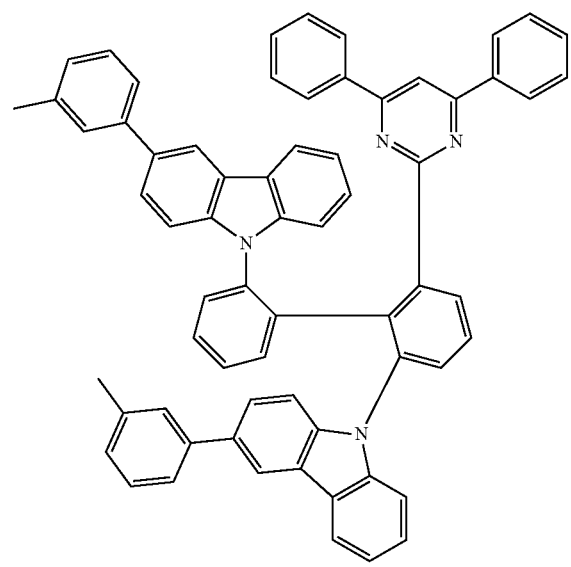
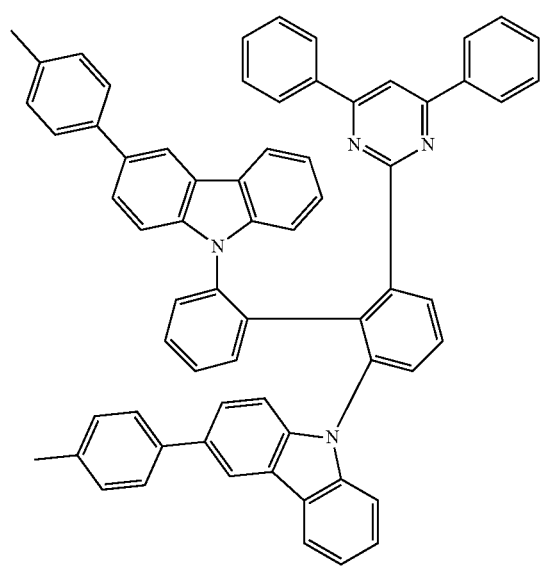
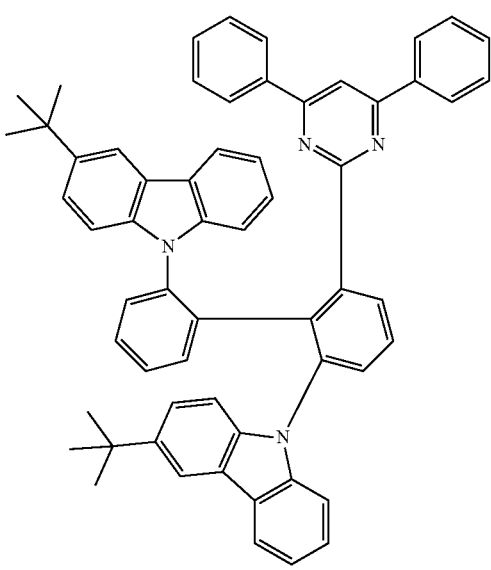

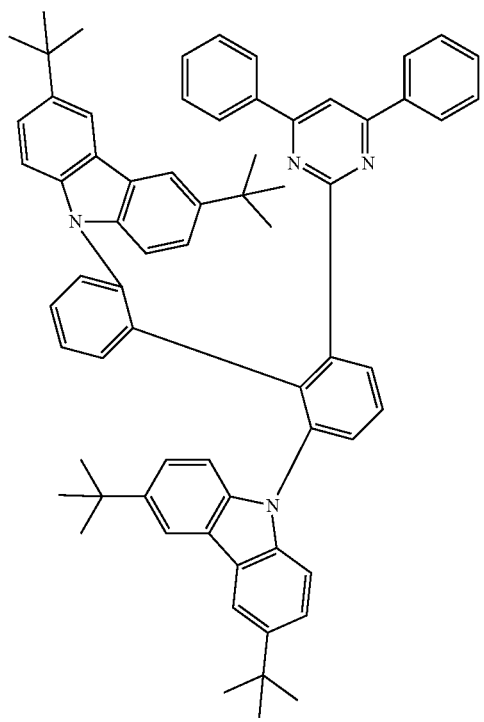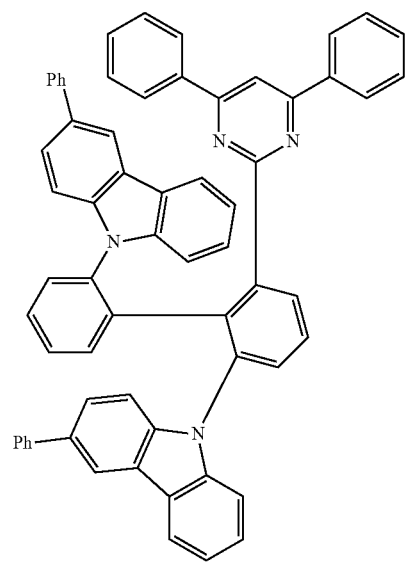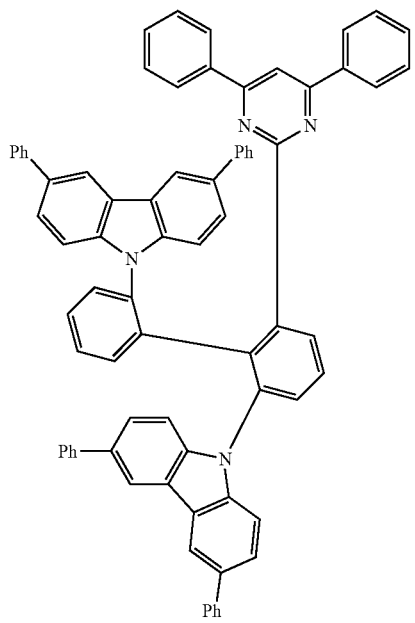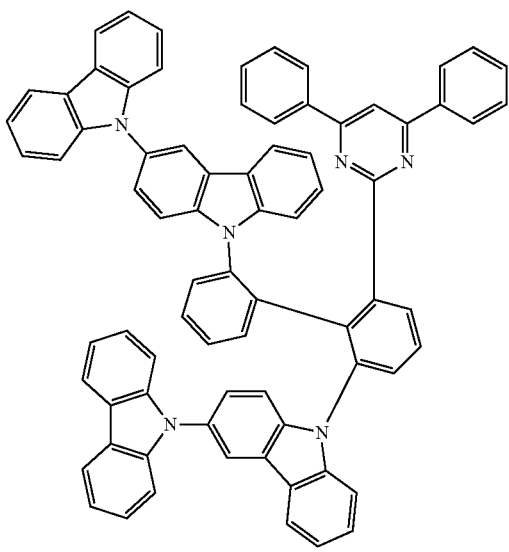

289 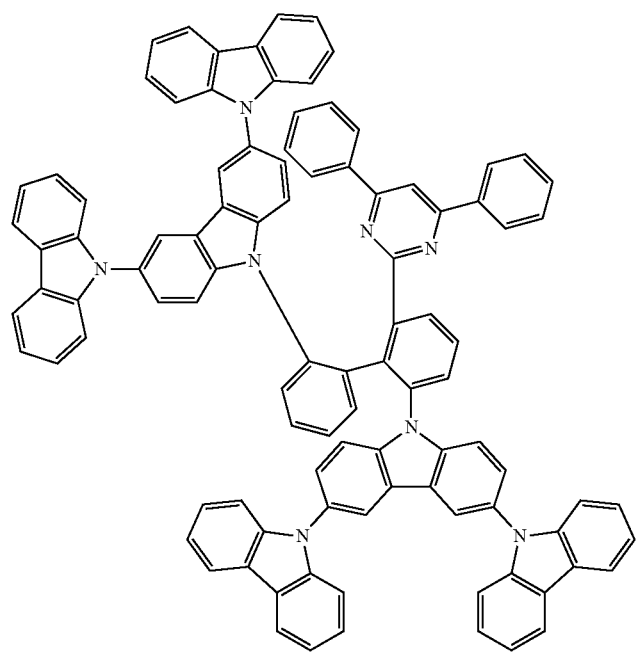 290 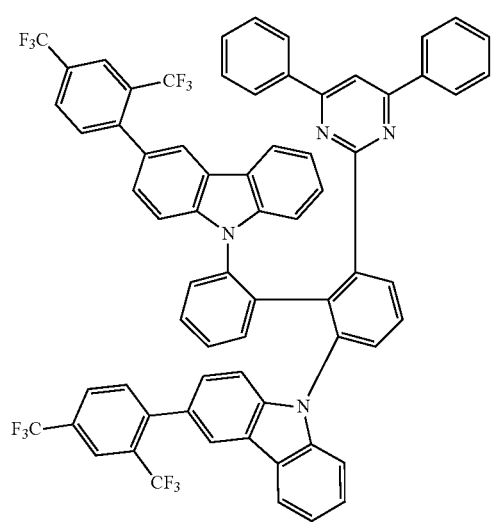
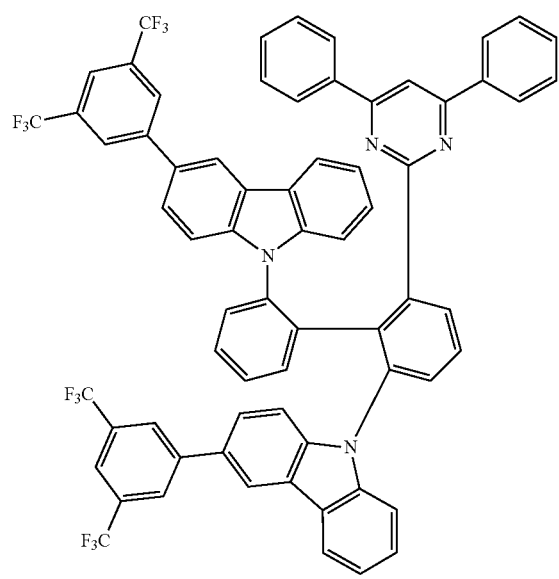 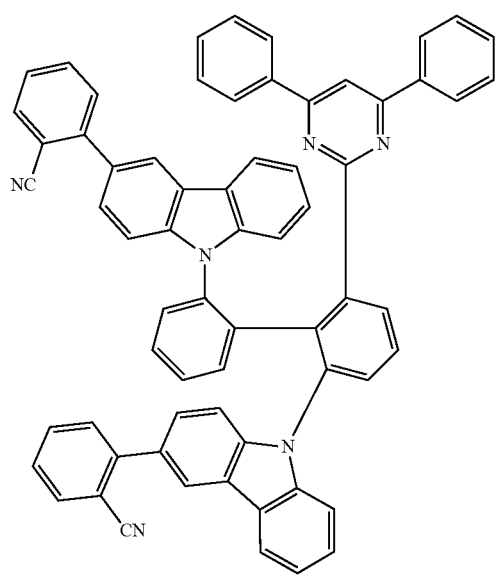

291 292
-continued
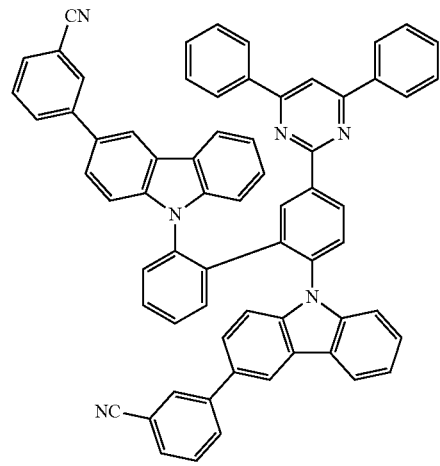
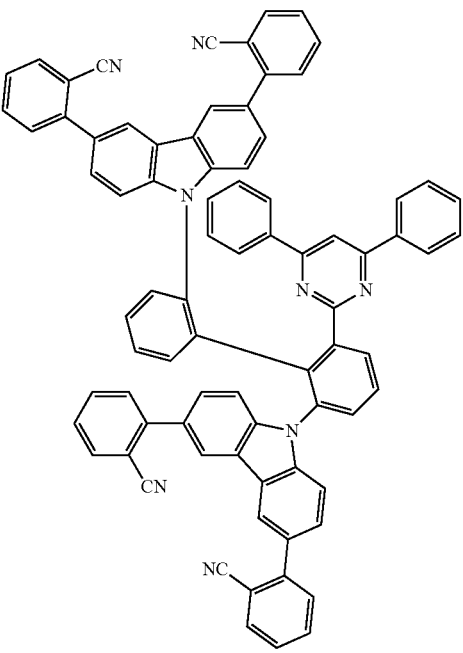
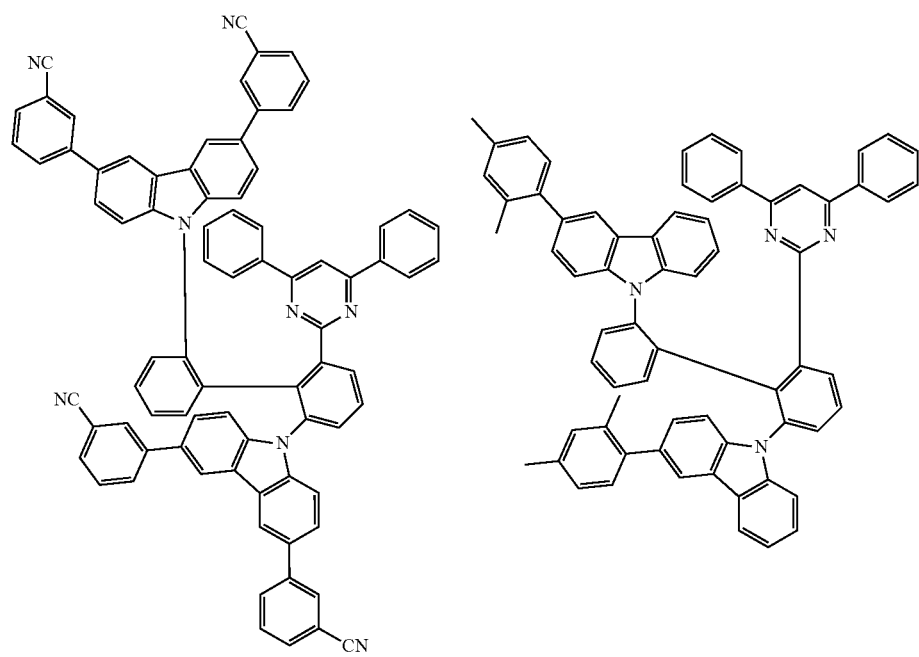

293 294
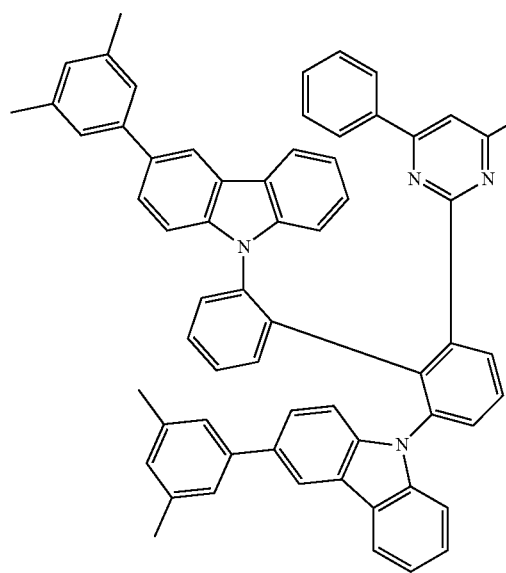 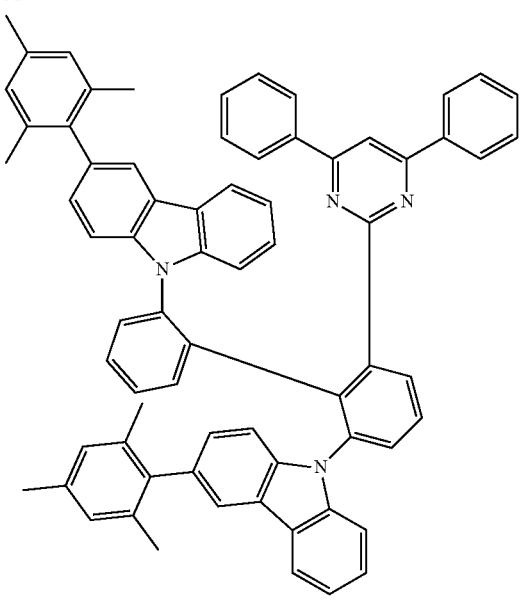
-continued
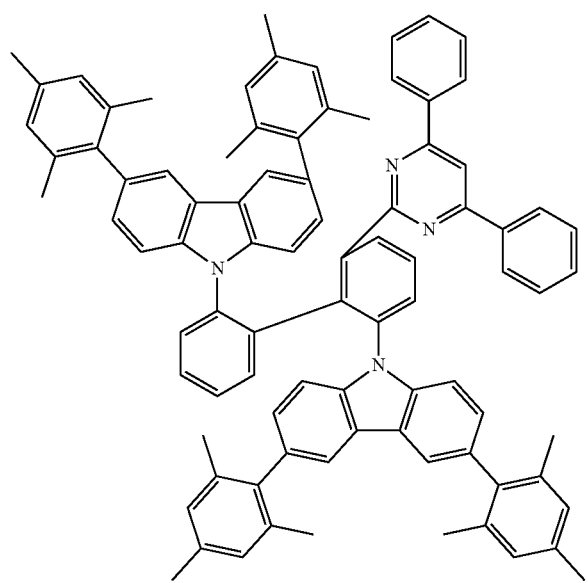

-continued
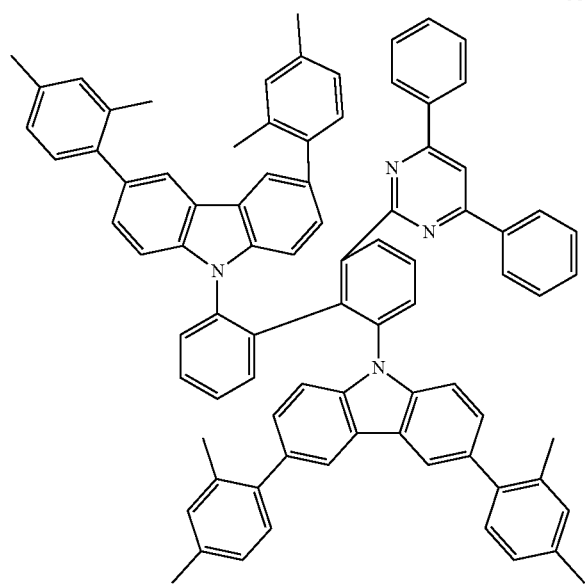
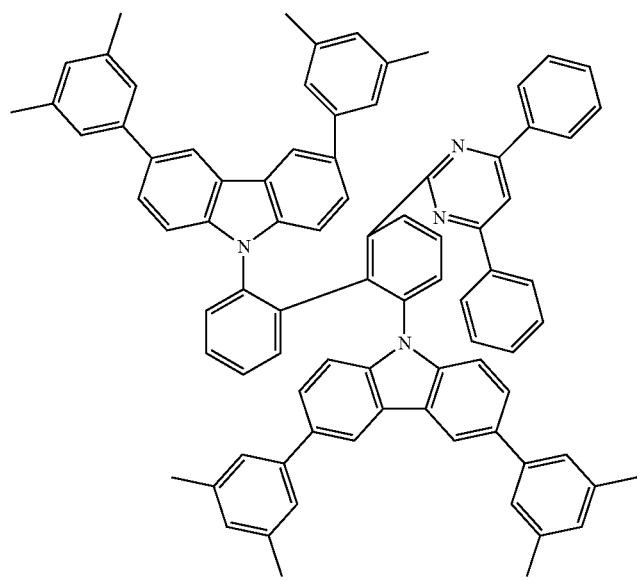
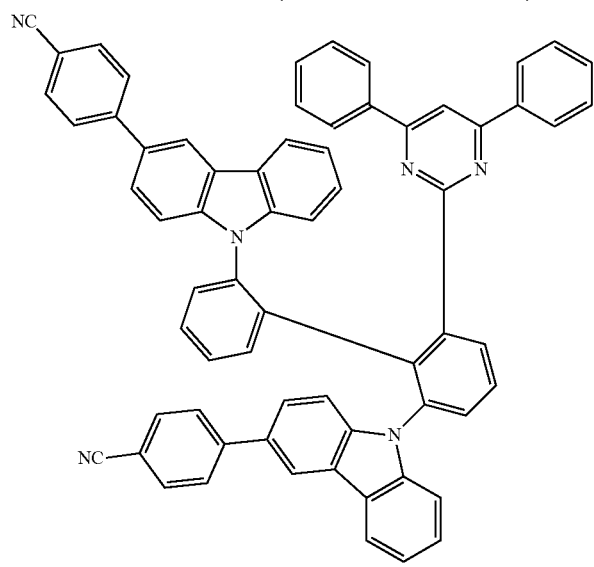

-continued
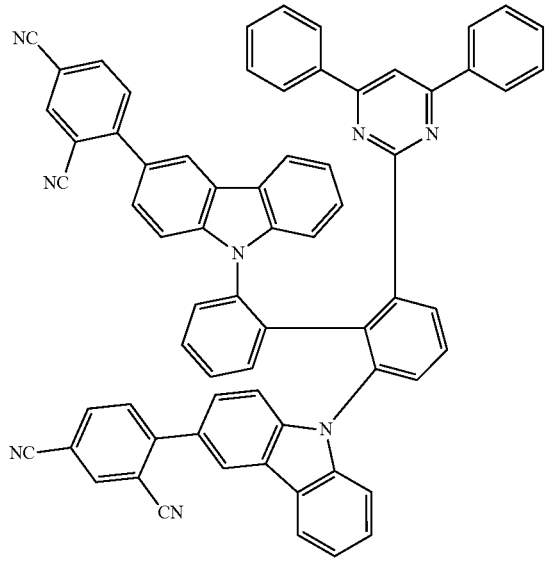
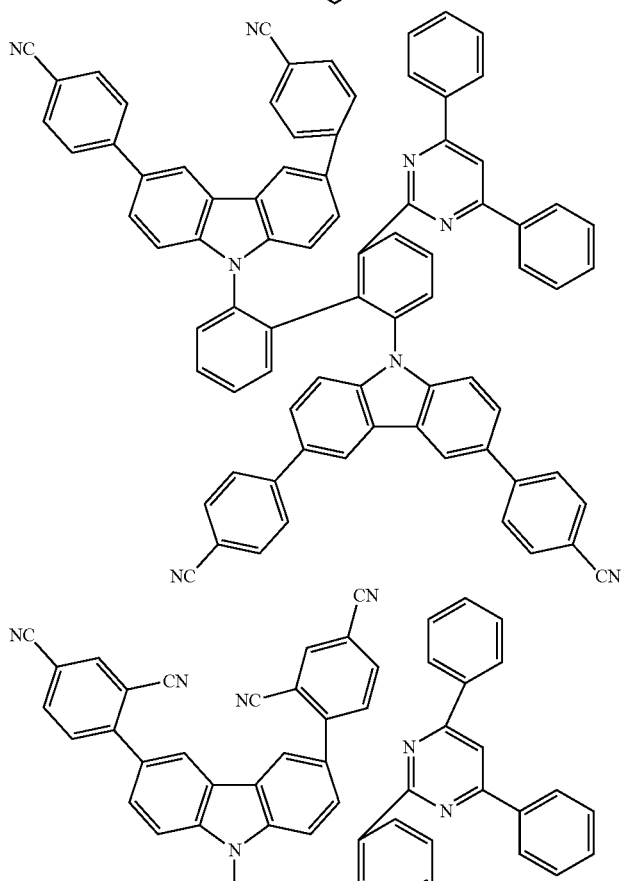
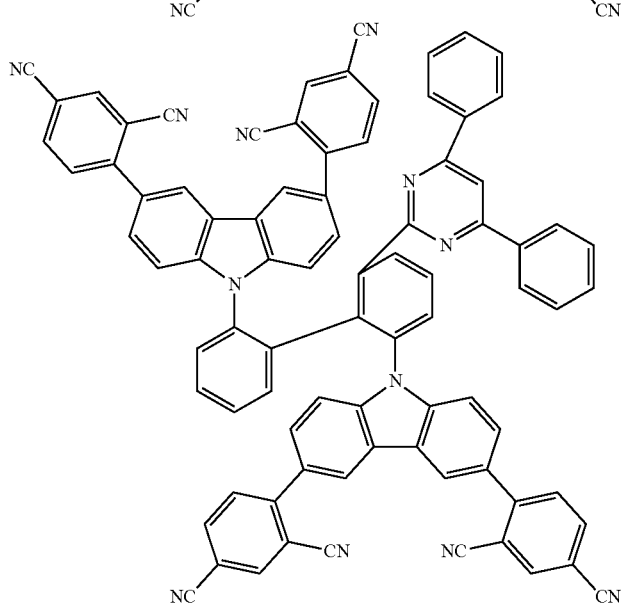

-continued
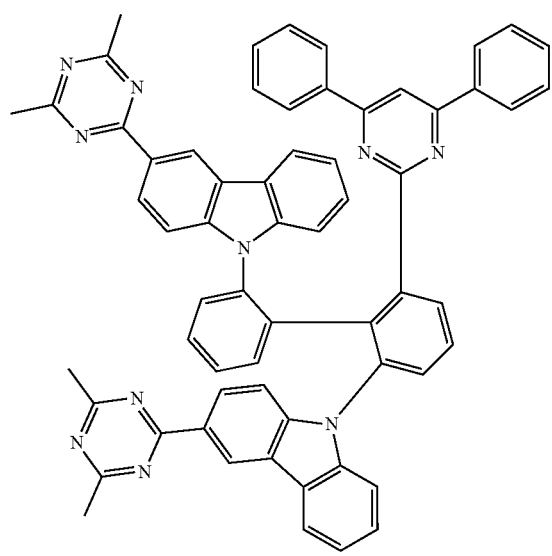
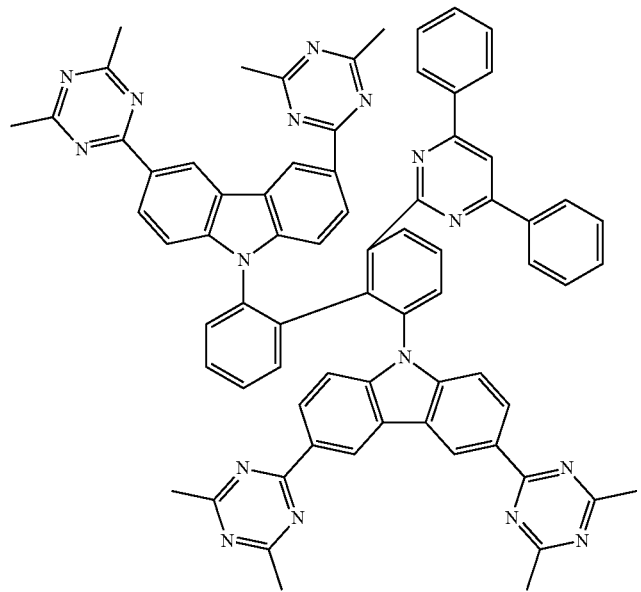
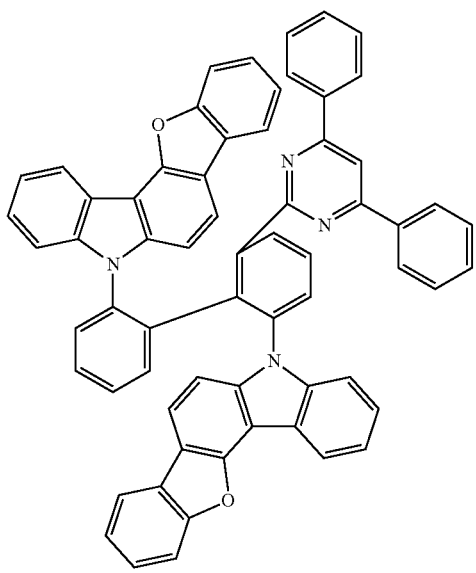
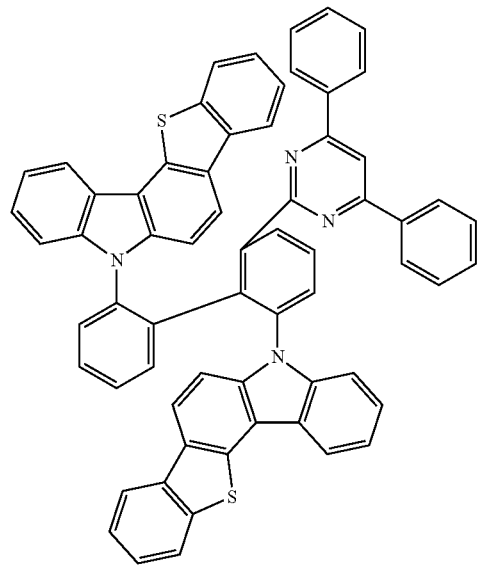
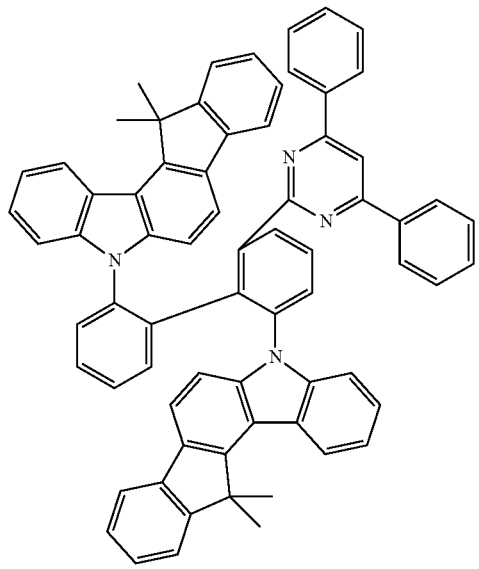

-continued
301
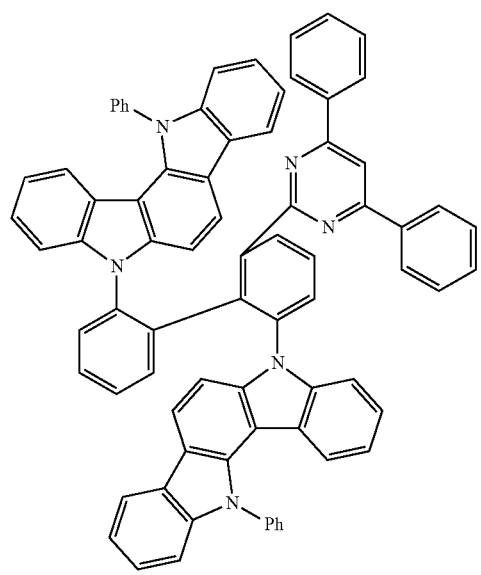
302
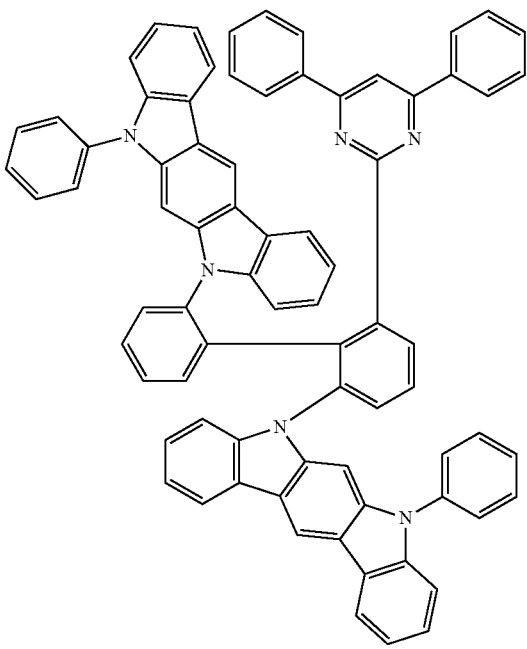
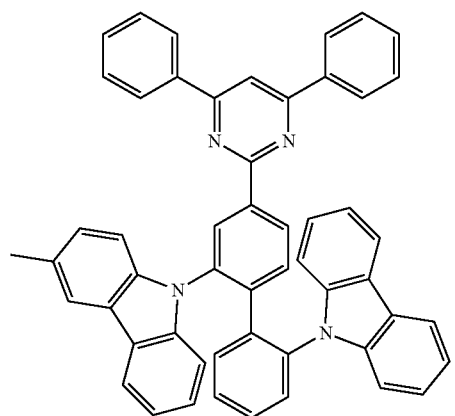
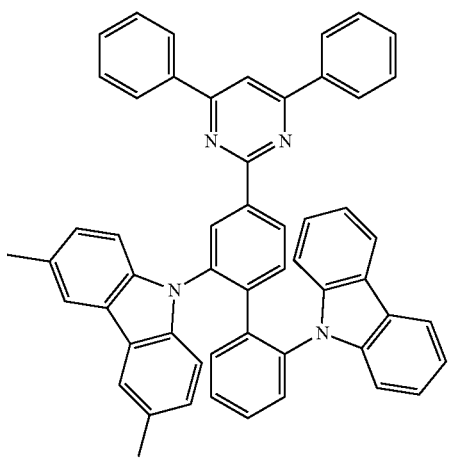
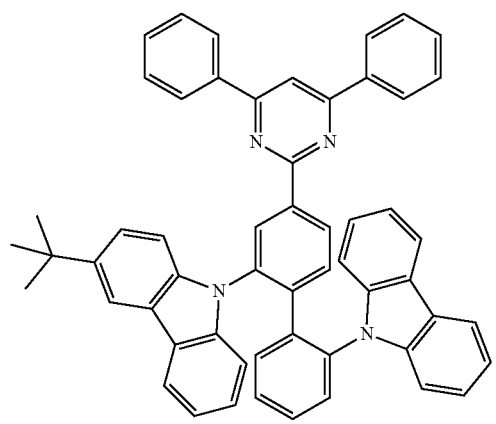
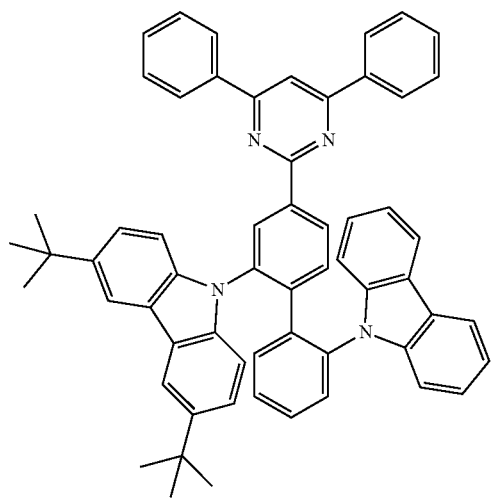

303
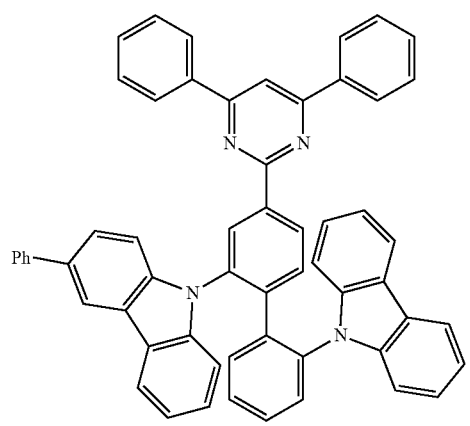
304
-continued
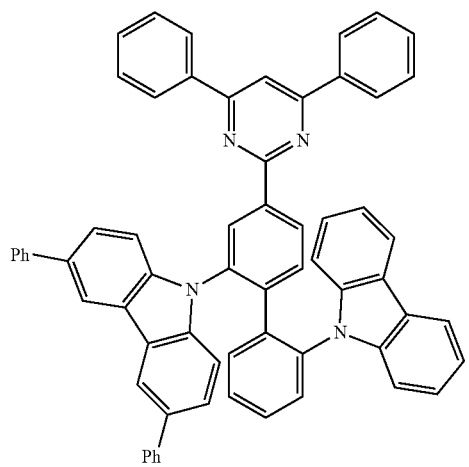
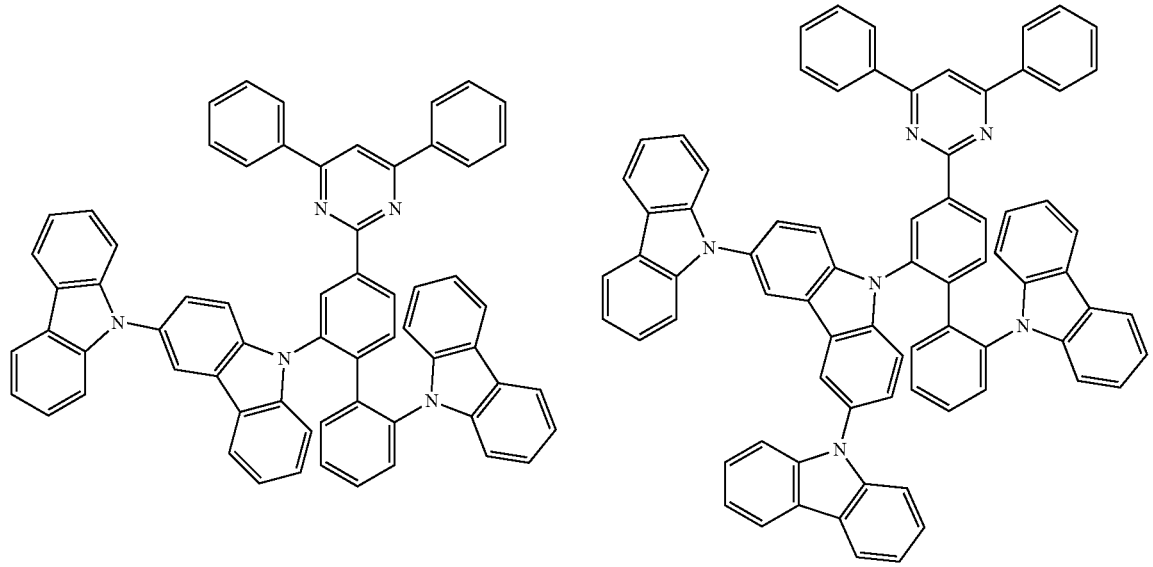
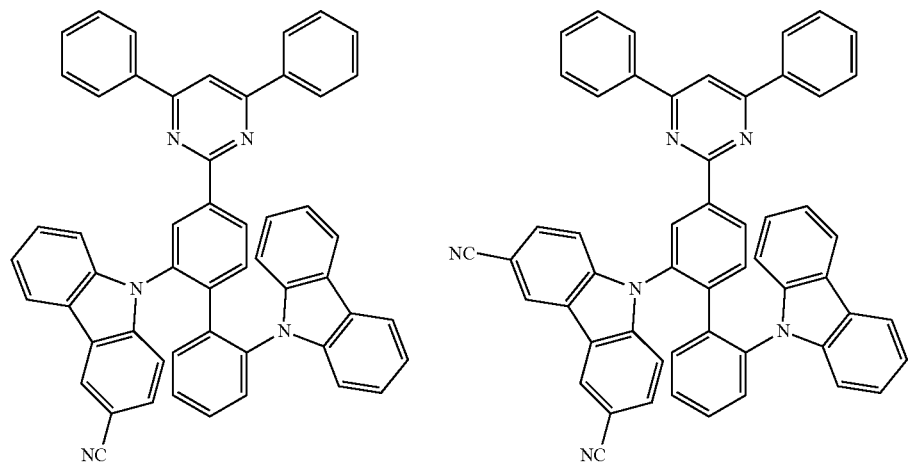

-continued
305
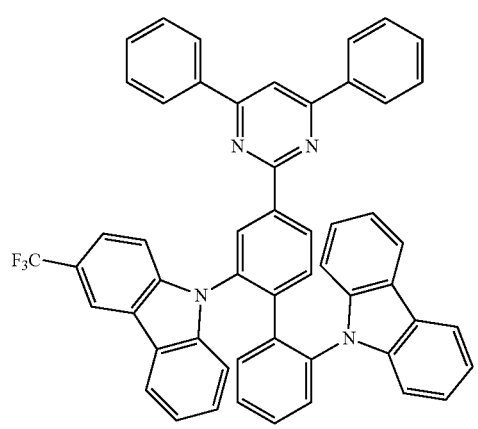
306
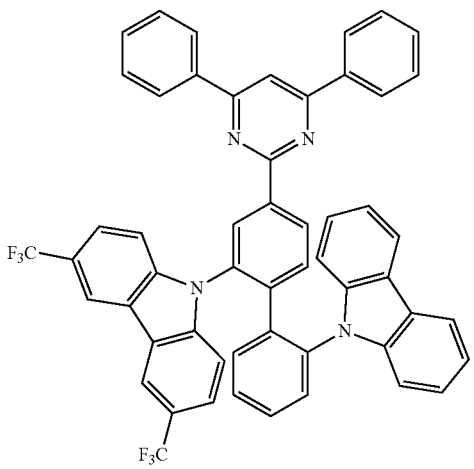
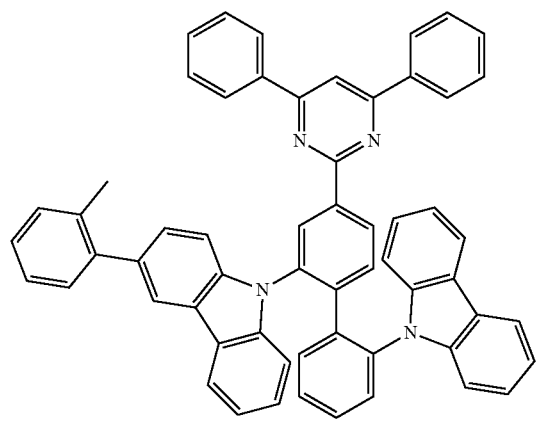
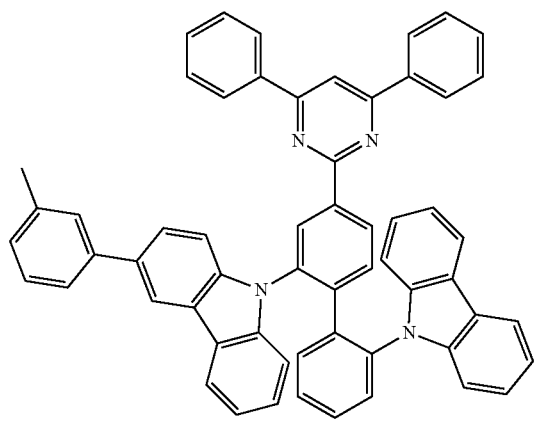
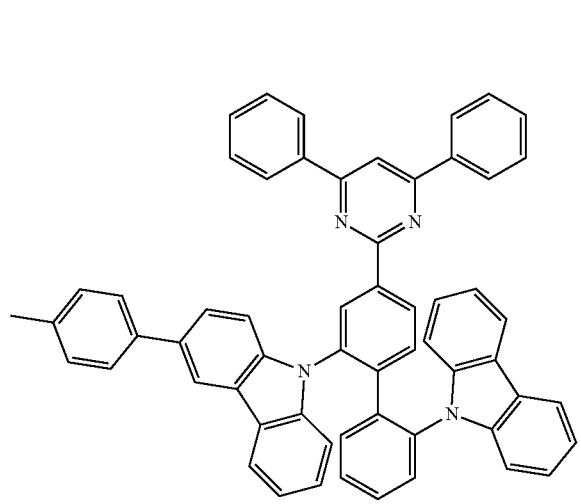
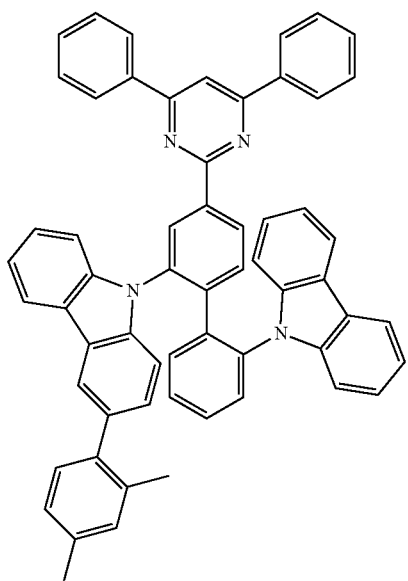

307 308
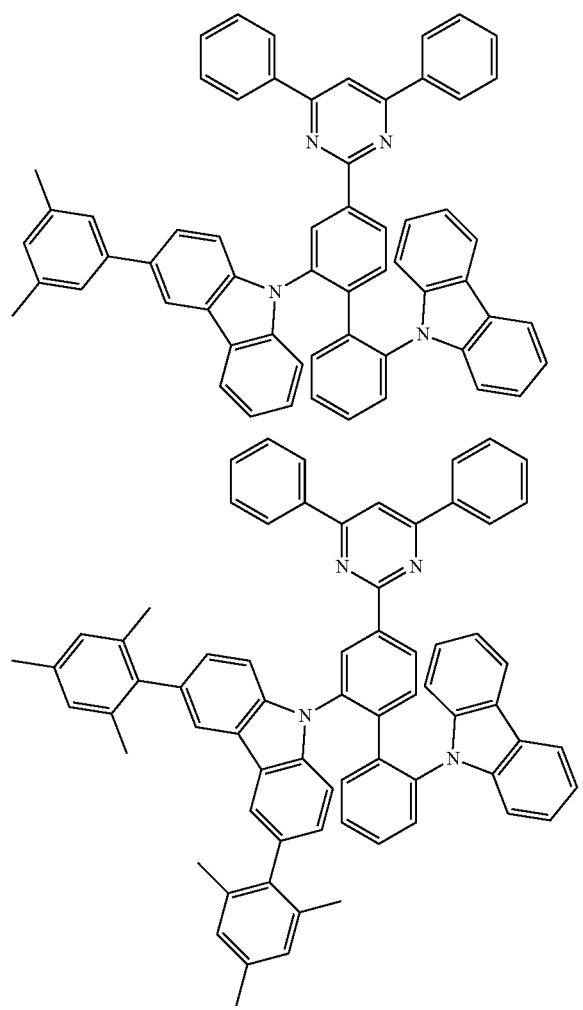 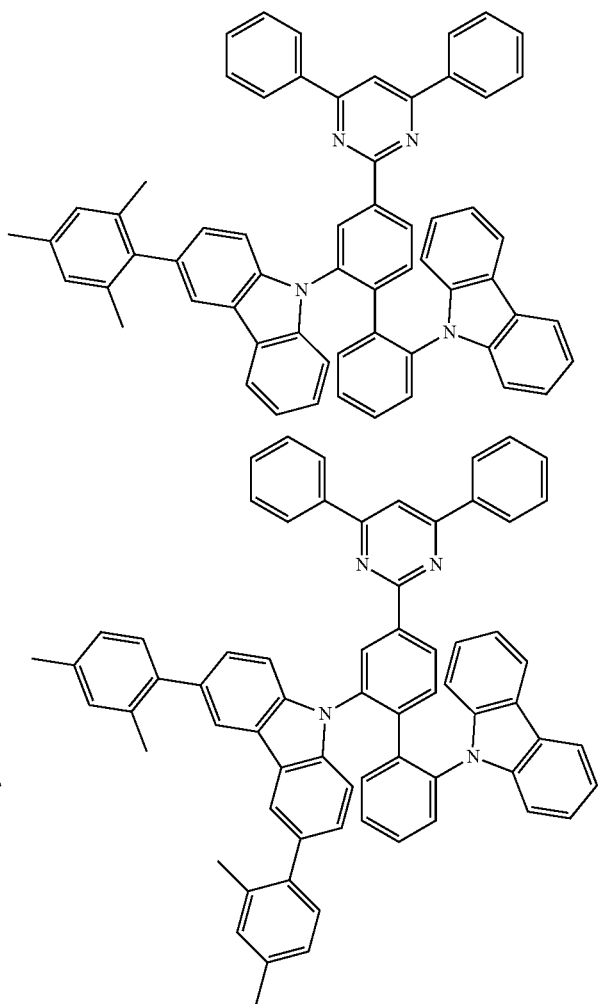
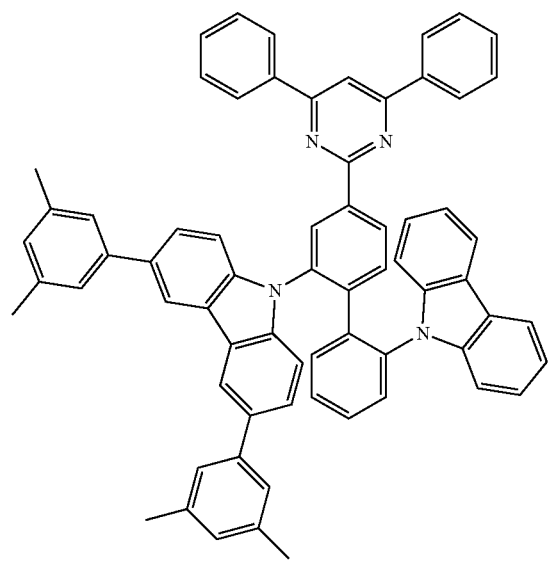

309
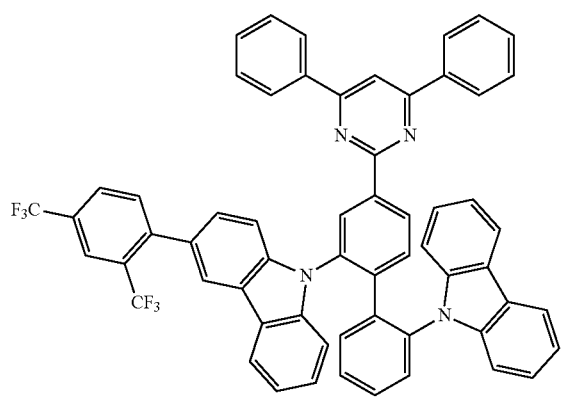
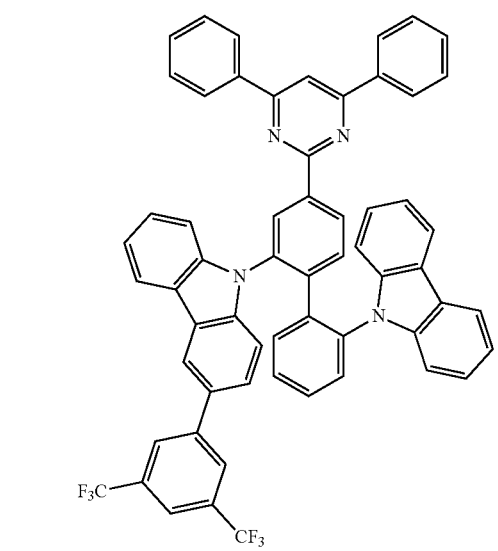
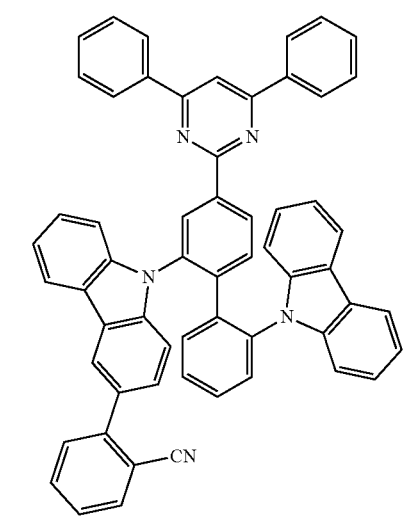
310
-continued
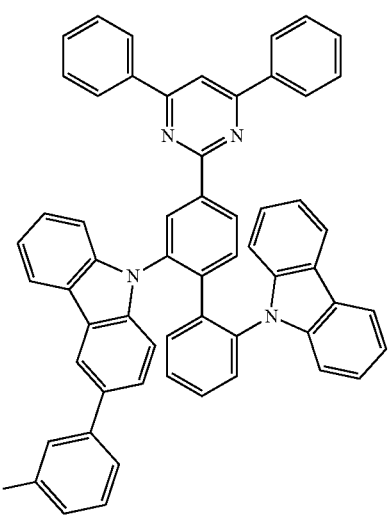
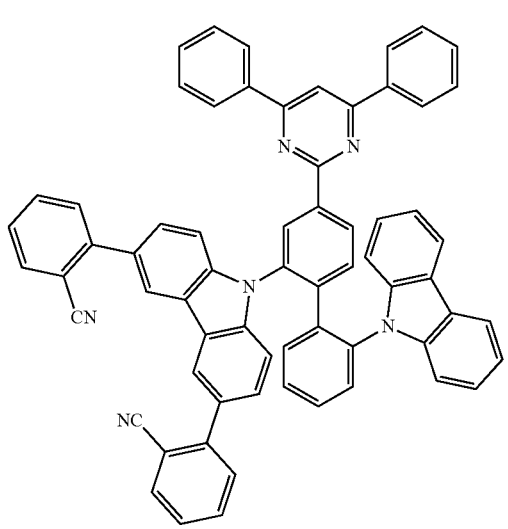
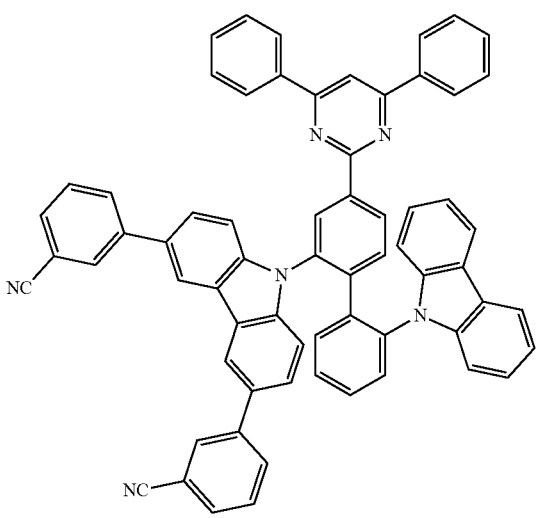

311
-continued
312
-continued
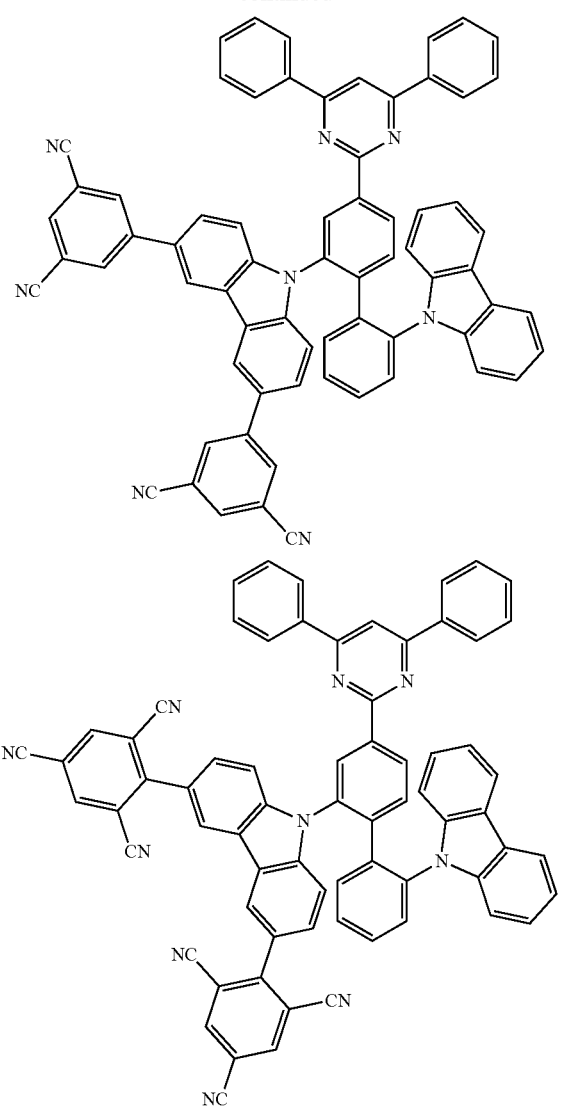
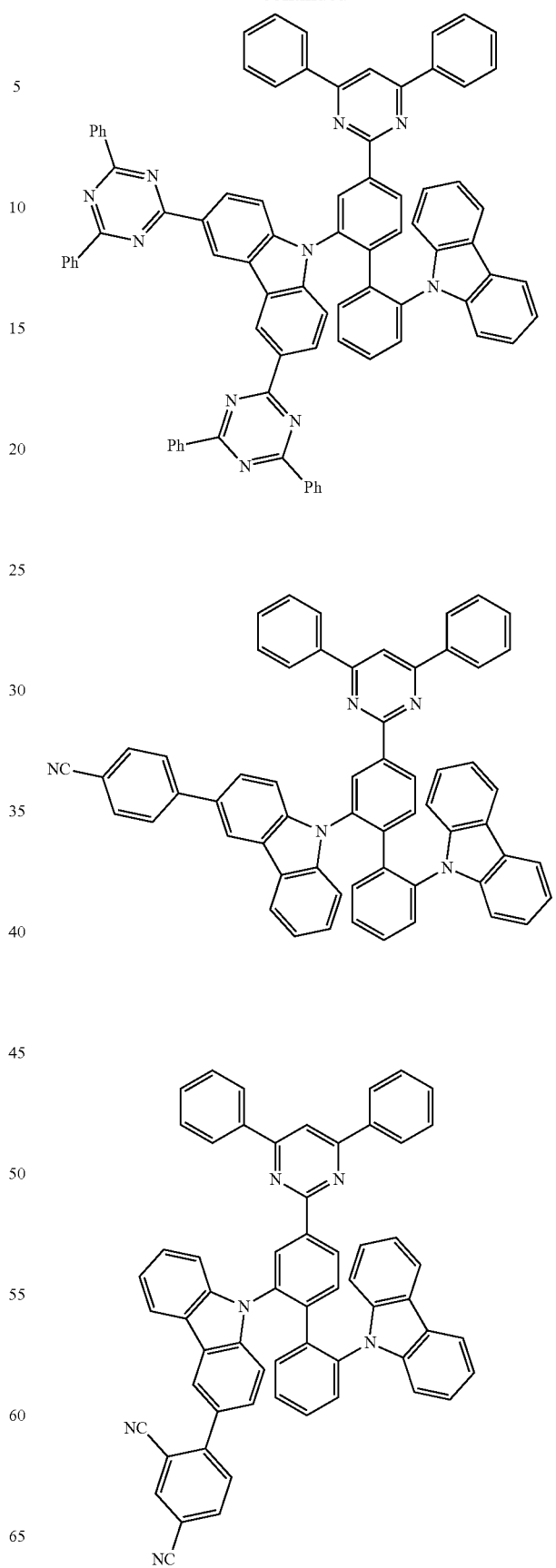

313
-continued
314
-continued
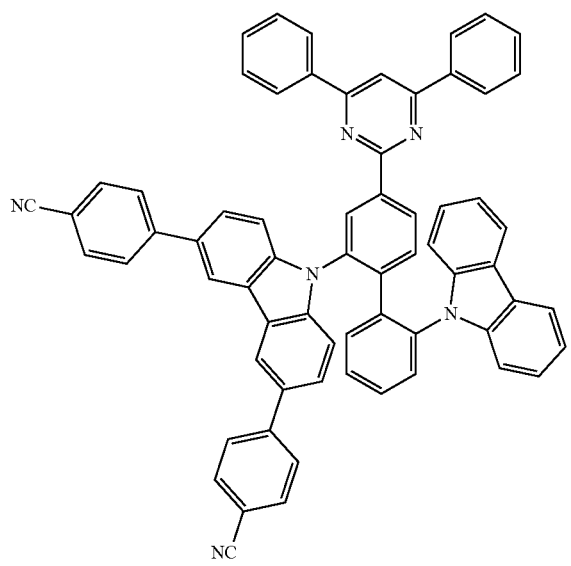
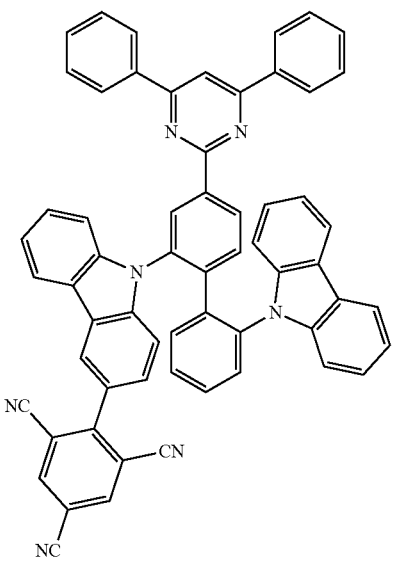
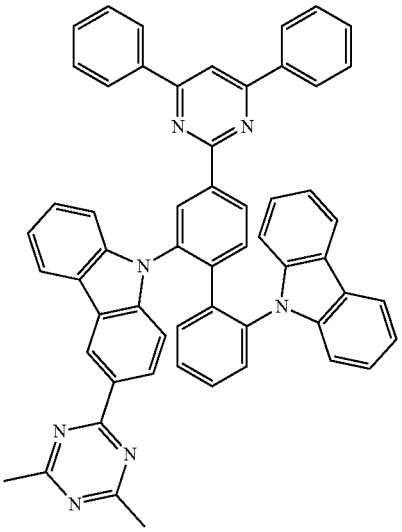
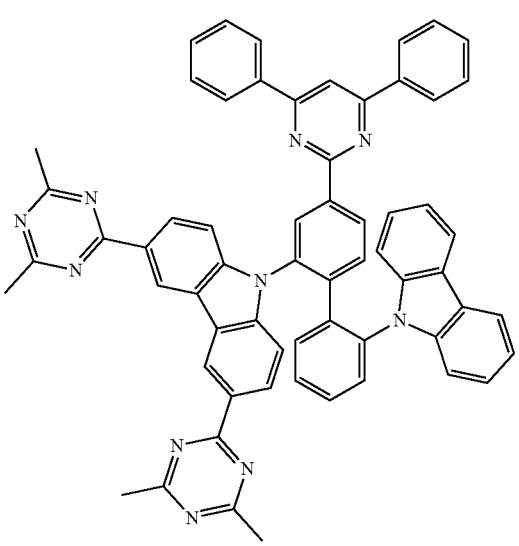

315
-continued
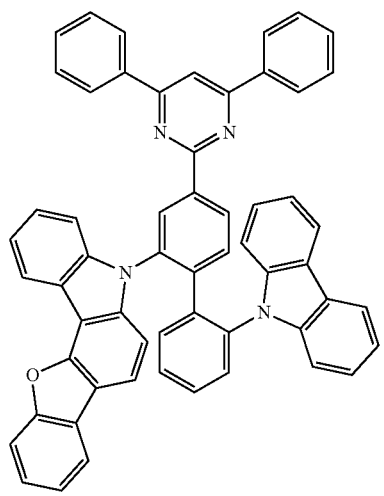
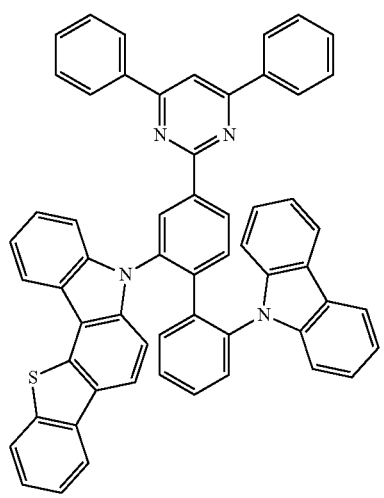
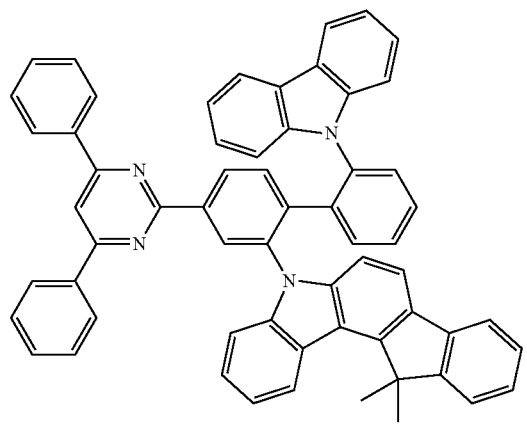
316
-continued
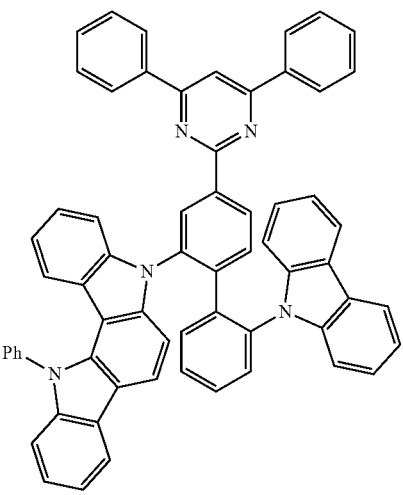
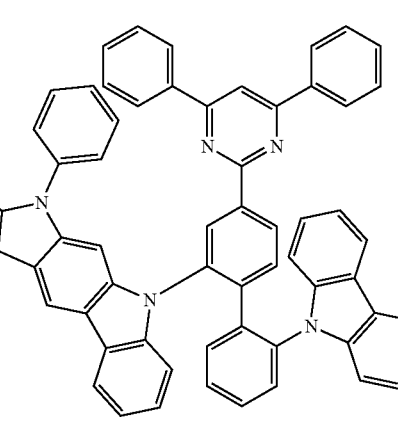
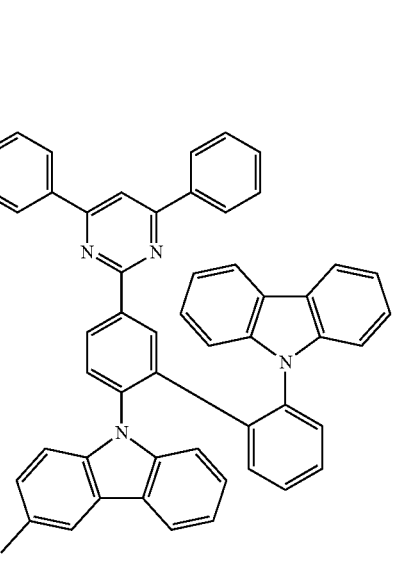

317
-continued
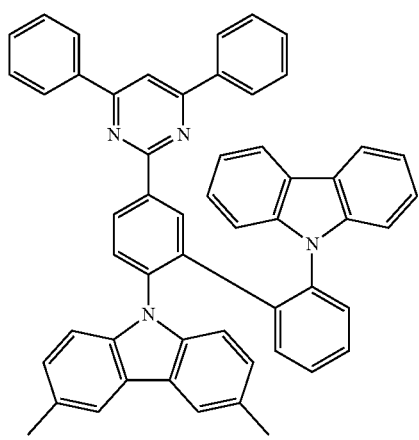
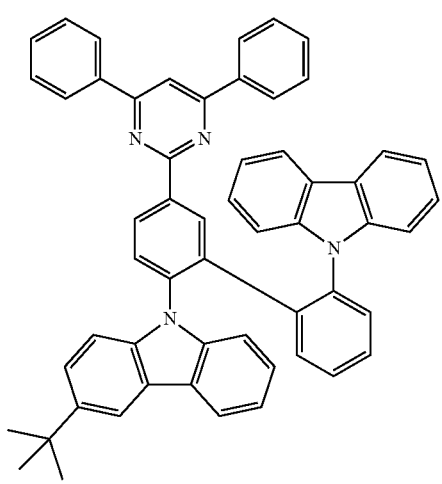
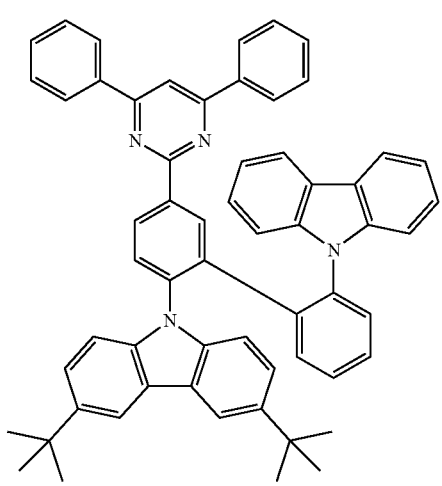
318
-continued
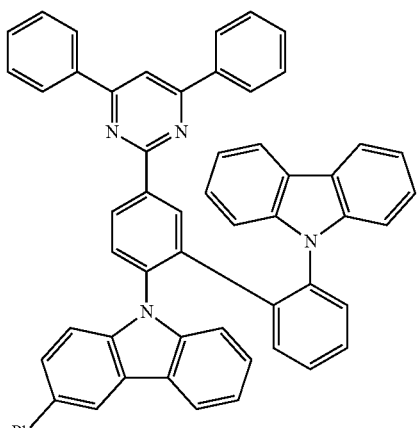
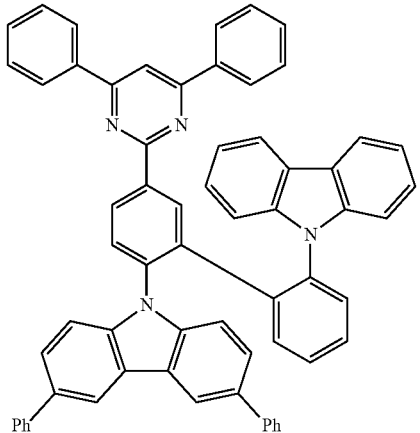
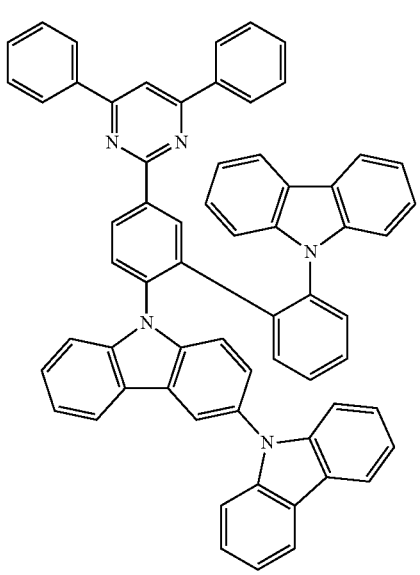

319
-continued
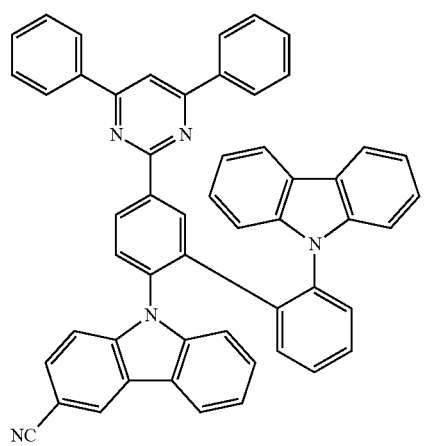
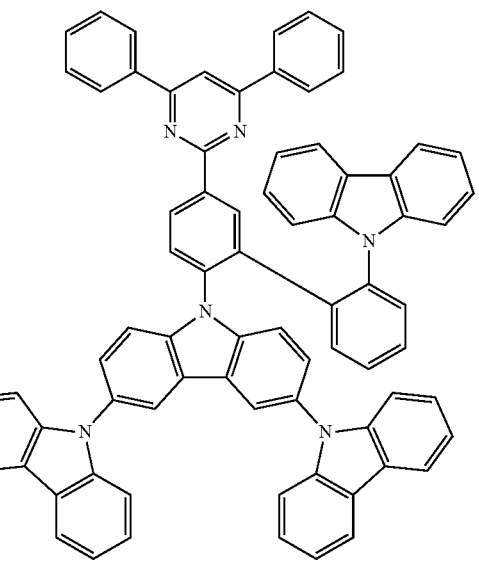
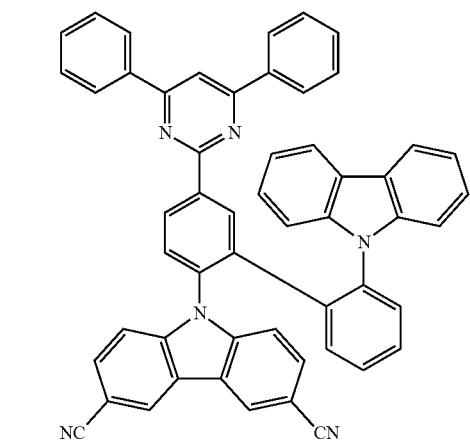
320
-continued
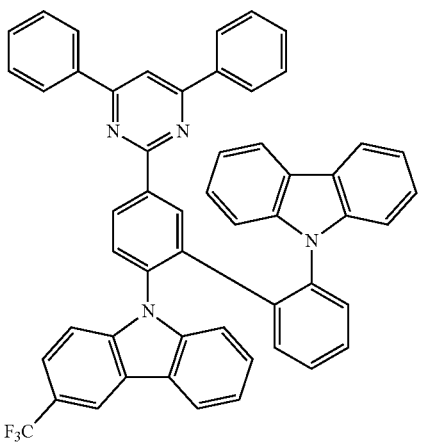
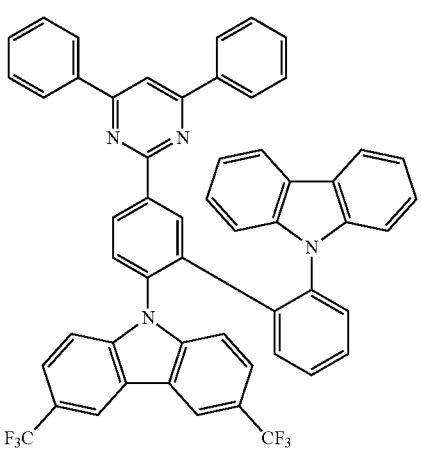
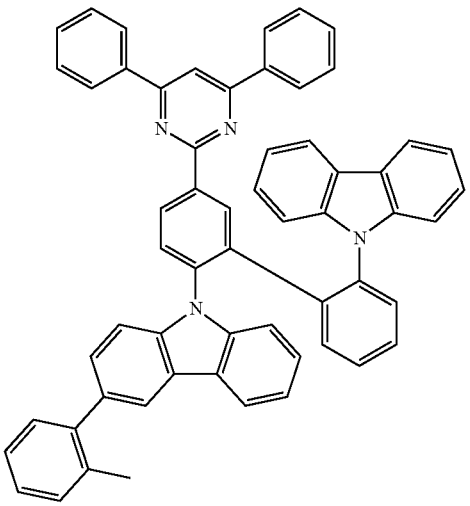

321
-continued
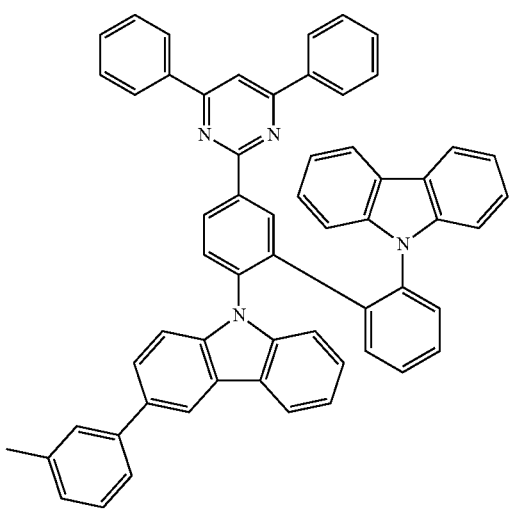
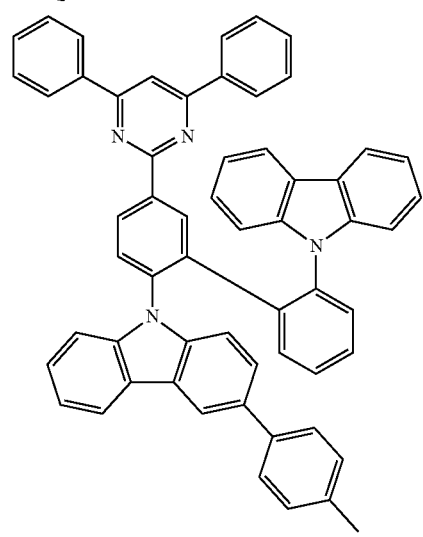
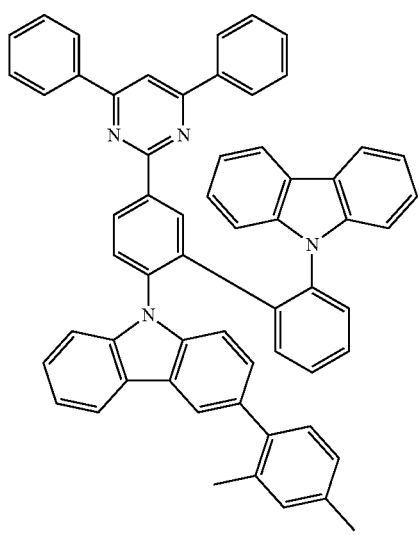
322
-continued
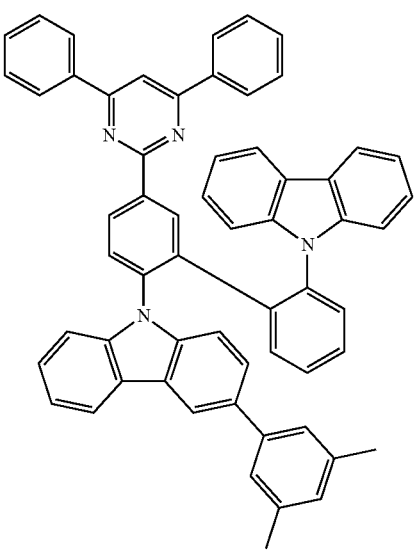
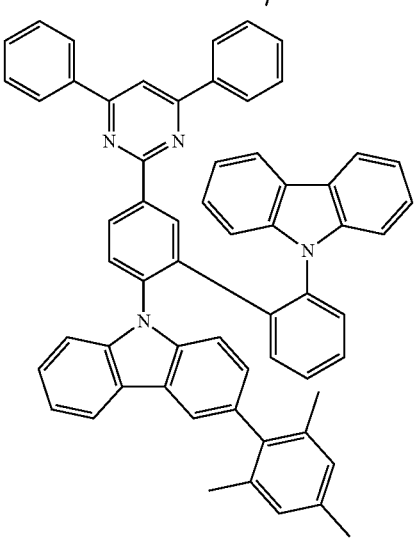
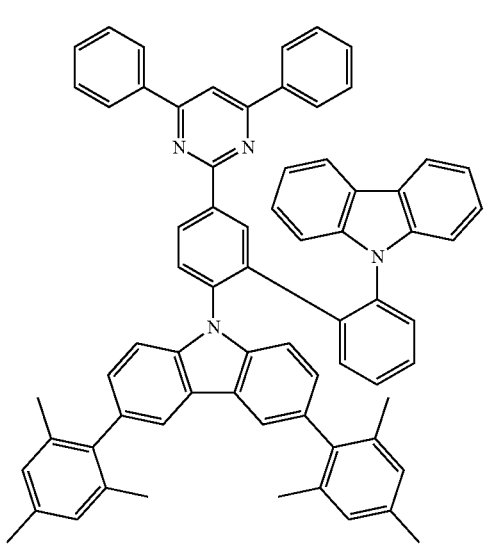

323
-continued
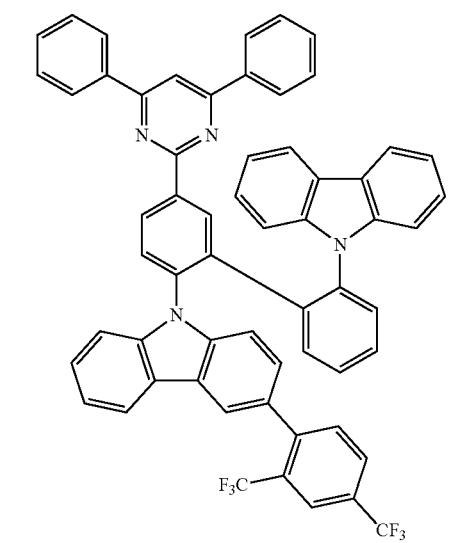
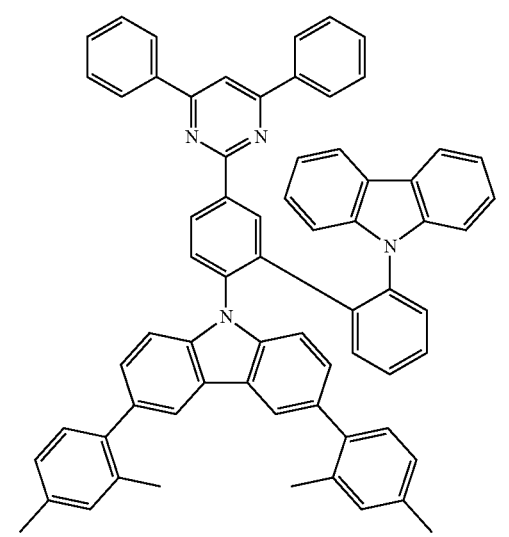
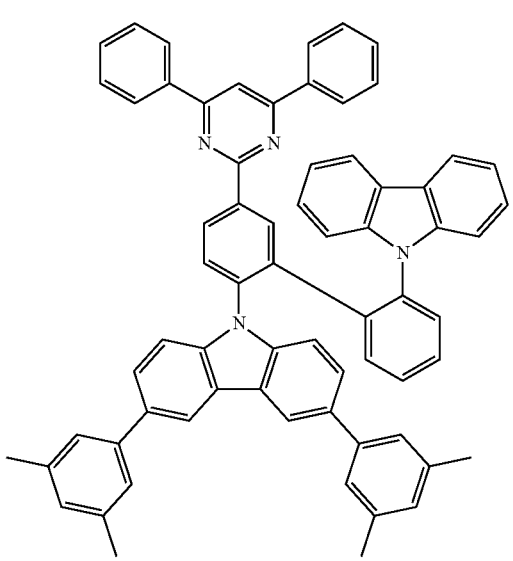
324
-continued
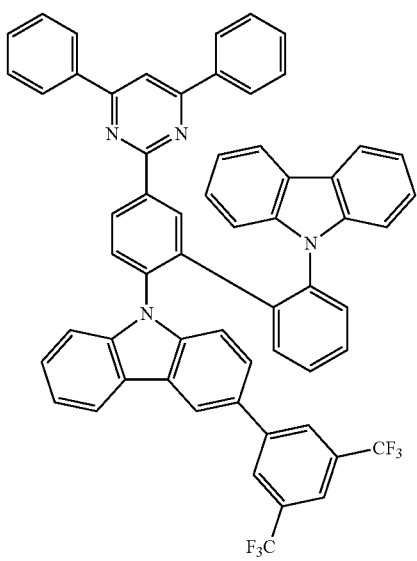
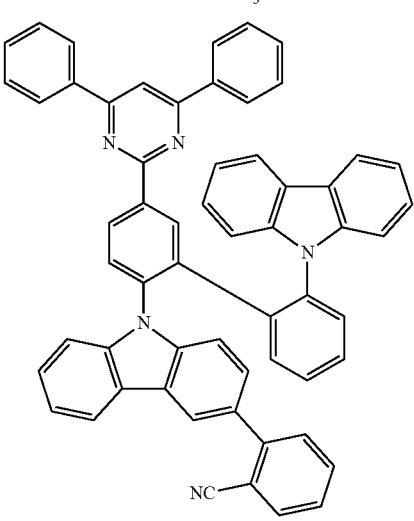
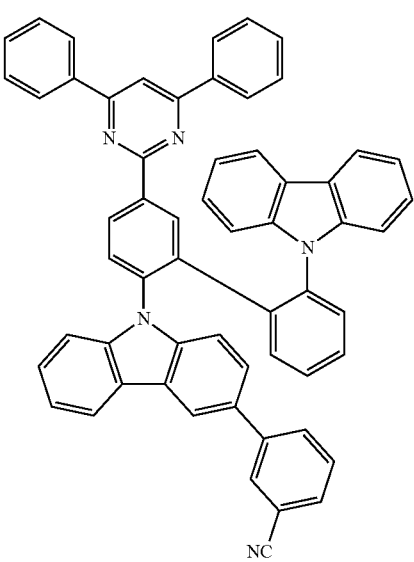

325
-continued
326
-continued
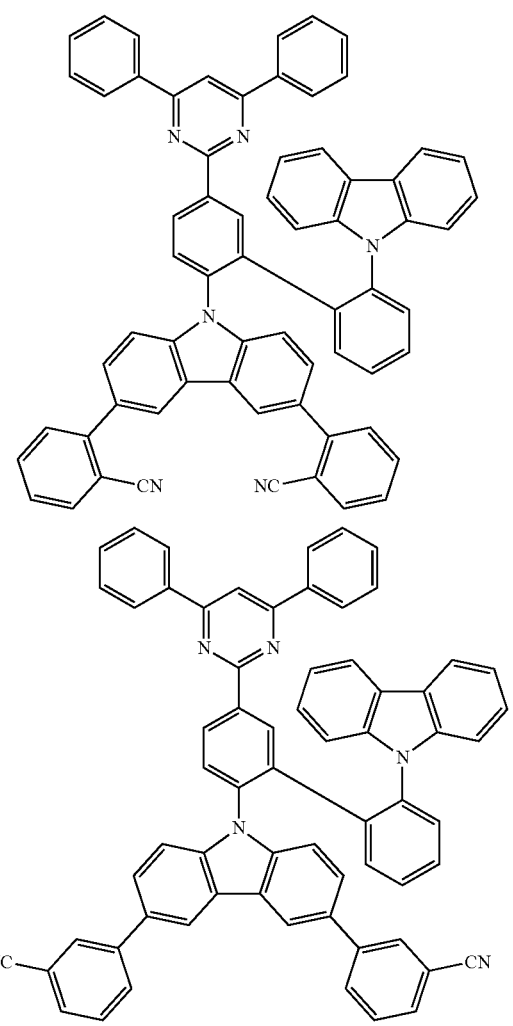
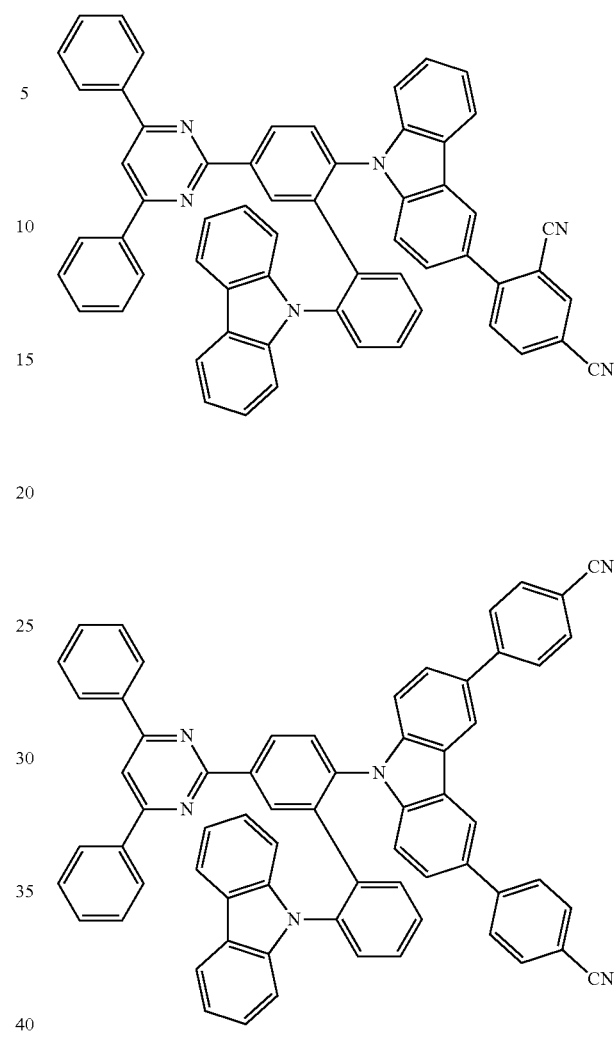
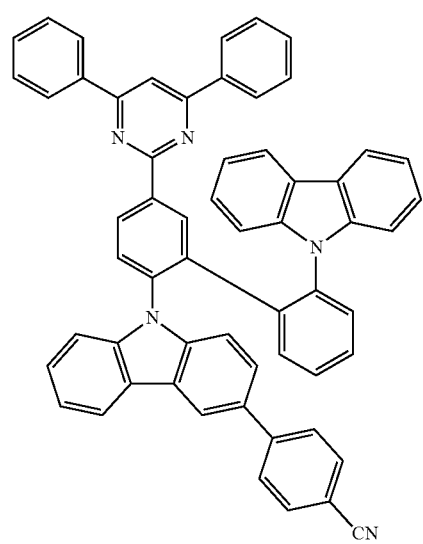
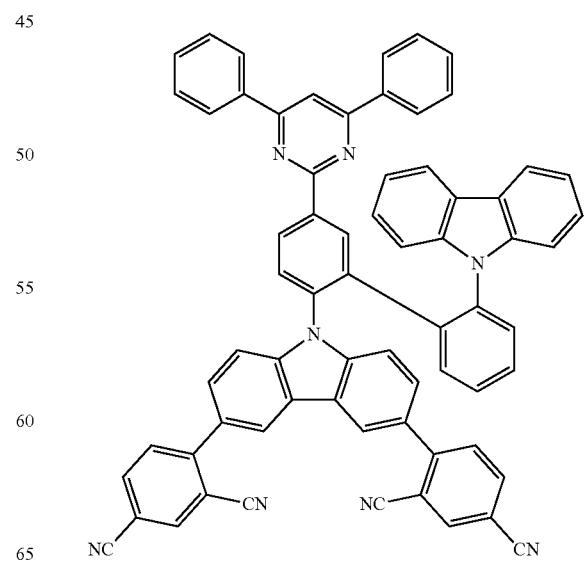

327
-continued
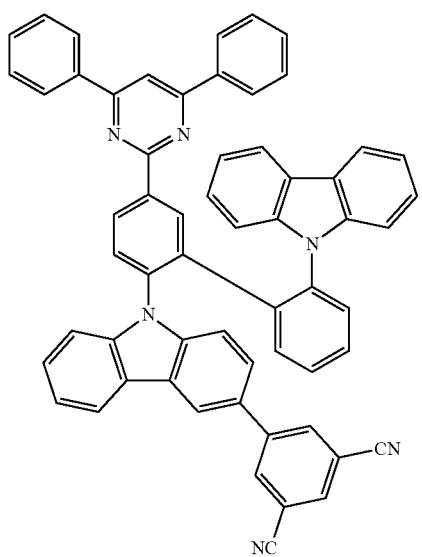
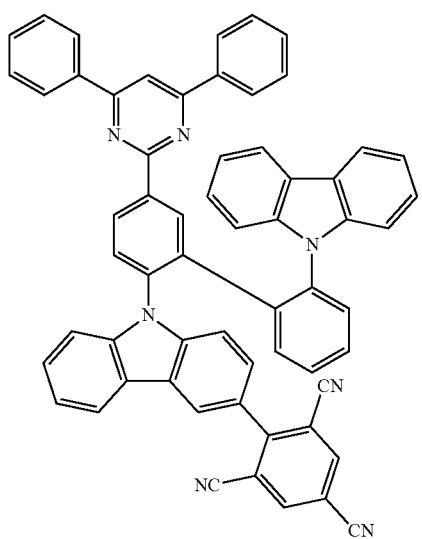
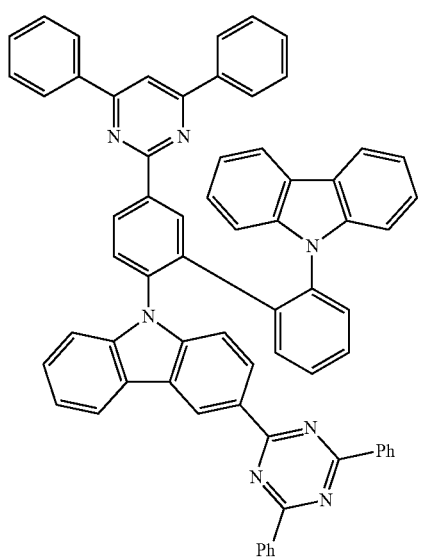
328
-continued
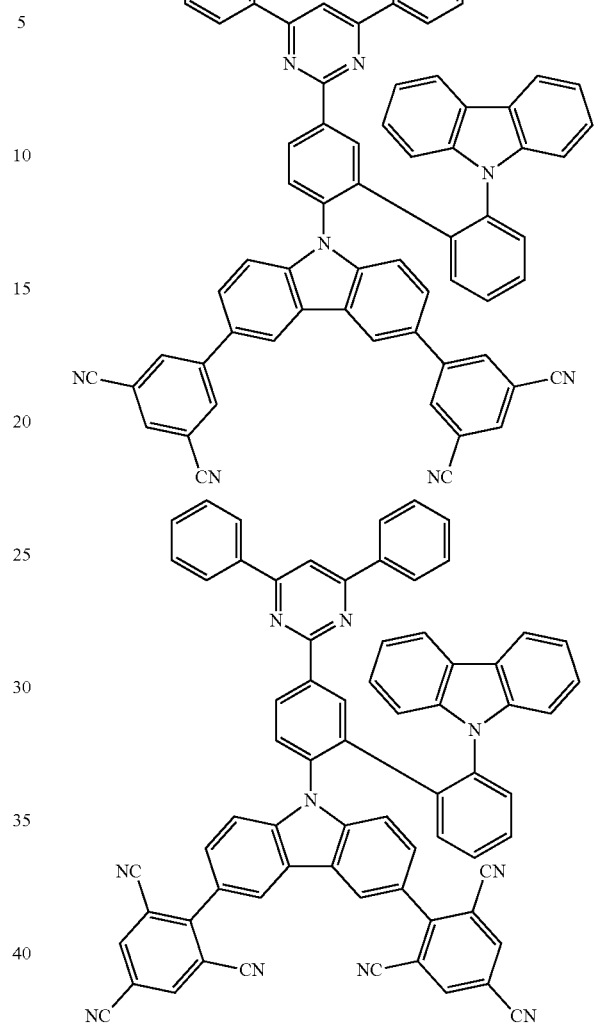
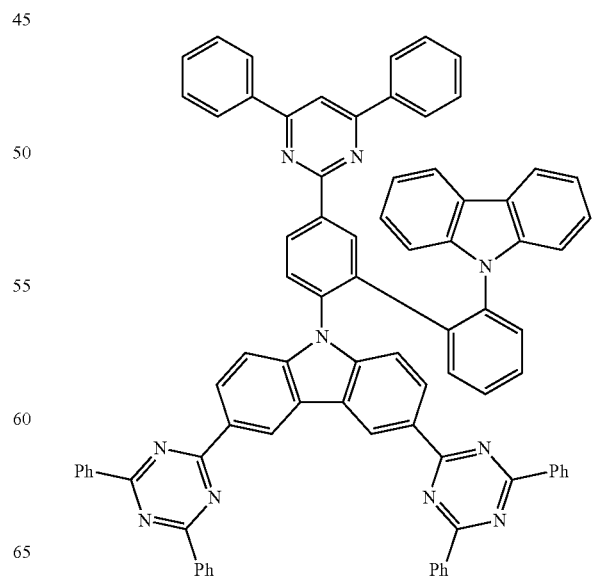

329
-continued
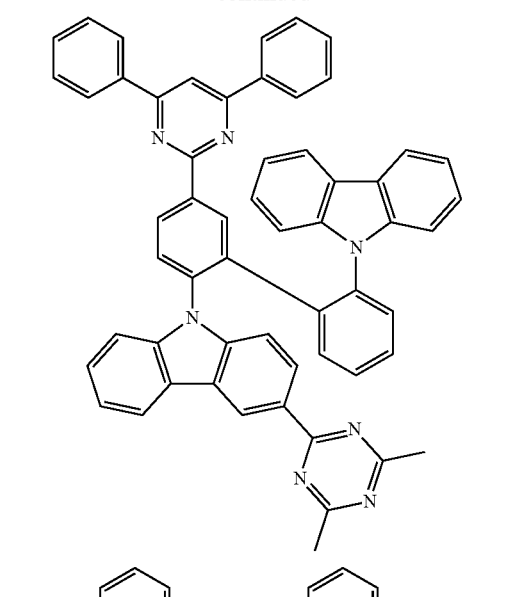
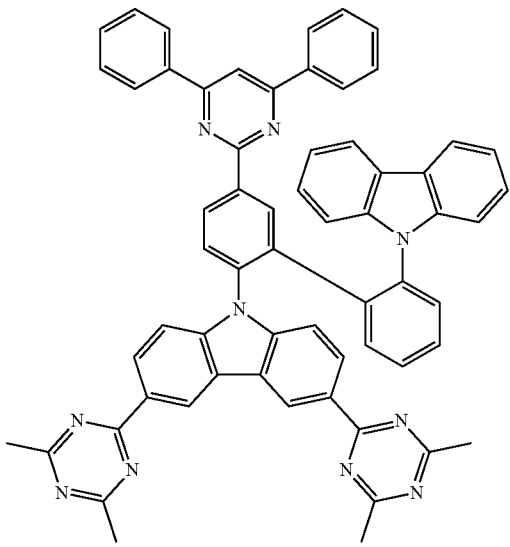
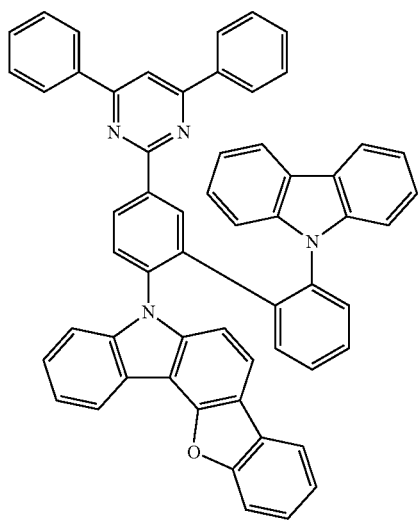
330
-continued
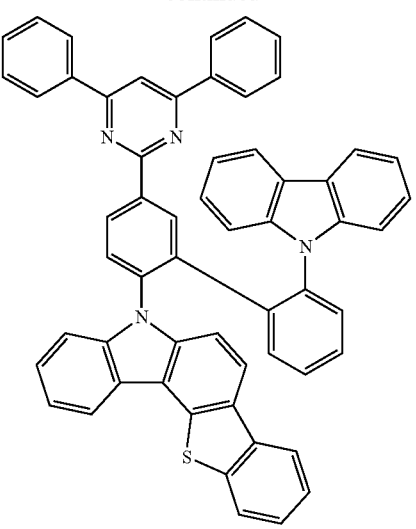
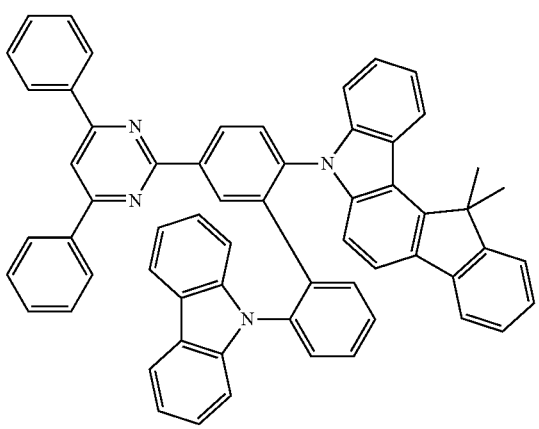

331
-continued
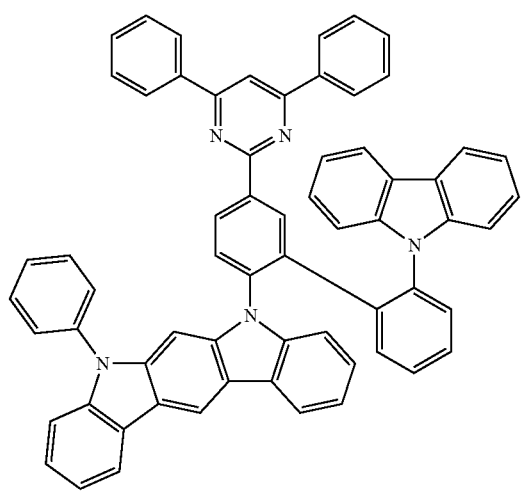
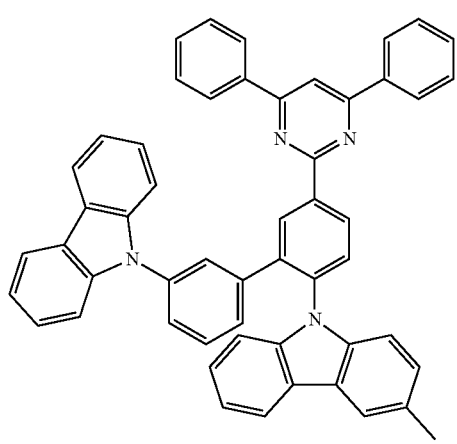
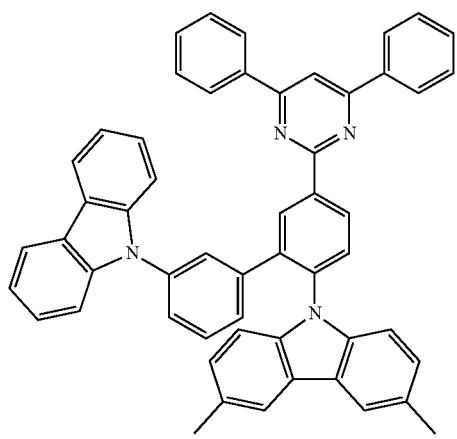
332
-continued
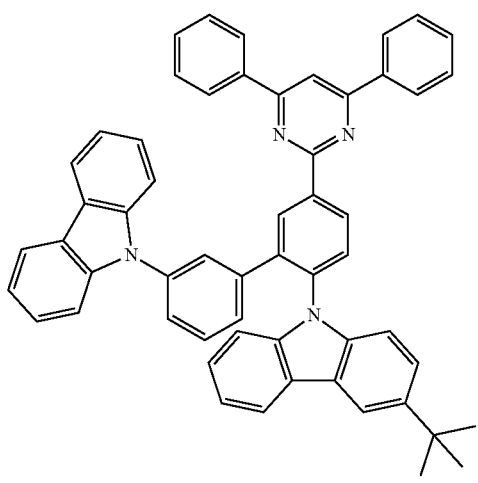
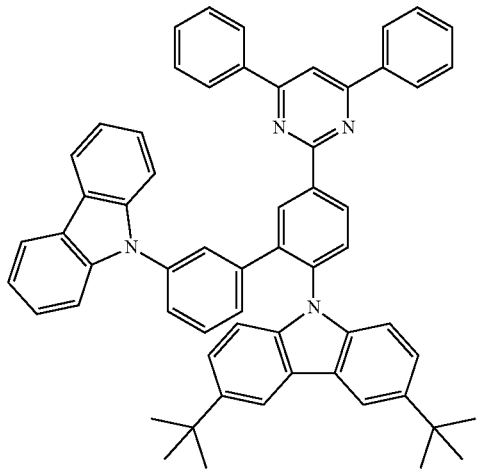
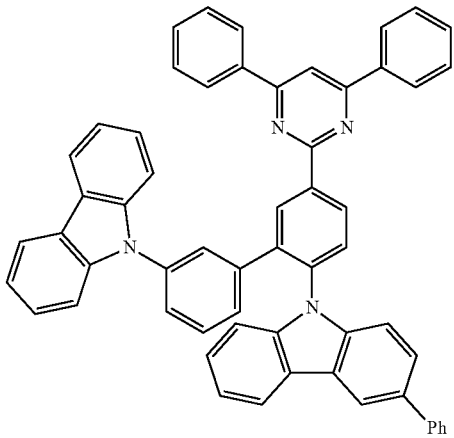

333
-continued
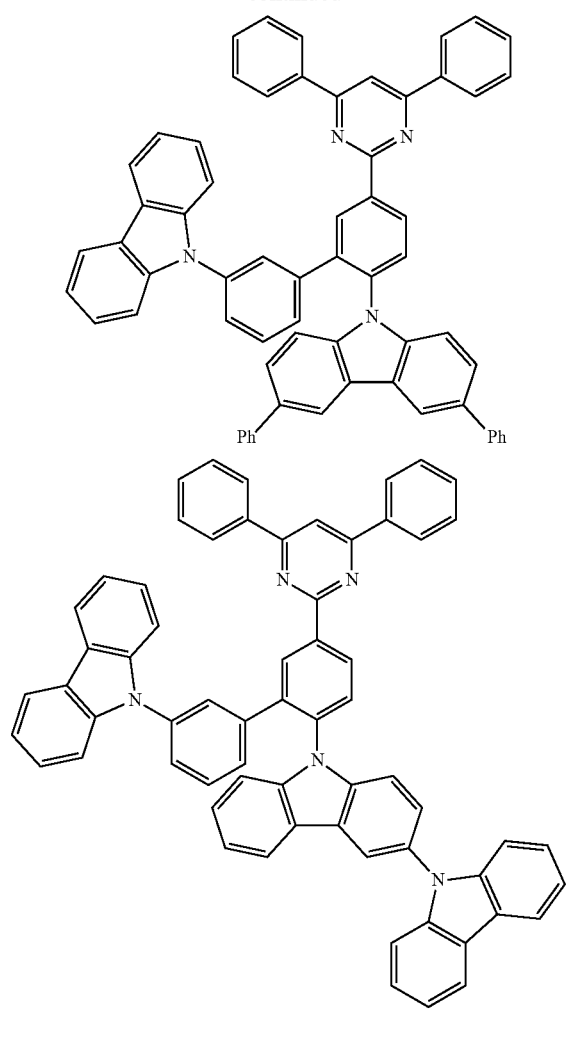
334
-continued
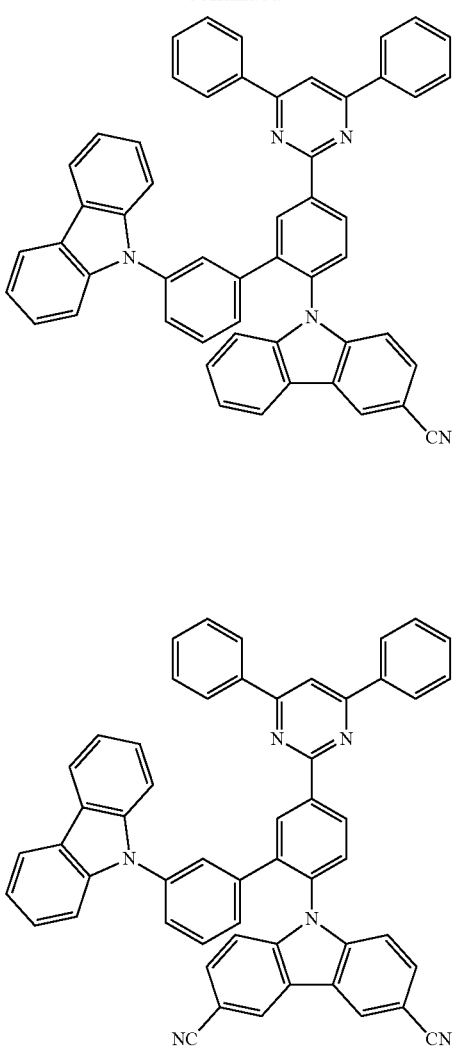
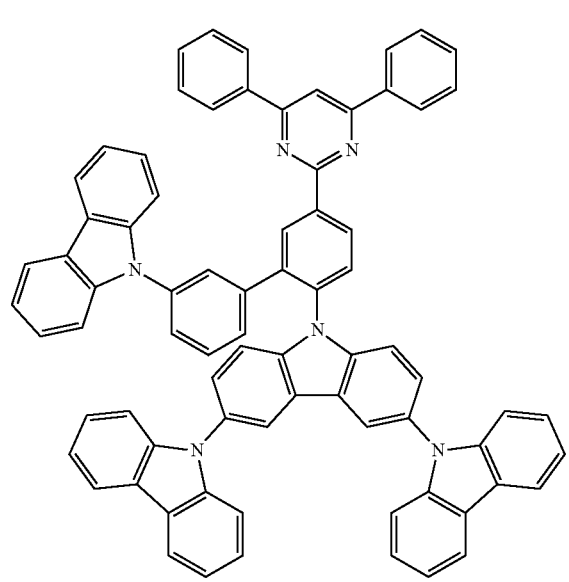
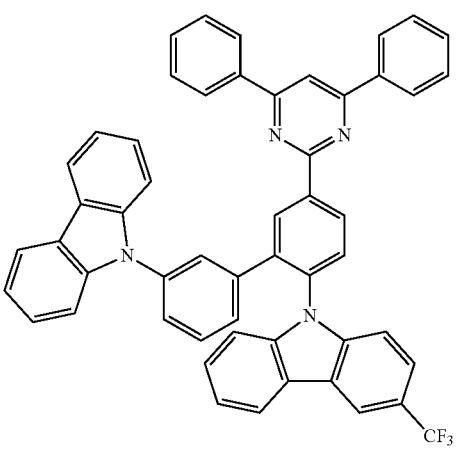

335
-continued
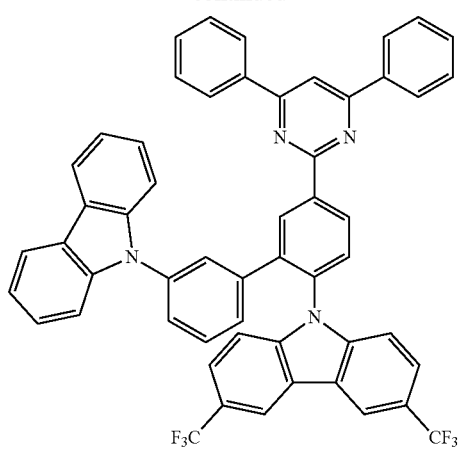
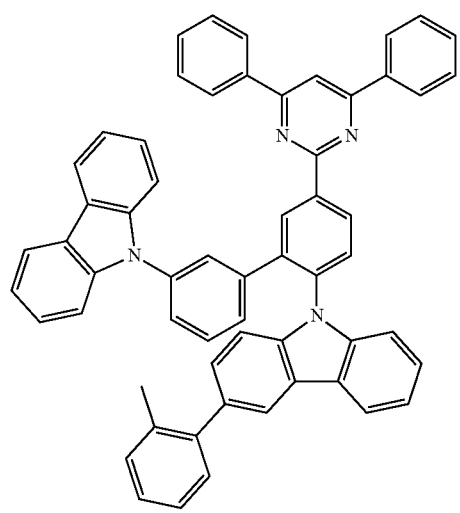
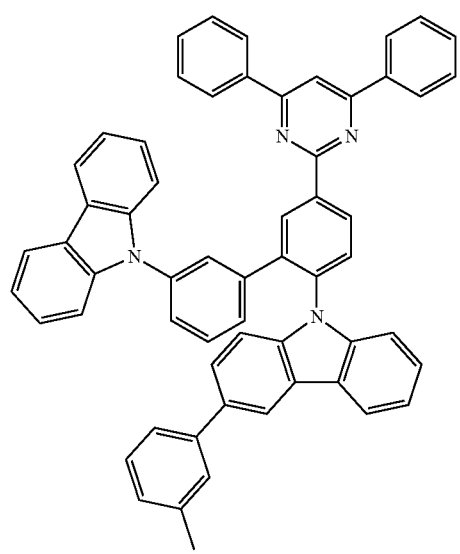
336
-continued
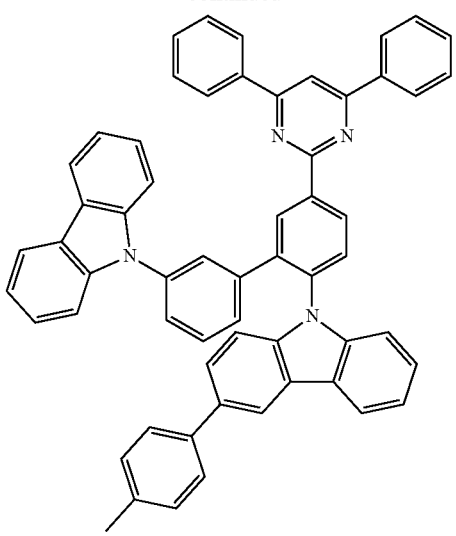
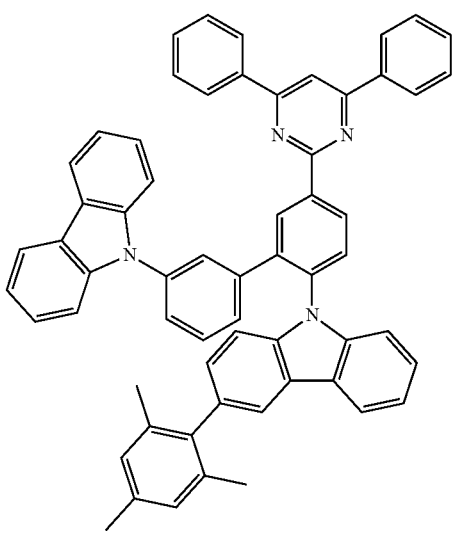
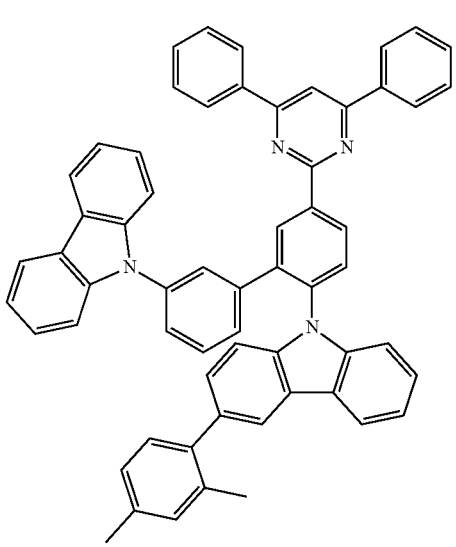

337
-continued
338
-continued
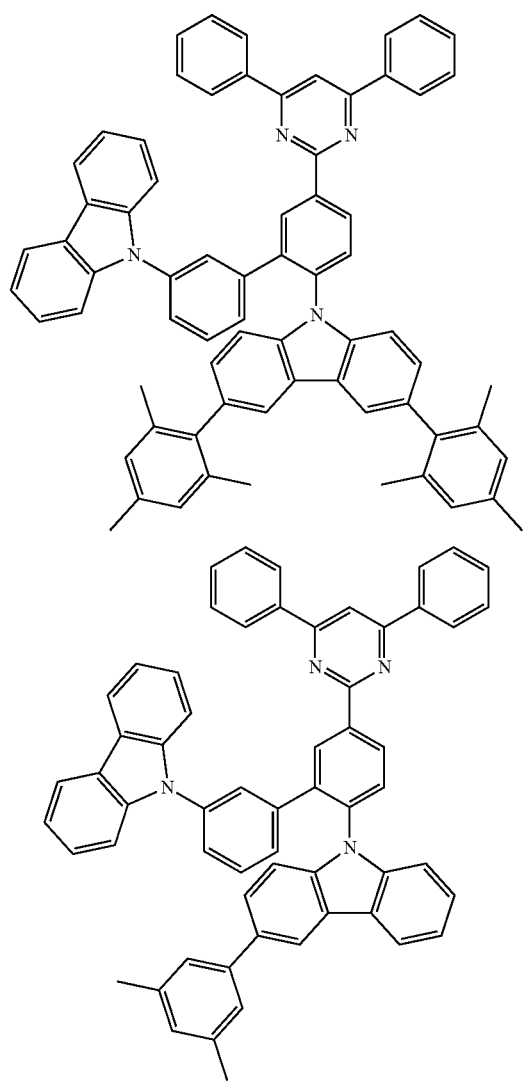
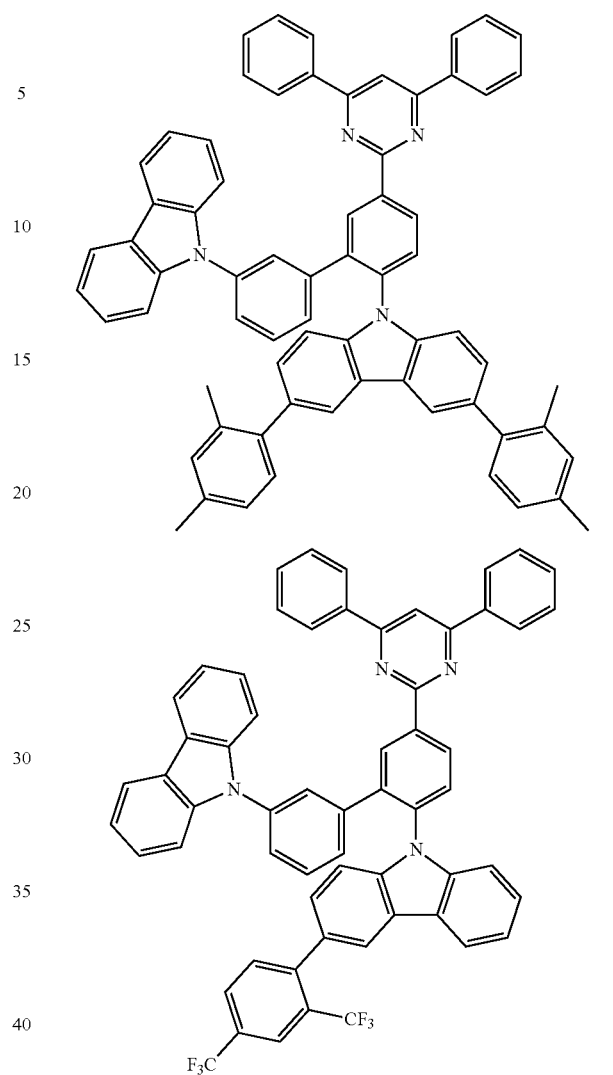
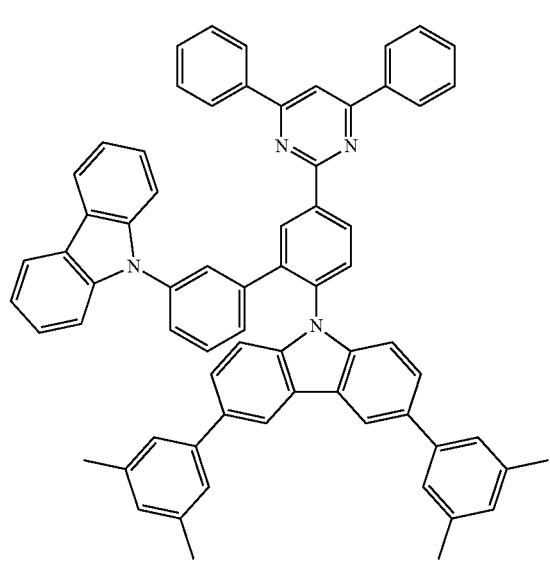
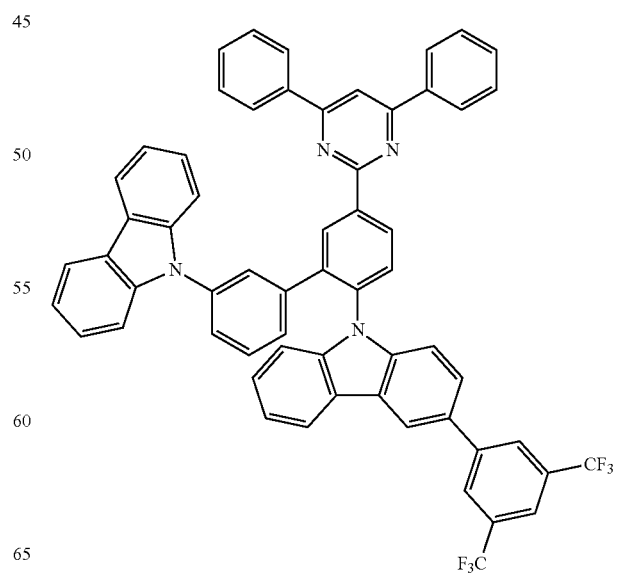

339
-continued
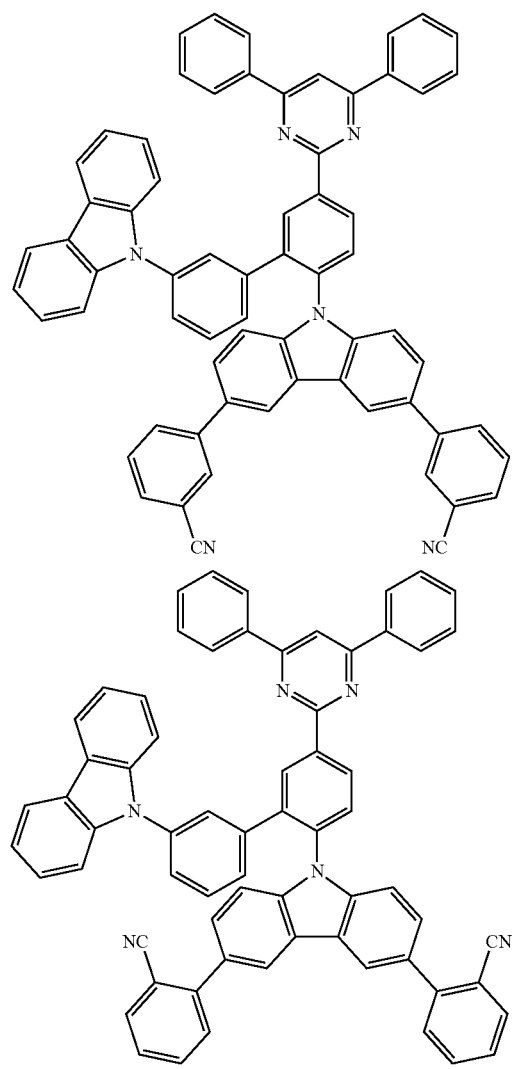
340
-continued
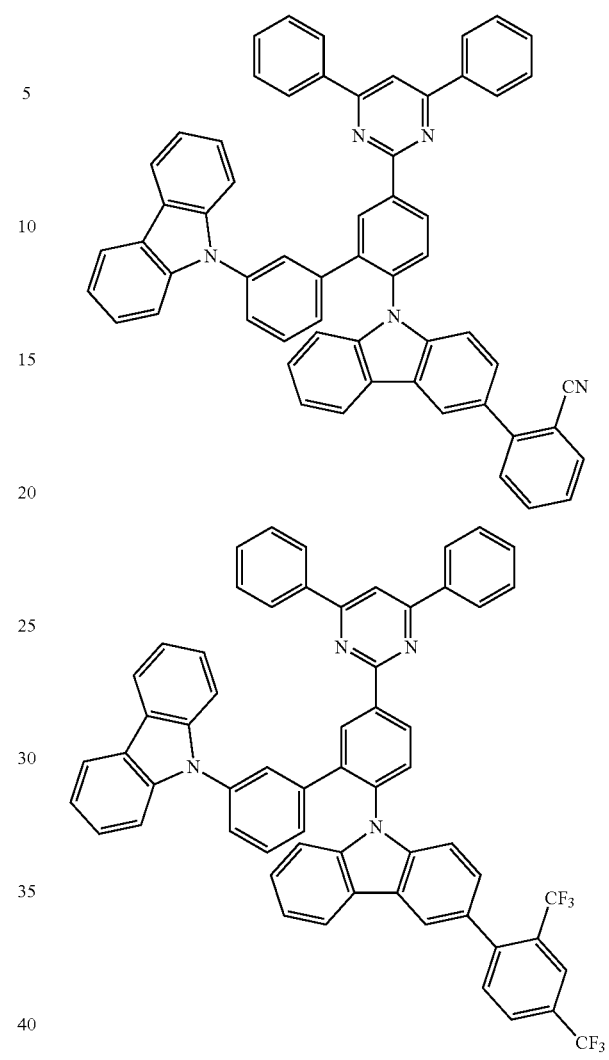
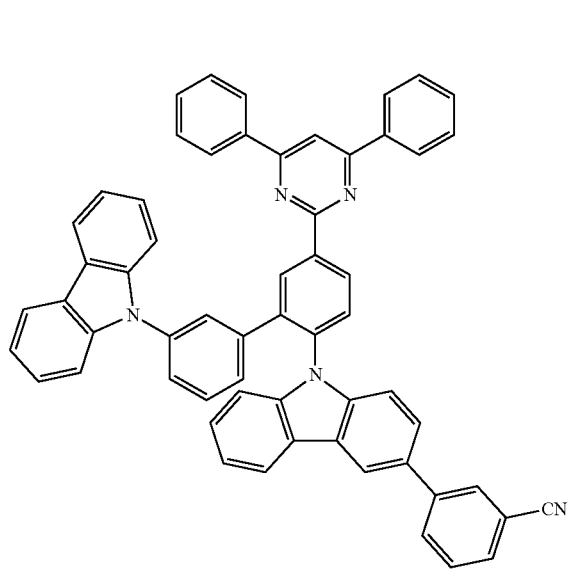
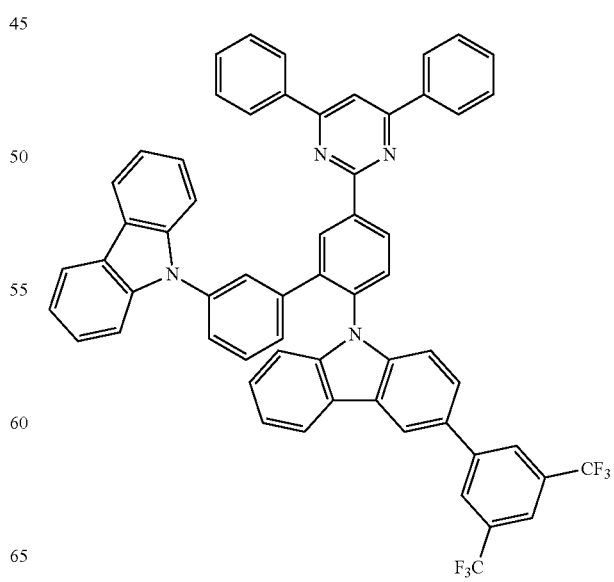

341
-continued
342
-continued
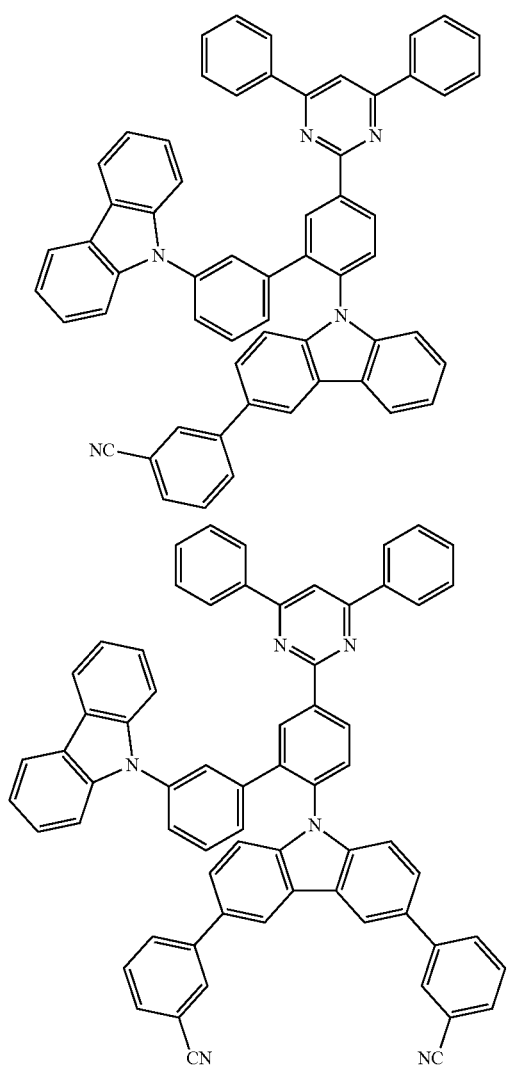
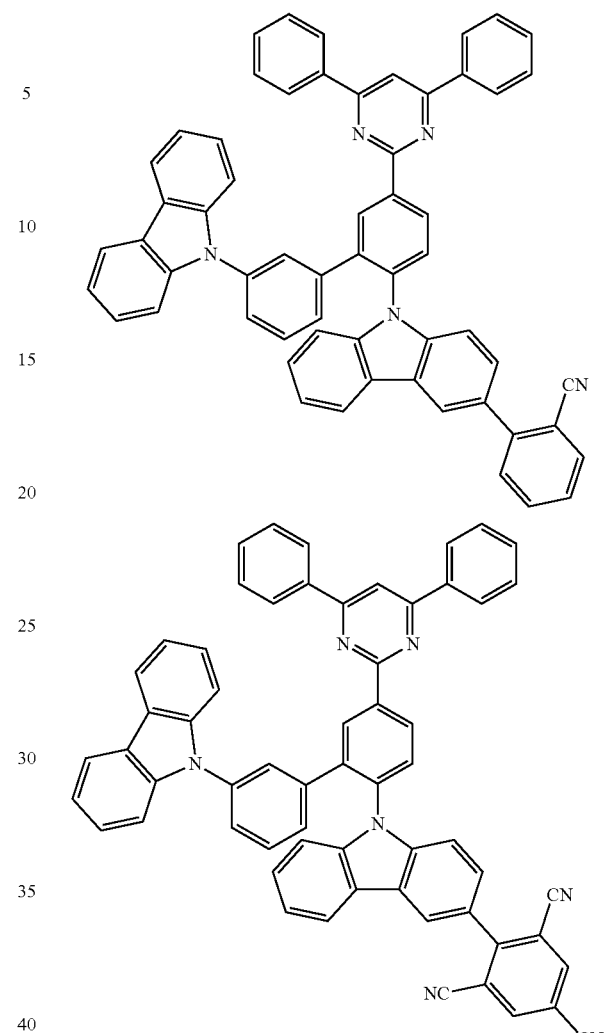
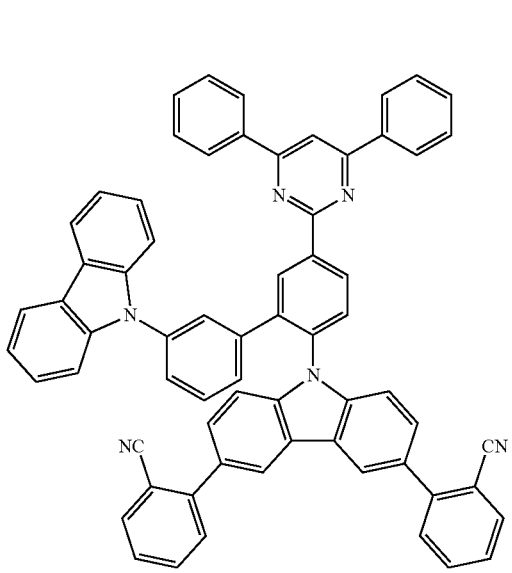
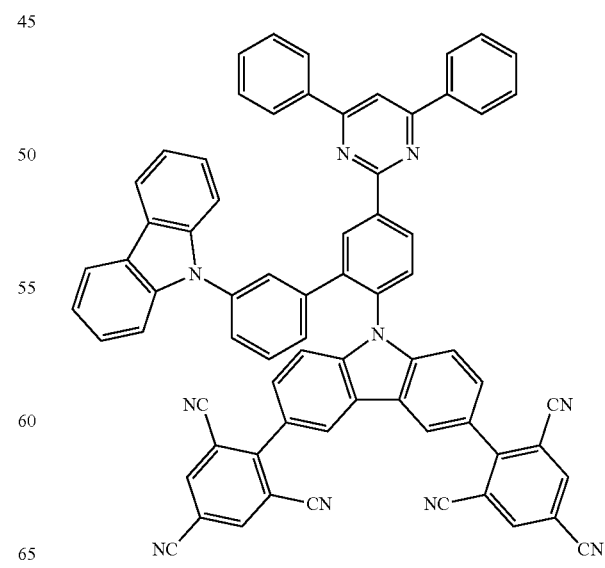

343
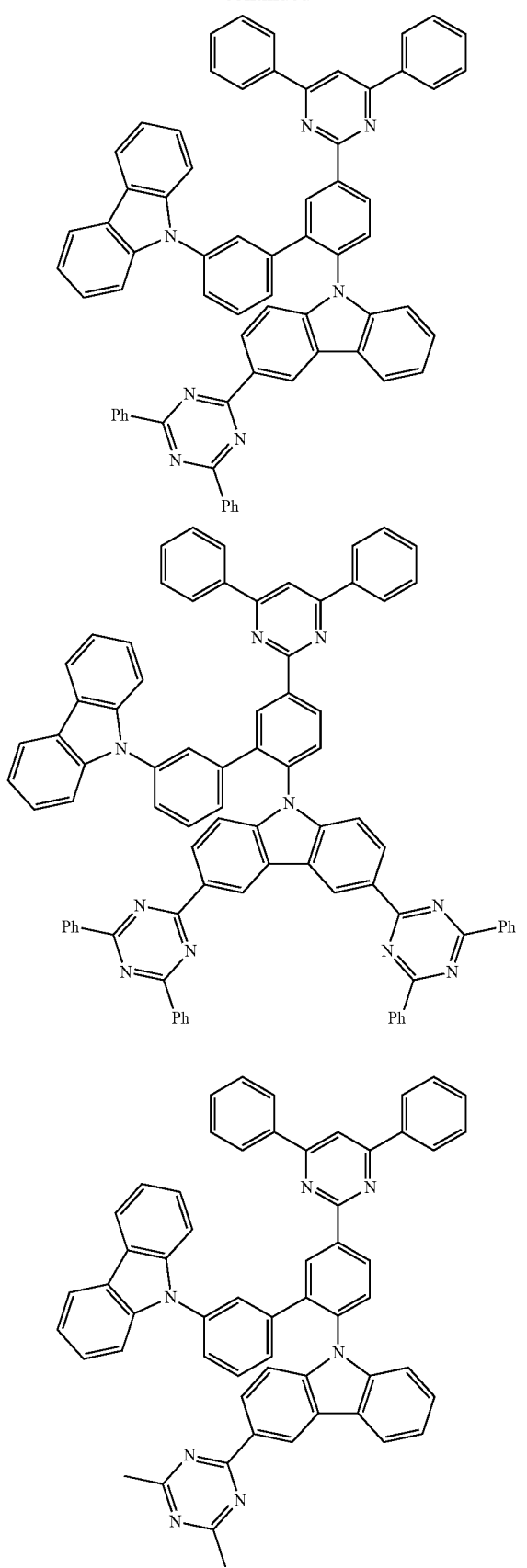
344
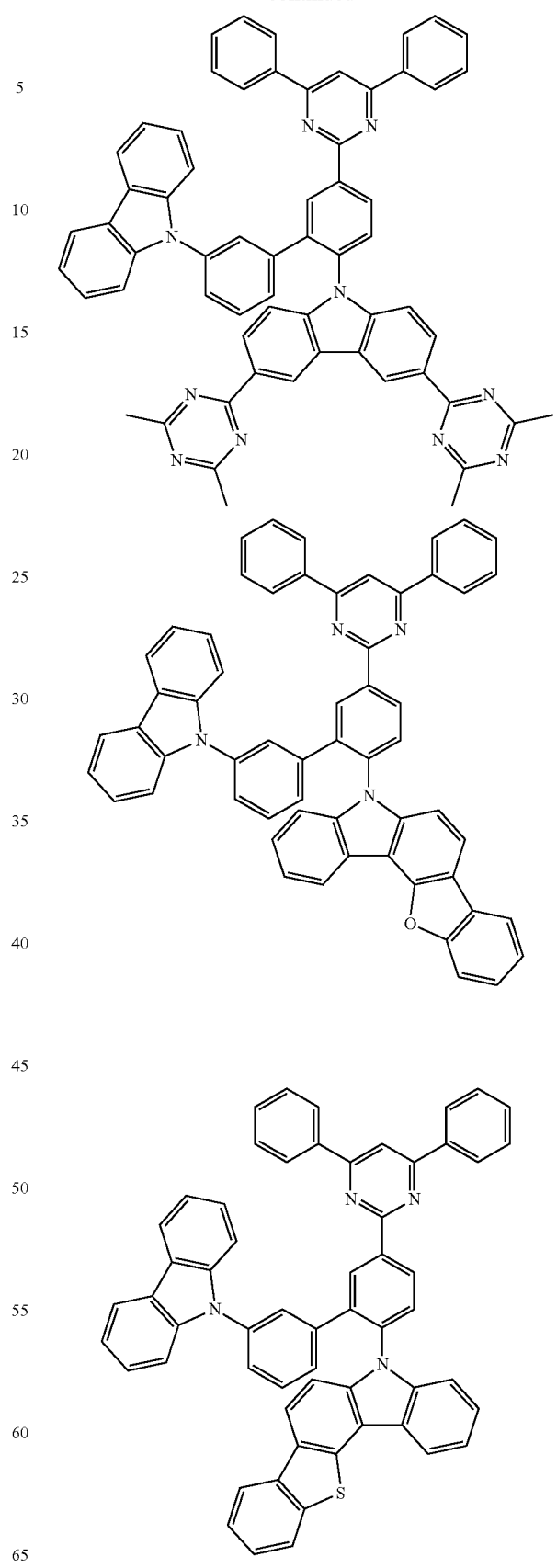

345
-continued
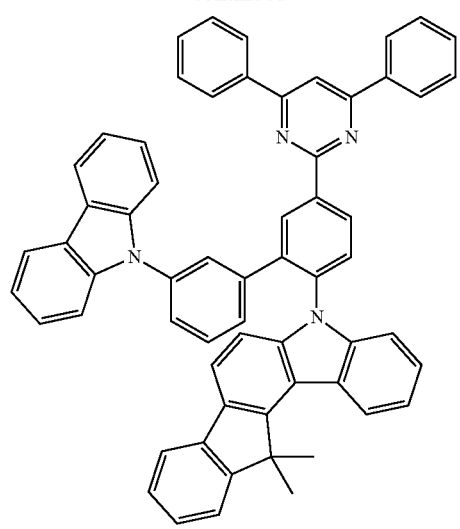
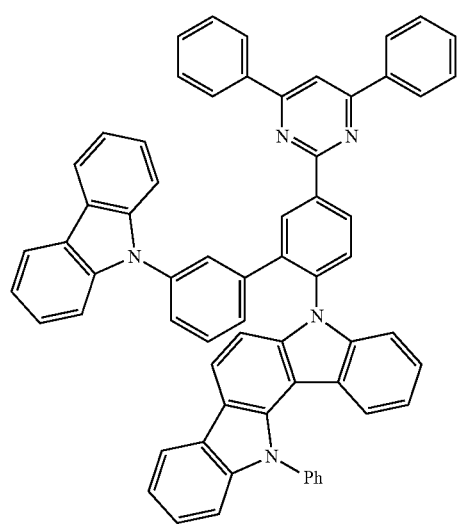
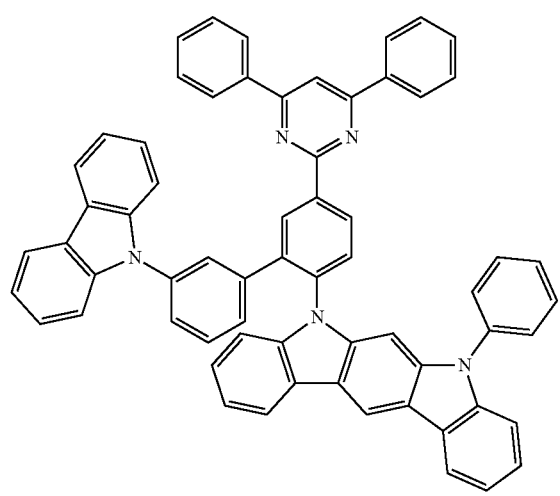
346
-continued
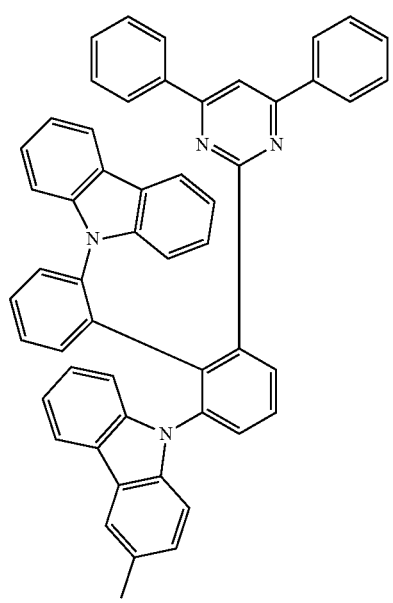
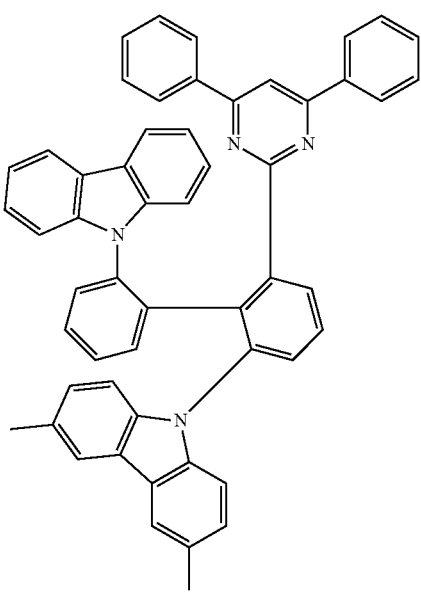

347
-continued
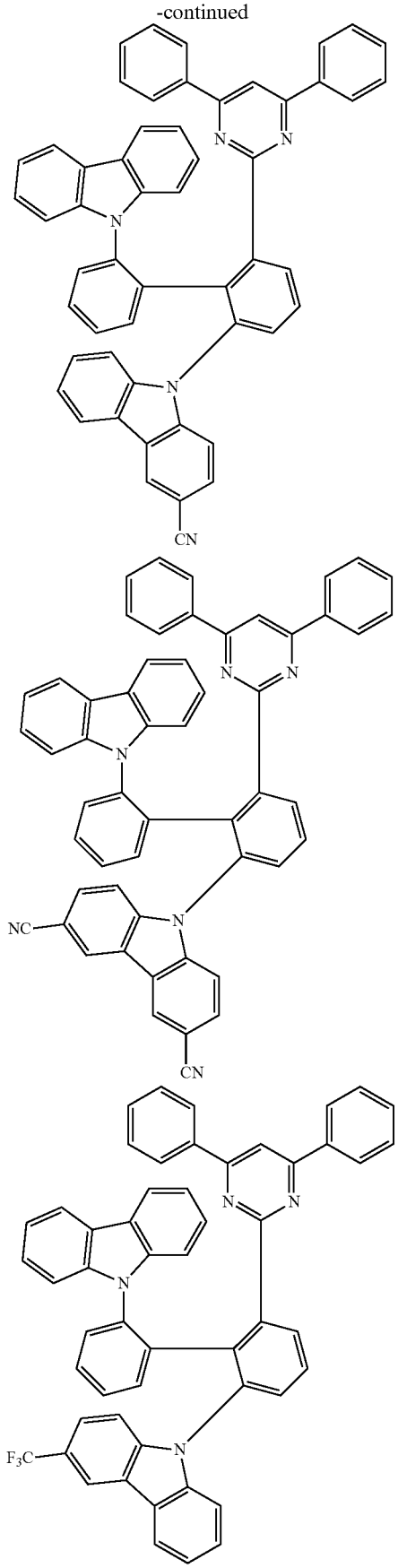
348
-continued
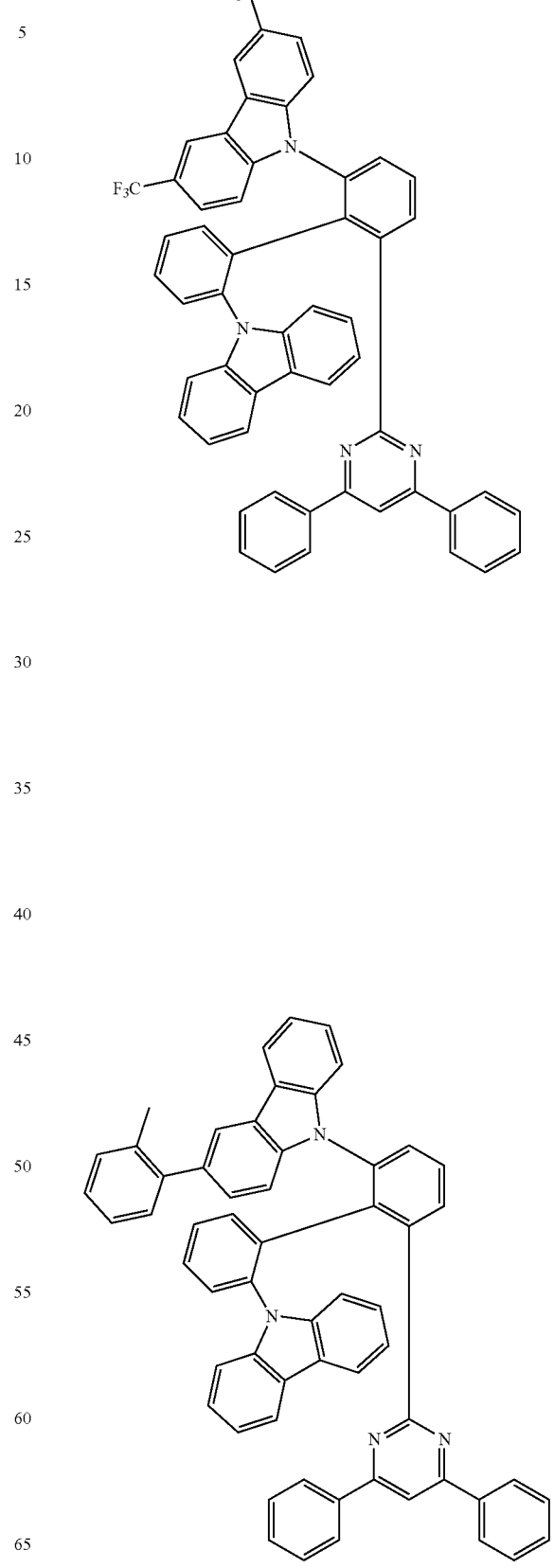

349
-continued
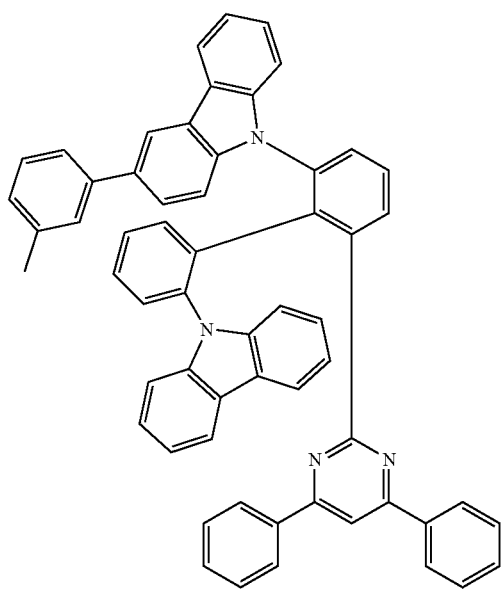
350
-continued
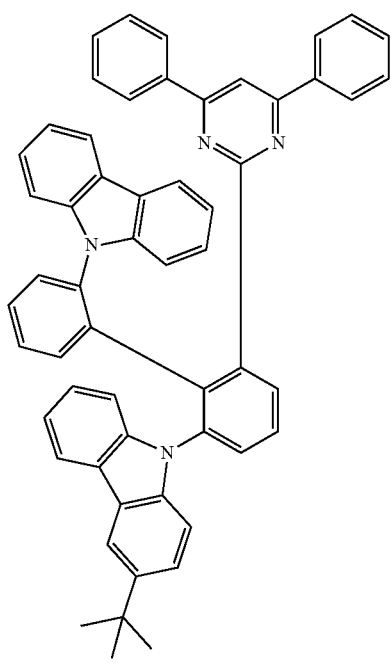
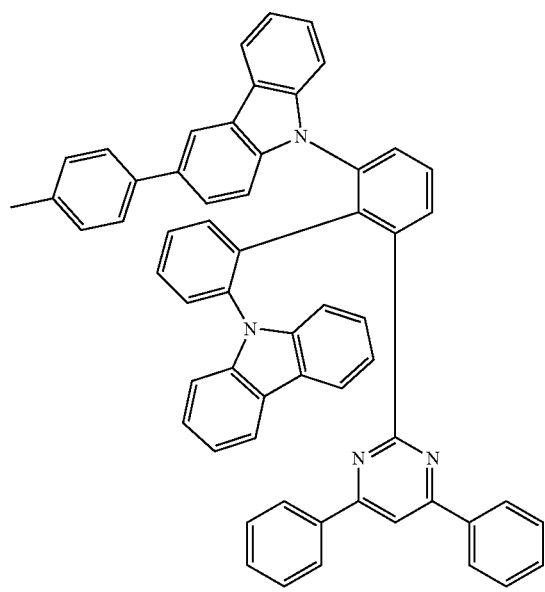
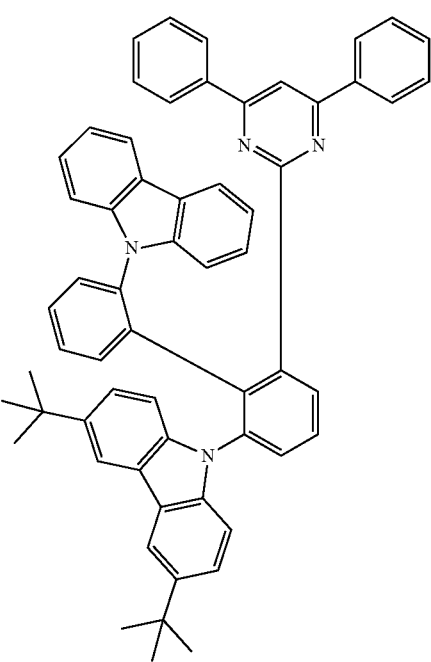

351
-continued
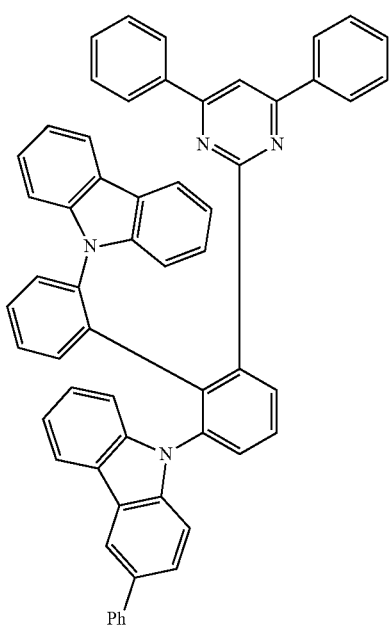
352
-continued
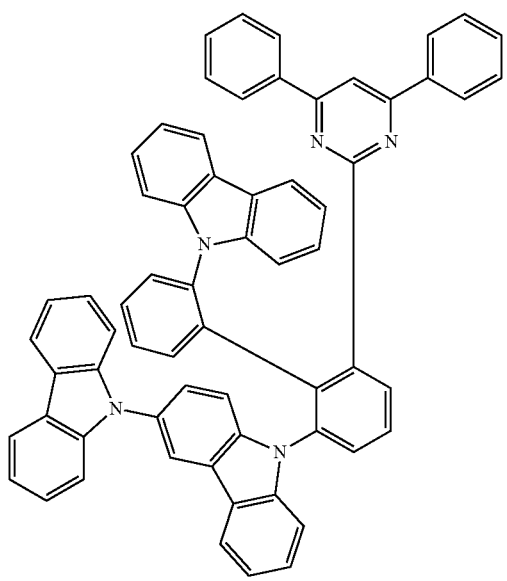
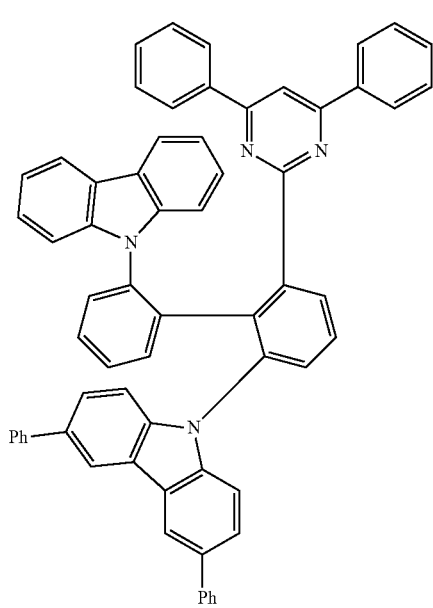
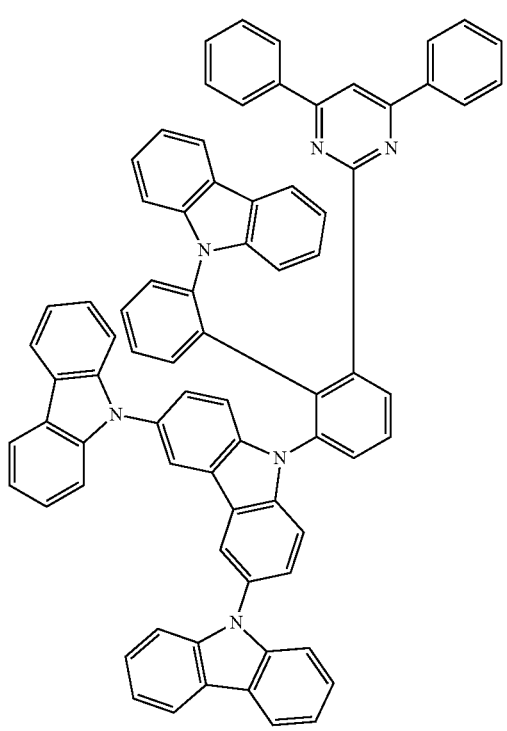

353
-continued
354
-continued
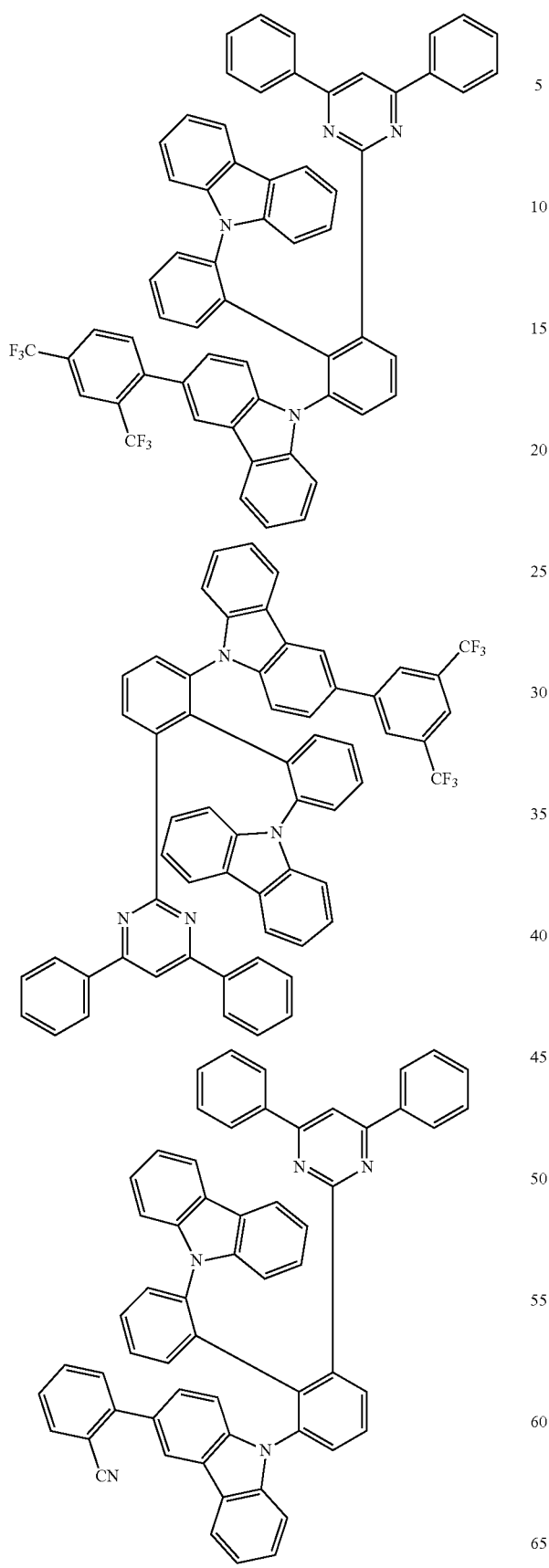
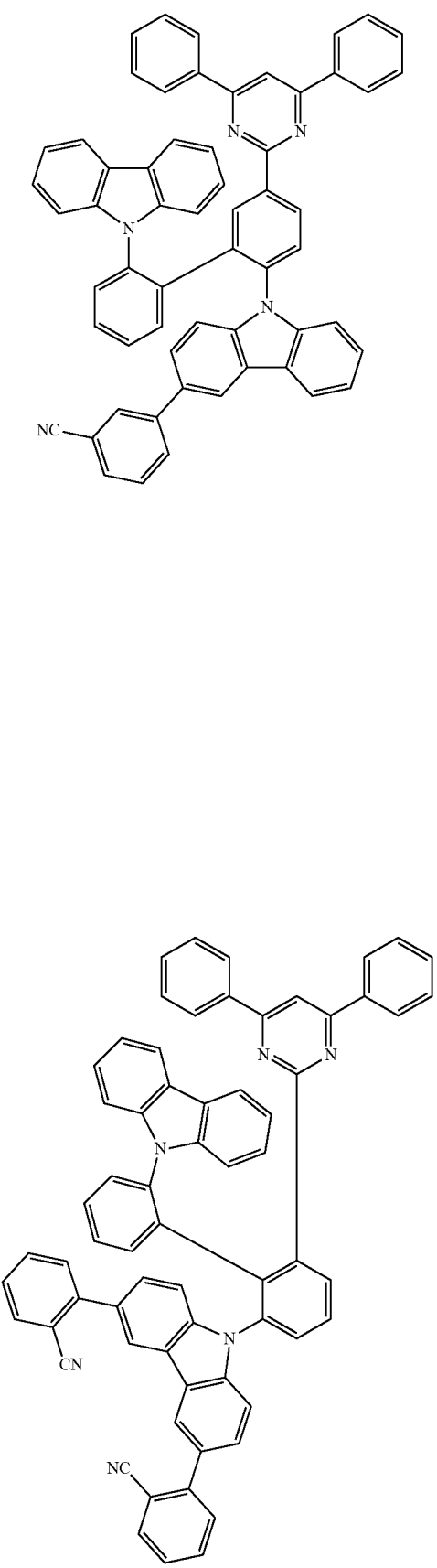

355
-continued
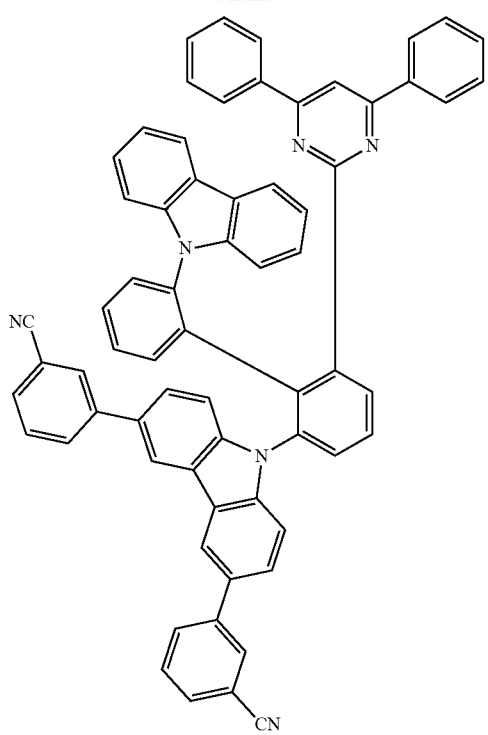
356
-continued
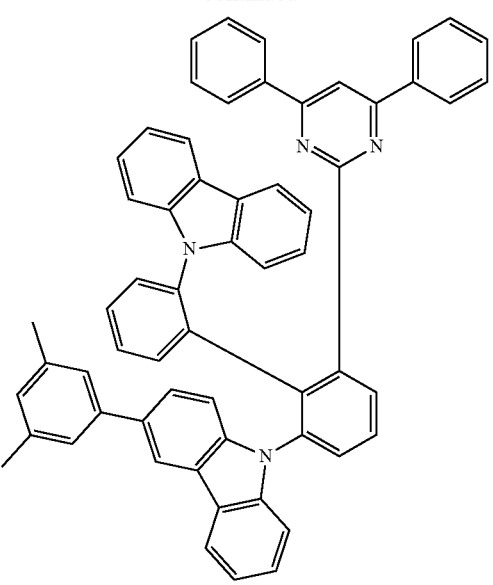
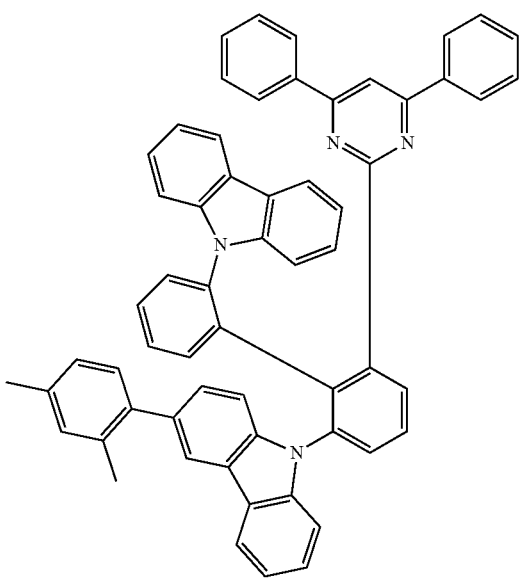

357
-continued
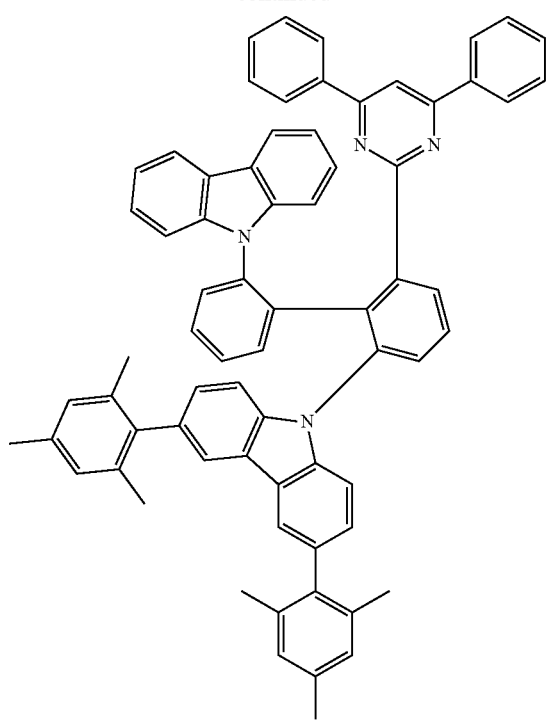
358
-continued
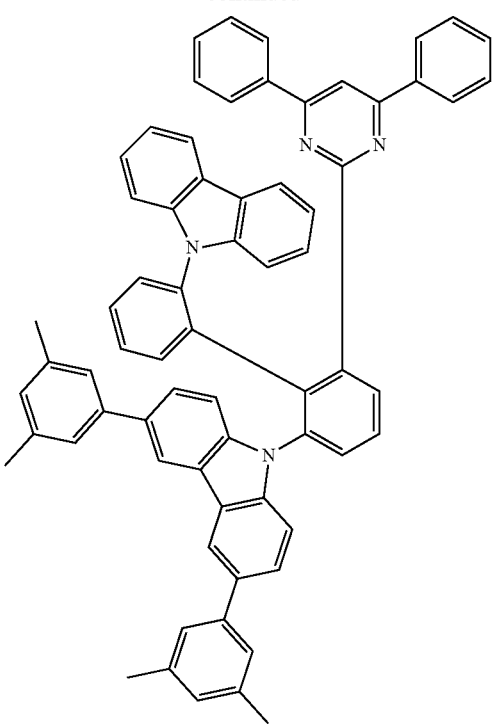
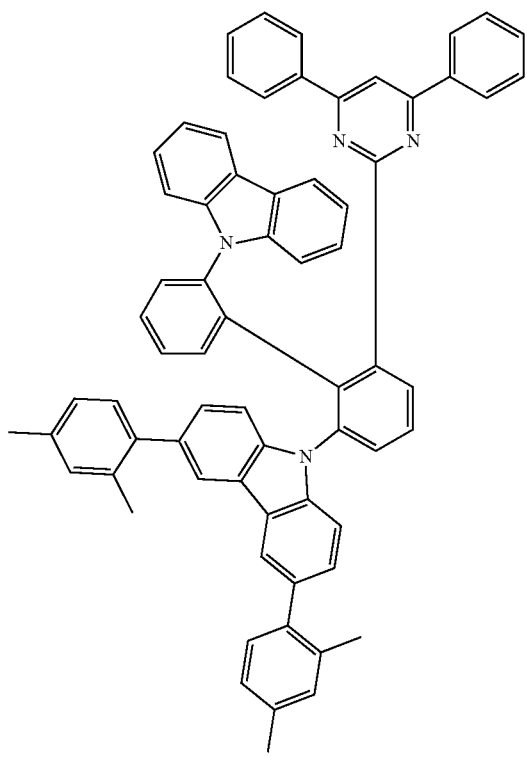

359
-continued
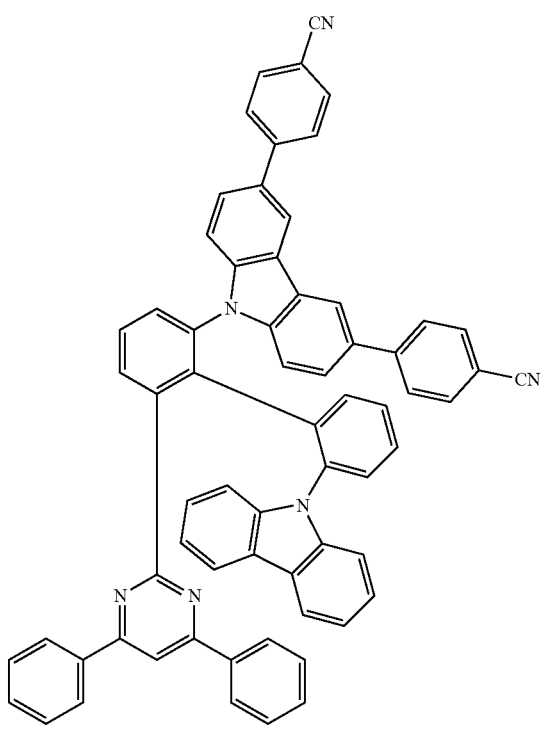
360
-continued
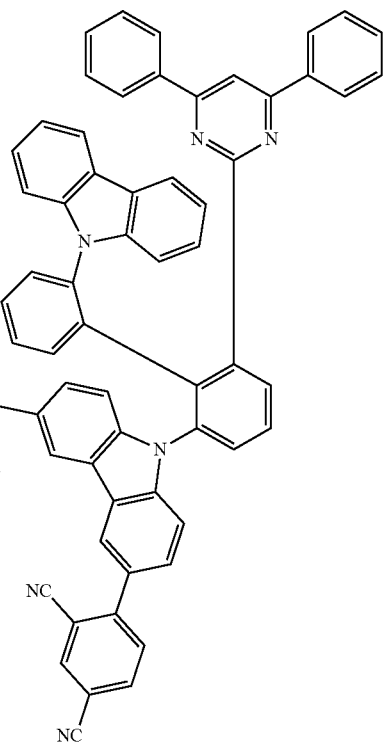
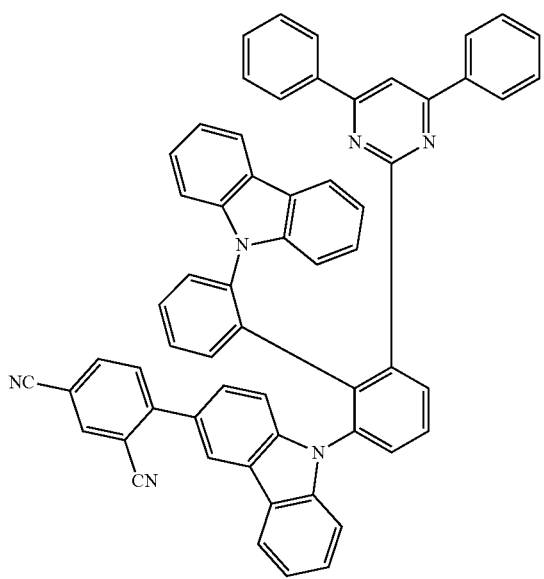
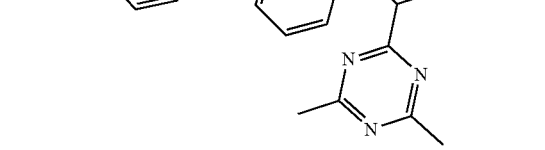

361
-continued

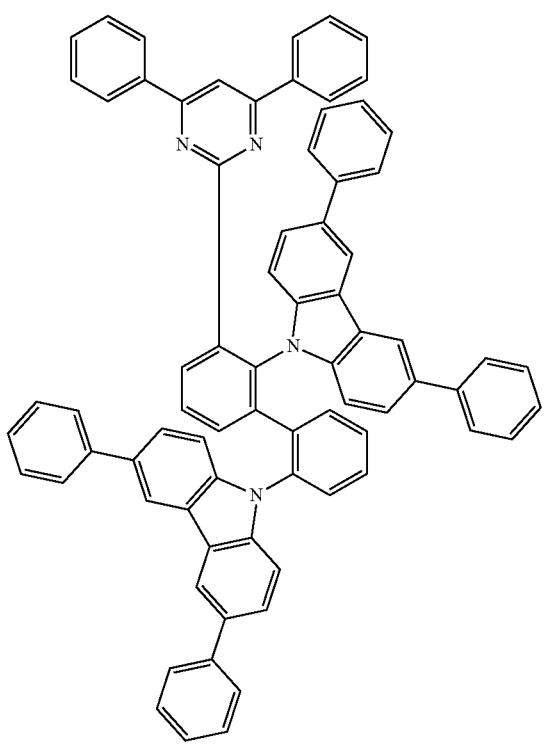

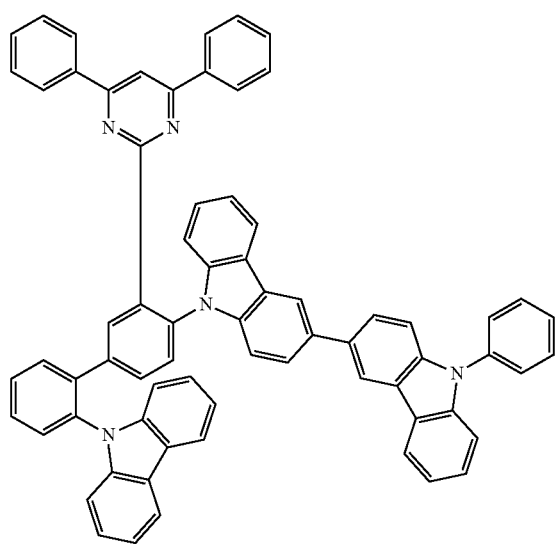 [SMILES: c1ccc(-c2cc(-c3cc(-c4ccccc4-n4c5ccccc5c5ccccc54)ccc3-n3c4ccccc4c4cc(-c5ccc6c(c5)c5ccccc5n6-c5ccccc5)ccc43)nc(-c3ccccc3)n2)cc1]

362
-continued

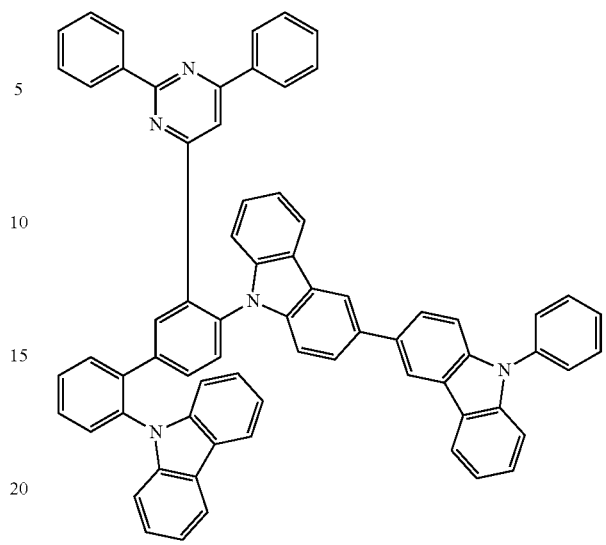

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule, comprising:
a first chemical moiety comprising a structure of Formula Iaa:

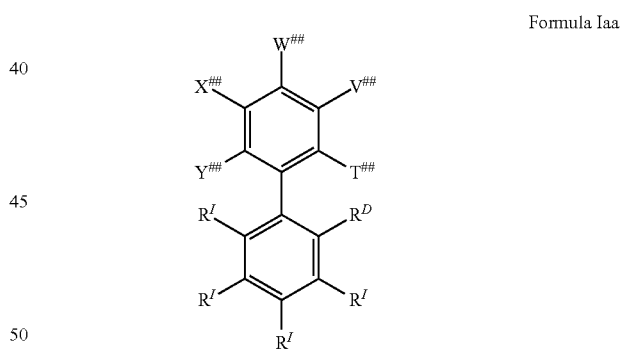

Formula Iaa and
two second chemical moieties, each independently from another comprising a structure of Formula IIa:

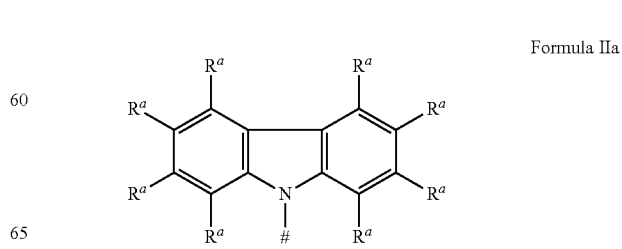

Formula IIa wherein
$R^D$ is the binding site of a single bond linking the first chemical moiety to one of the two second chemical moieties,
$T^{\#\#}$ is selected from the group consisting of $R^A$ and $R^1$,
$V^{\#\#}$ is selected from the group consisting of $R^A$ and $R^1$,
$W^{\#\#}$ is the binding site of a single bond linking the first chemical moiety to one of the two second chemical moieties or is selected from the group consisting of $R^A$ and $R^2$,
$X^{\#\#}$ is the binding site of a single bond linking the first chemical moiety to one of the two second chemical moieties or is $R^2$,
$Y^{\#\#}$ is the binding site of a single bond linking the first chemical moiety to one of the two second chemical moieties or is $R^2$,
wherein exactly one substituent selected from the group consisting of $W^{\#\#}$, $Y^{\#\#}$ and $X^{\#\#}$ represents the binding site of a single bond linking the first chemical moiety and one of the two second chemical moieties,
and wherein exactly one substituent selected from the group consisting of $T^{\#\#}$, $V^{\#\#}$ and $W^{\#\#}$ is $R^A$;
$R^A$ comprises a structure of Formula Py:

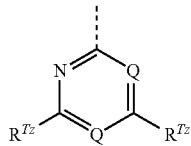

Formula Py wherein one Q is N and the other Q is C—$R^{PY}$, wherein the dashed bond represents the binding site of Py to the single bond linking the first chemical moiety and $R^A$;
\# represents the binding site of a single bond linking the second chemical moieties to the first chemical moiety;
$R^1$ is at each occurrence independently from another selected from the group consisting of:
hydrogen, deuterium,
$C_1$-$C_5$-alkyl,
  wherein one or more hydrogen atoms are optionally substituted by deuterium;
$C_2$-$C_8$-alkenyl,
  wherein one or more hydrogen atoms are optionally substituted by deuterium;
$C_2$-$C_8$-alkynyl,
  wherein one or more hydrogen atoms are optionally substituted by deuterium; and
$C_6$-$C_{18}$-aryl,
  which is optionally substituted with one or more substituents $R^6$;
$R^2$ is at each occurrence independently from another selected from the group consisting of:
hydrogen, deuterium,
$C_1$-$C_5$-alkyl,
  wherein one or more hydrogen atoms are optionally substituted by deuterium;
$C_2$-$C_8$-alkenyl,
  wherein one or more hydrogen atoms are optionally substituted by deuterium;
$C_2$-$C_8$-alkynyl,
  wherein one or more hydrogen atoms are optionally substituted by deuterium; and
$C_6$-$C_{18}$-aryl,
  which is optionally substituted with one or more substituents $R^6$;
$R^I$ is at each occurrence independently from another selected from the group consisting of:
hydrogen, deuterium,
$C_1$-$C_5$-alkyl,
  wherein one or more hydrogen atoms are optionally substituted by deuterium;
$C_2$-$C_8$-alkenyl,
  wherein one or more hydrogen atoms are optionally substituted by deuterium;
$C_2$-$C_8$-alkynyl,
  wherein one or more hydrogen atoms are optionally substituted by deuterium; and
$C_6$-$C_{18}$-aryl,
  which is optionally substituted with one or more substituents $R^6$;
$R^{Tz}$ is at each occurrence independently from another selected from the group consisting of
hydrogen,
deuterium,
$C_1$-$C_5$-alkyl,
  wherein one or more hydrogen atoms are optionally substituted by deuterium;
$C_6$-$C_{18}$-aryl,
  which is optionally substituted with one or more substituents $R^6$; and
$C_3$-$C_{17}$-heteroaryl,
  which is optionally substituted with one or more substituents $R^6$;
$R^{Py}$ is at each occurrence independently from another selected from the group consisting of:
hydrogen,
deuterium,
$C_1$-$C_5$-alkyl,
  wherein one or more hydrogen atoms are optionally substituted by deuterium;
$C_6$-$C_{18}$-aryl,
  which is optionally substituted with one or more substituents $R^6$; and
$C_3$-$C_{17}$-heteroaryl,
which is optionally substituted with one or more substituents $R^6$;
$R^a$ is at each occurrence independently from another selected from the group consisting of: hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;

$C_2$-$C_{40}$-alkenyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_2$-$C_{40}$-alkynyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$;

$C_6$-$C_{60}$-aryl,
  which is optionally substituted with one or more substituents $R^5$; and $C_3$-$C_{57}$-heteroaryl,
  which is optionally substituted with one or more substituents $R^5$;

$R^5$ is at each occurrence independently from another selected from the group consisting of hydrogen, deuterium, $N(R^6)_2$, $OR^6$, $Si(R^6)_3$, $B(OR^6)_2$, $OSO_2R^6$, $CF_3$, $CN$, $F$, $Br$, $I$, $C_1$-$C_{40}$-alkyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_1$-$C_{40}$-alkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_1$-$C_{40}$-thioalkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_2$-$C_{40}$-alkenyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_2$-$C_{40}$-alkynyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, $SO$, $SO_2$, $NR^6$, $O$, $S$ or $CONR^6$;

$C_6$-$C_{60}$-aryl,
  which is optionally substituted with one or more substituents $R^6$; and $C_3$-$C_{57}$-heteroaryl,
  which is optionally substituted with one or more substituents $R^6$; and $R^6$ is at each occurrence independently from another selected from the group consisting of: hydrogen, deuterium, $OPh$, $CF_3$, $CN$, $F$, $C_1$-$C_5$-alkyl,
  wherein one or more hydrogen atoms are optionally, independently from each other substituted by deuterium, $CN$, $CF_3$, or $F$;

$C_1$-$C_5$-alkoxy,
  wherein one or more hydrogen atoms are optionally, independently from each other substituted by deuterium, $CN$, $CF_3$, or $F$;

$C_1$-$C_5$-thioalkoxy,
  wherein one or more hydrogen atoms are optionally, independently from each other substituted by deuterium, $CN$, $CF_3$, or $F$;

$C_2$-$C_5$-alkenyl,
  wherein one or more hydrogen atoms are optionally, independently from each other substituted by deuterium, $CN$, $CF_3$, or $F$;

$C_2$-$C_5$-alkynyl,
  wherein one or more hydrogen atoms are optionally, independently from each other substituted by deuterium, $CN$, $CF_3$, or $F$;

$C_6$-$C_{18}$-aryl,
  which is optionally substituted with one or more $C_1$-$C_5$-alkyl substituents;

$C_3$-$C_{17}$-heteroaryl,
  which is optionally substituted with one or more $C_1$-$C_5$-alkyl substituents;

$N(C_6$-$C_{18}$-aryl$)_2$;
$N(C_3$-$C_{17}$-heteroaryl$)_2$,
and $N(C_3$-$C_{17}$-heteroaryl$)(C_6$-$C_{18}$-aryl);

wherein the substituents $R^a$ and/or $R^5$ independently from each other optionally form a mono- or polycyclic, aliphatic, aromatic and/or benzo-fused ring system with one or more substituents $R^a$ and/or $R^5$.

2. The organic molecule according to claim 1, wherein at each occurrence $R^1$, $R^2$ and $R^I$ is independently from each other selected from the group consisting of H, methyl, mesityl, tolyl, and phenyl.

3. The organic molecule according to claim 1, wherein $R^{Tz}$ and $R^{Py}$ is independently from each other at each occurrence selected from the group consisting of H, methyl, and phenyl.

4. The organic molecule according to claim 2, wherein $R^{Tz}$ and $R^{Py}$ is independently from each other at each occurrence selected from the group consisting of H, methyl, and phenyl.

5. The organic molecule according to claim 1, wherein $R^a$ is at each occurrence independently from another selected from the group consisting of H,
Me,
$^iPr$,
$^tBu$,
CN,
$CF_3$,
phenyl (Ph), which is optionally substituted with one or more substituents independently from each other selected from the group consisting of Me, $^iPr$, $^tBu$, CN, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph, carbazolyl, which is optionally substituted with one or more substituents independently from each other selected from the group consisting of Me, $^i$Pr, $^t$Bu, CN, CF$_3$, and Ph, triazinyl, which is optionally substituted with one or more substituents independently from each other selected from the group consisting of Me, $^i$Pr, $^t$Bu, CN, CF$_3$, and Ph, and N(Ph)$_2$.

6. The organic molecule according to claim 1, wherein R$^a$ is at each occurrence independently from another selected from the group consisting of H, Me, $^i$Pr, 1Bu,

CN,

CF$_3$,

Ph, which is optionally substituted with one or more substituents independently from each other selected from the group consisting of Me, $^i$Pr, $^t$Bu, CN, CF$_3$, and Ph, pyridinyl, which is optionally substituted with one or more substituents independently from each other selected from the group consisting of Me, $^i$Pr, $^t$Bu, CN, CF$_3$, and Ph, pyrimidinyl, which is optionally substituted with one or more substituents independently from each other selected from the group consisting of Me, $^i$Pr, $^t$Bu, CN, CF$_3$, and Ph, and triazinyl, which is optionally substituted with one or more substituents independently from each other selected from the group consisting of Me, $^i$Pr, $^t$Bu, CN, CF$_3$, and Ph.

7. The organic molecule according to claim 1, wherein R$^a$ is at each occurrence independently from another selected from the group consisting of H, Me, $^t$Bu, Ph, which is optionally substituted with one or more substituents independently from each other selected from the group consisting of Me, $^i$Pr, $^t$Bu, CN, CF$_3$, and Ph, and triazinyl, which is optionally substituted with one or more substituents independently from each other selected from the group consisting of Me, $^i$Pr, $^t$Bu, CN, CF$_3$, and Ph.

8. The organic molecule according to claim 1, wherein R$^a$ is H at each occurrence.

9. A composition comprising:
   (a) at least one organic molecule according to claim 1 as an emitter and/or a host;
   (b) one or more emitter and/or host materials different from the at least one organic molecule according to claim 1, and
   (c) optionally one or more dyes and/or one or more solvents.

10. An optoelectronic device comprising the organic molecule according to claim 1.

11. The optoelectronic device according to claim 10, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

12. The optoelectronic device according to claim 11, comprising:
    a substrate;
    an anode;
    a cathode, wherein the anode or the cathode is disposed on the substrate; and
    at least one light-emitting layer disposed between the anode and the cathode and which comprises the organic molecule.

13. An optoelectronic device comprising the organic molecule according to claim 1, wherein the organic molecule is one of a luminescent emitter, an electron transport material, a hole injection material or a hole blocking material in the optoelectronic device.

14. An optoelectronic device comprising the organic molecule according to claim 2, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

15. The optoelectronic device according to claim 14, comprising:
    a substrate;
    an anode;
    a cathode, wherein the anode or the cathode is applied to the substrate; and
    at least one light-emitting layer disposed between the anode and the cathode and which comprises the organic molecule.

16. An optoelectronic device comprising the composition according to claim 9.

17. The optoelectronic device according to claim 16, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

18. The optoelectronic device according to claim 17, comprising:
    a substrate;
    an anode;
    a cathode, wherein the anode or the cathode is disposed on the substrate; and
    at least one light-emitting layer disposed between the anode and the cathode and which comprises the composition.

19. A process for producing an optoelectronic device, comprising processing of the organic molecule according to claim 1 by a vacuum evaporation method or from a solution.

20. A process for producing an optoelectronic device, comprising processing of the composition according to claim 9 by a vacuum evaporation method or from a solution.

* * * * *